(12) United States Patent
Murphy et al.

(10) Patent No.: US 6,306,394 B1
(45) Date of Patent: Oct. 23, 2001

(54) NUCLEIC ACIDS, PROTEINS, AND METHODS OF USE OF GRANULOCYTIC EHRLICHIA

(75) Inventors: Cheryl Murphy, Hopkinton; James Storey, Linwood; Gerald A. Beltz, Lexington; Richard T. Coughlin, Leicester, all of MA (US)

(73) Assignee: Aquila Biopharmaceuticals Inc., Framingham, MA (US)

( * ) Notice: Subject to any disclaimer, the term of this patent is extended or adjusted under 35 U.S.C. 154(b) by 0 days.

(21) Appl. No.: 09/066,047

(22) Filed: Apr. 24, 1998

Related U.S. Application Data

(60) Provisional application No. 60/044,869, filed on Apr. 25, 1997.

(51) Int. Cl.[7] .......................... A61K 39/00; A61K 49/00; C12Q 1/68; C12N 1/00; C07K 14/00
(52) U.S. Cl. .......................... 424/184.1; 424/9.2; 435/6; 435/243; 435/252.1; 435/260; 530/300; 530/350
(58) Field of Search ................... 424/9.2, 184.1; 435/243, 252.1, 260, 6; 530/300, 350

(56) References Cited

FOREIGN PATENT DOCUMENTS

WO 96/39484   12/1996  (WO) .
WO 98/42740   10/1998  (WO) .

OTHER PUBLICATIONS

Asanovich, K.M. et al., "Partial Characterization of Cloned Genes Encoding Immunoreactive Proteins of *Ehrlichia equi* and the Agent of Human Granulocytic Ehrlichiosis (HGE)," Abstracts of the General Meeting of the American Society for Microbiology, May 19, 1996, p. D–22.

Dumler, J.S. et al., "Serologic Cross–Reactions Among *Ehrlichia equi*, *Ehrlichia phagocytophila*, and Human Granulocytic Ehrlichia," Journal of Clinical Microbiology, vol. 33, No. 5, May 1995, pp. 1098–1103.

*Primary Examiner*—Rodney P. Swart
(74) *Attorney, Agent, or Firm*—Pennie & Edmonds LLP

(57) ABSTRACT

Nucleic acids encoding eleven different proteins of granulocytic erhlichia (GE), a tick-borne intracellular bacteria, have been isolated and sequenced completely. These DNAs were isolated as immunoreactive clones from a Lambda Zap II genomic library of GE DNA purified from infected HL60 cells. Three of the clones, E8, E80, and E46, contain open reading frames for four highly homologous proteins which appear to be part of a multigene family resembling the MSP-2 gene family of *Anaplasma marginale*. One clone, B3, contained a gene encoding the heat shock 70 protein. The other clones (W20, E74, and E82) contain open reading frames for proteins which have some homology to other bacterial proteins present in the nucleotide and protein databases. These and other GE antigens identified by immunoscreening of the genomic library are potentially useful as diagnostic reagents and vaccine candidates for GE.

9 Claims, 63 Drawing Sheets

Sequence Range: 1 to 4833

```
              10         20         30         40         50
               *          *          *          *          *
         CCGCTCTAGA ACTAGTGGAT CCCCCGGGCT GCAGGAATTC C AAG GAA GTT GTC CTC
                                                       Lys Glu Val Val Leu>
                                                     a  ORF 1  a         >

60         70         80         90        100
               *          *          *          *          *
         AAG AAC ATG ATA GCC GAC ATG GTC GTT GAA AAG TTT GCT CAT GAC TTA
         Lys Asn Met Ile Ala Asp Met Val Val Glu Lys Phe Ala His Asp Leu>
          a   a   a   a   a   a  ORF 1  a   a   a   a   a   a   a   a  >

110        120        130        140        150
               *          *          *          *          *
         GGC ATA CGT GTT GGC TCA AAT AGC TTA CGG AGT CTG ATC AAA AAT ATA
         Gly Ile Arg Val Gly Ser Asn Ser Leu Arg Ser Leu Ile Lys Asn Ile>
          a   a   a   a   a   a  ORF 1  a   a   a   a   a   a   a   a  >

160        170        180        190        200
               *          *          *          *          *
         AGA ATA TTT CAG GAT GCT AAT GGT GTC TTC GAC CAG GAG AGA TAT GAA
         Arg Ile Phe Gln Asp Ala Asn Gly Val Phe Asp Gln Glu Arg Tyr Glu>
          a   a   a   a   a   a  ORF 1  a   a   a   a   a   a   a   a  >

210        220        230        240
               *          *          *          *
         GCC GTA TTG GCT GAC AGC GGA ATG ACT GAG TCG TCC TAT GTG AAT AAA
         Ala Val Leu Ala Asp Ser Gly Met Thr Glu Ser Ser Tyr Val Asn Lys>
          a   a   a   a   a   a  ORF 1  a   a   a   a   a   a   a   a  >

250        260        270        280        290
           *          *          *          *          *
         ATT CGC AAT GCT TTA CCT TCT ACT ATT CTA ATG GAG TGT TTA TTC CCT
         Ile Arg Asn Ala Leu Pro Ser Thr Ile Leu Met Glu Cys Leu Phe Pro>
          a   a   a   a   a   a  ORF 1  a   a   a   a   a   a   a   a  >

300        310        320        330        340
               *          *          *          *          *
         AAT AGG GCG GAA TTA CAT ATT CCT TAT TAT GAT GCA TTA GCA AAA GAT
         Asn Arg Ala Glu Leu His Ile Pro Tyr Tyr Asp Ala Leu Ala Lys Asp>
          a   a   a   a   a   a  ORF 1  a   a   a   a   a   a   a   a  >

350        360        370        380        390
               *          *          *          *          *
         GTT GTG TTG GGA TTG CTG CAG CAT CGT GTG GCA GAC ATA GTG GAA ATA
         Val Val Leu Gly Leu Leu Gln His Arg Val Ala Asp Ile Val Glu Ile>
          a   a   a   a   a   a  ORF 1  a   a   a   a   a   a   a   a  >

400        410        420        430        440
               *          *          *          *          *
         TCT TCT GAT GCC GTA GAC ATT TCA GGA AGT GAT ATA TCT GAT GAT GAA
         Ser Ser Asp Ala Val Asp Ile Ser Gly Ser Asp Ile Ser Asp Asp Glu>
          a   a   a   a   a   a  ORF 1  a   a   a   a   a   a   a   a  >

450        460        470        480
               *          *          *          *
         TTG CAA AAA TTG TTT GAG GAG CAG TAC AAG AAT TCT CTA AAT TTC CCT
         Leu Gln Lys Leu Phe Glu Glu Gln Tyr Lys Asn Ser Leu Asn Phe Pro>
          a   a   a   a   a   a  ORF 1  a   a   a   a   a   a   a   a  >
```

FIG. 1A

```
        490         500         510         520         530
         *           *           *           *           *
GAA TAT CGC AGT GCT GAT TAT ATA ATC ATG GCA GAA GAC GAC TTG CTT
Glu Tyr Arg Ser Ala Asp Tyr Ile Ile Met Ala Glu Asp Asp Leu Leu>
 a   a   a   a   a   a  ORF 1  a   a   a   a   a   a   a   a >

540         550         560         570         580
         *           *           *           *           *
GCT GAT GTC ATT GTT TCG GAT CAA GAG GTA GAC GTT GAG ATT AAA AAC
Ala Asp Val Ile Val Ser Asp Gln Glu Val Asp Val Glu Ile Lys Asn>
 a   a   a   a   a   a  ORF 1  a   a   a   a   a   a   a   a >

590         600         610         620         630
         *           *           *           *           *
AGT GAA CTA CAT GAT CAA AGA GAT GTT CTA AAT TTA GTA TTT ACA GAC
Ser Glu Leu His Asp Gln Arg Asp Val Leu Asn Leu Val Phe Thr Asp>
 a   a   a   a   a   a  ORF 1  a   a   a   a   a   a   a   a >

640         650         660         670         680
         *           *           *           *           *
AAA AAT GAA GCT GAG CTA GCT TAC AAA GCT TAC CAA GAG GGT AAG TCT
Lys Asn Glu Ala Glu Leu Ala Tyr Lys Ala Tyr Gln Glu Gly Lys Ser>
 a   a   a   a   a   a  ORF 1  a   a   a   a   a   a   a   a >

690         700         710         720
         *           *           *           *
TTT GAG GAA TTG GTT AGT GAT GCT GGC TAC ACC ATA GAG GAT ATT GCA
Phe Glu Glu Leu Val Ser Asp Ala Gly Tyr Thr Ile Glu Asp Ile Ala>
 a   a   a   a   a   a  ORF 1  a   a   a   a   a   a   a   a >

730         740         750         760         770
  *           *           *           *           *
CTC AAT AAT ATC TCT AAG GAT GTT CTT CCG GTA GGT GTG CGA AAT GTG
Leu Asn Asn Ile Ser Lys Asp Val Leu Pro Val Gly Val Arg Asn Val>
 a   a   a   a   a   a  ORF 1  a   a   a   a   a   a   a   a >

780         790         800         810         820
         *           *           *           *           *
GTG TTT GCA CTA AAT GAA GGA GAA GTC AGT GAA ATG TTC CGT AGC GTT
Val Phe Ala Leu Asn Glu Gly Glu Val Ser Glu Met Phe Arg Ser Val>
 a   a   a   a   a   a  ORF 1  a   a   a   a   a   a   a   a >

830         840         850         860         870
         *           *           *           *           *
GTC GGC TGG CAT ATC ATG AAG GTA ATA AGG AAG CAT GAG ATC ACT AAG
Val Gly Trp His Ile Met Lys Val Ile Arg Lys His Glu Ile Thr Lys>
 a   a   a   a   a   a  ORF 1  a   a   a   a   a   a   a   a >

880         890         900         910         920
         *           *           *           *           *
GAA GAC CTA GAA AAG CTG AAA GAG AAG ATA TCT TCA AAT ATT AGA AGG
Glu Asp Leu Glu Lys Leu Lys Glu Lys Ile Ser Ser Asn Ile Arg Arg>
 a   a   a   a   a   a  ORF 1  a   a   a   a   a   a   a   a >

930         940         950         960
         *           *           *           *
CAG AAG GCA GGT GAG TTG CTA GTT AGC AAT GTG AAA AAA GCA AAC GAT
Gln Lys Ala Gly Glu Leu Leu Val Ser Asn Val Lys Lys Ala Asn Asp>
 a   a   a   a   a   a  ORF 1  a   a   a   a   a   a   a   a >

```
ATG ATC AGC CGC GGG GCA TCG CTG AAT GAA CTA AAG GAT ATG TTT GGT
Met Ile Ser Arg Gly Ala Ser Leu Asn Glu Leu Lys Asp Met Phe Gly>
 a   a   a   a   a   a  ORF 1  a   a   a   a   a   a   a   >

1020        1030        1040        1050        1060
         *           *           *           *           *
GCG CGG ATC AGT GGT GTT TTG ACG AAT TTT GAT ATG CAT GGG CTC GAT
Ala Arg Ile Ser Gly Val Leu Thr Asn Phe Asp Met His Gly Leu Asp>
 a   a   a   a   a   a  ORF 1  a   a   a   a   a   a   a   >

1070        1080        1090        1100        1110
         *           *           *           *           *
AAA TCT GGC AAC TTA GTG AAA GAC TTT CCG TTG CAG CTT GGT ATA AAC
Lys Ser Gly Asn Leu Val Lys Asp Phe Pro Leu Gln Leu Gly Ile Asn>
 a   a   a   a   a   a  ORF 1  a   a   a   a   a   a   a   >

1120        1130        1140        1150        1160
         *           *           *           *           *
GCC TTT ACT ACT TTG GCG TTT TCA TCT GCC GTA GGA AAA CCG TCT CAT
Ala Phe Thr Thr Leu Ala Phe Ser Ser Ala Val Gly Lys Pro Ser His>
 a   a   a   a   a   a  ORF 1  a   a   a   a   a   a   a   >

1170        1180        1190        1200
             *           *           *           *
CTG GTT AGC AAT GGT GAC GCT TAT TTC GGC GTT CTT GTT ACT GAA GTA
Leu Val Ser Asn Gly Asp Ala Tyr Phe Gly Val Leu Val Thr Glu Val>
 a   a   a   a   a   a  ORF 1  a   a   a   a   a   a   a   >

1210        1220        1230        1240        1250
 *           *           *           *           *
GTG CCT CCA AGA CCA AGG ACA CTT GAA GAA AGC AGG TCT ATT CTT ACT
Val Pro Pro Arg Pro Arg Thr Leu Glu Glu Ser Arg Ser Ile Leu Thr>
 a   a   a   a   a   a  ORF 1  a   a   a   a   a   a   a   >

1260        1270        1280        1290        1300
         *           *           *           *           *
GAA GAA TGG AAG AGT GCA TTA CGT ATG AAG AAA ATA CGT GAA TTT GCT
Glu Glu Trp Lys Ser Ala Leu Arg Met Lys Lys Ile Arg Glu Phe Ala>
 a   a   a   a   a   a  ORF 1  a   a   a   a   a   a   a   >

1310        1320        1330        1340        1350
         *           *           *           *           *
GTG GAG TTG CGC TCG AAG CTA CAA AAT GGC ACT GAA TTG TCC GTT GTA
Val Glu Leu Arg Ser Lys Leu Gln Asn Gly Thr Glu Leu Ser Val Val>
 a   a   a   a   a   a  ORF 1  a   a   a   a   a   a   a   >

1360        1370        1380        1390        1400
         *           *           *           *           *
AAT GGA GTT TCT TTT AAA AAG AAT GTC ACG GTA AAA AAG TCA GAT GGC
Asn Gly Val Ser Phe Lys Lys Asn Val Thr Val Lys Lys Ser Asp Gly>
 a   a   a   a   a   a  ORF 1  a   a   a   a   a   a   a   >

1410        1420        1430        1440
             *           *           *           *
TCT ACC GAC AAT GAT AGC AAG TAT CCT GAA CGC TTA GTC GAT GAG ATA
Ser Thr Asp Asn Asp Ser Lys Tyr Pro Glu Arg Leu Val Asp Glu Ile>
 a   a   a   a   a   a  ORF 1  a   a   a   a   a   a   a   >

1450        1460        1470        1480        1490
 *           *           *           *           *
TTC GCC ATT AAC ATT GGT GGA GTA ACG AAA GAA GTT ATA GAT TCT GAA
Phe Ala Ile Asn Ile Gly Gly Val Thr Lys Glu Val Ile Asp Ser Glu>
```

FIG. 1C

```
          a   a   a   a   a   a     ORF 1   a   a   a   a   a   a   >
        1500            1510            1520            1530            1540
          *               *               *               *               *
        TCT GAG ACT GTA TAC ATT GCT CTG CTT AAA GAA ATA AAA GAT GCT GAA
        Ser Glu Thr Val Tyr Ile Ala Leu Leu Lys Glu Ile Lys Asp Ala Glu>
          a   a   a   a   a   a     ORF 1   a   a   a   a   a   a   >
        1550            1560            1570            1580            1590
          *               *               *               *               *
        ATA AGT GAG GAG GAT CTA GAG AGC TAC AAG GCA CAT TTT GTT AGT AGT
        Ile Ser Glu Glu Asp Leu Glu Ser Tyr Lys Ala His Phe Val Ser Ser>
          a   a   a   a   a   a     ORF 1   a   a   a   a   a   a   >
        1600            1610            1620            1630            1640
          *               *               *               *               *
        GGC ATC CTA TCT ATA AGA GAG CAG CTC TTA GGT TAT TTG ATG AAA AAA
        Gly Ile Leu Ser Ile Arg Glu Gln Leu Leu Gly Tyr Leu Met Lys Lys>
          a   a   a   a   a   a     ORF 1   a   a   a   a   a   a   >
        1650            1660            1670            1680            1690
          *               *               *               *               *
        TAC GGA GTA ACG ATC GAA AAT AGT TTG CTA GAG AAA GTG T AATTACGTAC
        Tyr Gly Val Thr Ile Glu Asn Ser Leu Leu Glu Lys Val>
          a   a   a   a   a     ORF 1   a   a   a   a   >
     1700         1710         1720         1730         1740         1750
        *            *            *            *            *            *
     TTTCCTAAGG   CTATTTTGTT   TTTAGGATGA   AGCGCGTTAG   TGGATTTTAG   TATCCTGTGT 1760         1770         1780         1790         1800         1810
        *            *            *            *            *            *
     GTGCATCGTA   TATGTACAGT   ATATGCTTCG   TTACATATGG   ATATGATATT   GTCGATGAAG 1820         1830         1840         1850         1860         1870
        *            *            *            *            *            *
     GTTTTGCTTT   CTGATATAGG   AAAACTCTTG   GCATTGCTGT   TATATTACGA   AGAGAGAGGC 1880         1890         1900         1910         1920         1930
        *            *            *            *            *            *
     GTTTCGCAAG   TAGGATAGTG   TGCACGCAGA   TAATGATTAA   CTGTAAACTC   ATGTGTCGCT 1940         1950         1960         1970         1980         1990
        *            *            *            *            *            *
     GCTAAGTAGC   TTATATTGCC   GGATGATGAA   ATTACAGGCA   TTTTCTTAGT   GCTGGGTAAC 2000         2010         2020         2030         2040         2050
        *            *            *            *            *            *
     ATTGTAATTA   AGTAAGTTAT   ACTTATAAAA   ATAATGAATA   TTTGCATGCT   GGTGGTGGAG 2060            2070            2080            2090            2100
          *               *               *               *               *
        CAAAACAT ATG AAG GGA GAA GTG GTA TCT TGG CCG TTT ATA GAA GCT GAA
                 Met Lys Gly Glu Val Val Ser Trp Pro Phe Ile Glu Ala Glu>
                  b   b   b   b   b     ORF 2   b   b   b   b   b   b   >
        2110            2120            2130            2140
          *               *               *               *
        AAA ATT TTA AAG GCA TTT GGT GAT AGC GAG GAA ATA ATA CTT GCT ACA
        Lys Ile Leu Lys Ala Phe Gly Asp Ser Glu Glu Ile Ile Leu Ala Thr>
          b   b   b   b   b   b     ORF 2   b   b   b   b   b   b   >
```

FIG. 1D

```
      2150          2160          2170          2180          2190
        *             *             *             *             *
 GGG TAT GGT CCG TCC GGA TTG CCT CAT ATA GGA ACT TTT GGT GAA GTA
 Gly Tyr Gly Pro Ser Gly Leu Pro His Ile Gly Thr Phe Gly Glu Val>
  b   b   b   b   b   b  ORF 2  b   b   b   b   b   b   b   >

2200          2210          2220          2230          2240
        *             *             *             *             *
 CAA AGA ACA GTA TAT GTA GCT AAT GCA CTG CGA GAG ATC TCT CCT AAA
 Gln Arg Thr Val Tyr Val Ala Asn Ala Leu Arg Glu Ile Ser Pro Lys>
  b   b   b   b   b   b  ORF 2  b   b   b   b   b   b   b   >

2250          2260          2270          2280          2290
        *             *             *             *             *
 ACT AAA ACA AGG ATT TTA GCA TTC TCT GAT GAT ATG GAT GGG TTG CGG
 Thr Lys Thr Arg Ile Leu Ala Phe Ser Asp Asp Met Asp Gly Leu Arg>
  b   b   b   b   b   b  ORF 2  b   b   b   b   b   b   b   >

2300          2310          2320          2330          2340
        *             *             *             *             *
 AAA GTT CCT GAT AAC GTA CCA AAC CGT GAA ATG CTA GAG AAA CAT CTG
 Lys Val Pro Asp Asn Val Pro Asn Arg Glu Met Leu Glu Lys His Leu>
  b   b   b   b   b   b  ORF 2  b   b   b   b   b   b   b   >

2350          2360          2370          2380
        *             *             *             *
 GGA CAG TTA CTG ACC TCA ATA CCT GAT CCG TTC GGC ACA TCC TCA AGC
 Gly Gln Leu Leu Thr Ser Ile Pro Asp Pro Phe Gly Thr Ser Ser Ser>
  b   b   b   b   b   b  ORF 2  b   b   b   b   b   b   b   >

2390          2400          2410          2420          2430
  *             *             *             *             *
 TAT GGC CAT CAT ATG AAC GGC ACT TTC TGT GCT TTT TTA GAC AGA TTT
 Tyr Gly His His Met Asn Gly Thr Phe Cys Ala Phe Leu Asp Arg Phe>
  b   b   b   b   b   b  ORF 2  b   b   b   b   b   b   b   >

2440          2450          2460          2470          2480
        *             *             *             *             *
 GGG TTT GAA TAC GAA TTT ATT AGT GCA ACA GAG TGC TAC AGA TCC GGT
 Gly Phe Glu Tyr Glu Phe Ile Ser Ala Thr Glu Cys Tyr Arg Ser Gly>
  b   b   b   b   b   b  ORF 2  b   b   b   b   b   b   b   >

2490          2500          2510          2520          2530
        *             *             *             *             *
 AGA TAT GAT GAT GTA CTG CTA CGG CTA CTA AGA AAT TAT GAT AAG GCC
 Arg Tyr Asp Asp Val Leu Leu Arg Leu Leu Arg Asn Tyr Asp Lys Ala>
  b   b   b   b   b   b  ORF 2  b   b   b   b   b   b   b   >

2540          2550          2560          2570          2580
        *             *             *             *             *
 GTA AGC ATA CTG TTG CCA ACA CTT GGC GAA GAG CGT CAA AAA ACT TAT
 Val Ser Ile Leu Leu Pro Thr Leu Gly Glu Glu Arg Gln Lys Thr Tyr>
  b   b   b   b   b   b  ORF 2  b   b   b   b   b   b   b   >

2590          2600          2610          2620
        *             *             *             *
 AGT CCG TTT CTG CCC ATA TGT GAA AAA ACA TCT AGA GTG CTG CAG GTG
 Ser Pro Phe Leu Pro Ile Cys Glu Lys Thr Ser Arg Val Leu Gln Val>
  b   b   b   b   b   b  ORF 2  b   b   b   b   b   b   b   >

```
              ACT ATA GTC AAA ACA GAC GTA GAA AAA GGA ACT ATT TTT TAT CAA AAT
              Thr Ile Val Lys Thr Asp Val Glu Lys Gly Thr Ile Phe Tyr Gln Asn>
               b   b   b   b   b   b  ORF 2  b   b   b   b   b   b   b    >

2680        2690        2700        2710        2720
            *           *           *           *           *
              GAA GAC GGA GAC TTG GTA GAG GTA AAA GTA ACC GGT GGA CAT TGT AAA
              Glu Asp Gly Asp Leu Val Glu Val Lys Val Thr Gly Gly His Cys Lys>
               b   b   b   b   b   b  ORF 2  b   b   b   b   b   b   b    >

2730        2740        2750        2760        2770
            *           *           *           *           *
              TTA CAG TGG AAA GCT GAT TGG GGA ATG CGT TGG GCC GCT TTT GGT GTG
              Leu Gln Trp Lys Ala Asp Trp Gly Met Arg Trp Ala Ala Phe Gly Val>
               b   b   b   b   b   b  ORF 2  b   b   b   b   b   b   b    >

2780        2790        2800        2810        2820
            *           *           *           *           *
              CAT TAT GAA TCT CAT GGT AAA GAC CTA ACT CCT TCT GCT AAA CCG TCT
              His Tyr Glu Ser His Gly Lys Asp Leu Thr Pro Ser Ala Lys Pro Ser>
               b   b   b   b   b   b  ORF 2  b   b   b   b   b   b   b    >

2830        2840        2850        2860
            *           *           *           *
              GCA GAA ATC TGT AAA CTC CTA GGT AGA AGG CCT CCT GTT CTG TTT CCA
              Ala Glu Ile Cys Lys Leu Leu Gly Arg Arg Pro Pro Val Leu Phe Pro>
               b   b   b   b   b   b  ORF 2  b   b   b   b   b   b   b    >

2870        2880        2890        2900        2910
     *           *           *           *           *
              TAT GAA CTT TTT CTT GAT AAA GAA GGG AAG AAA ATT TCC AAA TCT AAG
              Tyr Glu Leu Phe Leu Asp Lys Glu Gly Lys Lys Ile Ser Lys Ser Lys>
               b   b   b   b   b   b  ORF 2  b   b   b   b   b   b   b    >

2920        2930        2940        2950        2960
            *           *           *           *           *
              GGC AAT GGT TTC TCT GTA GAA GAG TGG CTT GCA TGC GCA CCG TAT GAG
              Gly Asn Gly Phe Ser Val Glu Glu Trp Leu Ala Cys Ala Pro Tyr Glu>
               b   b   b   b   b   b  ORF 2  b   b   b   b   b   b   b    >

2970        2980        2990        3000        3010
            *           *           *           *           *
              AGC CTA GCC CTC TAT ATG TTT CAA AAC CCG AAA AGG GCT AAG CGC TTG
              Ser Leu Ala Leu Tyr Met Phe Gln Asn Pro Lys Arg Ala Lys Arg Leu>
               b   b   b   b   b   b  ORF 2  b   b   b   b   b   b   b    >

3020        3030        3040        3050        3060
            *           *           *           *           *
              TGT TCT GAA GTA GTG CCA AAA TTT GTA GAT GAC TAT CTG TCA TTA TTA
              Cys Ser Glu Val Val Pro Lys Phe Val Asp Asp Tyr Leu Ser Leu Leu>
               b   b   b   b   b   b  ORF 2  b   b   b   b   b  b   b    >

3070        3080        3090        3100
            *           *           *           *
              CAT AAA TAC AAT GAG GCT CCT AGT ACT CAC AAT CCT GTA TGG CAT ATA
              His Lys Tyr Asn Glu Ala Pro Ser Thr His Asn Pro Val Trp His Ile>
               b   b   b   b   b   b  ORF 2  b   b   b   b   b   b   b    >

3110        3120        3130        3140        3150
     *           *           *           *           *
              CAC AAC GGT AAT GTT CCT AAA GTA GAG CTG TAT GGT TTA ACT TTT TGT
              His Asn Gly Asn Val Pro Lys Val Glu Leu Tyr Gly Leu Thr Phe Cys>
```

FIG. 1F

```
              b    b    b    b    b    b   ORF 2  b    b    b    b    b    b    b    >
           3160           3170           3180           3190           3200
             *              *              *              *              *
           CTA  CTC  ATC  AAC  ATA  GCA  TCA  GCG  TGC  AAT  GCA  AAC  GAT  GTT  GCG  ATG
           Leu  Leu  Ile  Asn  Ile  Ala  Ser  Ala  Cys  Asn  Ala  Asn  Asp  Val  Ala  Met>
              b    b    b    b    b    b   ORF 2  b    b    b    b    b    b    b    >
           3210           3220           3230           3240           3250
             *              *              *              *              *
           TTG  GAG  CAA  CTC  ATA  AAA  ATA  TAT  AGG  GAC  GGG  ATT  GAT  TTA  GAG  AAC
           Leu  Glu  Gln  Leu  Ile  Lys  Ile  Tyr  Arg  Asp  Gly  Ile  Asp  Leu  Glu  Asn>
              b    b    b    b    b    b   ORF 2  b    b    b    b    b    b    b    >
           3260           3270           3280           3290           3300
             *              *              *              *              *
           AAT  ACT  CTA  CTA  AGT  AGG  TTA  TTA  GAG  TTC  TCT  GTT  GCG  TAT  TGC  AGG
           Asn  Thr  Leu  Leu  Ser  Arg  Leu  Leu  Glu  Phe  Ser  Val  Ala  Tyr  Cys  Arg>
              b    b    b    b    b    b   ORF 2  b    b    b    b    b    b    b    >
                      3310           3320           3330           3340
                        *              *              *              *
           GCA  TTT  GTT  ATG  CCG  TCT  AGA  TCA  TAT  AAA  ACA  CCT  ACT  GCT  GAG  GAG
           Ala  Phe  Val  Met  Pro  Ser  Arg  Ser  Tyr  Lys  Thr  Pro  Thr  Ala  Glu  Glu>
              b    b    b    b    b    b   ORF 2  b    b    b    b    b    b    b    >
        3350           3360           3370           3380           3390
          *              *              *              *              *
        AGC  AAC  ATG  TTA  CTT  GAT  CTA  GCA  AAT  ACT  CTT  TCT  TGC  ATG  GAT  GAC
        Ser  Asn  Met  Leu  Leu  Asp  Leu  Ala  Asn  Thr  Leu  Ser  Cys  Met  Asp  Asp>
              b    b    b    b    b    b   ORF 2  b    b    b    b    b    b    b    >
           3400           3410           3420           3430           3440
             *              *              *              *              *
           AGT  AAA  TCA  CCT  GAT  GAA  ATA  CAA  AAT  GAA  GTA  TTT  GAG  GTT  GGA  AAG
           Ser  Lys  Ser  Pro  Asp  Glu  Ile  Gln  Asn  Glu  Val  Phe  Glu  Val  Gly  Lys>
              b    b    b    b    b    b   ORF 2  b    b    b    b    b    b    b    >
           3450           3460           3470           3480           3490
             *              *              *              *              *
           AAG  TAT  CTA  CAG  CCT  AGT  GAT  CTA  CGT  ATG  TGG  TTT  AAG  ATG  CTG  TAC
           Lys  Tyr  Leu  Gln  Pro  Ser  Asp  Leu  Arg  Met  Trp  Phe  Lys  Met  Leu  Tyr>
              b    b    b    b    b    b   ORF 2  b    b    b    b    b    b    b    >
                   3500           3510           3520           3530           3540
                     *              *              *              *              *
           GAA  GTG  TTA  CTT  GGA  CAG  AGT  GAT  GGG  CCT  AGA  TTT  GGG  TCT  TTT  GTA
           Glu  Val  Leu  Leu  Gly  Gln  Ser  Asp  Gly  Pro  Arg  Phe  Gly  Ser  Phe  Val>
              b    b    b    b    b    b   ORF 2  b    b    b    b    b    b    b    >
                      3550           3560           3570           3580
                        *              *              *              *
           AAA  TTG  TAT  GGT  ATT  GAG  AAT  ACA  GTA  CAG  TTA  ATA  AAG  CGT  AGT  ATT
           Lys  Leu  Tyr  Gly  Ile  Glu  Asn  Thr  Val  Gln  Leu  Ile  Lys  Arg  Ser  Ile>
              b    b    b    b    b    b   ORF 2  b    b    b    b    b    b    b    >
        3590           3600           3610           3620           3630           3640
          *              *              *              *              *              *
        TCT  GCT  ACT  GAA  TAGGAGGAGT  CACACCATAA  TATGAGTATT  GTAGCATCTA
        Ser  Ala  Thr  Glu>
              ORF 2  b    >
```

FIG. 1G

```
       3650        3660        3670        3680        3690        3700
         *           *           *           *           *           *
TTTTTGGGTT  GTTTTTTTGT  GAGTAATGTT  GACGAATCAG  AGCTGGTGAA  GTTCTCAAAT 3710        3720        3730        3740        3750        3760
         *           *           *           *           *           *
TTGGCTTCAG  AATGGTGGGA  TGGGGAGTCT  TTTTCAGCTT  TGCACAGGAT  AAATCCTTTG 3770        3780        3790        3800        3810        3820
         *           *           *           *           *           *
CGCGTTCAGT  ATATTCTTGA  AAATTTACAA  GAGGCTACTA  ACTCAGGTAA  AAGGCTTTTG 3830        3840        3850        3860        3870        3880
         *           *           *           *           *           *
GATATCGGTT  GTGGTGGTGG  GCTTATTTGC  GAAGCCATGG  CAAGGCTTGG  TTTTAGTGTC 3890        3900        3910        3920        3930        3940
         *           *           *           *           *           *
ACTGGAGTAG  ATCCATGTAG  AGAAGGAATA  GAAGCTGCTA  GACAGCACGC  TGCTATCGAA 3950        3960        3970        3980        3990        4000
         *           *           *           *           *           *
GGCTTAGATA  TAGAGTACCA  TTTTACGGAT  ATAGAGTCTT  TTATACACTC  CTCAGAGTGT 4010        4020        4030        4040        4050        4060
         *           *           *           *           *           *
TCTTCTTACG  ATATCATCAC  CTTAATGGAA  GTTGTAGAGC  ATATCCCTGA  TTTGACTGAA 4070        4080        4090        4100        4110        4120
         *           *           *           *           *           *
TTTTTATCTA  GCTCCTGTAA  GTTACTGAAA  CCTGGAGGTA  TGCTTTTCAT  TTCTACACTA 4130        4140        4150        4160        4170        4180
         *           *           *           *           *           *
AACAGAACTA  TCAAATCCAT  GTTACTTGGT  AAGATAGCTG  CGGAGTATAT  ACTTCGCATG 4190        4200        4210        4220        4230        4240
         *           *           *           *           *           *
GTGCCTCCTG  GCACGCACCA  GTGGAAGAAG  TTTGTCAAGC  CTTCAGAGAT  TCACGATGCC 4250        4260        4270        4280        4290        4300
         *           *           *           *           *           *
CTATTAAAAA  GCAGAGTGCT  CGTTAAAGAT  ATAAAAGGCA  TTACCTATAA  AATATTGCAT 4310        4320        4330        4340        4350        4360
         *           *           *           *           *           *
AACGATTGGG  TCTTAAATGA  TAGAGATATA  AGTGTAAACT  ACATATTAGC  CGCTCAAAAA 4370        4380        4390        4400        4410        4420
         *           *           *           *           *           *
GAGCAATAAT  CTACTTAGTG  ATGTTTATAC  GTAGTGTGTA  CCACAGAATG  TACTACTATT 4430        4440        4450        4460        4470        4480
         *           *           *           *           *           *
TAGGTTAGGT  GTTATAGGCA  TTTCTTTTGC  CGTCGTGAAT  ACCATATAGC  CTTATTCTCT 4490        4500        4510        4520        4530        4540
         *           *           *           *           *           *
TGTACAAAAA  TAGAGCTGCG  CGCGCAGCTT  CCACATACTT  GCCATAGCTC  TTACTTGCTT 4550        4560        4570        4580        4590        4600
         *           *           *           *           *           *
```

FIG. 1H

```
TTGCATCTTA  TAAACCTCGT  ATCTATGTTG  AAATGGGAAA  TTTAAATAGT  TACGACACTA
    4610        4620        4630        4640        4650        4660
      *           *           *           *           *           *
TATCCCCGCT  CGACAGTAAA  GCCCTCTTAG  CGACTGAACC  AGATATAGTA  GAAAGAAGTA
    4670        4680        4690        4700        4710        4720
      *           *           *           *           *           *
TTCAAGGGTT  AAATACTGAG  AAAAAACAAA  ACCACTCATT  TCATCTATAA  CTGCTCATGC
    4730        4740        4750        4760        4770        4780
      *           *           *           *           *           *
GAGGAAAAGG  ATGTTATATC  ACTATAAGTC  TGCATAGGCG  TAAACCAGGC  TCAATAGCAT
    4790        4800        4810        4820        4830
      *           *           *           *           *
TTTCGCGTGT  AAATAGTGGC  TAGGAATTCG  ATATCAAGCT  TATCGATACC  GTC
```

FIG. 1I

```
Sequence Range: 1 to 2515
                10          20          30          40          50          60
                *           *           *           *           *           *
        AAAATGTTGC  GGAGGTTGGA  GAGAGCGTGG  TTGCGGTGAC  TTGGGTTGAT  AAGTGGTTAA 70          80          90         100         110         120
                *           *           *           *           *           *
        CGCGGATGCT  CTCTAAAATA  TCGTAAGCAT  AGTTAGTGGG  GTATTTGAGG  CTTTTGGTGC 130         140         150         160         170         180
                *           *           *           *           *           *
        TTCAATATAG  AGCTAGTAAC  GGGGCGTGAT  GTTTGTTGGT  AGCGTTTGTA  TTACTAGTTT 190         200         210         220         230         240
                *           *           *           *           *           *
        CCTGACATGT  ATTGTGCATA  TCAGGTCTGT  TGTGGTGTAA  GGACACGTGT  GTTGCTAGGT 250         260         270         280         290         300
                *           *           *           *           *           *
        ATCAGGGACA  TATTTCTCTA  ATTTTTAAAT  AGGGGGTTGT  AATTTGCAGC  TTTGGTTATT 310         320         330         340         350
                *           *           *           *           *
        ATATCTACCG  TGTCTGAGTT  TTTTGTTTTT  TTCGA ATG GGG GTA GTC ATG GCG GCT
                                                 Met Gly Val Val Met Ala Ala>
                                                   a   a  B3 ORF  a   a    >
```

```
        360             370             380             390             400
         *               *               *               *               *
GAG CGT ATA ATA GGT ATA GAT CTA GGT ACT ACG AAT TCC TGT GTT GCT
Glu Arg Ile Ile Gly Ile Asp Leu Gly Thr Thr Asn Ser Cys Val Ala>
 a   a   a   a   a   a  B3 ORF a   a   a   a   a   a   a   a  >

410             420             430             440             450
         *               *               *               *               *
GTT ATG GAG GCT GGT ACC GCA AAG GTG ATA GAA AAC AGT GAA GGT TCG
Val Met Glu Ala Gly Thr Ala Lys Val Ile Glu Asn Ser Glu Gly Ser>
 a   a   a   a   a   a  B3 ORF a   a   a   a   a   a   a   a  >

460             470             480             490             500
         *               *               *               *               *
AGG ACC ACC CCG TCT GTT GTT GCG TTT ACT GAT AAT GAA AGG CTA GTA
Arg Thr Thr Pro Ser Val Val Ala Phe Thr Asp Asn Glu Arg Leu Val>
 a   a   a   a   a   a  B3 ORF a   a   a   a   a   a   a   a  >

510             520             530             540
         *               *               *               *
GGG GAA TTG GCT AAG CGG CAA GCA AAT ATC AAT GCT CAG AAC ACG ATA
Gly Glu Leu Ala Lys Arg Gln Ala Asn Ile Asn Ala Gln Asn Thr Ile>
 a   a   a   a   a   a  B3 ORF a   a   a   a   a   a   a   a  >

550             560             570             580             590
 *               *               *               *               *
TAT GCG AGC AAA AGG ATT ATC GGC CGC AGA TAC GAT GAC ATG AGG GAT
Tyr Ala Ser Lys Arg Ile Ile Gly Arg Arg Tyr Asp Asp Met Arg Asp>
 a   a   a   a   a   a  B3 ORF a   a   a   a   a   a   a   a  >

600             610             620             630             640
         *               *               *               *               *
TTG AAG TGT CCT TAT GAG GTG TTT CCT GCA AAG AAC GGT GAT GCT TGG
Leu Lys Cys Pro Tyr Glu Val Phe Pro Ala Lys Asn Gly Asp Ala Trp>
```

FIG. 5A

```
         a    a    a    a    a    a     B3 ORF a    a    a    a    a    a   >
         650            660            670            680            690
          *              *              *              *              *
        ATA  AGA  GCA  AAG  GGT  GAG  GGT  TAT  TCT  CCG  GTT  CAG  ATT  GGC  GCG  TTT
        Ile  Arg  Ala  Lys  Gly  Glu  Gly  Tyr  Ser  Pro  Val  Gln  Ile  Gly  Ala  Phe>
         a    a    a    a    a    a     B3 ORF a    a    a    a    a    a   >
         700            710            720            730            740
          *              *              *              *              *
        GTC  TTG  GAA  AAG  ATC  AAG  GAA  ACT  GCT  GAG  AGA  TAC  TTT  GGT  GCT  CCA
        Val  Leu  Glu  Lys  Ile  Lys  Glu  Thr  Ala  Glu  Arg  Tyr  Phe  Gly  Ala  Pro>
         a    a    a    a    a    a     B3 ORF a    a    a    a    a    a   >
                        750            760            770            780
                         *              *              *              *
        GTG  AAG  AAG  GCG  GTT  ATT  ACG  GTG  CCT  GCG  TAT  TTT  AAC  GAT  GCT  CAA
        Val  Lys  Lys  Ala  Val  Ile  Thr  Val  Pro  Ala  Tyr  Phe  Asn  Asp  Ala  Gln>
         a    a    a    a    a    a     B3 ORF a    a    a    a    a    a   >
        790            800            810            820            830
         *              *              *              *              *
        CGT  CAG  GCA  ACA  AAG  GAT  GCT  GGT  ACG  ATT  GCT  GGC  CTA  GAT  GTT  GTG
        Arg  Gln  Ala  Thr  Lys  Asp  Ala  Gly  Thr  Ile  Ala  Gly  Leu  Asp  Val  Val>
         a    a    a    a    a    a     B3 ORF a    a    a    a    a    a   >
                840            850            860            870            880
                 *              *              *              *              *
        AGA  ATA  ATT  AAT  GAA  CCT  ACA  GCA  GCA  GCT  TTG  GCG  TAC  GGG  TTA  GAT
        Arg  Ile  Ile  Asn  Glu  Pro  Thr  Ala  Ala  Ala  Leu  Ala  Tyr  Gly  Leu  Asp>
         a    a    a    a    a    a     B3 ORF a    a    a    a    a    a   >
                890            900            910            920            930
                 *              *              *              *              *
        AAG  GGT  GAC  AAG  CAA  AGG  ACT  ATA  GTA  GTA  TAC  GAT  CTT  GGT  GGT  GGT
        Lys  Gly  Asp  Lys  Gln  Arg  Thr  Ile  Val  Val  Tyr  Asp  Leu  Gly  Gly  Gly>
         a    a    a    a    a    a     B3 ORF a    a    a    a    a    a   >
                940            950            960            970            980
                 *              *              *              *              *
        ACA  TTT  GAC  GTA  TCT  GTT  TTG  GAG  ATA  GCT  GAC  GGT  GTA  TTT  GAA  GTT
        Thr  Phe  Asp  Val  Ser  Val  Leu  Glu  Ile  Ala  Asp  Gly  Val  Phe  Glu  Val>
         a    a    a    a    a    a     B3 ORF a    a    a    a    a    a   >
                        990           1000           1010           1020
                         *              *              *              *
        AAA  GCT  ACT  AAT  GGT  GAT  ACT  AAG  CTT  GGT  GGT  GAG  GAC  TTT  GAT  AAT
        Lys  Ala  Thr  Asn  Gly  Asp  Thr  Lys  Leu  Gly  Gly  Glu  Asp  Phe  Asp  Asn>
         a    a    a    a    a    a     B3 ORF a    a    a    a    a    a   >
        1030           1040           1050           1060           1070
          *              *              *              *              *
        GCC  ATC  ATG  GAA  CAT  ATG  ATG  GAG  AGT  TTC  CAA  AAA  GAA  ACA  GGT  ATA
        Ala  Ile  Met  Glu  His  Met  Met  Glu  Ser  Phe  Gln  Lys  Glu  Thr  Gly  Ile>
         a    a    a    a    a    a     B3 ORF a    a    a    a    a    a   >
                        1080           1090           1100           1110           1120
                         *              *              *              *              *
        AAT  CTA  CGT  AAT  GAC  CCT  ATG  GCT  GTT  CAG  CGG  GTC  AAG  GAG  GCT  GCG
        Asn  Leu  Arg  Asn  Asp  Pro  Met  Ala  Val  Gln  Arg  Val  Lys  Glu  Ala  Ala>
         a    a    a    a    a    a     B3 ORF a    a    a    a    a    a   >
```

FIG. 5B

```
              1130          1140          1150          1160          1170
                *             *             *             *             *
         GAG AAG GCT AAG ATT GAG TTA TCT ACC AGG TTA GAG ACA GAT ATA ACT
         Glu Lys Ala Lys Ile Glu Leu Ser Thr Arg Leu Glu Thr Asp Ile Thr>
          a   a   a   a   a   a  B3 ORF a   a   a   a   a   a   a   a  >

1180          1190          1200          1210          1220
                *             *             *             *             *
         CTT CCG TTT ATT TCT AGC GAC AGC ACT GGC GCG AAG CAC TTG AGT TTG
         Leu Pro Phe Ile Ser Ser Asp Ser Thr Gly Ala Lys His Leu Ser Leu>
          a   a   a   a   a   a  B3 ORF a   a   a   a   a   a   a   a  >

1230          1240          1250          1260
                        *             *             *             *
         AAG CTG AGT AGG GCT AAG TTT GAG GGT TTG GTA GAC GAG TTA ATC GAG
         Lys Leu Ser Arg Ala Lys Phe Glu Gly Leu Val Asp Glu Leu Ile Glu>
          a   a   a   a   a   a  B3 ORF a   a   a   a   a   a   a   a  >

1270          1280          1290          1300          1310
       *             *             *             *             *
     CGC ACT ATA GAG CCA TGT AAG AAG GCT TTG AGT GAT GCG GGT ATT AAG
     Arg Thr Ile Glu Pro Cys Lys Lys Ala Leu Ser Asp Ala Gly Ile Lys>
      a   a   a   a   a   a  B3 ORF a   a   a   a   a   a   a   a  >

1320          1330          1340          1350          1360
            *             *             *             *             *
         GAT AAC AGT AAG GTC GAC GAG GTT GTG CTA GTT GGT GGT ATG ACC AGG
         Asp Asn Ser Lys Val Asp Glu Val Val Leu Val Gly Gly Met Thr Arg>
          a   a   a   a   a   a  B3 ORF a   a   a   a   a   a   a   a  >

1370          1380          1390          1400          1410
                *             *             *             *             *
         GTT CCT AAG GTT ATT CAA AGG GTG AAA GAC TTC TTT GGG AAA GAG CCA
         Val Pro Lys Val Ile Gln Arg Val Lys Asp Phe Phe Gly Lys Glu Pro>
          a   a   a   a   a   a  B3 ORF a   a   a   a   a   a   a   a  >

1420          1430          1440          1450          1460
                *             *             *             *             *
         TGT CAA GGT GTA AAT CCA GAT GAA GTT GTA GCT GTA GGT GCT GCG ATA
         Cys Gln Gly Val Asn Pro Asp Glu Val Val Ala Val Gly Ala Ala Ile>
          a   a   a   a   a   a  B3 ORF a   a   a   a   a   a   a   a  >

1470          1480          1490          1500
                        *             *             *             *
         CAG GGT GGT ATC TTA ACA GGT GAT GTT CGT GAT GTC TTG TTG TTG GAT
         Gln Gly Gly Ile Leu Thr Gly Asp Val Arg Asp Val Leu Leu Leu Asp>
          a   a   a   a   a   a  B3 ORF a   a   a   a   a   a   a   a  >

1510          1520          1530          1540          1550
       *             *             *             *             *
     GTT GCT CCG CTA TCT TTG GGT ATA GAA ACT TTG GGT GGT GTA TTT ACG
     Val Ala Pro Leu Ser Leu Gly Ile Glu Thr Leu Gly Gly Val Phe Thr>
      a   a   a   a   a   a  B3 ORF a   a   a   a   a   a   a   a  >

1560          1570          1580          1590          1600
                *             *             *             *             *
         CCT TTG ATT GAG CGT AAT ACT ACA ATT CCT ACT AAG AAG TCG CAG GTG
         Pro Leu Ile Glu Arg Asn Thr Thr Ile Pro Thr Lys Lys Ser Gln Val>
          a   a   a   a   a   a  B3 ORF a   a   a   a   a   a   a   a  >

```
TTC TCT ACG GCT GAA GAT GGT CAA ACT GCG GTG ACT ATT AAG GTG TAC
Phe Ser Thr Ala Glu Asp Gly Gln Thr Ala Val Thr Ile Lys Val Tyr>
 a   a   a   a   a   a      B3 ORF a   a   a   a   a   a    >

1660         1670         1680         1690         1700
          *            *            *            *            *
CAA GGT GAG CGT AAG ATG GCA ATC GAC AAT AAG TTG TTG GGG CAG TTT
Gln Gly Glu Arg Lys Met Ala Ile Asp Asn Lys Leu Leu Gly Gln Phe>
 a   a   a   a   a   a   B3 ORF a   a   a   a   a   a   a    >

1710         1720         1730         1740
          *            *            *            *
AGT CTG GAG GGT ATT CCT CAT GCT CCA CGC GGA GTT CCT CAA ATT GAG
Ser Leu Glu Gly Ile Pro His Ala Pro Arg Gly Val Pro Gln Ile Glu>
 a   a   a   a   a   a   B3 ORF a   a   a   a   a   a   a    >

1750         1760         1770         1780         1790
  *            *            *            *            *
GTG ACT TTT GAC ATA GAC GCT AAT GGT ATA GTG CAC GTT TCA GCA AAG
Val Thr Phe Asp Ile Asp Ala Asn Gly Ile Val His Val Ser Ala Lys>
 a   a   a   a   a   a   B3 ORF a   a   a   a   a   a   a    >

1800         1810         1820         1830         1840
          *            *            *            *            *
GAT AAG GCT TCA GGT AAG GAG CAG ACT ATT AAG ATA CAG TCT TCT GGT
Asp Lys Ala Ser Gly Lys Glu Gln Thr Ile Lys Ile Gln Ser Ser Gly>
 a   a   a   a   a   a   B3 ORF a   a   a   a   a   a   a    >

1850         1860         1870         1880         1890
          *            *            *            *            *
GGC TTA AGT GAT GAA GAA ATC AAG AAG ATG GTC AAA GAT GCT CAG GAC
Gly Leu Ser Asp Glu Glu Ile Lys Lys Met Val Lys Asp Ala Gln Asp>
 a   a   a   a   a   a   B3 ORF a   a   a   a   a   a   a    >

1900         1910         1920         1930         1940
          *            *            *            *            *
CGG GCG GAA GAC GAT GAA AAG CGT AAG AAG CAT GTG GAG CTG AAG AAT
Arg Ala Glu Asp Asp Glu Lys Arg Lys Lys His Val Glu Leu Lys Asn>
 a   a   a   a   a   a   B3 ORF a   a   a   a   a   a   a    >

1950         1960         1970         1980
          *            *            *            *
AGT TCT GAG GGG CTG ATA CAT TCT GTA GAG AAG TCT TTG AAG GAT TAT
Ser Ser Glu Gly Leu Ile His Ser Val Glu Lys Ser Leu Lys Asp Tyr>
 a   a   a   a   a   a   B3 ORF a   a   a   a   a   a   a    >

1990         2000         2010         2020         2030
  *            *            *            *            *
GGA GAT AAG GTT GCG GGT GCT GAT AAG TCT AAT ATC GAG AGC GCT ATC
Gly Asp Lys Val Ala Gly Ala Asp Lys Ser Asn Ile Glu Ser Ala Ile>
 a   a   a   a   a   a   B3 ORF a   a   a   a   a   a   a    >

2040         2050         2060         2070         2080
          *            *            *            *            *
AAG GAT TTG AGA GAG TGC TTG AAT GAT AGC AAC TGT AGT ACT GAT ACT
Lys Asp Leu Arg Glu Cys Leu Asn Asp Ser Asn Cys Ser Thr Asp Thr>
 a   a   a   a   a   a   B3 ORF a   a   a   a   a   a   a    >

2090         2100         2110         2120         2130
          *            *            *            *            *
CTG CAG CAG AAG TAT GAT GCG CTT ATG AAT CTA TCC ATG AAG CTG GGA
Leu Gln Gln Lys Tyr Asp Ala Leu Met Asn Leu Ser Met Lys Leu Gly>
```

FIG. 5D

```
              a   a   a   a   a   a      B3 ORF a   a   a   a   a   a   >
                2140            2150            2160            2170            2180
                  *               *               *               *               *
            GAA GCT GCA TAT GCG GCT AAT AAG AAT GAC GGT GCG GGA AGT GCT GAT
            Glu Ala Ala Tyr Ala Ala Asn Lys Asn Asp Gly Ala Gly Ser Ala Asp>
              a   a   a   a   a   a      B3 ORF a   a   a   a   a   a   >
                      2190            2200            2210            2220
                        *               *               *               *
            CAA TCT GGA AGC AGT AGT GGG GGT TCT GAT GGT AAT CCG GAA GAG CGT
            Gln Ser Gly Ser Ser Ser Gly Gly Ser Asp Gly Asn Pro Glu Glu Arg>
              a   a   a   a   a   a      B3 ORF a   a   a   a   a   a   >
       2230            2240            2250            2260            2270
         *               *               *               *               *
     GTT GTA GAT TCC GAA TAT CAG GAG ATT AAT AAG GAC GAG GAC AAG AAG
     Val Val Asp Ser Glu Tyr Gln Glu Ile Asn Lys Asp Glu Asp Lys Lys>
       a   a   a   a   a   a      B3 ORF a   a   a   a   a   a   >
          2280            2290            2300            2310            2320            2330
            *               *               *               *               *               *
        AAT ACT TAGGTGTT GATAAGTATT GGGTAGTTTG GTATCCTCCT GCGGGGGTCT
        Asn Thr>
          a   >

2340         2350         2360         2370         2380         2390
                *            *            *            *            *            *
            GCGTTGTTCG TGTAGGTTGA AAGTGCCTCG AGCCCGATTT TGTTCTTATA GGGAGCCGTC 2400         2410         2420         2430         2440         2450
                *            *            *            *            *            *
            ACTGGTAACC TCGAGTAGGT TATTACACGG CGCCCACCTT AGCTTTAGTC TCAGGACACT 2460         2470         2480         2490         2500         2510
                *            *            *            *            *            *
            AAGCAAAGCG TTACGGCAAA TGCGGATCTC CTAGTTTCCT TTTTTAGCAG TGTGTGTAGG

AATTC
```

FIG. 5E

Sequence Range: 1 to 4804

```
          10          20          30              40              50
           *           *           *               *               *
AACTAGTGGA  TCCCCCGGGC  TGCAGGAATT  CC TCA GGT AAG GAG CAG ACT ATT
                                      Ser Gly Lys Glu Gln Thr Ile>
                                       a   a  ORF 1  a   a   a    >

60          70          80              90             100
               *           *           *               *               *
AAG ATA CAG TCT TCT GGT GGC TTA AGT GAT GAA GAA ATC AAG AAG ATG
Lys Ile Gln Ser Ser Gly Gly Leu Ser Asp Glu Glu Ile Lys Lys Met>
 a   a   a   a   a   a   a  ORF 1  a   a   a   a   a   a   a    >

110         120         130             140
              *           *           *               *
GTC AAA GAT GCT CAG GAC CGG GCG GAA GAC GAT GAA AAG CGT AAG AAG
Val Lys Asp Ala Gln Asp Arg Ala Glu Asp Asp Glu Lys Arg Lys Lys>
 a   a   a   a   a   a  ORF 1  a   a   a   a   a   a   a   a    >

150         160         170             180             190
  *           *           *               *               *
CAT GTG GAG CTG AAG AAT AGT TCT GAG GGG CTG ATA CAT TCT GTA GAG
His Val Glu Leu Lys Asn Ser Ser Glu Gly Leu Ile His Ser Val Glu>
 a   a   a   a   a   a  ORF 1  a   a   a   a   a   a   a   a    >

200         210         220             230             240
          *           *           *               *               *
AAG TCT TTG AAG GAT TAT GGA GAT AAG GTT GCG GGT GCT GAT AAG TCT
Lys Ser Leu Lys Asp Tyr Gly Asp Lys Val Ala Gly Ala Asp Lys Ser>
 a   a   a   a   a   a  ORF 1  a   a   a   a   a   a   a   a    >

250         260         270             280             290
          *           *           *               *               *
AAT ATC GAG AGC GCT ATC AAG GAT TTG AGA GAG TGC TTG AAT GAT AGC
Asn Ile Glu Ser Ala Ile Lys Asp Leu Arg Glu Cys Leu Asn Asp Ser>
 a   a   a   a   a   a  ORF 1  a   a   a   a   a   a   a   a    >

300         310         320             330             340
          *           *           *               *               *
AAC TGT AGT ACT GAT ACT CTG CAG CAG AAG TAT GAT GCG CTT ATG AAT
Asn Cys Ser Thr Asp Thr Leu Gln Gln Lys Tyr Asp Ala Leu Met Asn>
 a   a   a   a   a   a  ORF 1  a   a   a   a   a   a   a   a    >

350         360         370             380
          *           *           *               *
CTA TCC ATG AAG CTG GGA GAA GCT GCA TAT GCG GCT AAT AAG AAT GAC
Leu Ser Met Lys Leu Gly Glu Ala Ala Tyr Ala Ala Asn Lys Asn Asp>
 a   a   a   a   a   a  ORF 1  a   a   a   a   a   a   a   a    >

390         400         410             420             430
  *           *           *               *               *
GGT GCG GGA AGT GCT GAT CAA TCT GGA AGC AGT AGT GGG GGT TCT GAT
Gly Ala Gly Ser Ala Asp Gln Ser Gly Ser Ser Ser Gly Gly Ser Asp>
 a   a   a   a   a   a  ORF 1  a   a   a   a   a   a   a   a    >

440         450         460             470             480
  *           *           *               *               *
GGT AAT CCG GAA GAG CGT GTT GTA GAT TCC GAA TAT CAG GAG ATT AAT
Gly Asn Pro Glu Glu Arg Val Val Asp Ser Glu Tyr Gln Glu Ile Asn>
 a   a   a   a   a   a  ORF 1  a   a   a   a   a   a   a   a    >
```

FIG. 8A

```
          490           500           510           520           530           540
           *             *             *             *             *             *
AAG GAC GAG GAC AAG AAG AAT ACT T AGGTGTTGAT AAGTATTGGG TAGTTTGGTA
Lys Asp Glu Asp Lys Lys Asn Thr>
 a   a  ORF 1  a   a   a   >

550           560           570           580           590           600
           *             *             *             *             *             *
TCCTCCTGCG GGGGTCTGCG TTGTTCGTGT AGGTTGAAAG TGCCTCGAGC CCGATTTTGT 610           620           630           640           650           660
           *             *             *             *             *             *
TCTTATAGGG AGCCGTCACT GGTAACCTCG AGTAGGTTAT TACACGGCGG CCACCTTAGC 670           680           690           700           710
           *             *             *             *             *
TTTAGTCTCA GGA CAC TAA GCA AAG CGT TAC GGC AAA TGC GGA TCT CCT AGT
           <Ser Val Leu Cys Leu Thr Val Ala Phe Ala Ser Arg Arg Thr
           <   f   f   f   f   f  ORF 6  f   f   f   f   f   f 720           730           740           750           760
           *             *             *             *             *
TTC CTT TTT TAG CAG TGT GTG TAT GGT GCG AGC TAG GCG TGG GTT TAG
                        Met Val Arg Ala Arg Arg Gly Phe Ser>
                         b   b   b  ORF 2  b   b   b   >
<Glu Lys Lys Leu Leu Thr His Ile Thr Arg Ala Leu Arg Pro Asn Leu
<   f   f   f   f   f   f  ORF 6  f   f   f   f   f   f   f 770           780           790           800
           *             *             *             *
CAA GAG CGA AGT GCT TAG TTT TCC GGC AAA AGA TAT ATT TTC CAT TGT
Lys Ser Glu Val Leu Ser Phe Pro Ala Lys Asp Ile Phe Ser Ile Val>
 b   b   b   b   b   b  ORF 2  b   b   b   b   b   b   >
<Leu Leu Ser Thr Ser Leu Lys Gly Ala Phe Ser Ile Asn Glu Met Thr
<   f   f   f   f   f   f  ORF 6  f   f   f   f   f   f   f 810           820           830           840           850
 *             *             *             *             *
TCT TGA TGT TGA GAA GTA TCC CGC GTT TCT ACC GTG GTG TAA GGA AGT
Leu Asp Val Glu Lys Tyr Pro Ala Phe Leu Pro Trp Cys Lys Glu Val>
 b   b   b   b   b   b  ORF 2  b   b   b   b   b   b   >
<Arg Ser Thr Ser Phe Tyr Gly Ala Asn Arg Gly His His Leu Ser Thr
<   f   f   f   f   f   f  ORF 6  f   f   f   f   f   f   f 860           870           880           890           900
           *             *             *             *             *
AGT GAT TCT TGA AAG GCA TGA TGC TTC GAT GTT TGT GAA GTT GGT GGC
Val Ile Leu Glu Arg His Asp Ala Ser Met Phe Val Lys Leu Val Ala>
 b   b   b   b   b   b  ORF 2  b   b   b   b   b   b   >
<Thr Ile Arg Ser Leu Cys Ser Ala Glu Ile Asn Thr Phe Asn Thr Ala
<   f   f   f   f   f   f  ORF 6  f   f   f   f   f   f   f 910           920           930           940           950
           *             *             *             *             *
GCA ATT CAT GTC ACT TGA AGG TGC GTA TAC TTC CGA AGT TAG TTT CTC
Gln Phe Met Ser Leu Glu Gly Ala Tyr Thr Ser Glu Val Ser Phe Ser>
 b   b   b   b   b   b  ORF 2  b   b   b   b   b   b   >
<Cys Asn Met Asp Ser Ser Pro Ala Tyr Val Glu Ser Thr Leu Lys Glu
<   f   f   f   f   f   f  ORF 6  f   f   f   f   f   f 960           970           980           990          1000
           *             *             *             *             *
```

FIG. 8B

```
   TAC TCC GAC TTT AGA GAA CCC AGG GTG GAT AAG AGC TGT TTC TAC TGA
    Thr Pro Thr Leu Glu Asn Pro Gly Trp Ile Arg Ala Val Ser Thr Asp>
     b   b   b   b   b   b      ORF 2  b   b   b   b   b   b   b
<Val Gly Val Lys Ser Phe Gly Pro His Ile Leu Ala Thr Glu Val Ser
<    f   f   f   f   f   f      ORF 6  f   f   f   f   f   f   f 1010        1020        1030        1040
           *           *           *           *
   TGG AGT GTT TAA TAC TTT ATG TAG TGA GTG GAA TTT CCT GCC TAA AAA
    Gly Val Phe Asn Thr Leu Cys Ser Glu Trp Asn Phe Leu Pro Lys Asn>
     b   b   b   b   b   b      ORF 2  b   b   b   b   b   b   b   >
<Pro Thr Asn Leu Val Lys His Leu Ser His Phe Lys Arg Gly Leu Phe
<    f   f   f   f   f   f      ORF 6  f   f   f   f   f   f   f 1050        1060        1070        1080        1090
  *           *           *           *           *
   TGA AAG GGA GAC CTT GGT GAC GTT TTT TGT GAA TTT TTC TTT CAA AAA
    Glu Arg Glu Thr Leu Val Thr Phe Phe Val Asn Phe Ser Phe Lys Asn>
     b   b   b   b   b   b      ORF 2  b   b   b   b   b   b   b   >
<Ser Leu Ser Val Lys Thr Val Asn Lys Thr Phe Lys Glu Lys Leu Phe
<    f   f   f   f   f   f      ORF 6  f   f   f   f   f   f   f 1100        1110        1120        1130        1140
           *           *           *           *           *
   CAG AAT GTT GCA ATT TGC GTT CGA TAT GGC ATC AAG CAT GGC TAT TTC
    Arg Met Leu Gln Phe Ala Phe Asp Met Ala Ser Ser Met Ala Ile Ser>
     b   b   b   b   b   b      ORF 2  b   b   b   b   b   b   b   >
<Leu Ile Asn Cys Asn Ala Asn Ser Ile Ala Asp Leu Met Ala Ile Glu
<    f   f   f   f   f   f      ORF 6  f   f   f   f   f   f   f 1150        1160        1170        1180        1190
           *           *           *           *           *
   TAA CAT A TCT CGT GCG TTT AAA AAC AGG GCG TAC CAA TTG CTA AAA
    Asn Ile  Ser Arg Ala Phe Lys Asn Arg Ala Tyr Gln Leu Leu Lys>
     b   b b  b   b   b   b ORF 2  b   b   b   b   b   b   b   >
<Leu Met
<    f 1200        1210        1220        1230        1240        1250
           *           *           *           *           *           *
   TAAGGTATGT  GTGTAATTAG  CTGTTGCTAT  AACGCGCTGT  GTTATATGTG  CATGCTTTGG 1260        1270        1280        1290        1300        1310
           *           *           *           *           *           *
   GACATAGATA  TTGGAAGATT  TCAGCATACA  TTATGTGCTT  GCGCTGGTAC  AGCCAGCGTC 1320        1330        1340        1350        1360        1370
           *           *           *           *           *           *
   TGAGGTTTGT  GCTATAATGT  TCTAGGGTCA  GTAGCTTTTT  TGTCATATGA  GCCTGTAAAA 1380        1390        1400        1410        1420        1430
           *           *           *           *           *           *
   CAACTATCTG  CTGGAATGCT  TTCTCAAACA  AAAGCAAATA  TCTCGGCATA  AAATATAGCT 1440        1450        1460        1470        1480        1490
           *           *           *           *           *           *
   TCCTTACTAC  TATAAATACA  TCGCCTGTGG  GCAATAAGTG  TTTATATATC  TCAGCGTATA 1500        1510        1520        1530        1540        1550
           *           *           *           *           *           *
   GGTGCAGGTT  AGATCAGAAG  TTTCTATGGG  CATGCACTAT  TACAGCGTTT  GCAAAGAATT
```

FIG. 8C

```
         1560       1570       1580       1590       1600       1610
          *          *          *          *          *          *
   ATGACTTTGA TAATGAGTCC ATGACGTAAT TGCAATAAAG GCTATTATCC CTGGTATCTA 1620       1630       1640       1650       1660       1670
          *          *          *          *          *          *
   AATGGGTAGT TGTAAATTTG TGACGCAGCA TTGTGCTATA ATTCAGCAAA TAGTTACAGT 1680       1690       1700       1710       1720       1730
          *          *          *          *          *          *
   GCTTTTATAG GGGTGATATA CCGCAACCTA AGCGCATAGA TGAGGGGTTA TAGAGGCGTC 1740       1750       1760       1770       1780       1790
          *          *          *          *          *          *
   TATATATGCG TATTATATTG AGAAGTAGTT GATAAGAGCT ACAGCGGCGC AAAGTATTGG 1800       1810       1820       1830       1840       1850
          *          *          *          *          *          *
   AATTTGCAGT GATGTGTTTT TTTGGTGCAG AGGACATGCG TTTACTGATT CAAGTAACAC 1860       1870       1880       1890       1900       1910
          *          *          *          *          *          *
   GTGATGCATG TGCTATGATT CATGTCTTTG GTTTCGAAAT AATGTTTTAA CCTGTGGCGT 1920       1930       1940       1950       1960       1970
          *          *          *          *          *          *
   TGGATATTGA CTTGTTAGCG TAGGATTGTG CGGGTATATA GAGTACAGGG GCTAGATGTT 1980           1990           2000           2010           2020
               *              *              *              *              *
   ACATTTCC ATG GGT TCT TTG TAT AAT TTT ACG TTC AGT AAT ATT TTT CAG
            Met Gly Ser Leu Tyr Asn Phe Thr Phe Ser Asn Ile Phe Gln>
             c   c   c   c   c   ORF 3 c   c   c   c   c   c    >

2030           2040           2050           2060
           *              *              *              *
   GCA TTG GGT GGT GAG AAC GTG TTT TCA TTA GAC AAA GTC AGT GCT ATT
   Ala Leu Gly Gly Glu Asn Val Phe Ser Leu Asp Lys Val Ser Ala Ile>
    c   c   c   c   c   c   ORF 3  c   c   c   c   c   c   c    >

2070           2080           2090           2100           2110
 *              *              *              *              *
   CCG CTG ATT ATG TCG TTT CTT GCA TCT ATG TTT TGC ATA GTT TGT AGG
   Pro Leu Ile Met Ser Phe Leu Ala Ser Met Phe Cys Ile Val Cys Arg>
    c   c   c   c   c   c   ORF 3  c   c   c   c   c   c   c    >

2120           2130           2140           2150           2160
    *              *              *              *              *
   TGT AGG GTA GGT TTT AAG GAG CTC TTA TGT TCT CTG CTA TAT TGC ATT
   Cys Arg Val Gly Phe Lys Glu Leu Leu Cys Ser Leu Leu Tyr Cys Ile>
    c   c   c   c   c   c   ORF 3  c   c   c   c   c   c   c    >

2170           2180           2190           2200           2210
    *              *              *              *              *
   AGC AGT ATT GCA GTA TTG TTA TTT TCA AAT CTC ACA TTG GTA ACT ATT
   Ser Ser Ile Ala Val Leu Leu Phe Ser Asn Leu Thr Leu Val Thr Ile>
    c   c   c   c   c   c   ORF 3  c   c   c   c   c   c   c    >

2220           2230           2240           2250           2260
    *              *              *              *              *
   GGC TTT GAG ATT ATG GCG CTT ACT GCA GTA TGT ATT GTA GCA TTT GGG
   Gly Phe Glu Ile Met Ala Leu Thr Ala Val Cys Ile Val Ala Phe Gly>
```

FIG. 8D

```
                                    ORF 3  c   c   c   c   c   c   c   >
           2270        2280        2290        2300
            *           *           *           *
      GCA TAT AAA GGC AGG GAT TTT GCA TTT TTA CAT TAT GCA TGT TTG CAT
      Ala Tyr Lys Gly Arg Asp Phe Ala Phe Leu His Tyr Ala Cys Leu His>
        c   c   c   c   c   c   ORF 3  c   c   c   c   c   c   c   >
2310        2320        2330        2340        2350
  *           *           *           *           *
TTT ATT TCT GGC TTT TTG TTG CTT GTG GGT GCA AGT CAG CAT GCT CAT
Phe Ile Ser Gly Phe Leu Leu Leu Val Gly Ala Ser Gln His Ala His>
  c   c   c   c   c   c   ORF 3  c   c   c   c   c   c   c   >
2360        2370        2380        2390        2400
  *           *           *           *           *
TTA GGG GTT CTA GAG GGG ATA CCT AGA TGG TTT TTT ATG CTT GGT TTG
Leu Gly Val Leu Glu Gly Ile Pro Arg Trp Phe Phe Met Leu Gly Leu>
  c   c   c   c   c   c   ORF 3  c   c   c   c   c   c   c   >
2410        2420        2430        2440        2450
  *           *           *           *           *
ATA ATA AAT ACA GCA GCT TTT CCT GCA GCA TCA TGG CTT GTG CGC GCA
Ile Ile Asn Thr Ala Ala Phe Pro Ala Ala Ser Trp Leu Val Arg Ala>
  c   c   c   c   c   c   ORF 3  c   c   c   c   c   c   c   >
2460        2470        2480        2490        2500
  *           *           *           *           *
TAT CCG GTA TCG TCA AGT TTT GGG ATG CTG GTA CTT TCC TTG TTC ACA
Tyr Pro Val Ser Ser Ser Phe Gly Met Leu Val Leu Ser Leu Phe Thr>
  c   c   c   c   c   c   ORF 3  c   c   c   c   c   c   c   >
2510        2520        2530        2540
  *           *           *           *
ACT AAA GTG GCA TTG TAT GTT TTG TTA AAG TTC TTT TCT GGC GAG TCC
Thr Lys Val Ala Leu Tyr Val Leu Leu Lys Phe Phe Ser Gly Glu Ser>
  c   c   c   c   c   c   ORF 3  c   c   c   c   c   c   c   >
2550        2560        2570        2580        2590
  *           *           *           *           *
ATA ATT TTA TAC TTC GGT ATT TTC ACT TCT ATA TAT GCT GCG ATA TTT
Ile Ile Leu Tyr Phe Gly Ile Phe Thr Ser Ile Tyr Ala Ala Ile Phe>
  c   c   c   c   c   c   ORF 3  c   c   c   c   c   c   c   >
2600        2610        2620        2630        2640
  *           *           *           *           *
GCC TTT CTT GAG CAG AAT GTT CGT AGG CTG ATG GCT TAC ATG TTT GTA
Ala Phe Leu Glu Gln Asn Val Arg Arg Leu Met Ala Tyr Met Phe Val>
  c   c   c   c   c   c   ORF 3  c   c   c   c   c   c   c   >
2650        2660        2670        2680        2690
  *           *           *           *           *
GGG CAG GCA GGA TTG CTT ATG ATG GCT ATT GGG TGT CCG GGA ATA CCA
Gly Gln Ala Gly Leu Leu Met Met Ala Ile Gly Cys Pro Gly Ile Pro>
  c   c   c   c   c   c   ORF 3  c   c   c   c   c   c   c   >
2700        2710        2720        2730        2740
  *           *           *           *           *
TCA GAC CTT ATA ATC GTG CAG TTA TCA TTT TCA GTA TTA TAC CAG CTT
Ser Asp Leu Ile Ile Val Gln Leu Ser Phe Ser Val Leu Tyr Gln Leu>
  c   c   c   c   c   c   ORF 3  c   c   c   c   c   c   c   >
```

FIG. 8E

```
         2750            2760            2770            2780
           *               *               *               *
      CTT TTG GGG ATG TTT GCT GAT TCA GTG GTA AAA CGT TCT GGG CAT GTT
      Leu Leu Gly Met Phe Ala Asp Ser Val Val Lys Arg Ser Gly His Val>
        c   c   c   c   c   c ORF 3 c   c   c   c   c   c   c   >

2790            2800            2810            2820            2830
  *               *               *               *               *
 GAT ATT AAC AGA ATG GCT GGG TGT TTT AAA TTG GCA TCT ATG GAA GCT
 Asp Ile Asn Arg Met Ala Gly Cys Phe Lys Leu Ala Ser Met Glu Ala>
   c   c   c   c   c   c ORF 3 c   c   c   c   c   c   c   >

2840            2850            2860            2870            2880
           *               *               *               *               *
      ATG GGT TGT ATA GTG GCT CTG TTG AAT TTA GGG GGC TTC CCG TGG ACT
      Met Gly Cys Ile Val Ala Leu Leu Asn Leu Gly Gly Phe Pro Trp Thr>
        c   c   c   c   c   c ORF 3 c   c   c   c   c   c   c   >

2890            2900            2910            2920            2930
           *               *               *               *               *
      GCT GGT TTT GTG ACG AAA GGG CTA ATG TTA CAT ATG AAC TTG CAG AGT
      Ala Gly Phe Val Thr Lys Gly Leu Met Leu His Met Asn Leu Gln Ser>
        c   c   c   c   c   c ORF 3 c   c   c   c   c   c   c   >

2940            2950            2960            2970            2980
              *               *               *               *               *
         TTT GAC TAT ATG CTC CTA AAG TAT ATG CAG CCT ATG TTG GGA TGG TTG
         Phe Asp Tyr Met Leu Leu Lys Tyr Met Gln Pro Met Leu Gly Trp Leu>
           c   c   c   c   c   c ORF 3 c   c   c   c   c   c   c   >
             <Ile Ser Arg Phe Tyr Ile Cys Gly Ile Asn Pro His Asn
              <  e   e   e   e   e   e ORF 5 e   e   e   e   e   e 2990            3000            3010            3020
              *               *               *               *
         TTA TTT GCG AGT AAT GGA ATG AAG CTT TTT TGG TTG GCA TGC TTA AAG
         Leu Phe Ala Ser Asn Gly Met Lys Leu Phe Trp Leu Ala Cys Leu Lys>
           c   c   c   c   c   c ORF 3 c   c   c   c   c   c   c   >
     <Asn Asn Ala Leu Leu Pro Ile Phe Ser Lys Gln Asn Ala His Lys Phe
        <   e   e   e   e   e   e ORF 5 e   e   e   e   e   e 3030            3040            3050            3060            3070
  *               *               *               *               *
 CCG TGT TCT ACA ACT CCG GAG TAT GCG CCT AGT CCT TTT TCT TCT AAG
 Pro Cys Ser Thr Thr Pro Glu Tyr Ala Pro Ser Pro Phe Ser Ser Lys>
   c   c   c   c   c   c ORF 3 c   c   c   c   c   c   c   >
 <Gly His Glu Val Val Gly Ser Tyr Ala Gly Leu Gly Lys Glu Glu Leu
  <   e   e   e   e   e   e ORF 5 e   e   e   e   e   e 3080            3090            3100            3110            3120
           *               *               *               *               *
      CTC TCA ATT ATA ATG TTG TCG CTT ATT ATT ACG GTG TCT GGT GTA TTG
      Leu Ser Ile Ile Met Leu Ser Leu Ile Ile Thr Val Ser Gly Val Leu>
        c   c   c   c   c   c ORF 3 c   c   c   c   c   c   c   >
  <Ser Glu Ile Ile Ile Asn Asp Ser Ile Ile Val Thr Asp Pro Thr Asn
     <   e   e   e   e   e   e ORF 5 e   e   e   e   e   e 3130            3140            3150            3160            3170
           *               *               *               *               *
      TAT GGC GAG GGC TTG CTT TTT TCA GAG CAT AAA TTT GTA TAT ACA TTT
      Tyr Gly Glu Gly Leu Leu Phe Ser Glu His Lys Phe Val Tyr Thr Phe>
        c   c   c   c   c   c ORF 3 c   c   c   c   c   c   c   >
  <Tyr Pro Ser Pro Lys Ser Lys Glu Ser Cys Leu Asn Thr Tyr Val Asn
```

FIG. 8F

```
      <    e    e    e    e    e    e       ORF 5    e    e    e    e    e    e
                3180           3190           3200           3210           3220
                  *              *              *              *              *
         GGT  GCT  GTA  GCA  ACT  AAG  CTA  ATA  TGG  CTC  GGT  GGC  GTT  GTT  CTG  TTT
         Gly  Ala  Val  Ala  Thr  Lys  Leu  Ile  Trp  Leu  Gly  Gly  Val  Val  Leu  Phe>
           c    c    c    c    c    c       ORF 3    c    c    c    c    c    c    >
         <Pro Ala  Thr  Ala  Val  Leu  Ser  Ile  His  Ser  Pro  Pro  Thr  Thr  Arg  Asn
      <    e    e    e    e    e    e       ORF 5    e    e    e    e    e    e 3230           3240           3250           3260
                  *              *              *              *
         TTT  ATT  TTG  TTT  AGA  AGG  CAG  TTT  TTG  GGA  CGG  TAC  GAG  TCT  GCC  ATA
         Phe  Ile  Leu  Phe  Arg  Arg  Gln  Phe  Leu  Gly  Arg  Tyr  Glu  Ser  Ala  Ile>
           c    c    c    c    c    c       ORF 3    c    c    c    c    c    c    >
         <Lys Ile  Lys  Asn  Leu  Leu  Cys  Asn  Lys  Pro  Arg  Tyr  Ser  Asp  Ala  Met
      <    e    e    e    e    e    e       ORF 5    e    e    e    e    e    e 3270           3280           3290           3300           3310
         *              *              *              *              *
       GGT  GAT  AGC  TGG  GTC  TAT  CGG  CAG  TTT  TTT  ATA  ATG  GCG  GAA  AAG  TTT
       Gly  Asp  Ser  Trp  Val  Tyr  Arg  Gln  Phe  Phe  Ile  Met  Ala  Glu  Lys  Phe>
         c    c    c    c    c    c       ORF 3    c    c    c    c    c    c    >

3320           3330           3340           3350           3360
         *              *              *              *              *
       GCA  CAT  GCT  GCG  TCA  CGC  ATG  AGA  GAG  GTG  TTG  GGA  GGC  CTT  TTT  GCG
       Ala  His  Ala  Ala  Ser  Arg  Met  Arg  Glu  Val  Leu  Gly  Gly  Leu  Phe  Ala>
         c    c    c    c    c    c       ORF 3    c    c    c    c    c    c    >

3370           3380           3390           3400           3410
         *              *              *              *              *
       GGG  GGA  GCT  TTT  AGC  ATA  GAA  ACT  AGT  GGT  TCT  ACT  GTA  TTA  TCA  GCC
       Gly  Gly  Ala  Phe  Ser  Ile  Glu  Thr  Ser  Gly  Ser  Thr  Val  Leu  Ser  Ala>
         c    c    c    c    c    c       ORF 3    c    c    c    c    c    c    >

3420           3430           3440           3450           3460
         *              *              *              *              *
       AGG  TCG  CCA  TCT  GGG  GTT  GTT  AGC  TCT  ACA  TTG  CTT  TTG  GTT  ATG  TTG
       Arg  Ser  Pro  Ser  Gly  Val  Val  Ser  Ser  Thr  Leu  Leu  Leu  Val  Met  Leu>
         c    c    c    c    c    c       ORF 3    c    c    c    c    c    c    >

3470           3480           3490           3500           3510
         *              *              *              *              *
       AGT  ATT  TGT  ATT  ATT  GTT  TTG  GTA  TGG  GCT  TAT  GTT  T  AAC  TCT  TTA  ACC
       Ser  Ile  Cys  Ile  Ile  Val  Leu  Val  Trp  Ala  Tyr  Val>
         c    c    c    c       ORF 3    c    c    c    c    c    >
                                                            Met  Phe  Asn  Ser  Leu  Thr>
                                                              d    d  ORF 4    d    d    >

3520           3530           3540           3550
                  *              *              *              *
         AAG  GGG  TTT  TCT  TCT  GCG  CTG  CAA  AGG  TTA  AGT  GGA  AAG  CGG  GAG  ATA
         Lys  Gly  Phe  Ser  Ser  Ala  Leu  Gln  Arg  Leu  Ser  Gly  Lys  Arg  Glu  Ile>
           d    d    d    d    d    d       ORF 4    d    d    d    d    d    d    >

3560           3570           3580           3590           3600
         *              *              *              *              *
       TCC  AGC  AAG  GAT  TTT  GAT  CTT  GTA  ATA  GAA  GAT  ATA  ACT  CAG  GCA  TTG
       Ser  Ser  Lys  Asp  Phe  Asp  Leu  Val  Ile  Glu  Asp  Ile  Thr  Gln  Ala  Leu>
         d    d    d    d    d    d       ORF 4    d    d    d    d    d    d    >
```

FIG. 8G

```
        3610            3620            3630            3640            3650
         *               *               *               *               *
TTG GAT GCG GAT GTT AAT CTT GGT GTT GTT GAC GAA TTT ATA GAG AAC
Leu Asp Ala Asp Val Asn Leu Gly Val Val Asp Glu Phe Ile Glu Asn>
 d   d   d   d   d   d  ORF  4   d   d   d   d   d   d   d   >

3660            3670            3680            3690            3700
         *               *               *               *               *
GTA AAA AGC AAG ATC GTA GGG GGC GAT GTA GTT AAA GGG GTG CTC CCG
Val Lys Ser Lys Ile Val Gly Gly Asp Val Val Lys Gly Val Leu Pro>
 d   d   d   d   d   d  ORF  4   d   d   d   d   d   d   d   >

3710            3720            3730            3740            3750
         *               *               *               *               *
GAG CAA ATG GTC ATA AAG CGT ATA GAA GAG TGT TTG ATT GAA GTT TTA
Glu Gln Met Val Ile Lys Arg Ile Glu Glu Cys Leu Ile Glu Val Leu>
 d   d   d   d   d   d  ORF  4   d   d   d   d   d   d   d   >

3760            3770            3780            3790
         *               *               *               *
GGT AAT GAG AAG AGC GCT CTT GAT CTT AAG GGA AAG ATT CCT GCA GTA
Gly Asn Glu Lys Ser Ala Leu Asp Leu Lys Gly Lys Ile Pro Ala Val>
 d   d   d   d   d   d  ORF  4   d   d   d   d   d   d   d   >

3800            3810            3820            3830            3840
 *               *               *               *               *
ATC ATG ATG GTT GGG CTT CAA GGT GTT GGT AAG ACT ACT AAC ACA GTA
Ile Met Met Val Gly Leu Gln Gly Val Gly Lys Thr Thr Asn Thr Val>
 d   d   d   d   d   d  ORF  4   d   d   d   d   d   d   d   >

3850            3860            3870            3880            3890
         *               *               *               *               *
AAA GTT GCA CTG AGG TTA AAG AAG GAT TCT AAA AAC CCG TTG GTA GCG
Lys Val Ala Leu Arg Leu Lys Lys Asp Ser Lys Asn Pro Leu Val Ala>
 d   d   d   d   d   d  ORF  4   d   d   d   d   d   d   d   >

3900            3910            3920            3930            3940
         *               *               *               *               *
TCT TTA GAC GTA TAT CGT CCT GCA GCT CGA GAA CAG CTG AAG GTT TTG
Ser Leu Asp Val Tyr Arg Pro Ala Ala Arg Glu Gln Leu Lys Val Leu>
 d   d   d   d   d   d  ORF  4   d   d   d   d   d   d   d   >

3950            3960            3970            3980            3990
         *               *               *               *               *
GCT GAT GGA GTT GGT ATA GAC AGT CTT CCC ATC GTT GAG GAG CAA AAA
Ala Asp Gly Val Gly Ile Asp Ser Leu Pro Ile Val Glu Glu Gln Lys>
 d   d   d   d   d   d  ORF  4   d   d   d   d   d   d   d   >

4000            4010            4020            4030
                  *               *               *               *
CCA CTT GAT ATT GCG AAG CGT GCT ATG AGG GAA GCG AGG CTC AAA GGG
Pro Leu Asp Ile Ala Lys Arg Ala Met Arg Glu Ala Arg Leu Lys Gly>
 d   d   d   d   d   d  ORF  4   d   d   d   d   d   d   d   >

4040            4050            4060            4070            4080
 *               *               *               *               *
CAC GAT GTG GTG CTT TTG GAT ACA GCG GGG CGC TTG CAT ATC AAT CAG
His Asp Val Val Leu Leu Asp Thr Ala Gly Arg Leu His Ile Asn Gln>
 d   d   d   d   d   d  ORF  4   d   d   d   d   d   d   d   >

```
                GAC ATG ATA GAT GAG CTG AAG TGT GTA AAG AAG GAG GTA TCA CCA GCT
                Asp Met Ile Asp Glu Leu Lys Cys Val Lys Lys Glu Val Ser Pro Ala>
                 d   d   d   d   d   d  ORF  4   d   d   d   d   d   d   d   >

4140        4150        4160        4170        4180
                        *           *           *           *           *
                GAA ATT GTA TTG GTT GTA GAC TCC TTA ATG GGG CAA GAT GCC GTC ACT
                Glu Ile Val Leu Val Val Asp Ser Leu Met Gly Gln Asp Ala Val Thr>
                 d   d   d   d   d   d  ORF  4   d   d   d   d   d   d   d   >

4190        4200        4210        4220        4230
                        *           *           *           *           *
                ATG GTG CGC AAG TTC AAT GAG GAG TTA GGC ATT ACT GGG ACG ATC TTT
                Met Val Arg Lys Phe Asn Glu Glu Leu Gly Ile Thr Gly Thr Ile Phe>
                 d   d   d   d   d   d  ORF  4   d   d   d   d   d   d   d   >

4240        4250        4260        4270
                        *           *           *           *
                ACC AGG GCG GAT GGT GAT CCT AGG GGT GGT GCT ATC TTG TCT ATG AAG
                Thr Arg Ala Asp Gly Asp Pro Arg Gly Gly Ala Ile Leu Ser Met Lys>
                 d   d   d   d   d   d  ORF  4   d   d   d   d   d   d   d   >

4280        4290        4300        4310        4320
                 *           *           *           *           *
                TTG GTT GCT GGA TGT CCT ATA AAG TTC ATG TCT ACG GGA GAG AAG CCT
                Leu Val Ala Gly Cys Pro Ile Lys Phe Met Ser Thr Gly Glu Lys Pro>
                 d   d   d   d   d   d  ORF  4   d   d   d   d   d   d   d   >

4330        4340        4350        4360        4370
                        *           *           *           *           *
                GAA GAT TTG GAC GAT TTC TAT CCT GAT AGA ATA GCT CGT AGA ATG TTA
                Glu Asp Leu Asp Asp Phe Tyr Pro Asp Arg Ile Ala Arg Arg Met Leu>
                 d   d   d   d   d   d  ORF  4   d   d   d   d   d   d   d   >

4380        4390        4400        4410        4420
                        *           *           *           *           *
                AAT ATG GGA GAT GTC GCA TCT CTT GTA GAA AAG GCG GTA GAA GCG GTT
                Asn Met Gly Asp Val Ala Ser Leu Val Glu Lys Ala Val Glu Ala Val>
                 d   d   d   d   d   d  ORF  4   d   d   d   d   d   d   d   >

4430        4440        4450        4460        4470
                        *           *           *           *           *
                GGC AAG GAT ACA ATT AAT GAG CTA CAG GCG AAG GCC AAG AAG GGT AAA
                Gly Lys Asp Thr Ile Asn Glu Leu Gln Ala Lys Ala Lys Lys Gly Lys>
                 d   d   d   d   d   d  ORF  4   d   d   d   d   d   d   d   >

-      4480        4490        4500        4510
                              *           *           *           *
                TTC GAT TTG GAT GAT CTT GTT ATT CAG CTG AAA GCT TTG AAT AAA ATG
                Phe Asp Leu Asp Asp Leu Val Ile Gln Leu Lys Ala Leu Asn Lys Met>
                 d   d   d   d   d   d  ORF  4   d   d   d   d   d   d   d   >

4520        4530        4540        4550        4560
                 *           *           *           *           *
                GGT GGT ATT GCT AAT ATA ATG AAG TTT ATA CCC GCT TTC GGT AAC GAT
                Gly Gly Ile Ala Asn Ile Met Lys Phe Ile Pro Ala Phe Gly Asn Asp>
                 d   d   d   d   d   d  ORF  4   d   d   d   d   d   d   d   >

4570        4580        4590        4600        4610
                        *           *           *           *           *
                ATA AAA CGC AAA GTT GCG GGG ATA GCT GAT GAC AGC AAA GTC GAC ATG
                Ile Lys Arg Lys Val Ala Gly Ile Ala Asp Asp Ser Lys Val Asp Met>
```

FIG. 8I

```
      d   d   d   d   d   d  ORF 4  d   d   d   d   d   d   d  >
            4620            4630           4640            4650           4660
              *               *              *               *              *
     TAC ATT GCG ATT ATT AAC TCA ATG ACG AAG CAG GAG AGG GCG AAT CCT
     Tyr Ile Ala Ile Ile Asn Ser Met Thr Lys Gln Glu Arg Ala Asn Pro>
      d   d   d   d   d   d  ORF 4  d   d   d   d   d   d   d  >
            4670            4680           4690            4700           4710
              *               *              *               *              *
     GAG ATA CTG AAT GGT GCG AGG AAG GCA AGG ATA GCG AAG GGT GCG GGA
     Glu Ile Leu Asn Gly Ala Arg Lys Ala Arg Ile Ala Lys Gly Ala Gly>
      d   d   d   d   d   d  ORF 4  d   d   d   d   d   d   d  >
            4720            4730           4740            4750
              *               *              *               *
     GTT AAG GTT GAT GCT GTA AAT GCG TTG CTA AAG CAG TAT AAT CAG ATG
     Val Lys Val Asp Ala Val Asn Ala Leu Leu Lys Gln Tyr Asn Gln Met>
      d   d   d   d   d   d  ORF 4  d   d   d   d   d   d   d  >
     4760            4770            4780           4790            4800
       *               *               *              *               *
     AAT TCG ATA TCA AGC TTA TCG ATA CCG TCG ACC TCG AGG GGG CCC G
     Asn Ser Ile Ser Ser Leu Ser Ile Pro Ser Thr Ser Arg Gly Pro>
      d   d   d   d   d   d ORF 4   d   d   d   d   d   d  >
```

FIG. 8J

```
Sequence Range: 1 to 5174
                10          20          30              40          50
                 *           *           *               *           *
TCTAGAACTA GTGGATCCCC CGGGCTGAAT TCC GTA GAA GCT GGG GCA CAT ATA
                                    Val Glu Ala Gly Ala His Ile>
                                     b   b  ORF 1  b   b         >

60          70          80          90         100
          *           *           *           *           *
AAT ACT CCT ACC GGA TCT ATG AGC CCT TTA GCT GCT GCA GTT CAA GCG
Asn Thr Pro Thr Gly Ser Met Ser Pro Leu Ala Ala Ala Val Gln Ala>
 b   b   b   b   b   b  ORF 1  b   b   b   b   b   b   b       >

110         120         130         140         150
          *           *           *           *           *
GCA AAT GAG GCA AGT AAC CTT AAA GAG GCT AAT AAG ATT GTA AAT TTC
Ala Asn Glu Ala Ser Asn Leu Lys Glu Ala Asn Lys Ile Val Asn Phe>
 b   b   b   b   b   b  ORF 1  b   b   b   b   b   b   b       >

160         170         180         190
               *           *           *           *
CTT TTA CAT AGG GGT GCA GAT CTT TCG TCT ACG GAA CAC ACT GGA ACT
Leu Leu His Arg Gly Ala Asp Leu Ser Ser Thr Glu His Thr Gly Thr>
 b   b   b   b   b   b  ORF 1  b   b   b   b   b   b   b       >

200         210         220         230         240
  *           *           *           *           *
CCA GCC TTG CAT TTA GCA ACA GCT GCT GGC AAC CAT AGG ACT GCT ATG
Pro Ala Leu His Leu Ala Thr Ala Ala Gly Asn His Arg Thr Ala Met>
 b   b   b   b   b   b  ORF 1  b   b   b   b   b   b   b       >

250         260         270         280         290
          *           *           *           *           *
TTG CTC TTG GAT AAA GGG GCT CCA GCA ACG CAG AGA GAT GCT AGG GGT
Leu Leu Leu Asp Lys Gly Ala Pro Ala Thr Gln Arg Asp Ala Arg Gly>
 b   b   b   b   b   b  ORF 1  b   b   b   b   b   b   b       >

300         310         320         330         340
          *           *           *           *           *
AGG ACG GCT TTA CAT ATA GCA GCT GCT AAT GGT GAC GGT AAG CTA TAT
Arg Thr Ala Leu His Ile Ala Ala Ala Asn Gly Asp Gly Lys Leu Tyr>
 b   b   b   b   b   b  ORF 1  b   b   b   b   b   b   b       >

350         360         370         380         390
               *           *           *           *           *
AGG ATG ATT GCG AAA AAA TGC CCA GAT AGC TGT CAA CCA CTC TGT TCT
Arg Met Ile Ala Lys Lys Cys Pro Asp Ser Cys Gln Pro Leu Cys Ser>
 b   b   b   b   b   b  ORF 1  b   b   b   b   b   b   b       >

400         410         420         430
          *           *           *           *
GAT ATG GGA GAT ACA GCG TTA CAT GAG GCT TTA TAT TCT GAT AAT GTT
Asp Met Gly Asp Thr Ala Leu His Glu Ala Leu Tyr Ser Asp Asn Val>
 b   b   b   b   b   b  ORF 1  b   b   b   b   b   b   b       >

440         450         460         470         480
  *           *           *           *           *
ACA GAA AAA TGC TTT TTA AAG ATG CTT AAA GAG TCT CGA AAG CAT TTG
Thr Glu Lys Cys Phe Leu Lys Met Leu Lys Glu Ser Arg Lys His Leu>
 b   b   b   b   b   b  ORF 1  b   b   b   b   b   b   b       >
```

FIG. 10A

```
       490           500           510           520           530
        *             *             *             *             *
TCA AAC TCA TCT TTT TTC GGA GAC TTG CTT AAT ACT CCT CAA GAA GCA
Ser Asn Ser Ser Phe Phe Gly Asp Leu Leu Asn Thr Pro Gln Glu Ala>
 b   b   b   b   b   b  ORF 1 b   b   b   b   b   b   b    >

540           550           560           570           580
        *             *             *             *             *
AAT GGT GAC ACG TTA CTG CAT CTG GCT GCA TCG CGT GGT TTC GGT AAA
Asn Gly Asp Thr Leu Leu His Leu Ala Ala Ser Arg Gly Phe Gly Lys>
 b   b   b   b   b   b  ORF 1 b   b   b   b   b   b   b    >

590           600           610           620           630
        *             *             *             *             *
GCA TGT AAA ATA CTA CTA AAG GCT GGG GCG TCA GTA TCA GTC GTG AAT
Ala Cys Lys Ile Leu Leu Lys Ala Gly Ala Ser Val Ser Val Val Asn>
 b   b   b   b   b   b  ORF 1 b   b   b   b   b   b   b    >

640           650           660           670
               *             *             *             *
GTA GAG GGA AAA ACA CCG GTA GAT GTT GCG GAT CCA TCA TTG AAA ACT
Val Glu Gly Lys Thr Pro Val Asp Val Ala Asp Pro Ser Leu Lys Thr>
 b   b   b   b   b   b  ORF 1 b   b   b   b   b   b   b    >

680          690           700           710           720
  *            *             *             *             *
CGT CCG TGG TTT TTT GGA AAG TCC GTT GTC ACA ATG ATG GCT GAA CGT
Arg Pro Trp Phe Phe Gly Lys Ser Val Val Thr Met Met Ala Glu Arg>
 b   b   b   b   b   b  ORF 1 b   b   b   b   b   b   b    >

730           740           750           760           770
        *             *             *             *             *
GTT CAA GTT CCT GAA GGG GGA TTC CCA CCA TAT CTG CCG CCT GAA AGT
Val Gln Val Pro Glu Gly Gly Phe Pro Pro Tyr Leu Pro Pro Glu Ser>
 b   b   b   b   b   b  ORF 1 b   b   b   b   b   b   b    >

780           790           800           810           820
        *             *             *             *             *
CCA ACT CCT TCT TTA GGA TCT ATT TCA AGT TTT GAG AGT GTC TCT GCG
Pro Thr Pro Ser Leu Gly Ser Ile Ser Ser Phe Glu Ser Val Ser Ala>
 b   b   b   b   b   b  ORF 1 b   b   b   b   b   b   b    >

830           840           850           860           870
        *             *             *             *             *
CTA TCA TCC TTG GGT AGT GGC CTA GAT ACT GCA GGA GCT GAG GAG TCT
Leu Ser Ser Leu Gly Ser Gly Leu Asp Thr Ala Gly Ala Glu Glu Ser>
 b   b   b   b   b   b  ORF 1 b   b   b   b   b   b   b    >

880           890           900           910
               *             *             *             *
ATC TAC GAA GAA ATT AAG GAT ACA GCA AAA GGT ACA ACG GAA GTT GAA
Ile Tyr Glu Glu Ile Lys Asp Thr Ala Lys Gly Thr Thr Glu Val Glu>
 b   b   b   b   b   b  ORF 1 b   b   b   b   b   b   b    >

920          930           940           950           960
  *            *             *             *             *
AGC ACA TAT ACA ACT GTA GGA GCT GAG GAG TCT ATC TAC GAA GAA ATT
Ser Thr Tyr Thr Thr Val Gly Ala Glu Glu Ser Ile Tyr Glu Glu Ile>
 b   b   b   b   b   b  ORF 1 b   b   b   b   b   b   b    >

```
AAG GAT ACA GCA AAA GGT ACA ACG GAA GTT GAA AGC ACA TAT ACA ACT
Lys Asp Thr Ala Lys Gly Thr Thr Glu Val Glu Ser Thr Tyr Thr Thr>
 b   b   b   b   b   b   b  ORF1  b   b   b   b   b   b   b   >

1020        1030        1040        1050        1060
         *           *           *           *           *
GTA GGA GCT GAA GGT CCG AGA ACA CCA GAA GGT GAA GAT CTG TAT GCT
Val Gly Ala Glu Gly Pro Arg Thr Pro Glu Gly Glu Asp Leu Tyr Ala>
 b   b   b   b   b   b  ORF1  b   b   b   b   b   b   b   b   >

1070        1080        1090        1100        1110
         *           *           *           *           *
ACT GTG GGA GCT GCA ATT ACT TCC GAG GCG CAA GCA TCA GAT GCG GCG
Thr Val Gly Ala Ala Ile Thr Ser Glu Ala Gln Ala Ser Asp Ala Ala>
 b   b   b   b   b   b  ORF1  b   b   b   b   b   b   b   b   >

1120        1130        1140        1150
         *           *           *           *
TCA TCT AAG GGA GAA AGG CCG GAA TCC ATT TAT GCT GAT CCA TTT GAT
Ser Ser Lys Gly Glu Arg Pro Glu Ser Ile Tyr Ala Asp Pro Phe Asp>
 b   b   b   b   b   b  ORF1  b   b   b   b   b   b   b   b   >

1160        1170        1180        1190        1200
    *           *           *           *           *
ATA GTG AAA CCT AGG CAG GAA AGG CCT GAA TCT ATC TAT GCT GAC CCA
Ile Val Lys Pro Arg Gln Glu Arg Pro Glu Ser Ile Tyr Ala Asp Pro>
 b   b   b   b   b   b  ORF1  b   b   b   b   b   b   b   b   >

1210        1220        1230        1240        1250
         *           *           *           *           *
TTT GCT GCG GAA CGA ACA TCT TCT GGA GTA ACG ACA TTT GGC CCT AAG
Phe Ala Ala Glu Arg Thr Ser Ser Gly Val Thr Thr Phe Gly Pro Lys>
 b   b   b   b   b   b  ORF1  b   b   b   b   b   b   b   b   >

1260        1270        1280        1290        1300
         *           *           *           *           *
GAA GAG CCG ATT TAT GCA ACA GTG AAA AAG GGT CCT AAG AAG AGT GAT
Glu Glu Pro Ile Tyr Ala Thr Val Lys Lys Gly Pro Lys Lys Ser Asp>
 b   b   b   b   b   b  ORF1  b   b   b   b   b   b   b   b   >

1310        1320        1330        1340        1350
         *           *           *           *           *
ACT TCT CAA AAA GAA GGA ACA GCT TCT GAA AAA GTC TGC TCA ACA ATA
Thr Ser Gln Lys Glu Gly Thr Ala Ser Glu Lys Val Cys Ser Thr Ile>
 b   b   b   b   b   b  ORF1  b   b   b   b   b   b   b   b   >

1360        1370        1380        1390
              *           *           *           *
ACT GTG ATT AAG AAG AAA GTG AAA CCT CAG GTT CCA GCT AGG ACA AGT
Thr Val Ile Lys Lys Lys Val Lys Pro Gln Val Pro Ala Arg Thr Ser>
 b   b   b   b   b   b  ORF1  b   b   b   b   b   b   b   b   >

1400        1410        1420        1430        1440
 *           *           *           *           *
AGT TTG CCT ACT AAA GAA GGT ATA GGT TCT GAT AAA GAC CTG AGT TCA
Ser Leu Pro Thr Lys Glu Gly Ile Gly Ser Asp Lys Asp Leu Ser Ser>
 b   b   b   b   b   b  ORF1  b   b   b   b   b   b   b   b   >

1450        1460        1470        1480        1490
         *           *           *           *           *
GGA ACT AGT AGC TCT TTT GCA GCT GAG CTG CAA GCA CAA AGG GGT AAA
Gly Thr Ser Ser Ser Phe Ala Ala Glu Leu Gln Ala Gln Arg Gly Lys>
```

FIG. 10C

```
     b     b     b     b     b     b    ORF 1   b     b     b     b     b     b     >
    1500              1510              1520              1530              1540
     *                 *                 *                 *                 *
    TTG   CGT   CCT   GTG   AAG   GGA   GGT   GCT   CCG   GAT   TCT   ACC   AAA   GAC   AAA   ACA
    Leu   Arg   Pro   Val   Lys   Gly   Gly   Ala   Pro   Asp   Ser   Thr   Lys   Asp   Lys   Thr>
     b     b     b     b     b     b    ORF 1   b     b     b     b     b     b     >
          1550              1560              1570              1580              1590
           *                 *                 *                 *                 *
    GCT   ACT   TCT   ATA   TTC   TCC   AGT   AAA   GAG   TTC   AAA   AAG   GAA   CTA   ACA   AAA
    Ala   Thr   Ser   Ile   Phe   Ser   Ser   Lys   Glu   Phe   Lys   Lys   Glu   Leu   Thr   Lys>
     b     b     b     b     b     b    ORF 1   b     b     b     b     b     b     >
          1600              1610              1620              1630
           *                 *                 *                 *
    GCT   GCC   GAA   GGA   TTA   CAG   GGA   GCA   GTT   GAA   GAA   GCT   CAG   AAG   GGT   GAT
    Ala   Ala   Glu   Gly   Leu   Gln   Gly   Ala   Val   Glu   Glu   Ala   Gln   Lys   Gly   Asp>
     b     b     b     b     b     b    ORF 1   b     b     b     b     b     b     >
 1640              1650              1660              1670              1680
  *                 *                 *                 *                 *
 GGA   GGA   GCT   GCA   AAG   GCA   AAG   CAA   GAT   CTT   GGC   ATG   GAA   TCT   GGT   GCC
 Gly   Gly   Ala   Ala   Lys   Ala   Lys   Gln   Asp   Leu   Gly   Met   Glu   Ser   Gly   Ala>
  b     b     b     b     b     b    ORF 1   b     b     b     b     b     b     >
     1690              1700              1710              1720              1730
      *                 *                 *                 *                 *
    CCA   GGA   TCT   CAA   CCA   GAA   GCT   CCT   CAA   AGT   GAA   GGC   CCT   AAG   TCT   GTA
    Pro   Gly   Ser   Gln   Pro   Glu   Ala   Pro   Gln   Ser   Glu   Gly   Pro   Lys   Ser   Val>
     b     b     b     b     b     b    ORF 1   b     b     b     b     b     b     >
          1740              1750              1760              1770              1780              1790
           *                 *                 *                 *                 *                 *
         AAA   GGA   GGT   CGC   GGT   AGG   TAGAATTA    TACCGAAAAA   TCGCTGAGGT   ACTTTGATCA
         Lys   Gly   Gly   Arg   Gly   Arg>
          b         ORF 1   b     b     >
             1800         1810         1820         1830         1840         1850
              *            *            *            *            *            *
          ATATAATTCG   CGCTTCTGAG   TATTTAGGCG   ATGATCTCGC   CACTTTAATA   ATACCCCTTT
             1860         1870         1880         1890         1900         1910
              *            *            *            *            *            *
          TAGAGTACAT   AACGCTCTAA   AGGGGGCAGA   TTATTTTAAG   TAGTAGGGTT   TTGATTCTGA
             1920         1930         1940         1950         1960         1970
              *            *            *            *            *            *
          GATCTTTTGA   GTACAACTAT   TCCTTAGTGT   TTTTTTGGAA   TGCTATGTGC   TTGATAAAGA
             1980         1990         2000         2010         2020         2030
              *            *            *            *            *            *
          AAAAACTTGC   TCTGGGGTGG   GATGCACTCT   TGAGTACTTT   CCGCGCTCTG   TATATTCCTT
             2040         2050         2060         2070         2080         2090
              *            *            *            *            *            *
          TTTTTGCATC   TGCATAATCT   GCTGCATATG   TGATTATGTG   ATAATGACGG   AATTACCCAG
             2100         2110         2120         2130         2140         2150
              *            *            *            *            *            *
          AAAAGTTTTA   GCGTGTGAGG   CTATCATTCT   CAGTAAAGTT   ACAGTAGGAA   ACTTGTCATT
```

FIG. 10D

```
       2160       2170       2180       2190       2200       2210
         *          *          *          *          *          *
   TTCATCTTGT ATTTTTGTAA GTTGGCTAAG AGCACTAGCT ATAACAAATG CATCTATGGC 2220       2230       2240       2250       2260       2270
         *          *          *          *          *          *
   ATTTTTTGAG AGTTATAATA ATGAGCAACA AAGGGTGGTA CTATTGTTCA AAATTTGTTT 2280       2290       2300       2310       2320       2330
         *          *          *          *          *          *
   ATGTGCTTTG TCTCACAATG GAGTTTAAAG TCATCTCCGT GTAGTACTAC GACTTTAAGT 2340       2350       2360       2370       2380       2390
         *          *          *          *          *          *
   AGAGAATACT TTGTATTTTC TTTATAGAAG CTCAGAGATA TACTTCAGTA TGTGTCGGAG 2400       2410       2420       2430       2440       2450
         *          *          *          *          *          *
   GTTGTTCCCT TGGGAAAAAG GGCATTTTAT CAACTGTGAA CTATCGCTAC TATGGCTGAG 2460       2470       2480       2490       2500       2510
         *          *          *          *          *          *
   GAAAAGTAGA TAGCAACAAA GATAGTATTC TGGTTTTATA ATCAAACCGT AATCTTTCAA 2520       2530       2540       2550       2560       2570
         *          *          *          *          *          *
   CATGTTCGAA GATCGCTTTC ACTTTATAAT CCTTTTTGAC TGCCCTGCTG AAAGGGCTTT 2580       2590       2600       2610       2620       2630
         *          *          *          *          *          *
   TTTGTTATGA AACTATCCTC GCTCGATTTT CTTATCTTTG GATTCTATTA CCACGGATAA 2640       2650       2660       2670       2680       2690
         *          *          *          *          *          *
   TGTTTGTTGG AATTATTTTA GAAGAAGCTT AGGCATTGCG TTATTTCTTT AACTCTTATG 2700       2710       2720       2730       2740       2750
         *          *          *          *          *          *
   GTACTTGTAC AGTTTTCAGC AGCTTTAATT AAATCTTTTT CAATGTGGGC TCAAAGAGTT 2760       2770       2780       2790       2800       2810
         *          *          *          *          *          *
   GAGAATATAA GATTACGCTT ATACTGTGAC CATTTCTCTA CTTTGCGCTG TAAGGGAAGT 2820       2830       2840       2850       2860       2870
         *          *          *          *          *          *
   TCTTATGTTT GACTTCGTAT TTAAGGTGCT TTACGCGACC TCGCGTGTGG GTAGATAGAT 2880       2890       2900       2910       2920       2930
         *          *          *          *          *          *
   AAATTTGCTA TGGAGAGGAG GGATTTGCTT TGCATGCCAA ATGCCGCATA ATGTTCTGCA 2940       2950       2960       2970       2980       2990
         *          *          *          *          *          *
   TCGCGTGAAC GATACGTTAA TACTTTTTGC GTTGTTTTTG AGTTACGTAA TCAATAAATT 3000       3010       3020       3030       3040       3050
         *          *          *          *          *          *
   CACTGTTGTA ATTTAAGAGA TGCAAGATGT ACACTCAGGC GTATATACTT ATGGAATACT 3060       3070       3080       3090       3100       3110
         *          *          *          *          *          *
```

FIG. 10E

```
          TCACATACCG CGTGATTAGG TAATAAAAAG GCCTCAGCTT TTCTAGAAGA ATGTTCGCAG
             3120       3130       3140       3150       3160       3170
              *          *          *          *          *          *
          AAGCATTTAG TGATGTTTCA GGGTTTGTTT TTTATGCTAG GCGGACTTCC TTATGATCAT
             3180       3190       3200       3210       3220       3230
              *          *          *          *          *          *
          CCCATGTAGG TATGCGGTTT TCAAATGGGC ATGTAACGAA AAAATTCAAT TTTTTTATTT
             3240       3250       3260       3270       3280       3290
              *          *          *          *          *          *
          ATAAACATCT TGCTACTGTC TCAATAATTT GGTACATAGG AGAAAGTTGC ACGGGTTTGT
             3300       3310       3320       3330       3340       3350
              *          *          *          *          *          *
          ATGCAGCGCT TTCTTTTCGC GGGGTGGAGC AGTGGTAGCT CATCAGGCTC ATAACCTGAA
             3360       3370       3380       3390       3400       3410
              *          *          *          *          *          *
          GGTCGATGGT TCGAGTCCGT CCCCCGCAAC TTGTATTTCC TTAGTTCGCT ATGTAGTGTT
             3420       3430       3440       3450       3460       3470
              *          *          *          *          *          *
          GTCCTAAGGG GCGGAATGTC TTTATCTCTA GCTATTGCTT TATCTTTAAC TACTTGCGTG
             3480       3490       3500       3510       3520       3530
              *          *          *          *          *          *
          TTGTAGTAAA GCTGTTGTAT CTATTGCAGC TCAGTAGAGT TCGTGGGGTA GAAGTACTAA
             3540       3550       3560       3570       3580       3590
              *          *          *          *          *          *
          CGAAAAGTTT GAGATTAATA TCAAAATGGC GGCTAATTTT ATTCACCATC TACCGTATAC
             3600       3610       3620       3630       3640       3650
              *          *          *          *          *          *
          TAACGCTTGG CTGCGCAATA TCCGTATAGC TTAGCGGAAT TATACTGTGT AAATAATATT
             3660       3670       3680       3690       3700       3710
              *          *          *          *          *          *
          CACTCAAAAG TGTGATGATT TTAAGATAAC ACAGGTTTTC ACTTCGCTTA CCACTAAGTG
                 3720         3730       3740         3750         3760
                   *            *          *            *            *
          TTTATCTA CAT ACC TCT TCC TTC GGA ATG CTC TAT GAC GTT TGG CGA AGG
                 <Met Gly Arg Gly Glu Ser His Glu Ile Val Asn Pro Ser Pro
                  <    c   c   c   c   c ORF 2  c   c   c   c   c   c
                       3770         3780         3790             3800
                         *            *            *                *
          AGA AGG GGA GAC ATG GTG CTC ATG GCC TCT TTC TTC ATG TGA TAC ACC
          <Ser Pro Ser Val His His Glu His Gly Arg Glu Glu His Ser Val Gly
           <   c   c   c   c   c   c ORF 2  c   c   c   c   c   c   c
          3810         3820         3830         3840         3850
            *            *            *            *            *
          ATC TAA TCC TTG TGC TGC TCT TCC AAT AGA TTC GTC AGC ATG TGG ATA
          <Asp Leu Gly Gln Ala Ala Arg Gly Ile Ser Glu Asp Ala His Pro Tyr
           <   c   c   c   c   c   c ORF 2  c   c   c   c   c   c   c
          3860         3870         3880         3890         3900
            *            *            *            *            *
```

FIG. 10F

```
          CTG GTC AAA ATC CCA AGG ATC ATA TAG ATG CGG GTC ATT TCT TCC ATC
         <Gln Asp Phe Asp Trp Pro Asp Tyr Leu His Pro Asp Asn Arg Gly Asp
         <  c   c   c   c   c   c  ORF 2   c   c   c   c   c   c   c 3910        3920        3930        3940        3950
                *           *           *           *           *
          TAA ATA TCT CTC ATC ATC GCC ACC GTC AGT ATA ATC TTC TCC TCC TTC
         <Leu Tyr Arg Glu Asp Asp Gly Gly Asp Thr Tyr Asp Glu Gly Gly Glu
         <  c   c   c   c   c   c  ORF 2   c   c   c   c   c   c   c 3960        3970        3980        3990        4000
                *           *           *           *           *
          GCC ACC TCC TGA TGC TGC TTC ATC TCC TCC TTC TCC CCC TCC CTT TAT
         <Gly Gly Gly Ser Ala Ala Glu Asp Gly Gly Glu Gly Gly Gly Lys Ile
         <  c   c   c   c   c   c- ORF 2   c   c   c   c   c   c   c 4010        4020        4030        4040
                *           *           *           *
          GGA GTC AAA AAG TAT AGG AAA GCC AAA AGC TAA TGA TGT TTT AGA AGG
         <Ser Asp Phe Leu Ile Pro Phe Gly Phe Ala Leu Ser Thr Lys Ser Pro
         <  c   c   c   c   c   c  ORF 2   c   c   c   c   c   c   c 4050        4060        4070        4080        4090
           *           *           *           *           *
          TCC ATA TAT GCT AAA CTG CGC TGA TAG ATT AGC TCC TAA AGA CAT TGC
         <Gly Tyr Ile Ser Phe Gln Ala Ser Leu Asn Ala Gly Leu Ser Met Ala
         <  c   c   c   c   c   c  ORF 2   c   c   c   c   c   c   c 4100        4110        4120        4130        4140
                *           *           *           *           *
          TGC TTT GTC TAT ATT ACC AAG CAG GCT TCC TAC AAG ATC AGC TTC AT
         <Ala Lys Asp Ile Asn Gly Leu Leu Ser Gly Val Leu Asp Ala Lys Met
         <  c   c   c   c   c   c  ORF 2   c   c   c   c   c   c   c 4150        4160        4170        4180        4190
                *           *           *           *           *
          CGC TTC TAC AGG GGT TGC CAG TAC TGC ATT CAT TAT TGC TAG AGA AGA
         <Ala Glu Val Pro Thr Ala Leu Val Ala Asn Met Ile Ala Leu Ser Ser
         <  c   c   c   c   c   c  ORF 2   c   c   c   c   c   c   c 4200        4210        4220        4230        4240
                *           *           *           *           *
          TCT ATC ATC TCC TTC TTC ACC TCC TCC AGC GGC TTC AGC GCG CTC TTG
         <Arg Asp Asp Gly Glu Glu Gly Gly Gly Ala Ala Glu Ala Arg Glu Gln
         <  c   c   c   c   c   c  ORF 2   c   c   c   c   c   c   c 4250        4260        4270        4280
                     *           *           *           *
          AGT AGC ATG CAT TAA GGA CTG TAC ACT AGC TAT ATT TGG TCC CAT ACC
         <Thr Ala His Met Leu Ser Gln Val Ser Ala Ile Asn Pro Gly Met Gly
         <  c   c   c   c   c   c  ORF 2   c   c   c   c   c   c   c 4290        4300        4310        4320        4330        4340
                *           *           *           *           *           *
          CAT ATC GGC ACC GCC ACC ACC AGG TTT ATG CAT AATCACCTC TCAAGTAACA
         <Met Asp Ala Gly Gly Gly Gly Pro Lys His Met
         <  c   c   c   c  ORF 2   c   c   c   c 4350        4360        4370        4380        4390
                     *           *           *           *           *
          TAGAAAATTC AAGGCATATC CTAACTACAT CTACCATGCA ATAGTGAATA TTTTTA AAA
                                                                     <Phe
```

FIG. 10G

```
      4400          4410          4420          4430          4440
        *             *             *             *             *
   CGC CTC TTC CTC ATA TAT AAG GGC TGT CAT TTC TTT GCG CTG CTC TAG
  <Ala Glu Glu Glu Tyr Ile Leu Ala Thr Met Glu Lys Arg Gln Glu Leu
  <  a   a   a   a   a   a  ORF 3  a   a   a   a   a   a   a   a 4450          4460          4470          4480          4490
        *             *             *             *             *
   GAA TTT TGA ATC ATC TGA TAG TAA ATG TCT ATG GAG AAA ATA TCC TAG
  <Phe Lys Ser Asp Asp Ser Leu Leu His Arg His Leu Phe Tyr Gly Leu
  <  a   a   a   a   a   a  ORF 3  a   a   a   a   a   a   a   a 4500          4510          4520          4530          4540
         *             *             *             *             *
    GAT TTG TAA GCA GAG CAA AAA CTC TTT TCG TGA ACA CTG TTC GGT GTG
   <Ile Gln Leu Cys Leu Leu Phe Glu Lys Arg Ser Cys Gln Glu Thr His
   <  a   a   a   a   a   a  ORF 3  a   a   a   a   a   a   a   a 4550          4560          4570          4580          4590
          *             *             *             *             *
     AGT TCC ATT ATG AAG ATC GCG TAA TAT TTG TGG TAG AGG AAA TAA CAA
    <Thr Gly Asn His Leu Asp Arg Leu Ile Gln Pro Leu Pro Phe Leu Leu
    <  a   a   a   a   a   a  ORF 3  a   a   a   a   a   a   a   a 4600          4610          4620          4630
           *             *             *             *
      GTG CCG ATA TGA TAC GCC AGC TCT TTC AGA TAT TGC GCG ACC TGT TTT
     <His Arg Tyr Ser Val Gly Ala Arg Glu Ser Ile Ala Arg Gly Thr Lys
     <  a   a   a   a   a   a  ORF 3  a   a   a   a   a   a   a   a 4640          4650          4660          4670          4680
     *             *             *             *             *
  AGG AGA TAT GTA CAA TAG ATT ATC TTC GCA ATG GTA AAC AGC GCA TCT
 <Pro Ser Ile Tyr Leu Leu Asn Asp Glu Cys His Tyr Val Ala Cys Arg
 <  a   a   a   a   a   a  ORF 3  a   a   a   a   a   a   a   a 4690          4700          4710          4720          4730
         *             *             *             *             *
    TGA GAG ATC TAA GGC GAA GCC CAG CTG GGA TAA AAT TTC AAG TTC AAG
   <Ser Leu Asp Leu Ala Phe Gly Leu Gln Ser Leu Ile Glu Leu Glu Leu
   <  a   a   a   a   a   a  ORF 3  a   a   a   a   a   a   a   a 4740          4750          4760          4770          4780
            *             *             *             *             *
       CTT TAA GTA CTC GTT GTA CCA ATG GCC TCC ACA TTC TGC AGC TTC AGC
      <Lys Leu Tyr Glu Asn Tyr Trp His Gly Gly Cys Glu Ala Ala Glu Ala
      <  a   a   a   a   a   a  ORF 3  a   a   a   a   a   a   a   a 4790          4800          4810          4820          4830
               *             *             *             *             *
          AAA CTC TAT AAG ATA GTC ATA TAG TAT AGG ATG TGC ATC ATT TGT GGG
         <Phe Glu Ile Leu Tyr Asp Tyr Leu Ile Pro His Ala Asp Asn Thr Pro
         <  a   a   a   a   a   a  ORF 3  a   a   a   a   a   a   a   a 4840          4850          4860          4870
                  *             *             *             *
             GAC GGA CTT GTA TAT TGT GGA TGT AAC AGA GGA TAG ACA CAG CAA CTT
            <Val Ser Lys Tyr Ile Thr Ser Thr Val Ser Ser Leu Cys Leu Leu Lys
            <  a   a   a   a   a   a  ORF 3  a   a   a   a   a   a   a   a
```

FIG. 10H

```
      4880          4890          4900           4910          4920
        *             *             *              *             *
     TGA ATG ATC TTG AAA ATA CGC ATA AAA AGC TGA TGA AAT AAT TTC ACA
    <Ser His Asp Gln Phe Tyr Ala Tyr Phe Ala Ser Ser Ile Ile Glu Cys
    <  a   a   a   a   a   a  ORF 3  a   a   a   a   a   a   a   a 4930          4940          4950           4960          4970
        *             *             *              *             *
     GGA GTT AAA ATA CCC AAG GTT ATT AGC TAA TCT CGC ACG CCA CGT TAC
    <Ser Asn Phe Tyr Gly Leu Asn Asn Ala Leu Arg Ala Arg Trp Thr Val
    <  a   a   a   a   a   a  ORF 3  a   a   a   a   a   a   a   a 4980          4990          5000           5010          5020
           *             *             *              *             *
        GCA CAC TCT ATC TCC AAT CTG CAG AGA CTG CTT CTT TTT GTT TAG TCT
       <Cys Val Arg Asp Gly Ile Gln Leu Ser Gln Lys Lys Lys Asn Leu Arg
       <  a   a   a   a   a   a  ORF 3  a   a   a   a   a   a   a   a 5030          5040          5050           5060          5070
              *             *             *              *             *
           GAT CAT GGC ATT GCA AAT TCC GTG ATT ACG CGT AAA TAC AGA CAA TAT
          <Ile Met Ala Asn Cys Ile Gly His Asn Arg Thr Phe Val Ser Leu Ile
          <  a   a   a   a   a   a  ORF 3  a   a   a   a   a   a   a   a 5080          5090          5100           5110          5120
                   *             *             *              *             *
                ACT TCG AGT ATC CCC ATA AGG CGT CAT GCT TAC GAT CAT TCCATGGTCT
               <Ser Arg Thr Asp Gly Tyr Pro Thr Met Ser Val Ile Met
               <  a   a   a   a   a  ORF 3       a   a   a   a 5130          5140          5150           5160          5170
                        *             *             *              *             *
                     TGCCATGGAA TTCGATATCA AGCTTATCGA TACCGTCGAC CTCGAGGGGG GCCC
```

FIG. 10I

Sequence Range: 1 to 1843

```
           10         20         30         40         50         60
            *          *          *          *          *          *
       GGGCTATTCT GCAGCCTCAT AATAGATCCA CGCCCAAAAG CGCGTTCAAT CTGACCAATA 70         80         90        100        110        120
            *          *          *          *          *          *
       GCAGCATCAA CAGCCCGCTG CTTATCAGAG GGGGAGTCCT TCATTTCAAC CATGGGGTAT 130        140        150        160        170        180
            *          *          *          *          *          *
       CACAAGAATT TTAACTGCTC AACAATAGAC ATTGAAGCCA AAAGTGTCAA GATTTGTACA 190        200        210        220        230        240
            *          *          *          *          *          *
       AATGGGAGCG ATGCGATTTG CACTATAAAA ACACGCCAAA TCCCCATCAA GCACTGATAG 250        260        270        280        290        300
            *          *          *          *          *          *
       AAACCTTCTA ACCTGAGCAG CAAGAAAATA AATAATAGGA ACGGTCACGG AGTAATAATT 310        320        330        340        350        360
            *          *          *          *          *          *
       AATGGTAGCA GAACCAGAAG AAGTCAGGAA GAGGGTGAAG TACCGCAGGA AGTAGAATTA 370        380        390        400        410
            *          *          *          *          *
       AAGTAGAAAA GGGGAGCCCT TAGCCCCCCT CTTTAGATAA GCAAGCTTA AAA AGC AAA
                                                            <Phe Ala Phe
                                                            <  a    a
```

```
    420            430            440            450            460
     *              *              *              *              *
 CCT AAC ACC AAA TTC CCC ACC GAC ATA AGC CAT GGA GAA GTT AGC AAT
<Arg Val Gly Phe Glu Gly Gly Val Tyr Ala Met Ser Phe Asn Ala Ile
<  a   a   a   a   a   a  PROTEIN a   a   a   a   a   a   a   a 470            480            490            500            510
            *              *              *              *              *
 AGC AGT ATC CTT AGT ACG ACC CGC CGG ACT AGT ATC ATC TAC AAG ACG
<Ala Thr Asp Lys Thr Arg Gly Ala Pro Ser Thr Asp Asp Val Leu Arg
<  a   a   a   a   a   a  PROTEIN a   a   a   a   a   a   a   a 520            530            540            550            560
            *              *              *              *              *
 TTG AGC CGG CAG ATC ATC ATA AAC GCC ATC TCC CAC AAC GCG ATG GTA
<Gln Ala Pro Leu Asp Asp Tyr Val Gly Asp Gly Val Val Arg His Tyr
<  a   a   a   a   a   a  PROTEIN a   a   a   a   a   a   a   a 570            580            590            600            610
            *              *              *              *              *
 GAA TCC ACC CGC AAA AGC GGA GAT TAC AGG AGA GAG CTG ATA ACT CAA
<Phe Gly Gly Ala Phe Ala Ser Ile Val Pro Ser Leu Gln Tyr Ser Leu
<  a   a   a   a   a   a  PROTEIN a   a   a   a   a   a   a   a 620            630            640            650
            *              *              *              *
 CCC AGC CTT TAA TCT ATA AGC AAG CTT AGG AGT GAT ATG GCC ATC AAC
<Gly Ala Lys Leu Arg Tyr Ala Leu Lys Pro Thr Ile His Gly Asp Val
<  a   a   a   a   a   a  PROTEIN a   a   a   a   a   a   a   a
```

FIG. 12A

```
       660             670           680            690            700
        *               *             *              *              *
     CAC GCC CAC GAA GTT ACC GCC AAG ACC AAC ACA AGC ATA AGG AAC AAC
    <Val Gly Val Phe Asn Gly Gly Leu Gly Val Cys Ala Tyr Pro Val Val
    <  a   a   a   a   a   a PROTEIN a   a   a   a   a   a 710             720           730            740            750
        *               *             *              *              *
     ACC TAA ACC TTC ACT AAG AAG ATC ATA ACA AGC ATT GAC CAT TAC GGA
    <Gly Leu Gly Glu Ser Leu Leu Asp Tyr Cys Ala Asn Val Met Val Ser
    <  a   a   a   a   a   a PROTEIN a   a   a   a   a   a 760             770           780            790            800
        *               *             *              *              *
     AGT AGA AGA AAC CGC CCT GAT CTC AAC AAC TTC ACC CCC TTC AAT AGT
    <Thr Ser Ser Val Ala Arg Ile Glu Val Val Glu Gly Gly Glu Ile Thr
    <  a   a   a   a   a   a PROTEIN a   a   a   a   a   a 810             820           830            840            850
        *               *             *              *              *
     CTT AGC TAG TAA CCC TGC TAC TAT GGT TTT TTC TTC AGG GGT TAG CTC
    <Lys Ala Leu Leu Gly Ala Val Ile Thr Lys Glu Glu Pro Thr Leu Glu
    <  a   a   a   a   a   a PROTEIN a   a   a   a   a   a 860             870           880            890
           *               *             *              *
     CTG TAC TAG GTC TTT AGC TAC GGC TTC GGC GTT ACC ATT CGT ATC GCC
    <Gln Val Leu Asp Lys Ala Val Ala Glu Ala Asn Gly Asn Thr Asp Gly
    <  a   a   a   a   a   a PROTEIN a   a   a   a   a   a 900             910           920            930            940
      *               *             *              *              *
     GAG CAC ATT AAC GTT GTC GCC ATC ATT AAC GTA CCC CGT TGG CCA ATT
    <Leu Val Asn Val Asn Asp Gly Asp Asn Val Tyr Gly Thr Pro Trp Asn
    <  a   a   a   a   a   a PROTEIN a   a   a   a   a   a 950             960           970            980            990
         *               *             *              *              *
     CTT ACC TTC TCC AAC CTT TGT TTT GTT AAC AAA CTC AGT CAA GCC CAA
    <Lys Gly Glu Gly Val Lys Thr Lys Asn Val Phe Glu Thr Leu Gly Leu
    <  a   a   a   a   a   a PROTEIN a   a   a   a   a   a 1000            1010          1020           1030           1040
         *               *             *              *              *
     TCC TCT CTT GCC GGC TTT GCC GGT TCC CAT ACC ACT ACA CTG AGC CGT
    <Gly Arg Lys Gly Ala Lys Gly Thr Gly Met Gly Ser Cys Gln Ala Thr
    <  a   a   a   a   a   a PROTEIN a   a   a   a   a   a 1050            1060          1070           1080           1090
          *               *             *              *              *
     CTT ATT CGT CTG TGA CGC GCC ACC ATC CGT ATA GTC GGC CAG CGA GCC
    <Lys Asn Thr Gln Ser Ala Gly Gly Asp Thr Tyr Asp Ala Leu Ser Gly
    <  a   a   a   a   a   a PROTEIN a   a   a   a   a   a 1100            1110          1120           1130
              *               *             *              *
     ATT ATC TCC ACT CTT TTT TCC CCG TGC ATG ACC CCC ATC ACA AAC CTT
    <Asn Asp Gly Ser Lys Lys Gly Arg Ala His Gly Gly Asp Cys Val Lys
    <  a   a   a   a   a   a PROTEIN a   a   a   a   a   a 1140           1150         1160           1170          1180
         *              *             *              *             *
```

FIG. 12B

```
        CTT ATC AAT ACC GGG ATG AGA AAC CCC AAC CGC CTT AGC AAA CTG AAC
       <Lys Asp Ile Gly Pro His Ser Val Gly Val Ala Lys Ala Phe Gln Val
       <   a   a   a   a   a   a  PROTEIN a   a   a   a   a   a 1190          1200          1210          1220          1230
             *             *             *             *             *
        AAT ATC TTT ACC AGA GGT CTT GGC AAG AGC AGC AGC AAG GTT ATC AGT
       <Ile Asp Lys Gly Ser Thr Lys Ala Leu Ala Ala Ala Leu Asn Asp Thr
       <   a   a   a   a   a   a  PROTEIN a   a   a   a   a   a 1240          1250          1260          1270          1280
             *             *             *             *             *
        CTG CCC AGT AAC AAC ATC ATA AGC TAA CTC CTT AGC TAG TAG ATA TAC
       <Gln Gly Thr Val Val Asp Tyr Ala Leu Glu Lys Ala Leu Leu Tyr Val
       <   a   a   a   a   a   a  PROTEIN a   a   a   a   a   a 1290          1300          1310          1320          1330
             *             *             *             *             *
        TGT ATC AGC TTC ATC TTC CTT ACT ACC ACT ATC TCT AAT ACC CTT GGT
       <Thr Asp Ala Glu Asp Glu Lys Ser Gly Ser Asp Arg Ile Gly Lys Thr
       <   a   a   a   a   a   a  PROTEIN a   a   a   a   a   a 1340          1350          1360          1370
             *             *             *             *
        CTT GAA GCG CTC GTA ACC AAT CTC AAG CTC AAC CCT GGC ACC ACC AAT
       <Lys Phe Arg Glu Tyr Gly Ile Glu Leu Glu Val Arg Ala Gly Gly Ile
       <   a   a   a   a   a   a  PROTEIN a   a   a   a   a   a 1380          1390          1400          1410          1420
       *             *             *             *             *
        ACC ATA ACC AAC ACT ACC TTC CAT AGC TAC AAG CAT GTT GTC CTT AAA
       <Gly Tyr Gly Val Ser Gly Glu Met Ala Val Leu Met Asn Asp Lys Phe
       <   a   a   a   a   a   a  PROTEIN a   a   a   a   a   a 1430          1440          1450          1460          1470
             *             *             *             *             *
        CCC AAT CCG AGG ATC AGG AGT GTT CCA GTC AAA CTT GTG TGA CTC TAG
       <Gly Ile Arg Pro Asp Pro Thr Asn Trp Asp Phe Lys His Ser Glu Leu
       <   a   a   a   a   a   a  PROTEIN a   a   a   a   a   a 1480          1490          1500          1510          1520
             *             *             *             *             *
        CTT TAC ACT CTT TCC ATC CTT TAA GTA TGG ATA TAC TGC CTT AGT CTC
       <Lys Val Ser Lys Gly Asp Lys Leu Tyr Pro Tyr Val Ala Lys Thr Glu
       <   a   a   a   a   a   a  PROTEIN a   a   a   a   a   a 1530          1540          1550          1560          1570
             *             *             *             *             *
        TCC GTT ACT CTC CCT TAT ACT AAA ATC TCT TAT CTT GCT AAA CGC TGG
       <Gly Asn Ser Glu Arg Ile Ser Phe Asp Arg Ile Lys Ser Phe Ala Pro
       <   a   a   a   a   a   a  PROTEIN a   a   a   a   a   a 1580          1590          1600          1610
             *             *             *             *
        ACT GTA ATC CAA GCC AAC ATA GAA ATA TCC CGC ACC ACC AGT CTC CAA
       <Ser Tyr Asp Leu Gly Val Tyr Phe Tyr Gly Ala Gly Gly Thr Glu Leu
       <   a   a   a   a   a   a  PROTEIN a   a   a   a   a   a 1620          1630          1640          1650          1660
       *             *             *             *             *
        AGC GCT AAC GTC ATC ATG AGC CCT GAC ATC ATT CCC AGC CAT GAC TAT
       <Ala Ser Val Asp Asp His Ala Arg Val Asp Asn Gly Ala Met Val Ile
```

FIG. 12C

```
       <    a    a    a    a    a    a    PROTEIN a    a    a    a    a    a 1670           1680           1690           1700           1710
             *              *              *              *              *
       AGC CAT CGA CAT CAT TAC GCT TCC TAA GAT TAT CTT TCC TTT TCT CAT
       <Ala Met Ser Met Met Val Ser Gly Leu Ile Ile Lys Gly Lys Arg Met
       <    a    a    a    a    a    PROTEIN a    a    a    a    a 1720           1730           1740           1750           1760           1770
             *              *              *              *              *              *
       ACTTTT CAACTTCTCC AAATTCCTTC TTTTTCTTCG TCTCCTCACT TCAGCCGGTC 1780           1790           1800           1810           1820           1830
             *              *              *              *              *              *
       CACTCAAGGG CTAACCCCCT CTAACATCTC CAGCCAGGAA TTCGATATCA AGCTTATCGA

1840
             *
       TACCGTCGAC CTC
```

FIG. 12D

Sequence Range: 1 to 3435

```
              10         20         30         40         50         60
               *          *          *          *          *          *
      TTTTTATATC TGGAGCTCTT GTACTGTGTT TACCACGGGA TTTATTATTG GGTAGGCTTG 70         80         90        100        110        120
               *          *          *          *          *          *
      ATATTCAGGC TCTATCAACG CAGCTATTCA TGGCATTATT ACAGATAAAT TTGGCATTTT 130        140        150        160        170        180
               *          *          *          *          *          *
      GGAGATAGGC GATCTAGGGT TCTATTATTA GGAATCTATT ATTTAGATAT ATAGGGATAT 190        200        210        220        230        240
               *          *          *          *          *          *
      AAGGGAGAGT AACGGAGAGA CTAAGGCAGT ATATCCATAC TTAAAGGATG GAAAGAGTGT 250        260        270        280        290        300
               *          *          *          *          *          *
      AAAGCTAGAG TCACACAAGT TTGACTGGAA CACTCCTGAT CCTCGGATTG GGTTTAAGGA 310          320          330          340
                 *            *            *            *
       CAAC ATG CTT GTA GCT ATG GAA GGC AGT GTT GGT TAT GGT ATT GGT GGT
            Met Leu Val Ala Met Glu Gly Ser Val Gly Tyr Gly Ile Gly Gly>
             a   a   a   a   a   a ORF 1  a   a   a   a   a   a   >

350          360          370          380          390
         *            *            *            *            *
       GCC AGG GTT GAG CTT GAG ATT GGT TAC GAG CGC TTC AAG ACC AAG GGT
       Ala Arg Val Glu Leu Glu Ile Gly Tyr Glu Arg Phe Lys Thr Lys Gly>
        a   a   a   a   a   a ORF 1  a   a   a   a   a   a   a   >

400          410          420          430          440
               *            *            *            *            *
       ATT AGA GAT AGT GGT AGT AAG GAA GAT GAA GCA GAT ACA GTA TAT CTA
       Ile Arg Asp Ser Gly Ser Lys Glu Asp Glu Ala Asp Thr Val Tyr Leu>
        a   a   a   a   a   a ORF 1  a   a   a   a   a   a   a   >

450          460          470          480          490
               *            *            *            *            *
       CTA GCT AAG GAG TTA GCT TAT GAT GTT GTT ACT GGA CAG ACT GAT AAC
       Leu Ala Lys Glu Leu Ala Tyr Asp Val Val Thr Gly Gln Thr Asp Asn>
        a   a   a   a   a   a ORF 1  a   a   a   a   a   a   a   >

500          510          520          530          540
               *            *            *            *            *
       CTT GCC GCT GCT CTT GCC AAA ACC TCG GGG AAG GAC ATC GTT CAG TTT
       Leu Ala Ala Ala Leu Ala Lys Thr Ser Gly Lys Asp Ile Val Gln Phe>
        a   a   a   a   a   a ORF 1  a   a   a   a   a   a   a   >

550          560          570          580
               *            *            *            *
       GCC AAT GCT GTG AAA ATT TCT TAC CCT AAA ATT GAT GAG CAG GTT TGT
       Ala Asn Ala Val Lys Ile Ser Tyr Pro Lys Ile Asp Glu Gln Val Cys>
        a   a   a   a   a   a ORF 1  a   a   a   a   a   a   a   >

590          600          610          620          630
         *            *            *            *            *
       AAT AAA AAT CAT ACA GTG TTG AAT ACG GGG AAA GGG ACA ACC TTT AAT
       Asn Lys Asn His Thr Val Leu Asn Thr Gly Lys Gly Thr Thr Phe Asn>
```

FIG. 14A

```
              a   a   a   a   a   a   ORF 1 a   a   a   a   a   a   >
        640             650             660             670             680
         *               *               *               *               *
        CCA GAT CCC AAG ACA ACC GAA GAT AAT ACA GCG CAG TGC AGT GGG TTG
        Pro Asp Pro Lys Thr Thr Glu Asp Asn Thr Ala Gln Cys Ser Gly Leu>
          a   a   a   a   a   a   ORF 1 a   a   a   a   a   a   >

690             700             710             720             730
                 *               *               *               *               *
        AAC ACG AAG GGA ACG AAT AAG TTT AGC GAT TTT GCT GAA GGT GTA GGT
        Asn Thr Lys Gly Thr Asn Lys Phe Ser Asp Phe Ala Glu Gly Val Gly>
          a   a   a   a   a   a   ORF 1 a   a   a   a   a   a   >

740             750             760             770             780
                 *               *               *               *               *
        TTG AAA GAT AAT AAG AAT TGG CCT ACT GGT CAG GCT GGG AAG AGC AGT
        Leu Lys Asp Asn Lys Asn Trp Pro Thr Gly Gln Ala Gly Lys Ser Ser>
          a   a   a   a   a   a   ORF 1 a   a   a   a   a   a   >

790             800             810             820
                 *               *               *               *
        GGT GGT CCT GTG GTG GGT GCA TCT AAT AGT AAT GCC AAC GCT ATG GCT
        Gly Gly Pro Val Val Gly Ala Ser Asn Ser Asn Ala Asn Ala Met Ala>
          a   a   a   a   a   a   ORF 1 a   a   a   a   a   a   >

830             840             850             860             870
         *               *               *               *               *
        AGA GAC CTA GTA GAT CTT AAT CGA GAC GAA AAA ACC ATA GTA GCA GGG
        Arg Asp Leu Val Asp Leu Asn Arg Asp Glu Lys Thr Ile Val Ala Gly>
          a   a   a   a   a   a   ORF 1 a   a   a   a   a   a   >

880             890             900             910             920
         *               *               *               *               *
        TTA CTA GCT AAA ACT ATT GAA GGT GGT GAG GTT GTT GAG ATT AGG GCG
        Leu Leu Ala Lys Thr Ile Glu Gly Gly Glu Val Val Glu Ile Arg Ala>
          a   a   a   a   a   a   ORF 1 a   a   a   a   a   a   >

930             940             950             960             970
         *               *               *               *               *
        GTT TCT TCT ACT TCT GTA ATG GTC AAT GCT TGT TAT GAT CTT CTT AGT
        Val Ser Ser Thr Ser Val Met Val Asn Ala Cys Tyr Asp Leu Leu Ser>
          a   a   a   a   a   a   ORF 1 a   a   a   a   a   a   >

980             990             1000            1010            1020
                 *               *               *               *               *
        GAA GGT CTA GGC GTT GTT CCT TAC GCT TGT GTC GGT CTT GGA GGT AAC
        Glu Gly Leu Gly Val Val Pro Tyr Ala Cys Val Gly Leu Gly Gly Asn>
          a   a   a   a   a   a   ORF 1 a   a   a   a   a   a   >

1030            1040            1050            1060
                 *               *               *               *
        TTC GTG GGC GTT GTT GAT GGG CAT ATC ACT CCT AAG CTT GCT TAT AGA
        Phe Val Gly Val Val Asp Gly His Ile Thr Pro Lys Leu Ala Tyr Arg>
          a   a   a   a   a   a   ORF 1 a   a   a   a   a   a   >

1070            1080            1090            1100            1110
         *               *               *               *               *
        TTA AAG GCT GGG TTG AGT TAT CAG CTC TCT CCT GAA ATC TCC GCT TTT
        Leu Lys Ala Gly Leu Ser Tyr Gln Leu Ser Pro Glu Ile Ser Ala Phe>
          a   a   a   a   a   a   ORF 1 a   a   a   a   a   a   >
```

FIG. 14B

```
       1120           1130           1140           1150           1160
         *              *              *              *              *
   GCT GGG GGA TTC TAT CAT CGC GTT GTG GGA GAT GGT GTC TAT GAT GAT
   Ala Gly Gly Phe Tyr His Arg Val Val Gly Asp Gly Val Tyr Asp Asp>
    a   a   a   a   a   a  ORF 1  a   a   a   a   a   a   a   >

1170           1180           1190           1200           1210
         *              *              *              *              *
   CTT CCA GCT CAA CGT CTT GTA GAT GAT ACT AGT CCG GCG GGT CGT ACT
   Leu Pro Ala Gln Arg Leu Val Asp Asp Thr Ser Pro Ala Gly Arg Thr>
    a   a   a   a   a   a  ORF 1  a   a   a   a   a   a   a   >

1220           1230           1240           1250           1260
         *              *              *              *              *
   AAG GAT ACT GCT ATT GCT AAC TTC TCC ATG GCT TAT GTC GGT GGG GAA
   Lys Asp Thr Ala Ile Ala Asn Phe Ser Met Ala Tyr Val Gly Gly Glu>
    a   a   a   a   a   a  ORF 1  a   a   a   a   a   a   a   >

1270           1280           1290           1300           1310
         *              *              *              *              *
   TTT GGT GTT AGG TTT GCT TTT TAAGGTGG TTTGTTGGAA GCGGGGTAAG
   Phe Gly Val Arg Phe Ala Phe>
    a   a  ORF 1  a   a   >

1320           1330           1340           1350           1360
         *              *              *              *              *
   TCAAACTTAC CCCGCTTCTA TTAGGGAGTT AGTAT ATG AGA TCT AGA AGT AAG CTA
                                          Met Arg Ser Arg Ser Lys Leu>
                                           b   b  ORF 2  b   b   >

1370           1380           1390           1400           1410
         *              *              *              *              *
   TTT TTA GGA AGC GTA ATG ATG TCG TTG GCT ATA GTC ATG GCT GGG AAT
   Phe Leu Gly Ser Val Met Met Ser Leu Ala Ile Val Met Ala Gly Asn>
    b   b   b   b   b   b  ORF 2  b   b   b   b   b   b   b   >

1420           1430           1440           1450           1460
         *              *              *              *              *
   GAT GTC AGG GCT CAT GAT GAC GTT AGC GCT TTG GAT ACT GGT GGT GCG
   Asp Val Arg Ala His Asp Asp Val Ser Ala Leu Asp Thr Gly Gly Ala>
    b   b   b   b   b   b  ORF 2  b   b   b   b   b   b   b   >

1470           1480           1490           1500           1510
         *              *              *              *              *
   GGA TAT TTC TAT GTT GGT TTG GAT TAC AGT CCA GCG TTT AGC AAG ATA
   Gly Tyr Phe Tyr Val Gly Leu Asp Tyr Ser Pro Ala Phe Ser Lys Ile>
    b   b   b   b   b   b  ORF 2  b   b   b   b   b   b   b   >

1520           1530           1540           1550
         *              *              *              *
   AGA GAT TTT AGT ATA AGG GAG AGT AAC GGA GAG ACT AAG GCA GTA TAT
   Arg Asp Phe Ser Ile Arg Glu Ser Asn Gly Glu Thr Lys Ala Val Tyr>
    b   b   b   b   b   b  ORF 2  b   b   b   b   b   b   b   >

1560           1570           1580           1590           1600
    *              *              *              *              *
   CCA TAC TTA AAG GAT GGA AAG AGT GTA AAG CTA GAG TCA CAC AAG TTT
   Pro Tyr Leu Lys Asp Gly Lys Ser Val Lys Leu Glu Ser His Lys Phe>
    b   b   b   b   b   b  ORF 2  b   b   b   b   b   b   b   >

```
       GAC TGG AAC ACT CCT GAT CCT CGG ATT GGG TTT AAG GAC AAC ATG CTT
       Asp Trp Asn Thr Pro Asp Pro Arg Ile Gly Phe Lys Asp Asn Met Leu>
        b   b   b   b   b   b  ORF 2  b   b   b   b   b   b   b    >

1660        1670        1680        1690        1700
            *           *           *           *           *
       GTA GCT ATG GAA GGT AGT GTT GGT TAT GGT ATT GGT GGT GCC AGG GTT
       Val Ala Met Glu Gly Ser Val Gly Tyr Gly Ile Gly Gly Ala Arg Val>
        b   b   b   b   b   b  ORF 2  b   b   b   b   b   b   b    >

1710        1720        1730        1740        1750
            *           *           *           *           *
       GAG CTT GAG ATT GGT TAC GAG CGC TTC AAG ACC AAG GGT ATT AGA GAT
       Glu Leu Glu Ile Gly Tyr Glu Arg Phe Lys Thr Lys Gly Ile Arg Asp>
        b   b   b   b   b   b  ORF 2  b   b   b   b   b   b   b    >

1760        1770        1780        1790
            *           *           *           *
       AGT GGT AGT AAG GAA GAT GAA GCT GAT ACA GTA TAT CTA CTA GCT AAG
       Ser Gly Ser Lys Glu Asp Glu Ala Asp Thr Val Tyr Leu Leu Ala Lys>
        b   b   b   b   b   b  ORF 2  b   b   b   b   b   b   b    >

1800        1810        1820        1830        1840
   *           *           *           *           *
       GAG TTA GCT TAT GAT GTT GTT ACT GGG CAG ACT GAT AAC CTT GCC GCT
       Glu Leu Ala Tyr Asp Val Val Thr Gly Gln Thr Asp Asn Leu Ala Ala>
        b   b   b   b   b   b  ORF 2  b   b   b   b   b   b   b    >

1850        1860        1870        1880        1890
            *           *           *           *           *
       GCT CTG GCC AAA ACC TCC GGT AAA GAC TTT GTC CAG TTT GCT AAG GCG
       Ala Leu Ala Lys Thr Ser Gly Lys Asp Phe Val Gln Phe Ala Lys Ala>
        b   b   b   b   b   b  ORF 2  b   b   b   b   b   b   b    >

1900        1910        1920        1930        1940
            *           *           *           *           *
       GTT GGG GTT TCT CAT CCT AGT ATT GAT GGG AAG GTT TGT AAG ACG AAG
       Val Gly Val Ser His Pro Ser Ile Asp Gly Lys Val Cys Lys Thr Lys>
        b   b   b   b   b   b  ORF 2  b   b   b   b   b   b   b    >
                             <Gly Leu Ile Ser Pro Phe Thr Gln Leu Val Phe
                             < d   d   d   d   d ORF 4  d   d   d   d 1950        1960        1970        1980        1990
            *           *           *           *           *
       GCG GAT AGC TCG AAG AAA TTT CCG TTA TAT AGT GAC GAA ACG CAC ACG
       Ala Asp Ser Ser Lys Lys Phe Pro Leu Tyr Ser Asp Glu Thr His Thr>
        b   b   b   b   b   b  ORF 2  b   b   b   b   b   b   b    >
       <Ala Ser Leu Glu Phe Phe Asn Gly Asn Tyr Leu Ser Ser Val Cys Val
       <  d   d   d   d   d   d  ORF 4  d   d   d   d   d   d   d 2000        2010        2020        2030
            *           *           *           *
       AAG GGG GCA AGT GAG GGG AGA ACG TCT TTG TGC GGT GAC AAT GGT AGT
       Lys Gly Ala Ser Glu Gly Arg Thr Ser Leu Cys Gly Asp Asn Gly Ser>
        b   b   b   b   b   b  ORF 2  b   b   b   b   b   b   b    >
       <Phe Pro Ala Leu Ser Pro Leu Val Asp Lys His Pro Ser Leu Pro Leu
       <  d   d   d   d   d   d  ORF 4  d   d   d   d   d   d   d 2040        2050        2060        2070        2080
   *           *           *           *           *
       TCT ACG ATA ACA AAC AGT GGT GCG AAT GTA AGT GAA ACT GGG CAG GTT
       Ser Thr Ile Thr Asn Ser Gly Ala Asn Val Ser Glu Thr Gly Gln Val>
```

FIG. 14D

```
          b   b   b   b   b   b   ORF 2   b   b   b   b   b   b   b   >
    <Glu Val Ile Val Phe Leu Pro Ala Phe Thr Leu Ser Val Pro Cys Thr
     <   d   d   d   d   d   d   ORF 4   d   d   d   d   d   d   d 2090        2100        2110        2120        2130
             *           *           *           *           *
         TTT AGG GAT TTT ATC AGG GCA ACG CTG AAA GAG GAT GGT AGT AAA AAC
         Phe Arg Asp Phe Ile Arg Ala Thr Leu Lys Glu Asp Gly Ser Lys Asn>
          b   b   b   b   b   b   ORF 2   b   b   b   b   b   b   b   >
    <Lys Leu Ser Lys Ile Leu Ala Val Ser Phe Ser Ser Pro Leu Leu Phe
     <   d   d   d   d   d   d   ORF 4   d   d   d   d   d   d   d 2140        2150        2160        2170        2180
             *           *           *           *           *
         TGG CCA ACT TCA AGC GGC ACG GGA ACT CCA AAA CCT GTC ACG AAC GAC
         Trp Pro Thr Ser Ser Gly Thr Gly Thr Pro Lys Pro Val Thr Asn Asp>
          b   b   b   b   b   b   ORF 2   b   b   b   b   b   b   b   >
    <Gln Gly Val Glu Leu Pro Val Pro Val Gly Phe Gly Thr Val Phe Ser
     <   d   d   d   d   d   d   ORF 4   d   d   d   d   d   d   d 2190        2200        2210        2220        2230
             *           *           *           *           *
         AAC GCC AAA GCC GTA GCT AAA GAC CTA GTA CAG GAG CTA ACC CCT GAA
         Asn Ala Lys Ala Val Ala Lys Asp Leu Val Gln Glu Leu Thr Pro Glu>
          b   b   b   b   b   b   ORF 2   b   b   b   b   b   b   b   >
    <Leu Ala Leu Ala Thr Ala Leu Ser Arg Thr Cys Ser Ser Val Gly Ser
     <   d   d   d   d   d   d   ORF 4   d   d   d   d   d   d   d 2240        2250        2260        2270
             *           *           *           *
         GAA AAA ACC ATA GTA GCA GGG TTA CTA GCT AAA ACT ATT GAA GGT GGT
         Glu Lys Thr Ile Val Ala Gly Leu Leu Ala Lys Thr Ile Glu Gly Gly>
          b   b   b   b   b   b   ORF 2   b   b   b   b   b   b   b   >
    <Ser Phe Val Met
     <   d   d   d 2280        2290        2300        2310        2320
      *           *           *           *           *
    GAG GTT ATT GAA ATC AGG GCG GTT TCT TCT ACT TCT GTG ATG GTC AAT
    Glu Val Ile Glu Ile Arg Ala Val Ser Ser Thr Ser Val Met Val Asn>
     b   b   b   b   b   b   ORF 2   b   b   b   b   b   b   b   >

2330        2340        2350        2360        2370
          *           *           *           *           *
        GCT TGT TAT GAT CTT CTT AGT GAA GGT TTA GGT GTT GTC CCT TAT GCT
        Ala Cys Tyr Asp Leu Leu Ser Glu Gly Leu Gly Val Val Pro Tyr Ala>
         b   b   b   b   b   b   ORF 2   b   b   b   b   b   b   b   >

2380        2390        2400        2410        2420
              *           *           *           *           *
            TGT GTT GGT CTC GGT GGT AAC TTC GTG GGC GTG GTT GAT GGA ATT CAT
            Cys Val Gly Leu Gly Gly Asn Phe Val Gly Val Val Asp Gly Ile His>
             b   b   b   b   b   b   ORF 2   b   b   b   b   b   b   b   >

2430        2440        2450        2460        2470
                  *           *           *           *           *
                TAC ACA AAC CAT CTT TAA CTCTGAATAC CCTAGTTAAG GTAAGTGAAG
                Tyr Thr Asn His Leu>
                 b  ORF 2      b         >

```
          TAACTAGGCA AATTAGTGCT GCACCACTCG TGAAACAAAC TACGATCAGC GATTCACCAT
              2540       2550       2560       2570       2580       2590
               *          *          *          *          *          *
          ACTTAGTAAG TCCGTACAGT GGCTTTACGC TCTTACCCAT CATGAAAAAT ACTTGCTATC
              2600       2610       2620       2630       2640       2650
               *          *          *          *          *          *
          TAGGAATCTC CTCTAAAACT TTACAGAGGT TATCTGTACT TCGAGAGGAA GCTAATCTGT
              2660       2670       2680       2690       2700       2710
               *          *          *          *          *          *
          GGCTCATGAG GATGGTATTT AGCGTATCAC AGGTTCCAGC TGTCTTACAG TCTCTGGAGA
              2720       2730       2740       2750       2760       2770
               *          *          *          *          *          *
          TGTTATAAGG GTGCACATAT AAAACTATGC AATATTTCGC TGCAATACGA TTCCGATTCG
              2780       2790       2800       2810       2820       2830
               *          *          *          *          *          *
          AAAACACTGA AAAGTATTCC CATTATCTAT GAATCTCTGT GTAGATATAA ATAAGGGTAT
              2840       2850       2860       2870       2880       2890
               *          *          *          *          *          *
          ACGCAGTAAC TCTTACTTGT TAAAAACAAG ACCAATGGTA TAAGGAAAAA GCCTCAGTGT
              2900       2910       2920       2930       2940       2950
               *          *          *          *          *          *
          TGTTCCTCAT GCTTGCAGCT TACCCGATGC ACTCTTATTT AATAAGGTTG AATGTTAATC
              2960       2970       2980       2990       3000       3010
               *          *          *          *          *          *
          AGTGTTTCTG GGAAGGGAAT ATCTTATTGC AAAAACCTCA GCAGCTGCTT AGATATTGAA
              3020       3030       3040       3050       3060       3070
               *          *          *          *          *          *
          ACAAATGCGA TCATGCCGTC AGCACAATTA TGACATCTCT TAAGGCTCTG TAGTGCGCTT
              3080       3090       3100       3110       3120       3130
               *          *          *          *          *          *
          ATTTAGTCTA ACATGTGGTA AAGCTTGCC AGTTCTTTAC CACATGTTCA CCATCAGTTA
                         3140       3150       3160       3170
                          *          *          *          *
          ATT GAA AGC AAA TCT TGC TCC TAT GTT GAA GCC GTA ACT AGC TAT ATT
          <Asn Phe Ala Phe Arg Ala Gly Ile Asn Phe Gly Tyr Ser Ala Ile Asn
          <   c   c   c   c   c   c   ORF 3 c   c   c   c   c   c   c
          3180        3190         3200        3210        3220
            *           *            *           *           *
          TGC CTT TAC CTT GGC TGC AGC ACC ACC TGC TAT GTT TAC ACG GTT ACT
          <Ala Lys Val Lys Ala Ala Ala Gly Gly Ala Ile Asn Val Arg Asn Ser
          <   c   c   c   c   c   c   ORF 3 c   c   c   c   c   c   c
          3230        3240         3250        3260        3270
            *           *            *           *           *
          AGC GGG AAT ACC TGC ATA CTG TTC ATC GAA AAT TCC GTG GTA AAA ACC
          <Ala Pro Ile Gly Ala Tyr Gln Glu Asp Phe Ile Gly His Tyr Phe Gly
          <   c   c   c   c   c   c   ORF 3 c   c   c   c   c   c   c
          3280        3290         3300        3310        3320
            *           *            *           *           *
```

FIG. 14F

```
     TCC AGC TAT TAA AGA TAT TTC AGG AGT AAG CTT GTA ACT TAC GCC TAC
    <Gly Ala Ile Leu Ser Ile Glu Pro Thr Leu Lys Tyr Ser Val Gly Val
    <   c   c   c   c   c   c   ORF 3 c   c   c   c   c   c   c 3330            3340            3350            3360            3370
            *               *               *               *               *
     CTT TCC TCT ATA AGC CAA CTT ACT TGT AAC GTG ATC GGC GAT ATT AAT
    <Lys Gly Arg Tyr Ala Leu Lys Ser Thr Val His Asp Ala Ile Asn Ile
    <   c   c   c   c   c   c   ORF 3 c   c   c   c   c   c   c 3380            3390            3400            3410
            *               *               *               *
     AAA GCT CGC CCC TAA CCC AGC ACA CAT GTA AGG AGG GAA TTC GAT ATC
    <Phe Ser Ala Gly Leu Gly Ala Cys Met Tyr Pro Pro Phe Glu Ile Asp
    <   c   c   c   c   c   c   ORF 3 c   c   c   c   c   c   c 3420            3430
      *               *
     AAG CTT ATC GAT ACC GT
    <Leu Lys Asp Ile Gly
    <   c   ORF 3      c
```

FIG. 14G

Sequence Range: 1 to 2900

```
              10         20         30         40         50         60
               *          *          *          *          *          *
         CTCCACCGCG GTGGCGGCCG CTCTAGAACT AGTGGATCCC CCGGGCTGCA GGAATTCCGG 70         80         90        100        110
               *          *          *          *          *
         AATTCCGGAA TTC GGC CCT CCG GAC AGT ATA AAA GCT GCT ATT TTT TTC CCT
                     Gly Pro Pro Asp Ser Ile Lys Ala Ala Ile Phe Phe Pro>
                      a   a   a   a   a  ORF 1  a   a   a   a   a    >

120        130        140        150        160
              *          *          *          *          *
         TGC GCA AGT AAA GCA GGG AAG TCA GTA TCT ACA GAA AAA ACC TCA CTA
         Cys Ala Ser Lys Ala Gly Lys Ser Val Ser Thr Glu Lys Thr Ser Leu>
          a   a   a   a   a   a  ORF 1  a   a   a   a   a   a   a    >

170        180        190        200
              *          *          *          *
         TAC ACT CCA AGT TCT CTT ACT CTG CGT GCA ATC AGC TGG GTA ACC TGT
         Tyr Thr Pro Ser Ser Leu Thr Leu Arg Ala Ile Ser Trp Val Thr Cys>
          a   a   a   a   a   a  ORF 1  a   a   a   a   a   a   a    >

210        220        230        240        250
     *          *          *          *          *
   GAA CCA AAG TCA ATT ATG GCA ATC GTT AAC ACT TAC TAC TCC AAT ATA
   Glu Pro Lys Ser Ile Met Ala Ile Val Asn Thr Tyr Tyr Ser Asn Ile>
    a   a   a   a   a   a  ORF 1  a   a   a   a   a   a   a    >

260        270        280        290        300        310
              *          *          *          *          *          *
         CTC ACA CAC ATT GTA AGA CAT TAG TGCTCAGTGG ACAATGCACA TACACAGGGA
         Leu Thr His Ile Val Arg His>
          a   a  ORF 1  a   a       >

320        330        340        350        360        370
              *          *          *          *          *          *
         AGAGCAACGC TTATTGTTCA AAAGGAGAAG TAATCTCCCT CTTAGTATAG GGAAGAGGCT 380        390        400        410        420        430
              *          *          *          *          *          *
         ACCACGGAAG ATACAGGGTA TGTCACCTTG AGTGTTACCA CACTTAGACG CAAGCGAAGC
                                                                -
             440        450        460        470        480        490
              *          *          *          *          *          *
         ATGCAATAGC ATTTGGTGTA TTGATAGTAT AAATATTAAA ATTTTCTTTT TTTACTACTT 500        510        520        530        540        550
              *          *          *          *          *          *
         TACGTAGAGT GCGCCTATAG GGAATACCAC TTTCATTAGT TCTGTCATCA ATTTACTAAA 560        570        580        590        600        610
              *          *          *          *          *          *
         GTTATAAATT TATTAATGAA TTTCCCATAA CCTCGGTAGT GACAATATTT TGGTGAATGG 620        630        640        650
                     *          *          *          *
         T ATG AAA ACT GAA CCG CAA AGC CAC AAT TCT ACA ACA GTA AAT GAT ACT
           Met Lys Thr Glu Pro Gln Ser His Asn Ser Thr Thr Val Asn Asp Thr>
            b   b   b   b   b   b  ORF 2  b   b   b   b   b   b   b    >
```

FIG.16A

```
     660         670         680            690         700
      *           *           *              *           *
ACT TCT TCA TCT AGA ACA AGG AGT GAC GTT ATG AAA GGA AAG TCA GAT
Thr Ser Ser Ser Arg Thr Arg Ser Asp Val Met Lys Gly Lys Ser Asp>
 b   b   b   b   b   b  ORF 2  b   b   b   b   b   b   b   >

710         720         730            740         750
      *           *           *              *           *
TCT GAA ATA CGT ACG TCT TCT TCA ATA CGT ACA TCT TCT TCA GAC GAT
Ser Glu Ile Arg Thr Ser Ser Ser Ile Arg Thr Ser Ser Ser Asp Asp>
 b   b   b   b   b   b  ORF 2  b   b   b   b   b   b   b   >

760         770         780            790         800
      *           *           *              *           *
AGC AGG AGT TCG GAT GAC AGC ACA CGT ATT CGT GCT TCT AAA ACT CAT
Ser Arg Ser Ser Asp Asp Ser Thr Arg Ile Arg Ala Ser Lys Thr His>
 b   b   b   b   b   b  ORF 2  b   b   b   b   b   b   b   >

810         820         830            840         850
      *           *           *              *           *
CCT CAA GCA CCT AGC GAC AAC AGC AGC ATA CTC TCA TCT GAG GAT ATT
Pro Gln Ala Pro Ser Asp Asn Ser Ser Ile Leu Ser Ser Glu Asp Ile>
 b   b   b   b   b   b  ORF 2  b   b   b   b   b   b   b   >

860         870         880            890
      *           *           *              *
GAG AGC GTA ATG CGG TGC CTA GAA GAG GAA TAT GGC CAA AAG CTT AGC
Glu Ser Val Met Arg Cys Leu Glu Glu Glu Tyr Gly Gln Lys Leu Ser>
 b   b   b   b   b   b  ORF 2  b   b   b   b   b   b   b   >

900         910         920            930         940
  *           *           *              *           *
AGT GAG CTT AAG AAA TCA ATG CGT GAA GAA ATT TCT ACA GCT GTG CCA
Ser Glu Leu Lys Lys Ser Met Arg Glu Glu Ile Ser Thr Ala Val Pro>
 b   b   b   b   b   b  ORF 2  b   b   b   b   b   b   b   >

950         960         970            980         990
      *           *           *              *           *
GAA TTG ACA AGA GCG CTT ATA CCA TTA TTA GCA TCT GCT AGT GAT AGT
Glu Leu Thr Arg Ala Leu Ile Pro Leu Leu Ala Ser Ala Ser Asp Ser>
 b   b   b   b   b   b  ORF 2  b   b   b   b   b   b   b   >

1000        1010        1020           1030        1040
      *           *           *              *           *
GAT TCA AGC TCT AGA AAG CTG CAA GAA GAA TGG GTG AAA ACA TTC ATG
Asp Ser Ser Ser Arg Lys Leu Gln Glu Glu Trp Val Lys Thr Phe Met>
 -   b   b   b   b   b  ORF 2  b   b   b   b   b   b   b   >

1050        1060        1070           1080        1090
      *           *           *              *           *
GCT ATT ATG TTG CCG CAT ATG CAG AAA ATT GTG GCA TCG ACC CAA GGT
Ala Ile Met Leu Pro His Met Gln Lys Ile Val Ala Ser Thr Gln Gly>
 b   b   b   b   b   b  ORF 2  b   b   b   b   b   b   b   >

1100        1110        1120           1130        1140        1150
      *           *           *              *           *           *
TAGGTTTAG CCCAGGAGAC TGCTGCAGTT CAAGCACAGC GCCTAACCGG CAGCAGGTGC 1160        1170        1180           1190        1200        1210
      *           *           *              *           *           *
TGCATGCACA GTCAGTAAAT GTTGTTTGAT AGATGCCTGG AGCAGATCTA GTAGCATCGC
```

FIG.16B

```
      1220       1230       1240       1250       1260       1270
        *          *          *          *          *          *
CCCAGGCATC TCTCCCATTC CAAGCTCGCA ATTCTCTTCA GATTCTTTTT TCCACAAAGG 1280       1290       1300       1310       1320       1330
        *          *          *          *          *          *
ATATCTATAT ATTAGTCAGC TGCTTCTCGT TTTAGTGTGT GTGTAGAGCG GTGCTAAATC 1340       1350       1360       1370       1380       1390
        *          *          *          *          *          *
TCCTAATCTC CCATAGGTAG TAGCACCGTA CCTTTACCGA TATGCAAGTG TGTGCTGCGA 1400       1410       1420       1430       1440       1450
        *          *          *          *          *          *
GCGCTACCAT AGGCATATCG GTGGAGGTCT AACAAAACAA GGCGTATATC AAGTGCGTTT 1460       1470       1480       1490       1500       1510
        *          *          *          *          *          *
ATTACATAGA TCACGTCTGT ATTGATAGTG AGCGTGCACA CACAGTTCTA TCATTAGGTT 1520       1530       1540       1550       1560       1570
        *          *          *          *          *          *
GACACAGCTT TCATGTAGCG TCATAAACGT CGCATTTTAC TATGAAGTAG CTTATTTTAA 1580       1590       1600       1610       1620       1630
        *          *          *          *          *          *
CCATTCAAGT ATGTACTTTG TGCAAGAGAT TCTCCATTGG CATCACAGGA TTCGCTCTGT 1640       1650       1660       1670       1680       1690
        *          *          *          *          *          *
AAGTCTTGTG AGTACATTAC CATTGATTCC AGATTTTAAA TCTGTGCTTC CTTCCATACG 1700       1710       1720       1730       1740       1750
        *          *          *          *          *          *
TTCAGTGCCT TTGTAGCCTT ATAGGCAGGT ACTGGGTTTG TATCTATGGC TCGTGTATTT 1760       1770       1780       1790       1800       1810
        *          *          *          *          *          *
ACATTGAGTT TTGTAATCAG GTACAGGTTT TTATATCTGG AGCTCTTGTA CTGTGTTTAC 1820       1830       1840       1850       1860       1870
        *          *          *          *          *          *
CACGGGATTT ATTATTGGGT AGGCTTGATA TTCAGGCTCT ATCAACGCAG CTATTCATGG 1880       1890       1900       1910       1920       1930
        *          *          *          *          *          *
CATTATTACA GATAAATTTG GCATTTTGGA GATAGGCGAT CTAGGGTTCT ATTATTAGGA 1940       1950       1960       1970       1980       1990
        *          *          *          *          *          *
ATCTATTATT TAGATATATA GGGATATAAG GGAGAGTAAC GGAGAGACTA AGGCAGTATA 2000       2010       2020       2030       2040       2050
        *          *          *          *          *          *
TCCATACTTA AAGGATGGAA AGAGTGTAAA GCTAGAGTCA CACAAGTTTG ACTGGAACAC 2060       2070       2080       2090       2100
        *          *          *          *          *
TCCTGATCCT CGGATTGGGT TTAAGGACAA C ATG CTT GTA GCT ATG GAA GGC AGT
                                  Met Leu Val Ala Met Glu Gly Ser>
                                   c   c  ORF 3   c   c   c   >
```

FIG.16E

```
             2110         2120         2130         2140         2150
               *            *            *            *            *
        GTT GGT TAT GGT ATT GGT GGT GCC AGG GTT GAG CTT GAG ATT GGT TAC
        Val Gly Tyr Gly Ile Gly Gly Ala Arg Val Glu Leu Glu Ile Gly Tyr>
         c   c   c   c   c   c  ORF 3  c   c   c   c   c   c   c   >

2160         2170         2180         2190         2200
               *            *            *            *            *
        GAG CGC TTC AAG ACC AAG GGT ATT AGA GAT AGT GGT AGT AAG GAA GAT
        Glu Arg Phe Lys Thr Lys Gly Ile Arg Asp Ser Gly Ser Lys Glu Asp>
         c   c   c   c   c   c  ORF 3  c   c   c   c   c   c   c   >

2210         2220         2230         2240
               *            *            *            *
        GAA GCT GAT ACA GTA TAT CTA CTA GCT AAG GAG TTA GCT TAT GAT GTT
        Glu Ala Asp Thr Val Tyr Leu Leu Ala Lys Glu Leu Ala Tyr Asp Val>
         c   c   c   c   c   c  ORF 3  c   c   c   c   c   c   c   >

2250         2260         2270         2280         2290
     *            *            *            *            *
  GTT ACT GGG CAG ACT GAT AAC CTT GCC GCT GCT CTG GCC AAA ACC TCC
  Val Thr Gly Gln Thr Asp Asn Leu Ala Ala Ala Leu Ala Lys Thr Ser>
   c   c   c   c   c   c  ORF 3  c   c   c   c   c   c   c   >

2300         2310         2320         2330         2340
     *            *            *            *            *
  GGT AAA GAC TTT GTC CAG TTT GCT AAG GCG GTT GGG GTT TCT CAT CCT
  Gly Lys Asp Phe Val Gln Phe Ala Lys Ala Val Gly Val Ser His Pro>
   c   c   c   c   c   c  ORF 3  c   c   c   c   c   c   c   >
                                                              <Gly
                                                              < d 2350         2360         2370         2380         2390
         *            *            *            *            *
      AGT ATT GAT GGG AAG GTT TGT AAG ACG AAG GCG GAT AGC TCG AAG AAA
      Ser Ile Asp Gly Lys Val Cys Lys Thr Lys Ala Asp Ser Ser Lys Lys>
       c   c   c   c   c   c  ORF 3  c   c   c   c   c   c   c   >
      <Leu Ile Ser Pro Phe Thr Gln Leu Val Phe Ala Ser Leu Glu Phe Phe
      <  d   d   d   d   d   d  ORF 4  d   d   d   d   d   d   d 2400         2410         2420         2430         2440
            *            *            *            *            *
         TTT CCG TTA TAT AGT GAC GAA ACG CAC ACG AAG GGG GCA AGT GAG GGG
         Phe Pro Leu Tyr Ser Asp Glu Thr His Thr Lys Gly Ala Ser Glu Gly>
          c   c   c   c   c   c  ORF 3  c   c   c   c   c   c   c   >
         <Asn Gly Asn Tyr Leu Ser Ser Val Cys Val Phe Pro Ala Leu Ser Pro
         <-   d   d   d   d   d  ORF 4  d   d   d   d   d   d   d 2450         2460         2470         2480
               *            *            *            *
            AGA AGC TCT TTG TGC GGT GAC AAT GGT AGT TCT ACG ATA ACA AAC AGT
            Arg Ser Ser Leu Cys Gly Asp Asn Gly Ser Ser Thr Ile Thr Asn Ser>
             c   c   c   c   c   c  ORF 3  c   c   c   c   c   c   c   >
            <Leu Leu Glu Lys His Pro Ser Leu Pro Leu Glu Val Ile Val Phe Leu
            <  d   d   d   d   d   d  ORF 4  d   d   d   d   d   d   d 2490         2500         2510         2520         2530
     *            *            *            *            *
  GGT GCG AAT GTA AGT GAA ACT GGG CAG GTT TTT AGG GAT TTT ATC AGG
  Gly Ala Asn Val Ser Glu Thr Gly Gln Val Phe Arg Asp Phe Ile Arg>
   c   c   c   c   c   c  ORF 3  c   c   c   c   c   c   c   >
  <Pro Ala Phe Thr Leu Ser Val Pro Cys Thr Lys Leu Ser Lys Ile Leu
```

FIG.16D

```
         <   d   d   d   d   d   d   ORF 4  d   d   d   d   d   d   d
          2540        2550        2560        2570        2580
            *           *           *           *           *
         GCA ACG CTG AAA GAG GAT GGT AGT AAA AAC TGG CCA ACT TCA AGC GGC
         Ala Thr Leu Lys Glu Asp Gly Ser Lys Asn Trp Pro Thr Ser Ser Gly>
           c   c   c   c   c   c   ORF 3  c   c   c   c   c   c   >
         <Ala Val Ser Phe Ser Ser Pro Leu Leu Phe Gln Gly Val Glu Leu Pro
         <   d   d   d   d   d   d   ORF 4  d   d   d   d   d   d
          2590        2600        2610        2620        2630
            *           *           *           *           *
         ACG GGA ACT CCA AAA CCT GTC ACG AAC GAC AAC GCC AAA GCC GTA GCT
         Thr Gly Thr Pro Lys Pro Val Thr Asn Asp Asn Ala Lys Ala Val Ala>
           c   c   c   c   c   c·  ORF 3  c   c   c   c   c   c   >
         <Val Pro Val Gly Phe Gly Thr Val Phe Ser Leu Ala Leu Ala Thr Ala
         <   d   d   d   d   d   d   ORF 4  d   d   d   d   d   d
          2640        2650        2660        2670        2680
            *           *           *           *           *
         AAA GAC CTA GTA CAG GAG CTA ACC CCT GAA GAA AAA ACC ATA GTA GCA
         Lys Asp Leu Val Gln Glu Leu Thr Pro Glu Glu Lys Thr Ile Val Ala>
           c   c   c   c   c   c   ORF 3  c   c   c   c   c   c   >
         <Leu Ser Arg Thr Cys Ser Ser Val Gly Ser Ser Phe Val Met
         <   d   d   d   d       ORF 4  d   d   d   d   d
          2690        2700        2710        2720
            *           *           *           *
         GGG TTA CTA GCT AAA ACT ATT GAA GGT GGT GAG GTT ATT GAA ATC AGG
         Gly Leu Leu Ala Lys Thr Ile Glu Gly Gly Glu Val Ile Glu Ile Arg>
           c   c   c   c   c   c   ORF 3  c   c   c   c   c   c   >
  2730        2740        2750        2760        2770
     *           *           *           *           *
  GCG GTT TCT TCT ACT TCT GTG ATG GTC AAT GCT TGT TAT GAT CTT CTT
  Ala Val Ser Ser Thr Ser Val Met Val Asn Ala Cys Tyr Asp Leu Leu>
    c   c   c   c   c   c   ORF 3  c   c   c   c   c   c   >
  2780        2790        2800        2810        2820
     *           *           *           *           *
  AGT GAA GGT TTA GGT GTT GTC CCT TAT GCT TGT GTT GGT CTC GGT GGT
  Ser Glu Gly Leu Gly Val Val Pro Tyr Ala Cys Val Gly Leu Gly Gly>
    c   c   c   c   c   c   ORF 3  c   c   c   c   c   c   >
  2830        2840        2850        2860        2870
     *           *           *           *           *
  AAC TTC GTG GGC GTG GTT GAT GGA ATT CGA TAT CAA GCT TAT CGA TAC
  Asn Phe Val Gly Val Val Asp Gly Ile Arg Tyr Gln Ala Tyr Arg Tyr>
    c   c   c   c   c   c   ORF 3  c   c   c   c   c   c   >
  2880        2890        2900
     *           *           *
  CGT CGA CCT CGA GGG GGG GCC CGG TAC
  Arg Arg Pro Arg Gly Gly Ala Arg Tyr>
    c   c   c   ORF 3       c   c   c   >
```

GE MSP Alignments

```
                         10                  20                  30                  40
E8 pept
E80 ORF 3         m r k g k i i i l g s v m m s m a i v m s g n d v r a h d d v s n l c t g g a g y f y v g
E46 orf 2         m r i r s k l f l g s v m m s l s i v m s g n d v r a h d d v s l d t g g a g y f y v g
E46 orf 1

50                  60                  70                  80                  90
E8 pept
E80 ORF 3         l d y s p a f s k i r d f s i r c s n g c t k a v y p y l k d g k s v k l c s h k f d w n
E46 orf 2         l d y s p a f s k i r d f s i r c s n g c t k a v y p y l k d g k s v k l c s h k f d w n
E46 orf 1

100                 110                 120                 130
E8 pept           t p d d p r i g f k d n M L V A M E G S V G Y G I G G A R V E L E I G Y E R F K T K G I R D
E80 ORF 3                               M L V A M E G S V G Y G I G G A R V E L E I G Y E R F K T K G I R D
E46 orf 2         t p d d p r i g f k d   M L V A M E G S V G Y G I G G A R V E L E I G Y E R F K T K G I R D
E46 orf 1                                 M L V A M E G S V G Y G I G G A R V E L E I G Y E R F K T K G I R D 140                 150                 160                 170                 180
E8 pept           S G S K E D E A D T V Y L L A K E L A Y D V V T G Q T D N L A A A L A K T S G K D i V Q F
E80 ORF 3         S G S K E D E A D T V Y L L A K E L A Y D V V T G Q T D N L A A A L A K T S G K D f V Q F
E46 orf 2         S G S K E D E A D T V Y L L A K E L A Y D V V T G Q T D N L A A A L A K T S G K D f V Q F
E46 orf 1         S G S K E D E A D T V Y L L A K E L A Y D V V T G Q T D N L A A A L A K T S G K D i V Q F 190                 200                 210                 220
E8 pept           A K A V G V S H P g I D k K V C d g g h a r g l A d y t d g g s           - - r s s     - l
E80 ORF 3         A K A V G V S H P - I D g K V C k t k a d s   T h t k g a s c g            r s s l
E46 orf 2         A K A V G V S H P - I D g K V C k t k a d s   T h t k g a s c g            r s s l
E46 orf 1         A n A V k I S y P k I D e Q V C n k n h t v l n - - - t k g T f f n p d p k - - - - -
```

FIG. 18B

E8/MSP-2 Alignments

```
                      10              20              30              40
AMmsp2 pept  m s V n r K L p L G g V L M A L A s s V A p i h s l l s s p s A g s g A G G
E8 pept            M r g K I i L G s V M M S M A i v M A g n d v r s h d d v S s l c T G G 50              60              70              80
AMmsp2 pept  e g l f s g s s A G s F Y I G L D Y S P A F g s I K D F k V Q E A G G t T R g V
E8 pept      - - - - - - - - A G y F Y V G L D Y S P A F s k I R D F s I R E S N G c T K s V 90              100             110             120
AMmsp2 pept  F P Y k R D s s g r V d f k v H n F D W s A P E P K I s F K D s M L t A L E G S
E8 pept      Y P Y l K D g k - s V k l e s H k F D W n T P D P R I s F K D n M L v A M E G S 130             140             150             160
AMmsp2 pept  I G Y s I G G A R V E V E V G Y E R F v i K G s K k S N - - E D - T s V F L L
E8 pept      V G Y s I G G A R V E L E I G Y E R F k t K G i R d S G s k E D e A d T V Y L L 170             180             190             200
AMmsp2 pept  s K E L A Y h t s r G Q v D s L A T A L g K m T k s E s k K W g n A I e s - - -
E8 pept      s K E L A Y d v v t G Q t D n L A A A L s K t S g k D i v Q f s k A V g v s h p 210             220             230             240
AMmsp2 pept  - - - - - - - - - A t G t t S G D e - - L s k k v c G k g T t S G s T n Q C
E8 pept      g i d k k v c d g g h A r G k k S G D n g s L A d y t d G g s S q T N k T s Q C 250             260             270             280
AMmsp2 pept  g t t d S t s T t K i s a v f T E d s s s q l s - - - - - - - - - - t m D N t T
E8 pept      s g m g T g k A s K r g l g l T E f v n k t k v g e g k n w p t g y v n D G d N 290             300             310             320
AMmsp2 pept  I N t t G m A N N - - - - - - - - - - I N s L T k D E K A I V A G s f A R A V E G
E8 pept      V N v l g d T N G n s e s v s k d l V Q e L T p E E K T I V A G l l A K T I E G 330             340             350             360
AMmsp2 pept  s E V I E V R A I s S T S V M L N A C Y D L L T D G I G V V P Y A C s G I G G N
E8 pept      g E V V E I R A V s S T S V M V N A C Y D L L S E G L G V V P Y A C v G L G G N 370             380             390             400
AMmsp2 pept  F V s V V D G H I N P K f A Y R V K A G L S Y s L T P e I S A F A G s F Y H K V
E8 pept      F V g V V D G H I T P K l A Y R L K A G L S Y q L S P v I S A F A G s F Y H R V 410             420             430             440
AMmsp2 pept  L G D G d Y D E L P l s H I s D y T s s A G K N K D T s I A s F n f A Y f G G E
E8 pept      V G D G v Y D D L P s q R L v D d T s p A G R T K D T s I A n F s m A Y v G G E AMmsp2 pept  l G V R F A F
E8 pept      f G V R F A F
```

FIG. 19

E8 Peptide Sequence

```
              10          20          30          40          50          60
               *           *           *           *           *           *
      MRKGKIILGS  VMMSMAIVMA  GNDVRAHDDV  SALETGGAGY  FYVGLDYSPA  FSKIRDFSIR 70          80          90         100         110         120
               *           *           *           *           *           *
      ESNGETKAVY  PYLKDGKSVK  LESHKFDWNT  PDPRIGFKDN  MLVAMEGSVG  YGIGGARVEL 130         140         150         160         170         180
               *           *           *           *           *           *
      EIGYERFKTK  GIRDSGSKED  EADTVYLLAK  ELAYDVVTGQ  TDNLAAALAK  TSGKDIVQFA 190         200         210         220         230         240
               *           *           *           *           *           *
      KAVGVSHPGI  DKKVCDGGHA  RGKKSGDNGS  LADYTDGGAS  QTNKTAQCSG  MGTGKAGKRG 250         260         270         280         290         300
               *           *           *           *           *           *
      LGLTEFVNKT  KVGEGKNWPT  GYVNDGDNVN  VLGDTNGNAE  AVAKDLVQEL  TPEEKTIVAG 310         320         330         340         350         360
               *           *           *           *           *           *
      LLAKTIEGGE  VVEIRAVSST  SVMVNACYDL  LSEGLGVVPY  ACVGLGGNFV  GVVDGHITPK 370         380         390         400         410         420
               *           *           *           *           *           *
      LAYRLKAGLS  YQLSPVISAF  AGGFYHRVVG  DGVYDDLPAQ  RLVDDTSPAG  RTKDTAIANF

430
               *
      SMAYVGGEFG  VRFAF
```

FIG. 20

NUCLEIC ACIDS, PROTEINS, AND METHODS OF USE OF GRANULOCYTIC EHRLICHIA

CROSS-REFERENCE TO RELATED APPLICATIONS

This U.S. Utility Patent Application claims priority from U.S. Provisional Patent Application Ser. No. 60/044,869, filed on Apr. 25, 1997.

BACKGROUND OF THE INVENTION

1. Field of the Invention

The present invention relates, in general, to granulocytic ehrlichia (GE) proteins. In particular, the present invention relates to nucleic acid molecules coding for GE W20.1, W20.2, B3, E74.3, E74.4, E82.2, E82.3, E8, E46.1, E46.2, and E80 proteins; purified GE W20.1, W20.2, B3, E74.3, E74.4, E82.2, E82.3, E8, E46.1, E46.2, and E80 proteins and polypeptides; recombinant nucleic acid molecules; cells containing the recombinant nucleic acid molecules; antibodies having binding affinity specifically to GE W20.1, W20.2, B3, E74.3, E74.4, E82.2, E82.3, E8, E46.1, E46.2, and E80 proteins and polypeptides; hybridomas containing the antibodies; nucleic acid probes for the detection of nucleic acids encoding GE W20.1, W20.2, B3, E74.3, E74.4, E82.2, E82.3, E8, E46.1, E46.2, and E80 proteins; a method of detecting nucleic acids encoding GE W20.1, W20.2, B3, E74.3, E74.4, E82.2, E82.3, E8, E46.1, E46.2, and E80 proteins or polypeptides in a sample; kits containing nucleic acid probes or antibodies; bioassays using the nucleic acid sequence, protein or antibodies of this invention to diagnose, assess, or prognose a mammal afflicted with ehrlichiosis; therapeutic uses, specifically vaccines comprising W20.1, W20.2, B3, E74.3, E74.4, E82.2, E82.3, E8, E46.1, E46.2, and E80 proteins or polypeptides; and methods of preventing or inhibiting ehrlichiosis in an animal.

2. Related Art

GE is an acute, potentially fatal tick-borne infection. The causative agent, GE, has been identified by the polymerase chain reaction (PCR) using universal primers for eubacterial 16S ribosomal RNA to amplify the DNA of infected patients' blood (Chen et al., *J. Clin. Micro.* 32:589–595, 1994). Comparison of the 16S rRNA gene sequence of GE to other known 16S rDNA sequences revealed a nearly identical match to the 16S genes of *Ehrlichia phagocytophila* and *Ehrlichia equi* (Chen et al., 1994). Two other groups of Ehrlichia species have also been categorized according to their 16S rRNA gene sequences, the *Ehrlichia canis* and *Ehrlichia sennetsu* groups. The *E. canis* and *E. sennetsu* species predominantly infect mononuclear phagocytes (Dumler et al., *N. Eng. J. Med.* 325:1109–1110 (1991)) whereas members of the *E. phagocytophila* group including GE are tropic for granulocytes (Ristic et al., in *Bergey's Manual of Systemic Bacteriology*, Kreig et al., eds., (1984), pp. 704–709). The near identity of the 16S rRNA gene sequences and the sharing of significant antigenicity by IFA and immunoblot (Dumler et al., *J. Clin. Micro.* 33:1098–1103 (1995)) indicate that *E. phagocytophila*, *E. equi* and GE are closely related.

Full classification of the *E. phagocytophila* Ehrlichia species including antigenic relationships among the individual isolates has been impeded by the inability to cultivate these organisms in cell culture. It has been shown that GE can be successfully cultivated in HL60 cells, a human promyelocytic leukemia cell line (Coughlin et al., PCT Application No. PCT/US96/10117; Goodman et al., *N. Eng. J. Med.* 334:209–215 (1996)). Walker et al., PCT Application No. PCT/US97/09147 teaches an isolated gene encoding a 120 kDa immunodominant antigen of *E. chaffeensis* that stimulates production of specific antibodies in infected humans.

The present invention describes GE specific genes encoding eleven different proteins (W20.1, W20.2, B3, E74.3, E74.4, E82.2, E82.3, E8, E46.1, E46.2, and E80 proteins) which can be used as diagnostic reagents and vaccines.

SUMMARY OF THE INVENTION

The invention provides isolated nucleic acid molecules coding for polypeptides comprising amino acid sequences corresponding to GE W20.1, W20.2, B3, E74.3, E74.4, E82.2, E82.3, E8, E46.1, E46.2, and E80 proteins.

The invention further provides purified polypeptides comprising amino acid sequences corresponding to GE W20.1, W20.2, B3, E74.3, E74.4, E82.2, E82.3, E8, E46.1, E46.2, and E80 proteins.

The invention also provides nucleic acid probes for the specific detection of the presence of GE W20.1, W20.2, B3, E74.3, E74.4, E82.2, E82.3, E8, E46.1, E46.2, and E80 proteins or polypeptides in a sample.

The invention further provides a method of detecting nucleic acid encoding GE W20.1, W20.2, B3, E74.3, E74.4, E82.2, E82.3, E8, E46.1, E46.2, and E80 protein in a sample.

The invention also provides a kit for detecting the presence of nucleic acid encoding GE W20.1, W20.2, B3, E74.3, E74.4, E82.2, E82.3, E8, E46.1, E46.2, and E80 protein in a sample.

The invention further provides a recombinant nucleic acid molecule comprising, 5' to 3', a promoter effective to initiate transcription in a host cell and the above-described isolated nucleic acid molecule.

The invention also provides a recombinant nucleic acid molecule comprising a vector and the above-described isolated nucleic acid molecule.

The invention further provides a recombinant nucleic acid molecule comprising a sequence complimentary to an RNA sequence encoding an amino acid sequence corresponding to the above-described polypeptide.

The invention also provides a cell that contains the above-described recombinant nucleic acid molecule.

The invention further provides a non-human organism that contains the above-described recombinant nucleic acid molecule.

The invention also provides an antibody having binding affinity specifically to a GE W20.1, W20.2, B3, E74.3, E74.4, E82.2, E82.3, E8, E46.1, E46.2, and E80 protein or polypeptide.

The invention further provides a method of detecting GE W20.1, W20.2, B3, E74.3, E74.4, E82.2, E82.3, E8, E46.1, E46.2, and E80 protein or polypeptide in a sample.

The invention also provides a method of measuring the amount of GE W20.1, W20.2, B3, E74.3, E74.4, E82.2, E82.3, E8, E46.1, E46.2, and E80 protein or polypeptide in a sample.

The invention further provides a method of detecting antibodies having binding affinity specifically to a GE W20.1, W20.2, B3, E74.3, E74.4, E82.2, E82.3, E8, E46.1, E46.2, and E80 protein or polypeptide.

The invention further provides a diagnostic kit comprising a first container means containing the above-described antibody, and a second container means containing a conjugate comprising a binding partner of the monoclonal antibody and a label.

The invention also provides a hybridoma which produces the above-described monoclonal antibody.

The invention further provides diagnostic methods for ehrlichiosis. More specifically, the invention further provides a method for identifying granulocytic Ehrlichia in an animal comprising analyzing tissue or body fluid from the animal for a W20.1, W20.2, B3, E74.3, E74.4, E82.2, E82.3, E8, E46.1, E46.2, and E80 nucleic acid, protein, polysaccharide, or antibody.

The invention also provides methods for therapeutic uses involving all or part of the GE W20.1, W20.2, B3, E74.3, E74.4, E82.2, E82.3, E8, E46.1, E46.2, and E80 nucleic acid or protein. More specifically, the invention further provides a vaccine comprising a W20.1, W20.2, B3, E74.3, E74.4, E82.2, E82.3, E8, E46.1, E46.2, and E80 protein or nucleic acid together with a pharmaceutically acceptable diluent, carrier, or excipient, wherein the protein or nucleic acid is present in an amount effective to elicit a beneficial immune response in an animal to the protein.

The invention also provides a method of preventing or inhibiting ehrlichiosis in an animal comprising administering to the animal the above-described vaccine.

Further objects and advantages of the present invention will be clear from the description that follows.

DEFINITIONS

In the description that follows, a number of terms used in recombinant DNA (rDNA) technology are extensively utilized. In order to provide a clear and consistent understanding of the specification and claims, including the scope to be given such terms, the following definitions are provided.

Isolated Nucleic Acid Molecule. An "isolated nucleic acid molecule", as is generally understood and used herein, refers to a polymer of nucleotides, and includes but should not be limited to DNA and RNA.

Recombinant DNA. Any DNA molecule formed by joining DNA segments from different sources and produced using "recombinant DNA" technology (also known as "molecular genetic engineering").

DNA Segment. A "DNA segment," as is generally understood and used herein, refers to a molecule comprising a linear stretch of nucleotides wherein the nucleotides are present in a sequence that can encode, through the genetic code, a molecule comprising a linear sequence of amino acid residues that is referred to as a protein, a protein fragment or a polypeptide.

Gene. A DNA sequence related to a single polypeptide chain or protein, and as used herein includes the 5' and 3' untranslated ends. The polypeptide can be encoded by a full-length sequence or any portion of the coding sequence, so long as the functional activity of the protein is retained.

Complementary DNA ("cDNA"). Recombinant nucleic acid molecules synthesized by reverse transcription of messenger RNA ("mRNA").

Structural Gene. A DNA sequence that is transcribed into mRNA that is then translated into a sequence of amino acids characteristic of a specific polypeptide.

Open Reading Frame ("orf"). The property of some nucleic acid sequences to encode for more than one peptide within the same sequence, which is possible because these sequences contain a series of triplets coding for amino acids without any termination codons interrupting the relevant reading frames.

Restriction Endonuclease. A "restriction endonuclease" (also "restriction enzyme") is an enzyme that has the capacity to recognize a specific base sequence (usually 4, 5, or 6 base pairs in length) in a DNA molecule, and to cleave the DNA molecule at every place where this sequence appears. For example, EcoRI recognizes the base sequence GAATTC/CTTAAG.

Restriction Fragment. The DNA molecules produced by digestion with a restriction endonuclease are referred to as "restriction fragments." Any given genome can be digested by a particular restriction endonuclease into a discrete set of restriction fragments.

Agarose Gel Electrophoresis. To determine the length of restriction fragments, an analytical method for fractionating double-stranded DNA molecules on the basis of size is required. The most commonly used technique (though not the only one) for achieving such a fractionation is "agarose gel electrophoresis." The principle of this method is that DNA molecules migrate through the gel as though it were a sieve that retards the movement of the largest molecules to the greatest extent and the movement of the smallest molecules to the least extent. Note that the smaller the DNA fragment, the greater the mobility under electrophoresis in the agarose gel.

The DNA fragments fractionated by "agarose gel electrophoresis" can be visualized directly by a staining procedure if the number of fragments included in the pattern is small. The DNA fragments of genomes can be visualized successfully. However, most genomes, including the human genome, contain far too many DNA sequences to produce a simple pattern of restriction fragments. For example, the human genome is digested into approximately 1,000,000 different DNA fragments by EcoRI. In order to visualize a small subset of these fragments, a methodology referred to as the Southern hybridization procedure can be applied.

Southern Transfer Procedure. The purpose of the "Southern transfer procedure" (also "Southern blotting") is to physically transfer DNA fractionated by agarose gel electrophoresis onto a nitrocellulose filter paper or another appropriate surface or method, while retaining the relative positions of DNA fragments resulting from the fractionation procedure. The methodology used to accomplish the transfer from agarose gel to nitrocellulose involves drawing the DNA from the gel into the nitrocellulose paper by capillary action or electrophoretic transfer.

Nucleic Acid Hybridization. "Nucleic acid hybridization" depends on the principle that two single-stranded nucleic acid molecules that have complementary base sequences will reform the thermodynamically favored double-stranded structure if they are mixed under the proper conditions. The double-stranded structure will be formed between two complementary single-stranded nucleic acids even if one is immobilized on a nitrocellulose filter. In the Southern hybridization procedure, the latter situation occurs. As noted previously, the DNA of the individual to be tested is digested with a restriction endonuclease, fractionated by agarose gel electrophoresis, converted to the single-stranded form, and transferred to nitrocellulose paper, making it available for reannealing to the hybridization probe. Examples of hybridization conditions can be found in Ausubel, F. M. et al., *Current Protocols in Molecular Biology*, John Wiley & Sons, Inc., New York, N.Y. (1989). For example, a nitrocellulose filter is incubated overnight at 68° C. with labeled probe in a solution containing 50% formamide, high salt (either 5×SSC[20×: 3M NaCl/0.3M trisodium citrate] or 5×SSPE [20×: 3.6M NaCl/0.2M $NaH_2PO_4$/0.02M EDTA, pH 7.7]), 5×Denhardt's solution, 1% SDS, and 100 µg/ml denatured salmon sperm DNA. This is followed by several washes in 0.2×SSC/0.1% SDS at a temperature selected based on the desired stringency: room temperature (low stringency), 42° C. (moderate stringency) or 68° C. (high stringency). The temperature selected is determined based on the melting temperature (Tm) of the DNA hybrid.

Hybridization Probe. To visualize a particular DNA sequence in the Southern hybridization procedure, a labeled DNA molecule or "hybridization probe" is reacted to the fractionated DNA bound to the nitrocellulose filter. The areas on the filter that carry DNA sequences complementary to the labeled DNA probe become labeled themselves as a consequence of the reannealing reaction. The areas of the filter that exhibit such labeling are visualized. The hybridization probe is generally produced by molecular cloning of a specific DNA sequence.

Oligonucleotide or Oligomer. A molecule comprised of two or more deoxyribonucleotides or ribonucleotides, preferably more than three. Its exact size will depend on many factors, which in turn depend on the ultimate function or use of the "oligonucleotide." An "oligonucleotide" can be derived synthetically or by cloning.

Sequence Amplification. A method for generating large amounts of a target sequence. In general, one or more amplification primers are annealed to a nucleic acid sequence. Using appropriate enzymes, sequences found adjacent to, or in between the primers are amplified.

Amplification Primer. An oligonucleotide which is capable of annealing adjacent to a target sequence and serving as an initiation point for DNA synthesis when placed under conditions in which synthesis of a primer extension product which is complementary to a nucleic acid strand is initiated.

Vector. A plasmid or phage DNA or other DNA sequence into which DNA can be inserted to be cloned. The "vector" can replicate autonomously in a host cell, and can be further characterized by one or a small number of endonuclease recognition sites at which such DNA sequences can be cut in a determinable fashion and into which DNA can be inserted. The "vector" can further contain a marker suitable for use in the identification of cells transformed with the "vector". Markers, for example, are tetracycline resistance or ampicillin resistance. The words "cloning vehicle" are sometimes used for "vector."

Expression. "Expression" is the process by which a structural gene produces a polypeptide. It involves transcription of the gene into mRNA, and the translation of such mRNA into polypeptide(s).

Expression Vector. A vector or vehicle similar to a cloning vector but which is capable of expressing a gene which has been cloned into it, after transformation into a host. The cloned gene is usually placed under the control of (i.e., operably linked to) certain control sequences such as promoter sequences.

Expression control sequences will vary depending on whether the vector is designed to express the operably linked gene in a prokaryotic or eukaryotic host and can additionally contain transcriptional elements such as enhancer elements, termination sequences, tissue-specificity elements, and/or translational initiation and termination sites.

Functional Derivative. A "functional derivative" of a sequence, either protein or nucleic acid, is a molecule that possesses a biological activity (either functional or structural) that is substantially similar to a biological activity of the protein or nucleic acid sequence. A "functional derivative" of a protein can contain post-translational modifications such as covalently linked carbohydrate, depending on the necessity of such modifications for the performance of a specific function. The term "functional derivative" is intended to include the "fragments," "segments," "variants," "analogs," or "chemical derivatives" of a molecule.

As used herein, a molecule is said to be a "chemical derivative" of another molecule when it contains additional chemical moieties not normally a part of the molecule. Such moieties can improve the molecule's solubility, absorption, biological half life, and the like. The moieties can alternatively decrease the toxicity of the molecule, eliminate or attenuate any undesirable side effect of the molecule, and the like. Moieties capable of mediating such effects are disclosed in *Remington's Pharmaceutical Sciences* (1980). Procedures for coupling such moieties to a molecule are well known in the art.

Variant. A "variant" of a protein or nucleic acid is meant to refer to a molecule substantially similar in structure and biological activity to either the protein or nucleic acid. Thus, provided that two molecules possess a common activity and can substitute for each other, they are considered "variants" as that term is used herein even if the composition or secondary, tertiary, or quaternary structure of one of the molecules is not identical to that found in the other, or if the amino acid or nucleotide sequence is not identical.

Allele. An "allele" is an alternative form of a gene occupying a given locus on the chromosome.

Mutation. A "mutation" is any detectable change in the genetic material which can be transmitted to daughter cells and possibly even to succeeding generations giving rise to mutant cells or mutant individuals. If the descendants of a mutant cell give rise only to somatic cells in multicellular organisms, a mutant spot or area of cells arises. "Mutations" in the germ line of sexually reproducing organisms can be transmitted by the gametes to the next generation resulting in an individual with the new mutant condition in both its somatic and germ cells. A "mutation" can be any (or a combination of) detectable, unnatural change affecting the chemical or physical constitution, mutability, replication, phenotypic function, or recombination of one or more deoxyribonucleotides; nucleotides can be added, deleted, substituted for, inverted, or transposed to new positions with and without inversion. "Mutations" can occur spontaneously and can be induced experimentally by application of mutagens. A mutant variation of a nucleic acid molecule results from a mutation. A mutant polypeptide can result from a mutant nucleic acid molecule.

Species. A "species" is a group of actually or potentially interbreeding natural populations. A species variation within a nucleic acid molecule or protein is a change in the nucleic acid or amino acid sequence that occurs among species and can be determined by DNA sequencing of the molecule in question.

Purified. A "purified" protein or nucleic acid is a protein or nucleic acid that has been separated from a cellular component. "Purified" proteins or nucleic acids have been purified to a level of purity not found in nature.

BRIEF DESCRIPTION OF THE FIGURES

FIG. 1. Complete sequence of W20. The nucleotide number is indicated above the sequences. The complete DNA sequence of the W20 insert in Lambda Zap II is shown (SEQ ID NO:1). The translated amino acid sequences for the open reading frames ("orf") are displayed underneath the DNA sequences. Orf 1 of W20, which begins at nucleotide 42 and ends at nucleotide 1679, is shown (SEQ ID NO:2). The translated amino acid sequence for orf 2 of W20, which begins at nucleotide 2059 and ends at nucleotide 3600, is shown (SEQ ID NO:3).

FIG. 3. PCR analysis of GE clones. PCR reactions were performed and the products analyzed using 4% Nusieve gels. Primer sequences are listed in Table 2.

FIG. 4. Expression of seven GE clones by Western blot.

FIG. 5. Complete sequence of B3. The nucleotide number is indicated above the sequences. The complete DNA sequence of the B3 insert in Lambda Zap II is shown (SEQ ID NO:4). The translated amino acid sequences for the opening reading frame are displayed underneath the DNA sequence. The amino acid sequence of B3 orf, which begins at nucleotide 336 and ends at nucleotide 2282, is shown (SEQ ID NO:5).

FIG. 8. Complete sequence of E74. The nucleotide number is indicated above the sequences. The complete DNA sequence of the E74 insert in Lambda Zap II is shown (SEQ ID NO:6). The translated amino acid sequences for the open reading frames are displayed underneath the DNA sequences. The amino acid sequence of E74.3, which begins at nucleotide 1980 and ends at nucleotide 3497, is shown (SEQ ID NO:7). The amino acid sequence the E74.4 orf, which begins at nucleotide 3491 and ends at nucleotide 4803, is shown (SEQ ID NO:8).

FIG. 10. Complete sequence of E82. The nucleotide number is indicated above the sequences. The complete DNA sequence of the E82 insert in Lambda Zap II is shown (SEQ ID NO:9). The translated amino acid sequences for the open reading frames are displayed underneath the DNA sequences. The amino acid sequence of E82.2, which begins at nucleotide 3719 and ends at nucleotide 4321, is shown (SEQ ID NO:10). The amino acid sequence of E82.3, which begins at nucleotide 4397 and ends at nucleotide 5110, is also shown (SEQ ID NO:11).

FIG. 12. Complete sequence of E8. The nucleotide number is indicated above the sequences. The complete DNA sequence of the E8 insert in Lambda Zap II is shown (SEQ ID NO:12). The translated amino acid sequences for the open reading frame are displayed underneath the DNA sequences. The amino acid sequence of the E8 orf, which begins at nucleotide 410 and ends at nucleotide 1714, is shown (SEQ ID NO:13).

FIG. 14. Complete sequence of E46. The nucleotide number is indicated above the sequences. The complete DNA sequence of the E46 insert in Lambda Zap II is shown (SEQ ID NO:14). The translated amino acid sequences for the open reading frames are displayed underneath the DNA sequences. The amino acid sequence of E46.1, which begins at nucleotide 305 and ends at nucleotide 1282, is shown (SEQ ID NO:15). The amino acid sequence of E46.2, which begins at nucleotide 1346 and ends at nucleotide 2437, is shown (SEQ ID NO:16).

FIG. 16. Complete sequence of E80. The nucleotide number is indicated above the sequences. The complete DNA sequence of the E80 insert in Lambda Zap II is shown (SEQ ID NO:17). The translated amino acid sequences of the open reading frames are displayed underneath the DNA sequences. The amino acid sequences of the E80 orf 3, which begins at nucleotide 2082 and ends at nucleotide 2900, is shown (SEQ ID NO:18).

FIG. 18. Sequence homology of various GE proteins. The amino acid sequences of E8 (SEQ ID NO:13), E80 (SEQ ID NO:18), E46.1 (SEQ ID NO:15), and E46.2 (SEQ ID NO:16) were aligned using Clustal W software.

FIG. 19. Sequence homology of the E8 protein and the *A. marginale* MSP-2 protein. The amino acid sequences of E8 and *A. marginale* MSP-2 were aligned using Clustal W software.

FIG. 20. Amino acid sequence of the E8 (SEQ ID NO:13) protein. Three different GE proteins were isolated by SDS-PAGE for peptide sequencing as discussed in the specification, e.g., 54.7, 51, and 32.4 kDa. Sequences of the N-terminal peptides and internal peptides were compared with the amino acid sequences obtained from the genomic library DNA sequences. When compared with the protein sequence of E8, all the peptides except for the 32.4 kDa peptide could be found in E8. These peptides are underlined in FIG. 20.

DETAILED DESCRIPTION OF THE PREFERRED EMBODIMENTS

Figure 2:
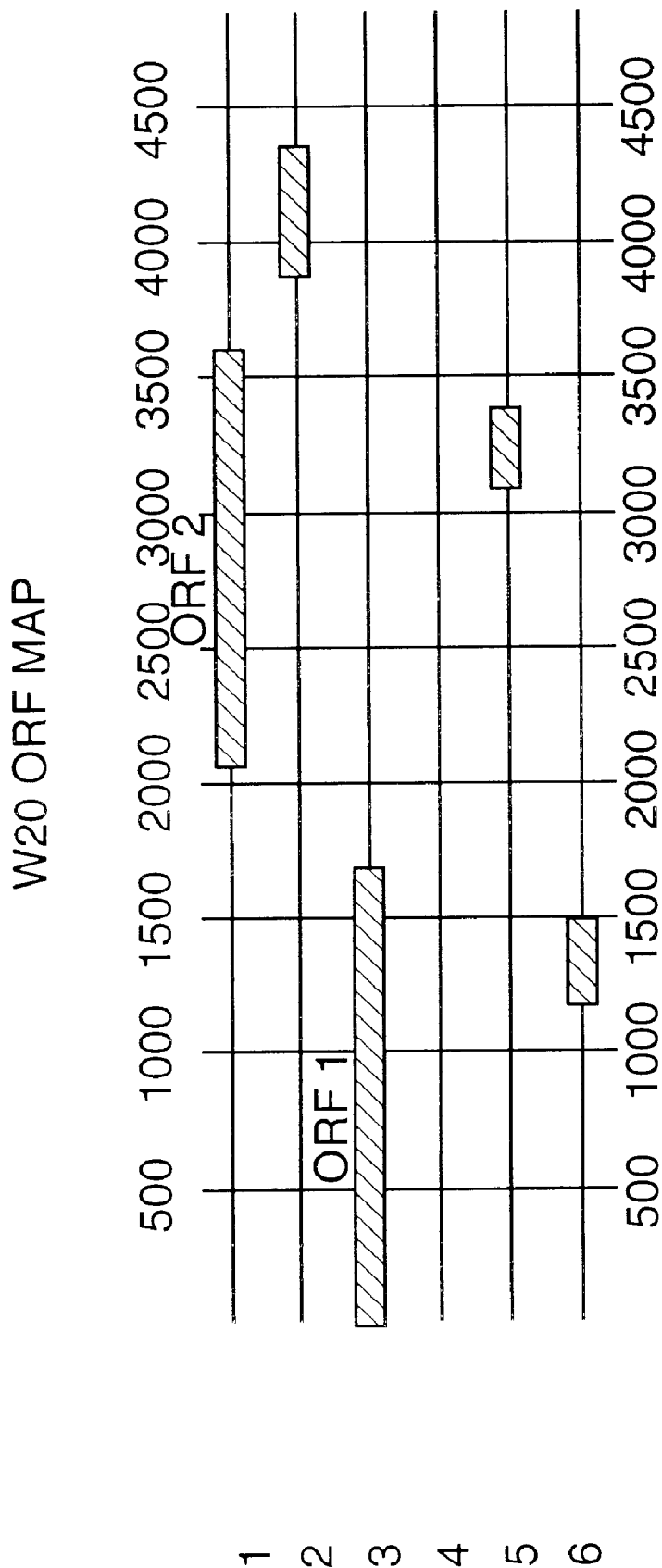
FIG. 2. The ORF map of W20 is shown. Numbers 1–3 on the left of the map represent the three different reading frames for the plus strand and numbers 4–6 represent the three different reading frames for the minus strand. The clone contains two large and one small orfs (solid bars) encoded by the plus strand of the insert, as well as two small orfs (hatched bars) on the minus strand.

The sequencing and protein analysis of seven recombinant clones (W20, B3, E74, E82, E8, E46, and E80) identified by immunological screening of a GE genomic library is described. Several clones contain two open reading frames. In particular, E74 encodes E74.3 and E74.4; E46 encodes E46.1 and E46.2; W20 encodes W20.1 and W20.2; and E82 encodes E82.2 and E82.3. These genomic DNA isolates were proven to be specific to GE based on PCR analysis of GE DNA and HL60 DNA.

These genes most likely encode immunodominant GE antigens which may also be present in more than one copy in the GE genome. Other immunodominant rickettsial antigens have been shown to be important diagnostic reagents and vaccine targets including the outer membrane polypeptides of *Anaplasma marginale* (Tebele et al., *Infect. Immun.* 59:3199–3204 (1991)), immunogenic proteins of *Cowdria rumantiun* (Mahan et al., *Microbiology* 140:2135–2142 (1994); van Vliet et al., *Infect. Immun.* 62:1451–1456 (1994)), the 120 kDa immunodominant protein of *E. chaffeensis* (Yu et al., *J. Clin. Micro.* 34:2853–2855 (1996)), the immuno-dominant surface protein antigen of *Rickettsia prowazekii* (Dasch et al., in *Microbiology*, D. Schlessinger (ed.), American Society for Microbiology, Washington, D.C., (1984), p. 251–256,) and two *Rickettsia rickettsii* surface proteins (Anacker et al., *Infect. Immun.* 55:825–827 (1987); Sumner et al., *Vaccine* 13:29–35 (1995)). Many of these proteins contain highly repeated regions similar to those found for GE proteins. Repetitive protein domains have been shown to function in ligand binding (Wren, *Mol. Microbiol.* 5:797–803 (1991)) and may function to facilitate rickettsial uptake by host cell membranes.

For purposes of clarity of disclosure, and not by way of limitation, the detailed description of the invention is divided into the following subsections:

I. Isolated Nucleic Acid Molecules Coding for W20.1, W20.2, B3, E74.3, E74.4, E82.2, E82.3, E8, E46.1, E46.2, and E80 Polypeptides.

II. Recombinantly Produced W20.1, W20.2, B3, E74.3, E74.4, E82.2, E82.3, E8, E46.1, E46.2, and E80 Polypeptides.

III. A Nucleic Acid Probe for the Specific Detection of W20.1, W20.2, B3, E74.3, E74.4, E82.2, E82.3, E8, E46.1, E46.2, and E80.

IV. A Method of Detecting The Presence of W20.1, W20.2, B3, E74.3, E74.4, E82.2, E82.3, E8, E46.1, E46.2, and E80 in a Sample.

V. A Kit for Detecting the Presence of W20.1, W20.2, B3, E74.3, E74.4, E82.2, E82.3, E8, E46.1, E46.2, and E80 in a Sample.

VI. DNA Constructs Comprising a W20.1, W20.2, B3, E74.3, E74.4, E82.2, E82.3, E8, E46.1, E46.2, and E80 Nucleic Acid Molecule and Cells Containing These Constructs.

VII. An Antibody Having Binding Affinity to a W20.1, W20.2, B3, E74.3, E74.4, E82.2, E82.3, E8, E46.1, E46.2, and E80 Polypeptide and a Hybridoma Containing the Antibody.

VIII. A Method of Detecting a W20.1, W20.2, B3, E74.3, E74.4, E82.2, E82.3, E8, E46.1, E46.2, and E80 Polypeptide or Antibody in a Sample.

IX. A Diagnostic Kit Comprising W20.1, W20.2, B3, E74.3, E74.4, E82.2, E82.3, E8, E46.1, E46.2, and E80 Protein or Antibody.

X. Diagnostic Screening.

XI. Vaccines.

I. Isolated Nucleic Acid Molecules Coding for W20.1, W20.2, B3, E74.3, E74.4, E82.2, E82.3, E8, E46.1, E46.2, and E80 Polypeptides In one embodiment, the present invention relates to isolated nucleic acid molecules comprising a polynucleotide sequence at least 90% identical (more preferably, 95%, 96%, 97%, 98%, 99% or 100% identical) to a sequence selected from the group consisting of:

(a) a nucleotide sequence encoding the W20.1, W20.2, B3, E74.3, E74.4, E82.2, E82.3, E8, E46.1, E46.2, and E80 polypeptide comprising the complete amino acid sequence in SEQ ID NO:2, 3, 5, 7, 8, 10, 11, 13, 15, 16, or 18.

(b) a nucleotide sequence encoding the W20.1, W20.2, B3, E74.3, E74.4, E82.2, E82.3, E8, E46.1, E46.2, and E80 polypeptide comprising the complete amino acid sequence; and (c) a nucleotide sequence complementary to any of the nucleotide sequences in (a) or (b).

In one preferred embodiment, the isolated nucleic acid molecule comprises a GE W20.1, W20.2, B3, E74.3, E74.4, E82.2, E82.3, E8, E46.1, E46.2, and E80 nucleotide sequence with greater than 90% identity or similarity to the nucleotide sequence present in SEQ ID NO: 1, 4, 6, 9, 12, 14, or 17 (preferably greater than 95%, 96%, 97%, 98%, 99% or 100%). In another preferred embodiment, the isolated nucleic acid molecule comprises the W20.1, W20.2, B3, E74.3, E74.4, E82.2, E82.3, E8, E46.1, E46.2, and E80 nucleotide sequence present in SEQ ID NO: 1, 4, 6, 9, 12, 14, or 17. In another embodiment, the isolated nucleic acid molecule encodes the W20.1, W20.2, B3, E74.3, E74.4, E82.2, E82.3, E8, E46.1, E46.2, and E80 proteins amino acid sequence present in SEQ ID NO:2, 3, 5, 7, 8, 10, 11, 13, 15, 16, or 18.

Also included within the scope of this invention are the functional equivalents of the herein-described isolated nucleic acid molecules and derivatives thereof. For example, the nucleic acid sequences depicted in SEQ ID NO:1, 4, 6, 9, 12, 14, or 17 can be altered by substitutions, additions or deletions that provide for functionally equivalent molecules. Due to the degeneracy of nucleotide coding sequences, other DNA sequences which encode substantially the same amino acid sequence as depicted in SEQ ID NO: 2, 4, 6, 8, 10, or 11 can be used in the practice of the present invention. These include but are not limited to nucleotide sequences comprising all or portions of W20.1, W20.2, B3, E74.3, E74.4, E82.2, E82.3, E8, E46.1, E46.2, and E80 nucleic acid depicted in SEQ ID NO:1, 4, 6, 9, 12, 14, or 17 which are altered by the substitution of different codons that encode a functionally equivalent amino acid residue within the sequence.

In addition, the nucleic acid sequence can comprise a nucleotide sequence which results from the addition, deletion or substitution of at least one nucleotide to the 5'-end and/or the 3'-end of the nucleic acid formula shown in SEQ ID NO:1, 4, 6, 9, 12, 14, or 17 or a derivative thereof. Any nucleotide or polynucleotide can be used in this regard, provided that its addition, deletion or substitution does not substantially alter the amino acid sequence of SEQ ID NO:2, 4, 6, 8, 10, or 11 which is encoded by the nucleotide sequence. Moreover, the nucleic acid molecule of the present invention can, as necessary, have restriction endonuclease recognition sites added to its 5'-end and/or 3'-end. All variations of the nucleotide sequence of the W20.1, W20.2, B3, E74.3, E74.4, E82.2, E82.3, E8, E46.1, E46.2, and E80 gene and fragments thereof permitted by the genetic code are, therefore, included in this invention.

Further, it is possible to delete codons or to substitute one or more codons by codons other than degenerate codons to produce a structurally modified polypeptide, but one which has substantially the same utility or activity of the polypeptide produced by the unmodified nucleic acid molecule. As recognized in the art, the two polypeptides are functionally equivalent, as are the two nucleic acid molecules which give rise to their production, even though the differences between the nucleic acid molecules are not related to degeneracy of the genetic code.

A Isolation of Nucleic Acid

In one aspect of the present invention, isolated nucleic acid molecules coding for polypeptides having amino acid sequences corresponding to W20.1, W20.2, B3, E74.3, E74.4, E82.2, E82.3, E8, E46.1, E46.2, and E80 are provided. In particular, the nucleic acid molecule can be isolated from a biological sample (preferably of mammalian or tick origin) containing GE RNA or DNA.

The nucleic acid molecule can be isolated from a biological sample containing GE RNA using the techniques of cDNA cloning and subtractive hybridization. The nucleic acid molecule can also be isolated from a cDNA library using a homologous probe.

The nucleic acid molecule can be isolated from a biological sample containing genomic DNA or from a genomic library. Suitable biological samples include, but are not limited to, whole organisms, organs, tissues, blood and cells. The method of obtaining the biological sample will vary depending upon the nature of the sample.

One skilled in the art will realize that genomes can be subject to slight allelic variations between individuals. Therefore, the isolated nucleic acid molecule is also intended to include allelic variations, so long as the sequence is a functional derivative of the W20.1, W20.2, B3, E74.3, E74.4, E82.2, E82.3, E8, E46.1, E46.2, and E80 coding sequence. When an W20.1, W20.2, B3, E74.3, E74.4, E82.2, E82.3, E8, E46.1, E46.2, and E80 allele does not encode the identical sequence to that found in SEQ ID NO:1, 4, 6, 9, 12, 14, or 17, it can be isolated and identified as W20.1, W20.2, B3, E74.3, E74.4, E82.2, E82.3, E8, E46.1, E46.2, and E80 using the same techniques used herein, and especially PCR techniques to amplify the appropriate gene with primers based on the sequences disclosed herein.

One skilled in the art will realize that organisms other than GE will also contain W20.1, W20.2, B3, E74.3, E74.4, E82.2, E82.3, E8, E46.1, E46.2, and E80 genes. The invention is intended to include, but not be limited to, W20.1, W20.2, B3, E74.3, E74.4, E82.2, E82.3, E8, E46.1, E46.2, and E80 nucleic acid molecules isolated from the above-described organisms. Also, infected eukaryotes (for example, mammals, birds, fish and humans) may contain the W20.1, W20.2, B3, E74.3, E74.4, E82.2, E82.3, E8, E46.1, E46.2, and E80 proteins genes.

B. Synthesis of Nucleic Acid

Isolated nucleic acid molecules of the present invention are also meant to include those chemically synthesized. For example, a nucleic acid molecule with the nucleotide sequence which codes for the expression product of an W20.1, W20.2, B3, E74.3, E74.4, E82.2, E82.3, E8, E46.1, E46.2, and E80 gene can be designed and, if necessary, divided into appropriate smaller fragments. Then an oligomer which corresponds to the nucleic acid molecule, or to each of the divided fragments, can be synthesized. Such synthetic oligonucleotides can be prepared, for example, by the triester method of Matteucci et al., *J. Am. Chem. Soc.* 103:3185–3191 (1981) or by using an automated DNA synthesizer.

An oligonucleotide can be derived synthetically or by cloning. If necessary, the 5'-ends of the oligomers can be phosphorylated using T4 polynucleotide kinase. Kinasing of single strands prior to annealing or for labeling can be achieved using an excess of the enzyme. If kinasing is for the labeling of probe, the ATP can contain high specific activity radioisotopes. Then, the DNA oligomer can be subjected to annealing and ligation with T4 ligase or the like.

II. Recombinantly Produced W20.1, W20.2, B3, E74.3, E74.4, E82.2, E82.3, E8, E46.1, E46.2, and E80 Polypeptides In another embodiment, the present invention relates to a purified polypeptide (preferably, substantially pure) having an amino acid sequence corresponding to W20.1, W20.2, B3, E74.3, E74.4, E82.2, E82.3, E8, E46.1, E46.2, and E80, or a functional derivative thereof. In a preferred embodiment, the polypeptide has the amino acid sequence set forth in SEQ ID NO:2, 3, 5, 7, 8, 10, 11, 13, 15, 16, or 18 or mutant or species variation thereof, or at least 60% identity or at least 85% similarity thereof (preferably, at least 90%, 95%, 96%, 97%, 98%, or 99% identity or at least 95%, 96%, 97%, 98%, or 99% similarity thereof), or at least 6 contiguous amino acids thereof (preferably, at least 10, 15, 20, 25, or 50 contiguous amino acids thereof).

In a preferred embodiment, the invention relates to W20.1, W20.2, B3, E74.3, E74.4, E82.2, E82.3, E8, E46.1, E46.2, and E80 epitopes. The epitope of these polypeptides is an immunogenic or antigenic epitope. An immunogenic epitope is that part of the protein which elicits an antibody response when the whole protein is the immunogen. An antigenic epitope is a fragment of the protein which can elicit an antibody response. Methods of selecting antigenic epitope fragments are well known in the art. See, Sutcliffe et al., *Science* 219:660–666 (1983). Antigenic epitope-bearing peptides and polypeptides of the invention are useful to raise an immune response that specifically recognizes the polypeptides.

Amino acid sequence variants of W20.1, W20.2, B3, E74.3, E74.4, E82.2, E82.3, E8, E46.1, E46.2, and E80 can be prepared by mutations in the DNA. Such variants include, for example, deletions from, or insertions or substitutions of, residues within the amino acid sequence shown in SEQ ID NO:2, 3, 5, 7, 8, 10, 11, 13, 15, 16, or 18. Any combination of deletion, insertion, and substitution can also be made to arrive at the final construct, provided that the final construct possesses the desired activity.

While the site for introducing an amino acid sequence variation is predetermined, the mutation per se need not be predetermined. For example, to optimize the performance of a mutation at a given site, random mutagenesis can be conducted at the target codon or region and the expressed W20.1, W20.2, B3, E74.3, E74.4, E82.2, E82.3, E8, E46.1, E46.2, and E80 variants screened for the optimal combination of desired activity. Techniques for making substitution mutations at predetermined sites in DNA having a known sequence are well known, for example, site-specific mutagenesis.

Preparation of a W20.1, W20.2, B3, E74.3, E74.4, E82.2, E82.3, E8, E46.1, E46.2, and E80 variant in accordance herewith is preferably achieved by site-specific mutagenesis of DNA that encodes an earlier prepared variant or a nonvariant version of the protein. Site-specific mutagenesis allows the production of W20.1, W20.2, B3, E74.3, E74.4, E82.2, E82.3, E8, E46.1, E46.2, and E80 variants through the use of specific oligonucleotide sequences that encode the DNA sequence of the desired mutation. In general, the technique of site-specific mutagenesis is well known in the art, as exemplified by publications such as Adelman et al., *DNA* 2:183 (1983) and Ausubel et al. "Current Protocols in Molecular Biology", J. Wiley & Sons, NY, N.Y., 1996. As will be appreciated, the site-specific mutagenesis technique can employ a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, Editor A. Walton, Elsevier, Amsterdam (1981). These phage are readily commercially available and their use is generally well known to those skilled in the art. Alternatively, plasmid vectors that contain a single-stranded phage origin of replication (Vieira et al., *Meth. Enzymol.* 153:3 (1987)) can be employed to obtain single-stranded DNA.

In general, site-directed mutagenesis in accordance herewith is performed by first obtaining a single-stranded vector that includes within its sequence a DNA sequence that encodes the relevant protein. An oligonucleotide primer bearing the desired mutated sequence is prepared, generally synthetically, for example, by the method of Crea et al., *Proc. Natl. Acad. Sci.* (USA) 75:5765 (1978). This primer is then annealed with the single-stranded protein-sequence-containing vector, and subjected to DNA-polymerizing enzymes such as *E. coli* polymerase I Klenow fragment, to complete the synthesis of the mutation-bearing strand. Thus, a mutated sequence and the second strand bears the desired mutation. This heteroduplex vector is then used to transform appropriate cells and clones are selected that include recombinant vectors bearing the mutated sequence arrangement.

After such a clone is selected, the mutated protein region can be removed and placed in an appropriate vector for protein production, generally an expression vector of the type that can be employed for transformation of an appropriate host.

Amino acid sequence deletions generally range from about 1 to 30 residues, more preferably 1 to 10 residues, and typically are contiguous.

Amino acid sequence insertions include amino and/or carboxyl- terminal fusions of from one residue to polypeptides of essentially unrestricted length, as well as intrasequence insertions of single or multiple amino acid residues. Intrasequence insertions (i.e., insertions within the complete W20.1, W20.2, B3, E74.3, E74.4, E82.2, E82.3, E8, E46.1 and E80 sequence) can range generally from about 1 to 10 residues, more preferably 1 to 5.

The third group of variants are those in which at least one amino acid residue in the W20.1, W20.2, B3, E74.3, E74.4, E82.2, E82.3, E8, E46.1, E46.2, and E80 molecule, and preferably, only one, has been removed and a different residue inserted in its place. Such substitutions preferably are made in accordance with the following non-limiting examples in Table 1 when it is desired to modulate finely the characteristics of W20.1, W20.2, B3, E74.3, E74.4, E82.2, E82.3, E8, E46.1, E46.2, and E80.

TABLE 1

| Original Residue | Exemplary Substitutions |
| --- | --- |
| Ala | gly; ser |
| Arg | lys |
| Asn | gin; his |
| Asp | glu |
| Cys | ser |
| Gln | asn |
| Glu | asp |
| Gly | ala; pro |
| His | asn; gin |
| Ile | leu; val |
| Leu | ile; val |
| Lys | arg; gln; glu |
| Met | leu; tyr; ile |
| Phe | met; leu; tyr |
| Ser | thr |
| Thr | ser |
| Trp | tyr |
| Tyr | trp; phe |
| Val | ile; leu |

Substantial changes in functional or immunological identity are made by selecting substitutions that are less conservative than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected are those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine.

Some deletions and insertions, and substitutions are not expected to produce radical changes in the characteristics of W20.1, W20.2, B3, E74.3, E74.4, E82.2, E82.3, E8, E46.1, E46.2, and E80. However, when it is difficult to predict the exact effect of the substitution, deletion, or insertion in advance of doing so, one skilled in the art will appreciate that the effect will be evaluated by routine screening assays. For example, a variant typically is made by site-specific mutagenesis of the native W20.1, W20.2, B3, E74.3, E74.4, E82.2, E82.3, E8, E46.1, E46.2, and E80 encoding- nucleic acid, expression of the variant nucleic acid in recombinant cell culture, and, optionally, purification from the cell culture, for example, by immunoaffinity adsorption on a column (to absorb the variant by binding it to at least one remaining immune epitope). The activity of the cell lysate or purified W20.1, W20.2, B3, E74.3, E74.4, E82.2, E82.3, E8, E46.1, E46.2, and E80 molecule variant is then screened in a suitable screening assay for the desired characteristic. For example, a change in the immunological character of the W20.1, W20.2, B3, E74.3, E74.4, E82.2, E82.3, E8, E46.1, E46.2, and E80 molecule, such as affinity for a given antibody, is measured by a competitive type immunoassay. Changes in immunomodulation activity are measured by the appropriate assay. Modifications of such protein properties as redox or thermal stability, hydrophobicity, susceptibility to proteolytic degradation or the tendency to aggregate with carriers or into multimers are assayed by methods well known to the ordinarily skilled artisan.

A variety of methodologies known in the art can be utilized to obtain the peptide of the present invention. In one embodiment, the peptide is purified from tissues or cells which naturally produce the peptide. Alternatively, the above-described isolated nucleic acid fragments can be used to express the W20.1, W20.2, B3, E74.3, E74.4, E82.2, E82.3, E8, E46.1, E46.2, and E80 protein in any organism. The samples of the present invention include cells, protein extracts or membrane extracts of cells, or biological fluids. The sample will vary based on the assay format, the detection method and the nature of the tissues, cells or extracts used as the sample.

Any prokaryotic (preferably, a GE) organism can be used as a source for the peptide of the invention, as long as the source organism naturally contains such a peptide. A eukaryotic organism infected with GE can also be used as the source organism. As used herein, "source organism" refers to the original organism from which the amino acid sequence of the subunit is derived, regardless of the organism the subunit is expressed in and ultimately isolated from.

One skilled in the art can readily follow known methods for isolating proteins in order to obtain the peptide free of natural contaminants. These include, but are not limited to: immunochromotography, size-exclusion chromatography, HPLC, ion-exchange chromatography, and immuno-affinity chromatography.

III. A Nucleic Acid Probe for the Specific Detection of W20.1, W20.2, B3, E74.3, E74.4, E82.2, E82.3, E8, E46.1, E46.2, and E80

In another embodiment, the present invention relates to a nucleic acid probe for the specific detection of the presence of W20.1, W20.2, B3, E74.3, E74.4, E82.2, E82.3, E8, E46.1, E46.2, and E80 nucleic acid in a sample comprising the above-described nucleic acid molecules or at least a fragment thereof which binds under stringent conditions to W20.1, W20.2, B3, E74.3, E74.4, E82.2, E82.3, E8, E46.1, E46.2, and E80 nucleic acid.

In one preferred embodiment, the present invention relates to an isolated nucleic acid probe consisting of 10 to 1000 nucleotides (preferably, 10 to 500, 10 to 100, 10 to 50, 10 to 35, 20 to 1000, 20 to 500, 20 to 100, 20 to 50, or 20 to 35) which hybridizes preferentially to RNA or DNA of GE but not to RNA or DNA of non-GE organisms (example, humans), wherein said nucleic acid probe is or is complementary to a nucleotide sequence consisting of at least 10 consecutive nucleotides (preferably, 15, 20, 25, or 30) from the nucleic acid molecule comprising a polynucleotide sequence at least 90% identical to a sequence selected from the group consisting of:

(a) a nucleotide sequence encoding the W20.1, W20.2, B3, E74.3, E74.4, E82.2, E82.3, E8, E46.1, E46.2, and E80 polypeptide comprising the complete amino acid sequence in SEQ ID NO:2, 3, 5, 7, 8, 10, 11, 13, 15, 16, or 18;

(b) a nucleotide sequence encoding the W20.1, W20.2, B3, E74.3, E74.4, E82.2, E82.3, E8, E46.1, E46.2, and E80 polypeptide comprising the complete amino acid sequence;

(c) a nucleotide sequence complementary to any of the nucleotide sequences in (a) or (b); and (d) a nucleotide sequence as previously described above.

The nucleic acid probe can be used to probe an appropriate chromosomal or cDNA library by usual hybridization methods to obtain another nucleic acid molecule of the present invention. A chromosomal DNA or cDNA library can be prepared from appropriate cells according to recognized methods in the art (cf. *Molecular Cloning: A Laboratory Manual, second edition,* edited by Sambrook, Fritsch, & Maniatis, Cold Spring Harbor Laboratory, 1989).

In the alternative, chemical synthesis is carried out in order to obtain nucleic acid probes having nucleotide sequences which correspond to N-terminal and C-terminal portions of the W20.1, W20.2, B3, E74.3, E74.4, E82.2, E82.3, E8, E46.1, E46.2, and E80 amino acid sequence. Thus, the synthesized nucleic acid probes can be used as primers in a polymerase chain reaction (PCR) carried out in accordance with recognized PCR techniques, essentially according to *PCR Protocols, A Guide to Methods and Applications,* edited by Michael et al., Academic Press, 1990, utilizing the appropriate chromosomal, cDNA or cell line library to obtain the fragment of the present invention.

One skilled in the art can readily design such probes based on the sequence disclosed herein using methods of computer alignment and sequence analysis known in the art (cf. *Molecular Cloning: A Laboratory Manual, second edition,* edited by Sambrook, Fritsch, & Maniatis, Cold Spring Harbor Laboratory, 1989).

The hybridization probes of the present invention can be labeled by standard labeling techniques such as with a radiolabel, enzyme label, fluorescent label, biotin-avidin label, chemiluminescence, and the like. After hybridization, the probes can be visualized using known methods.

The nucleic acid probes of the present invention include RNA, as well as DNA probes, such probes being generated using techniques known in the art.

In one embodiment of the above described method, a nucleic acid probe is immobilized on a solid support. Examples of such solid supports include, but are not limited to, plastics such as polycarbonate, complex carbohydrates such as agarose and sepharose, and acrylic resins, such as polyacrylamide and latex beads. Techniques for coupling nucleic acid probes to such solid supports are well known in the art.

The test samples suitable for nucleic acid probing methods of the present invention include, for example, cells or nucleic acid extracts of cells, or biological fluids. The sample used in the above-described methods will vary based on the assay format, the detection method and the nature of the tissues, cells or extracts to be assayed. Methods for preparing nucleic acid extracts of cells are well known in the art and can be readily adapted in order to obtain a sample which is compatible with the method utilized.

IV. A Method of Detecting The Presence of W20.1, W20.2, B3, E74.3, E74.4, E82.2, E82.3, E8, E46.1, E46.2, and E80 in a Sample In another embodiment, the present invention relates to a method of detecting the presence of W20.1, W20.2, B3, E74.3, E74.4, E82.2, E82.3, E8, E46.1, E46.2, and E80 nucleic acid in a sample comprising a) contacting the sample with the above-described nucleic acid probe, under specific hybridization conditions such that hybridization occurs, and b) detecting the presence of the probe bound to the nucleic acid molecule. Alternatively, in another preferred embodiment, the method of detecting the presence of W20.1, W20.2, B3, E74.3, E74.4, E82.2, E82.3, E8, E46.1, E46.2, and E80 nucleic acid in a sample may comprise a) amplifying the nucleic acid in the sample with the above-described nucleic acid probe wherein the amplification uses PCR techiniques and b) detecting the presence of the amplified nucleic acid molecules. One skilled in the art would select the nucleic acid probe according to techniques known in the art as described above. Samples to be tested include but should not be limited to RNA samples from human tissue.

V. A Kit for Detecting the Presence of W20.1, W20.2, B3, E74.3, E74.4, E82.2, E82.3, E8, E46.1, E46.2, and E80 in a Sample In another embodiment, the present invention relates to a kit for detecting the presence of W20.1, W20.2, B3, E74.3, E74.4, E82.2, E82.3, E8, E46.1, E46.2, and E80 nucleic acid in a sample comprising at least one container means having disposed therein the above-described nucleic acid probe. In a preferred embodiment, the kit further comprises other containers comprising one or more of the following: wash reagents and reagents capable of detecting the presence of bound nucleic acid probe. Examples of detection reagents include, but are not limited to radiolabelled probes, enzymatic labeled probes (horseradish peroxidase, alkaline phosphatase), and affinity labeled probes (biotin, avidin, or steptavidin).

In detail, a compartmentalized kit includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which contain wash reagents (such as phosphate buffered saline, Tris-buffers, and the like), and containers which contain the reagents used to detect the hybridized probe, bound antibody, amplified product, or the like.

One skilled in the art will readily recognize that the nucleic acid probes described in the present invention can readily be incorporated into one of the established kit formats which are well known in the art.

VI. DNA Constructs Comprising a W20.1, W20.2, B3, E74.3, E74.4, E82.2, E82.3, E8, E46.1, E46.2, and E80 Nucleic Acid Molecule and Cells Containing These Constructs In another embodiment, the present invention relates to a recombinant DNA molecule comprising, 5' to 3', a promoter effective to initiate transcription in a host cell and the above-described nucleic acid molecules. In another embodiment, the present invention relates to a recombinant DNA molecule comprising a vector and an above-described nucleic acid molecule.

In another embodiment, the present invention relates to a nucleic acid molecule comprising a transcriptional control region functional in a cell, a sequence complimentary to an RNA sequence encoding an amino acid sequence corresponding to the above-described polypeptide, and a transcriptional termination region functional in the cell.

Preferably, the above-described molecules are isolated and/or purified DNA molecules.

In another embodiment, the present invention relates to a cell or non-human organism that contains an above-described nucleic acid molecule.

In another embodiment, the peptide is purified from cells which have been altered to express the peptide.

As used herein, a cell is said to be "altered to express a desired peptide" when the cell, through genetic manipulation, is made to produce a protein which it normally does not produce or which the cell normally produces at low levels. One skilled in the art can readily adapt procedures for introducing and expressing either genomic, cDNA, or synthetic sequences into either eukaryotic or prokaryotic cells.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression can vary from organism to organism, but shall in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

If desired, the non-coding region 3' to the W20.1, W20.2, B3, E74.3, E74.4, E82.2, E82.3, E8, E46.1, E46.2, or E80 coding sequence can be obtained by the above-described methods. This region can be retained for its transcriptional termination regulatory sequences, such as termination and polyadenylation. Thus, by retaining the 3'-region naturally contiguous to the DNA sequence encoding an W20.1, W20.2, B3, E74.3, E74.4, E82.2, E82.3, E8, E46.1, E46.2, or E80 gene, the transcriptional termination signals can be provided. Where the transcriptional termination signals are not satisfactorily functional in the expression host cell, then a 3' region functional in the host cell can be substituted.

Two DNA sequences (such as a promoter region sequence and a W20.1, W20.2, B3, E74.3, E74.4, E82.2, E82.3, E8, E46.1, E46.2, and E80 coding sequence) are said to be operably linked if the nature of the linkage between the two DNA sequences does not (1) result in the introduction of a frame-shift mutation, (2) interfere with the ability of the promoter region sequence to direct the transcription of a W20.1, W20.2, B3, E74.3, E74.4, E82.2, E82.3, E8, E46.1, E46.2, and E80 coding sequence, or (3) interfere with the ability of the W20.1, W20.2, B3, E74.3, E74.4, E82.2, E82.3, E8, E46.1, E46.2, and E80 coding sequence to be transcribed by the promoter region sequence. Thus, a promoter region would be operably linked to a DNA sequence if the promoter were capable of effecting transcription of that DNA sequence.

The present invention encompasses the expression of the W20.1, W20.2, B3, E74.3, E74.4, E82.2, E82.3, E8, E46.1, E46.2, and E80 coding sequence (or a functional derivative thereof) in either prokaryotic or eukaryotic cells. Prokaryotic hosts are, generally, the most efficient and convenient for the production of recombinant proteins and, therefore, are preferred for the expression of the W20.1, W20.2, B3, E74.3, E74.4, E82.2, E82.3, E8, E46.1, E46.2, and E80 coding sequence.

Prokaryotes most frequently are represented by various strains of E. coli. However, other microbial strains can also be used, including other bacterial strains. In prokaryotic systems, plasmid vectors that contain replication sites and control sequences derived from a species compatible with the host can be used. Examples of suitable plasmid vectors include pBR322, pUC18, pUC19, pUC118, pUC119 and the like; suitable phage or bacteriophage vectors include λgt10, λgt11 and the like; and suitable virus vectors include pMAM-neo, pKRC and the like. Preferably, the selected vector of the present invention has the capacity to replicate in the selected host cell.

Recognized prokaryotic hosts include bacteria such as E. coli, Bacillus, Streptomyces, Pseudomonas, Salmonella, Serratia, and the like. However, under such conditions, the peptide will not be glycosylated. The prokaryotic host must be compatible with the replicon and control sequences in the expression plasmid.

To express W20.1, W20.2, B3, E74.3, E74.4, E82.2, E82.3, E8, E46.1, E46.2, and E80 in a prokaryotic cell, it is necessary to operably link the W20.1, W20.2, B3, E74.3, E74.4, E82.2, E82.3, E8, E46.1, E46.2, and E80 coding sequence to a functional prokaryotic promoter. Such promoters can be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pBR325, and the like. Examples of inducible prokaryotic promoters include the major right and left promoters of bacteriophage λ ($P_L$ and $P_R$), the trp, recA, lacZ, lacI, and gal promoters of E. coli, the α-amylase (Ulmanen et al., *J. Bacteriol.* 162:176–182 (1985)) and the ζ-28-specific promoters of *B. subtilis* (Gilman et al., *Gene sequence* 32:11–20 (1984)), the promoters of the bacteriophages of Bacillus (Gryczan, In: *The Molecular Biology of the Bacilli*, Academic Press, Inc., NY (1982)), and Streptomyces promoters (Ward et al., *Mol. Gen. Genet.* 203:468–478 (1986)). Prokaryotic promoters are reviewed by Glick (*J. Ind. Microbiol.* 1:277–282 (1987)); Cenatiempo (*Biochimie* 68:505–516 (1986)); and Gottesman (*Ann. Rev. Genet.* 18:415–442 (1984)).

Proper expression in a prokaryotic cell also requires the presence of a ribosome binding site upstream of the gene sequence-encoding sequence. Such ribosome binding sites are disclosed, for example, by Gold et al (*Ann. Rev. Microbiol.* 35:365–404 (1981)).

The selection of control sequences, expression vectors, transformation methods, and the like, are dependent on the type of host cell used to express the gene. As used herein, "cell", "cell line", and "cell culture" can be used interchangeably and all such designations include progeny. Thus, the words "transformants" or "transformed cells" include the primary subject cell and cultures derived therefrom, without regard to the number of transfers. It is also understood that all progeny can not be precisely identical in DNA content, due to deliberate or inadvertent mutations. However, as defined, mutant progeny have the same functionality as that of the originally transformed cell. Host cells which can be used in the expression systems of the present invention are not strictly limited, provided that they are suitable for use in the expression of the W20.1, W20.2, B3, E74.3, E74.4, E82.2, E82.3, E8, E46.1, E46.2, and E80 peptide of interest. Suitable hosts include eukaryotic cells.

Preferred eukaryotic hosts include, for example, yeast, fungi, insect cells, mammalian cells either in vivo, or in tissue culture. Preferred mammalian cells include HeLa cells, cells of fibroblast origin such as VERO or CHO-K1, or cells of lymphoid origin and their derivatives.

In addition, plant cells are also available as hosts, and control sequences compatible with plant cells are available, such as the cauliflower mosaic virus 35S and 19S, and nopaline synthase promoter and polyadenylation signal sequences.

Another preferred host is an insect cell, for example Drosophila larvae. Using insect cells as hosts, the Drosophila alcohol dehydrogenase promoter can be used, Rubin, *Science* 240:1453–1459 (1988). Alternatively, baculovirus vectors can be engineered to express large amounts of W20.1, W20.2, B3, E74.3, E74.4, E82.2, E82.3, E8, E46.1, E46.2, and E80 in insect cells (Jasny, *Science* 238:1653 (1987); Miller et al., In: *Genetic Engineering* (1986), Setlow, J. K., et al., eds., *Plenum*, Vol. 8, pp. 277–297).

Different host cells have characteristic and specific mechanisms for the translational and post-translational processing and modification (e.g., glycosylation, cleavage) of proteins. Appropriate cell lines or host systems can be chosen to ensure the desired modification and processing of the foreign protein expressed.

Any of a series of yeast gene sequence expression systems can be utilized which incorporate promoter and termination elements from the actively expressed gene sequences coding for glycolytic enzymes. These enzymes are produced in large quantities when yeast are grown in mediums rich in glucose. Known glycolytic gene sequences can also provide very efficient transcriptional control signals.

Yeast provides substantial advantages in that it can also carry out post-translational peptide modifications. A number of recombinant DNA strategies exist which utilize strong promoter sequences and high copy number of plasmids which can be utilized for production of the desired proteins in yeast. Yeast recognizes leader sequences on cloned mammalian gene sequence products and secretes peptides bearing leader sequences (i.e., pre-peptides). For a mammalian host, several possible vector systems are available for the expression of W20.1, W20.2, B3, E74.3, E74.4, E82.2, E82.3, E8, E46.1, E46.2, and E80.

A wide variety of transcriptional and translational regulatory sequences can be employed, depending upon the nature of the host. The transcriptional and translational regulatory signals can be derived from viral sources, such as adenovirus, bovine papilloma virus, simian virus, or the like, where the regulatory signals are associated with a particular gene sequence which has a high level of expression. Alternatively, promoters from mammalian expression products, such as actin, collagen, myosin, and the like, can be employed. Transcriptional initiation regulatory signals can be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

As discussed above, expression of W20.1, W20.2, B3, E74.3, E74.4, E82.2, E82.3, E8, E46.1, E46.2, and E80 in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., *J. Mol. Appl. Gen.* 1:273–288 (1982)); the TK promoter of Herpes virus (McKnight, Cell 31:355–365 (1982)); the SV40 early promoter (Benoist et al., *Nature* (*London*) 290:304–310 (1981)); the yeast gal4 gene sequence promoter (Johnston et al., *Proc. Natl. Acad. Sci. (USA)* 79:6971–6975 (1982); Silver et al., *Proc. Natl. Acad. Sci. (USA)* 81:5951–5955 (1984)) and the CMV immediate-early gene promoter (Thomsen et al., *Proc. Natl. Acad. Sci (USA)* 81:659–663 (1984)).

As is widely known, translation of eukaryotic mRNA is initiated at the codon which encodes the first methionine. For this reason, it is preferable to ensure that the linkage between a eukaryotic promoter and a W20.1, W20.2, B3, E74.3, E74.4, E82.2, E82.3, E8, E46.1, E46.2, and E80 coding sequence does not contain any intervening codons which are capable of encoding a methionine (i.e., AUG). The presence of such codons results either in a formation of a fusion protein (if the AUG codon is in the same reading frame as the W20.1, W20.2, B3, E74.3, E74.4, E82.2, E82.3, E8, E46.1, E46.2, and E80 coding sequence) or a frame-shift mutation (if the AUG codon is not in the same reading frame as the W20.1, W20.2, B3, E74.3, E74.4, E82.2, E82.3, E8, E46.1, E46.2, and E80 coding sequence).

A W20.1, W20.2, B3, E74.3, E74.4, E82.2, E82.3, E8, E46.1, E46.2, and E80 nucleic acid molecule and an operably linked promoter can be introduced into a recipient prokaryotic or eukaryotic cell either as a non-replicating DNA (or RNA) molecule, which can either be a linear molecule or, more preferably, a closed covalent circular molecule. Since such molecules are incapable of autonomous replication, the expression of the gene can occur through the transient expression of the introduced sequence. Alternatively, permanent expression can occur through the integration of the introduced DNA sequence into the host chromosome.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker can provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements can also be needed for optimal synthesis of single chain binding protein mRNA. These elements can include splice signals, as well as transcription promoters, enhancer signal sequences, and termination signals. cDNA expression vectors incorporating such elements include those described by Okayama, *Molec. Cell. Biol.* 3:280 (1983).

In a preferred embodiment, the introduced nucleic acid molecule will be incorporated into a plasmid or viral vector capable of autonomous replication in the recipient host. Any of a wide variety of vectors can be employed for this purpose. Factors of importance in selecting a particular plasmid or viral vector include: the ease with which recipient cells that contain the vector can be recognized and selected from those recipient cells which do not contain the vector; the number of copies of the vector which are desired in a particular host; and whether it is desirable to be able to "shuttle" the vector between host cells of different species.

Preferred prokaryotic vectors include plasmids such as those capable of replication in *E. coli* (such as, for example, pBR322, ColE1, pSC101, pACYC 184, πVX. Such plasmids are, for example, disclosed by Sambrook (cf. *Molecular Cloning: A Laboratory Manual*, second edition, edited by Sambrook, Fritsch, & Maniatis, Cold Spring Harbor Laboratory, 1989). Bacillus plasmids include pC194, pC221, pT127, and the like. Such plasmids are disclosed by Gryczan (In: *The Molecular Biology of the Bacilli*, Academic Press, NY (1982), pp. 307–329). Suitable Streptomyces plasmids include pIJ101 (Kendall et al., *J. Bacteriol.* 169:4177–4183 (1987)), and streptomyces bacteriophages such as φC31 (Chater et al., In: *Sixth International Symposium on Actinomycetales Biology*, Akaderniai Kaido, Budapest, Hungary (1986), pp. 45–54). Pseudomonas plasmids are reviewed by John et al (*Rev. Infect. Dis.* 8:693–704 (1986)), and Izaki (*Jpn. J. Bacteriol.* 33:729–742 (1978)).

Preferred eukaryotic plasmids include, for example, BPV, vaccinia, SV40, 2-micron circle, and the like, or their derivatives. Such plasmids are well known in the art (Botstein et al., *Miami Wntr. Symp.* 19:265–274 (1982); Broach, In: *The Molecular Biology of the Yeast Saccharomyces: Life Cycle and Inheritance*, Cold Spring Harbor Laboratory, Cold Spring Harbor, N.Y., p. 445–470 (1981); Broach, *Cell* 28:203–204 (1982); Bollon et al., *J. Clin. Hematol. Oncol.* 10:39–48 (1980); Maniatis, In: *Cell Biology: A Comprehensive Treatise*, Vol. 3, Gene Sequence Expression, Academic Press, NY, pp. 563–608 (1980)).

Once the vector or nucleic acid molecule containing the construct(s) has been prepared for expression, the DNA construct(s) can be introduced into an appropriate host cell by any of a variety of suitable means, i.e., transformation, transfection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells. Expression of the cloned gene molecule(s) results in the production of W20.1, W20.2, B3, E74.3, E74.4, E82.2, E82.3, E8, E46.1, E46.2, and E80. This can take place in the transformed cells as such, or following the induction of these cells to differentiate (for example, by administration of bromodeoxyuracil to neuroblastoma cells or the like).

VII. An Antibody Having Binding Affinity to a W20.1, W20.2, B3, E74.3, E74.4, E82.2, E82.3, E8, E46.1, E46.2, and E80 Polypeptide and a Hybridoma Containing the Antibody In another embodiment, the present invention relates to an antibody having binding affinity specifically to a W20.1, W20.2, B3, E74.3, E74.4, E82.2, E82.3, E8, E46.1, E46.2, and E80 polypeptide as described above or specifically to a W20.1, W20.2, B3, E74.3, E74.4, E82.2, E82.3, E8, E46.1, E46.2, and E80 polypeptide binding fragment thereof. An antibody binds specifically to a W20.1, W20.2, B3, E74.3, E74.4, E82.2, E82.3, E8, E46.1, E46.2, and E80 polypeptide or binding fragment thereof if it does not bind to non-W20.1, W20.2, B3, E74.3, E74.4, E82.2, E82.3, E8, E46.1, E46.2, and E80 polypeptides. Those which bind selectively to W20.1, W20.2, B3, E74.3, E74.4, E82.2, E82.3, E8, E46.1, E46.2, and E80 would be chosen for use in methods which could include, but should not be limited to, the analysis of altered W20.1, W20.2, B3, E74.3, E74.4, E82.2, E82.3, E8, E46.1, E46.2, and E80 expression in tissue containing W20.1, W20.2, B3, E74.3, E74.4, E82.2, E82.3, E8, E46.1, E46.2, and E80.

The W20.1, W20.2, B3, E74.3, E74.4, E82.2, E82.3, E8, E46.1, E46.2, and E80 of the present invention can be used in a variety of procedures and methods, such as for the generation of antibodies, for use in identifying pharmaceutical compositions, and for studying DNA/protein interaction.

The W20.1, W20.2, B3, E74.3, E74.4, E82.2, E82.3, E8, E46.1, E46.2, and E80 peptide of the present invention can be used to produce antibodies or hybridomas. One skilled in the art will recognize that if an antibody is desired, such a peptide would be generated as described herein and used as an immunogen.

The antibodies of the present invention include monoclonal and polyclonal antibodies, as well as fragments of these antibodies. The invention further includes single chain antibodies. Antibody fragments which contain the idiotype of the molecule can be generated by known techniques. For example, such fragments include but are not limited to: the F(ab')$_2$ fragment; the Fab' fragments, Fab fragments, and Fv fragments.

Of special interest to the present invention are antibodies to W20.1, W20.2, B3, E74.3, E74.4, E82.2, E82.3, E8, E46.1, E46.2, and E80 which are produced in humans, or are "humanized" (i.e. non-immunogenic in a human) by recombinant or other technology. Humanized antibodies can be produced, for example by replacing an immunogenic portion of an antibody with a corresponding, but non-immunogenic portion (i.e. chimeric antibodies) (Robinson, R. R. et al., International Patent Publication PCT/US86/02269; Akira, K. et al., European Patent Application 184,187; Taniguchi, M., European Patent Application 171,496; Morrison, S. L. et al., European Patent Application 173,494; Neuberger, M. S. et al., PCT Application WO 86/01533; Cabilly, S. et al., European Patent Application 125,023; Better, M. et al., Science 240:1041–1043 (1988); Liu, A. Y. et al., Proc. Natl. Acad. Sci. USA 84:3439–3443 (1987); Liu, A. Y. et al., J. Immunol. 139:3521–3526 (1987); Sun, L. K. et al., Proc. Natl. Acad. Sci. USA 84:214–218 (1987); Nishimura, Y. et al., Canc. Res. 47:999–1005 (1987); Wood, C. R. et al., Nature 314:446–449 (1985); Shaw et al., J. Natl. Cancer Inst. 80:1553–1559 (1988)). General reviews of "humanized" chimeric antibodies are provided by Morrison, S. L. (Science, 229:1202–1207 (1985)) and by Oi, V. T. et al., BioTechniques 4:214 (1986)). Suitable "humanized" antibodies can be alternatively produced by CDR or CEA substitution (Jones, P. T. et al., Nature 321:552–525 (1986); Verhoeyan et al., Science 239:1534 (1988); Beidler, C. B. et al., J. Immunol. 141:4053–4060 (1988)).

In another embodiment, the present invention relates to a hybridoma which produces the above-described monoclonal antibody. A hybridoma is an immortalized cell line which is capable of secreting a specific monoclonal antibody.

In general, techniques for preparing monoclonal antibodies and hybridomas are well known in the art (Campbell, "Monoclonal Antibody Technology: Laboratory Techniques in Biochemistry and Molecular Biology," Elsevier Science Publishers, Amsterdam, The Netherlands (1984); St. Groth et al., J. Immunol. Methods 35:1–21 (1980)).

Any animal (mouse, rabbit, and the like) which is known to produce antibodies can be immunized with the selected polypeptide. Methods for immunization are well known in the art. Such methods include subcutaneous or interperitoneal injection of the polypeptide. One skilled in the art will recognize that the amount of polypeptide used for immunization will vary based on the animal which is immunized, the antigenicity of the polypeptide and the site of injection.

The polypeptide can be modified or administered in an adjuvant in order to increase the peptide antigenicity. Methods of increasing the antigenicity of a polypeptide are well known in the art. Such procedures include coupling the antigen with a heterologous protein (such as globulin or β-galactosidase) or through the inclusion of an adjuvant during immunization.

For monoclonal antibodies, spleen cells from the immunized animals are removed, fused with myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz et al., Exp. Cell Res. 175:109–124 (1988)).

Hybridomas secreting the desired antibodies are cloned and the class and subclass is determined using procedures known in the art (Campbell, Monoclonal Antibody Technology: Laboratory Techniques in Biochemistry and Molecular Biology, supra (1984)).

For polyclonal antibodies, antibody containing antisera is isolated from the immunized animal and is screened for the presence of antibodies with the desired specificity using one of the above-described procedures.

In another embodiment of the present invention, the above-described antibodies are detectably labeled. Antibodies can be detectably labeled through the use of radioisotopes, affinity labels (such as biotin, avidin, and the like), enzymatic labels (such as horseradish peroxidase, alkaline phosphatase, and the like) fluorescent labels (such as FITC or rhodamine, and the like), paramagnetic atoms, and the like. Procedures for accomplishing such labeling are well-known in the art, for example, see (Stemberger et al., J. Histochem. Cytochem. 18:315 (1970); Bayer et al., Meth. Enzym. 62:308 (1979); Engval et al., Immunol. 109:129 (1972); Goding, J. Immunol. Meth. 13:215 (1976)). The labeled antibodies of the present invention can be used for in vitro, in vivo, and in situ assays to identify cells or tissues which express a specific peptide.

In another embodiment of the present invention the above-described antibodies are immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "Handbook of Experimental Immunology" 4th Ed., Blackwell Scientific Publications, Oxford, England, Chapter 10 (1986); Jacoby et al., Meth. Enzym. 34 Academic Press, N.Y. (1974)). The immobilized antibodies of the present invention can be used for in vitro, in vivo, and in situ assays as well as in immunochromatography.

Furthermore, one skilled in the art can readily adapt currently available procedures, as well as the techniques, methods and kits disclosed above with regard to antibodies, to generate peptides capable of binding to a specific peptide sequence in order to generate rationally designed antipeptide peptides, for example see Hurby et al., "Application of Synthetic Peptides: Antisense Peptides", In Synthetic Peptides, A User's Guide, W. H. Freeman, NY, pp. 289–307 (1992), and Kaspczak et al., Biochemistry 28:9230–8 (1989).

Anti-peptide peptides can be generated in one of two fashions. First, the anti-peptide peptides can be generated by replacing the basic amino acid residues found in the W20.1, W20.2, B3, E74.3, E74.4, E82.2, E82.3, E8, E46.1, E46.2, and E80 peptide sequence with acidic residues, while maintaining hydrophobic and uncharged polar groups. For example, lysine, arginine, and/or histidine residues are replaced with aspartic acid or glutamic acid and glutamic acid residues are replaced by lysine, arginine or histidine.

VIII. A Method of Detecting a W20.1, W20.2, B3, E74.3, E74.4, E82.2, E82.3, E8, E46.1, E46.2, and E80 Polypeptide or Antibody in a Sample In another embodiment, the present invention relates to a method of detecting a W20.1, W20.2, B3, E74.3, E74.4, E82.2, E82.3, E8, E46.1, E46.2, and E80 polypeptide in a sample, comprising: a) contacting the sample with an above-described antibody (or protein), under conditions such that immunocomplexes form, and b) detecting the presence of the antibody bound to the polypeptide. In detail, the methods comprise incubating a test sample with one or more of the antibodies of the present invention and assaying whether the antibody binds to the test sample. Altered levels of W20.1, W20.2, B3, E74.3, E74.4, E82.2, E82.3, E8, E46.1, E46.2, and E80 in a sample as compared to normal levels can indicate a specific disease.

In a further embodiment, the present invention relates to a method of detecting a W20.1, W20.2, B3, E74.3, E74.4, E82.2, E82.3, E8, E46.1, E46.2, and E80 antibody in a sample, comprising: a) contacting the sample with an above-described W20.1, W20.2, B3, E74.3, E74.4, E82.2, E82.3, E8, E46.1, E46.2, and E80 protein, under conditions such that immunocomplexes form, and b) detecting the presence of the protein bound to the antibody or antibody bound to the protein. In detail, the methods comprise incubating a test sample with one or more of the proteins of the present invention and assaying whether the antibody binds to the test sample. The presence of antibodies to W20.1, W20.2, B3, E74.3, E74.4, E82.2, E82.3, E8, E46.1, E46.2, and E80 may indicate exposure to GE, the potential need for therapy of the affected individual, or GE contamination of a biological sample.

Conditions for incubating an antibody with a test sample vary. Incubation conditions depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard, *An Introduction to Radioimmunoassay and Related Techniques,* Elsevier Science Publishers, Amsterdam, The Netherlands (1986); Bullock et al., *Techniques in Immunocytochemistry,* Academic Press, Orlando, Fla. Vol. 1 (1982), Vol. 2 (1983), Vol. 3 (1985); Tijssen, *Practice and Theory of Enzyme Immunoassays: Laboratory Techniques in Biochemistry and Molecular Biology,* Elsevier Science Publishers, Amsterdam, The Netherlands (1985).

The immunological assay test samples of the present invention include cells, protein or membrane extracts of cells, or biological fluids such as blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is capable with the system utilized.

IX. A Diagnostic Kit Comprising W20.1, W20.2, B3, E74.3, E74.4, E82.2, E82.3, E8, E46.1, E46.2, and E80 Protein or Antibody In another embodiment of the present invention, a kit is provided which contains all the necessary reagents to carry out the previously described methods of detection.

The kit can comprise: i) a first container means containing an above-described antibody, and ii) second container means containing a conjugate comprising a binding partner of the antibody and a label.

The kit can comprise: i) a first container means containing an above-described protein, and preferably, ii) second container means containing a conjugate comprising a binding partner of the protein and a label. More specifically, a diagnostic kit comprises W20.1, W20.2, B3, E74.3, E74.4, E82.2, E82.3, E8, E46.1, E46.2, and E80 protein as described above, to detect antibodies in the serum of potentially infected animals or humans.

In another preferred embodiment, the kit further comprises one or more other containers comprising one or more of the following: wash reagents and reagents capable of detecting the presence of bound antibodies. Examples of detection reagents include, but are not limited to, labeled secondary antibodies, or in the alternative, if the primary antibody is labeled, the chromophoric, enzymatic, or antibody binding reagents which are capable of reacting with the labeled antibody. The compartmentalized kit can be as described above for nucleic acid probe kits.

One skilled in the art will readily recognize that the antibodies described in the present invention can readily be incorporated into one of the established kit formats which are well known in the art.

X. Diagnostic Screening

It is to be understood that although the following discussion is specifically directed to human patients, the teachings are also applicable to any animal which can be infected with GE.

The diagnostic and screening methods of the invention are especially useful for a patient suspected of being at risk for developing ehrlichiosis.

According to the invention, a pre- and post-symptomatic screening of an individual in need of such screening is now possible using DNA encoding the W20.1, W20.2, B3, E74.3, E74.4, E82.2, E82.3, E8, E46.1, E46.2, and E80 protein or fragment thereof of the invention. The screening method of the invention allows a presymptomatic diagnosis of the presence of W20.1, W20.2, B3, E74.3, E74.4, E82.2, E82.3, E8, E46.1, E46.2, and E80 protein or DNA in individuals, and thus an opinion concerning the likelihood that such individual would develop or has developed ehrlichiosis. Early diagnosis is desired to maximize appropriate timely intervention.

In one preferred embodiment of the method of screening, a tissue sample would be taken from an individual, and screened for (1) the presence of the W20.1, W20.2, B3, E74.3, E74.4, E82.2, E82.3, E8, E46.1, E46.2, and E80 DNA coding sequence; (2) the presence of W20.1, W20.2, B3, E74.3, E74.4, E82.2, E82.3, E8, E46.1, E46.2, and E80 mRNA; (3) the presence of W20.1, W20.2, B3, E74.3, E74.4, E82.2, E82.3, E8, E46.1, E46.2, and E80 protein; and/or (4) the presence of antibody to W20.1, W20.2, B3, E74.3, E74.4, E82.2, E82.3, E8, E46.1, E46.2, and E80 protein.

A preferred method of detecting the presence of W20.1, W20.2, B3, E74.3, E74.4, E82.2, E82.3, E8, E46.1, E46.2, and E80 and/or the presence of antibody to W20.1, W20.2, B3, E74.3, E74.4, E82.2, E82.3, E8, E46.1, E46.2, and E80 protein comprises a) contacting the ample with a polypeptide or antibody to a polypeptide having the amino acid sequence of W20.1, W20.2, B3, E74.3, E74.4, E82.2, E82.3, E8, E46.1, E46.2, or E80, or a fragment thereof, under conditions such that immunocomplexes form, and b) detecting the presence of the bound immunocomplexes of antibody and polypeptide.

Individuals not infected with GE do not have GEW20.1, W20.2, B3, E74.3, E74.4, E82.2, E82.3, E8, E46.1, E46.2, and E80 DNA, mRNA, or protein.

The screening and diagnostic methods of the invention do not require that the entire W20.1, W20.2, B3, E74.3, E74.4, E82.2, E82.3, E8, E46.1, E46.2, and E80 coding sequence be used for the probe. Rather, it is only necessary to use a fragment or length of nucleic acid that is sufficient to detect the presence of the W20.1, W20.2, B3, E74.3, E74.4, E82.2, E82.3, E8, E46.1, E46.2, and E80 nucleic acid in a DNA preparation from an individual.

Analysis of nucleic acid specific to GE can be by PCR techniques or hybridization techniques (cf. *Molecular Cloning: A Laboratory Manual, second edition,* edited by Sambrook, Fritsch, & Maniatis, Cold Spring Harbor Laboratory, 1989; Eremeeva et al., *J. Clin. Microbiol.* 32:803–810 (1994) which describes differentiation among spotted fever group Rickettsiae species by analysis of restriction fragment length polymorphism of PCR-amplified DNA). Nucleic acid probes used to analyze GE genomic DNA via PCR analysis have been described in Chen et al., *J. Clin. Microbiol.* 32:589–595 (1994).

XI. Vaccines

In another embodiment, the present invention relates to a vaccine comprising a GE W20.1, W20.2, B3, E74.3, E74.4, E82.2, E82.3, E8, E46.1, E46.2, and E80 protein or a fragment thereof (preferably, an immunologically active fragment) together with a pharmaceutically acceptable diluent, carrier, or excipient, wherein the protein is present in an amount effective to elicit a beneficial immune response in an animal to GE. W20.1, W20.2, B3, E74.3, E74.4, E82.2, E82.3, E8, E46.1, E46.2, and E80 protein may be obtained as described above and using methods well known in the art. An immunologically active fragment comprises an epitope-bearing portion of the protein.

In a further preferred embodiment, the present invention relates to a composition comprising a GE W20.1, W20.2, B3, E74.3, E74.4, E82.2, E82.3, E8, E46.1, E46.2, and E80 protein or fragment thereof (preferably, an immunologically reactive fragment- antigenic epitope) and a carrier.

In another embodiment, the present invention relates to a vaccine comprising a GE W20.1, W20.2, B3, E74.3, E74.4, E82.2, E82.3, E8, E46.1, E46.2, and E80 nucleic acid (preferably, DNA) or a fragment thereof (preferably, a fragment encoding an immunologically active protein or peptide) together with a pharmaceutically acceptable diluent, carrier, or excipient, wherein the nucleic acid is present in an amount effective to elicit a beneficial immune response in an animal to GE. W20.1, W20.2, B3, E74.3, E74.4, E82.2, E82.3, E8, E46.1, E46.2, and E80 nucleic acid may be obtained as described above and using methods well known in the art. An immunologically active fragment comprises an epitope-bearing portion of the nucleic acid.

In a further preferred embodiment, the present invention relates to a composition comprising a GE W20.1, W20.2, B3, E74.3, E74.4, E82.2, E82.3, E8, E46.1, E46.2, and E80 nucleic acid (preferably, DNA) or fragment thereof (preferably, encoding an immunologically reactive protein or fragment—antigenic epitope) and a carrier.

In a further preferred embodiment, the present invention relates to a method of producing an immune response which recognizes GE in a host comprising administering to the host the above-described composition.

In a preferred embodiment, the animal to be protected is selected from the group consisting of humans, horses, deer, cattle, pigs, sheep, dogs, and chickens. In a more preferred embodiment, the animal is a human or a dog.

In a further embodiment, the present invention relates to a method of preventing or inhibiting ehrlichiosis in an animal comprising administering to the animal the above-described vaccine, wherein the vaccine is administered in an amount effective to prevent or inhibit Ehrlichiosis. The vaccine of the invention is used in an amount effective depending on the route of administration. Although intranasal, subcutaneous or intramuscular routes of administration are preferred, the vaccine of the present invention can also be administered by an oral, intraperitoneal or intravenous route. One skilled in the art will appreciate that the amounts to be administered for any particular treatment protocol can be readily determined without undue experimentation. Suitable amounts are within the range of 2 $\mu$g of the W20.1, W20.2, B3, E74.3, E74.4, E82.2, E82.3, E8, E46.1, E46.2, and E80 protein per kg body weight to 100 micrograms per kg body weight (preferably, 2 $\mu$g to 50 $\mu$g, 2 $\mu$g to 25 $\mu$g, 5 $\mu$g to 50 $\mu$g, or 5 $\mu$g to 10 $\mu$g).

Examples of vaccine formulations including antigen amounts, route of administration and addition of adjuvants can be found in Kensil, *Therapeutic Drug Carrier Systems* 13:1–55 (1996), Livingston et al., *Vaccine* 12:1275 (1994), and Powell et al., *AIDS RES, Human Retroviruses* 10:5105 (1994). The vaccine of the present invention may be employed in such forms as capsules, liquid solutions, suspensions or elixirs for oral administration, or sterile liquid forms such as solutions or suspensions. Any inert carrier is preferably used, such as saline, phosphate-buffered saline, or any such carrier in which the vaccine has suitable solubility properties. The vaccines may be in the form of single dose preparations or in multi-dose flasks which can be used for mass vaccination programs. Reference is made to *Remington's Pharmaceutical Sciences,* Mack Publishing Co., Easton, Pa., Osol (ed.) (1980); and *New Trends and Developments in Vaccines,* Voller et al (eds.), University Park Press, Baltimore, Md. (1978), for methods of preparing and using vaccines.

The vaccines of the present invention may further comprise adjuvants which enhance production of antibodies and immune cells. Such adjuvants include, but are not limited to, various oil formulations such as Freund's complete adjuvant (CFA), the dipeptide known as MDP, saponins (ex. QS-21, U.S. Pat. No. 5,047,540), aluminum hydroxide, or lymphatic cytokines. Freund's adjuvant is an emulsion of mineral oil and water which is mixed with the immunogenic substance. Although Freund's adjuvant is powerful, it is usually not administered to humans. Instead, the adjuvant alum (aluminum hydroxide) may be used for administration to a human. Vaccine may be absorbed onto the aluminum hydroxide from which it is slowly released after injection. The vaccine may also be encapsulated within liposomes according to Fullerton, U.S. Pat. No. 4,235,877.

The present invention is described in further detail in the following non-limiting examples.

EXAMPLES

The following protocols and experimental details are referenced in the examples that follow.

Cultivation of GE in HL60 Cells

The GE-infected HL60 cell line, USG3 (ATCC CRL-12239), was obtained by co-culturing HL60 cells (CCL 240) with blood cells from dogs challenged with field collected *Ixodes scapularis* ticks. After degenerative cell morphology became noticeable, the infected cells were passed over fresh uninfected HL60 cells to maintain the culture. USG3 was grown in RPMI 1640 containing 10–20% heat-inactivated fetal bovine serum, 2 mM 1-glutamine, 1 mM sodium pyruvate, 0.1 mM MEM non-essential amino acids and was split into fresh HL60 cells two to three times per week. This procedure is also outlined in Coughlin et al., PCT Application No. PCT/US96/10117 and has also been demonstrated by Goodman et al., N. Eng. J. Med. 334:209–215 (1996).

Purification of GE and DNA Isolation

Two liters of USG3 culture at approximately 80% host cell lysis was centrifuged at 500×g for 15 min at 4° C. to remove host HL60 cell debris. The supernatant was filtered through a Poretics 5 μm polycarbonate membrane, 47 mm in diameter, and a Poretics draining disk under negative pressure. The USG3 filtrate was centrifuged at 8500×g in the RC5B centrifuge for 30 min at 4° C. Following centrifugation, the GE pellet was resuspended in 5 ml 25 mM Tris, pH 8.0, 10 mM $MgCl_2$, and 0.9% NaCl. DNase I was added to a final concentration of 9 μg per ml and the solution was incubated for 15 min at 37° C. Following the incubation, the DNase was inactivated by the addition of EDTA (0.5 ml of 0.5 M EDTA) and the GE was pelleted at 13,000×g in the RC5B centrifuge for 30 min at 4° C.

DNA was isolated from the GE pellet and an uninfected HL60 cell pellet used as a control by the Qiagen genomic DNA isolation method using Genomic tip-100/G (Cat # 10243) and Genomic DNA buffer set #19060.

Preparation of a GE Genomic DNA Library

The GE genomic library was custom prepared by Stratagene, La Jolla, Calif. In brief, the DNA was sheared, ligated to Eco RI linkers and size selected to give fragments 4 to 10 kb in length. The DNA fragments were ligated into the Eco RI site of Lambda Zap II (Bullock et al., *Biotechniques* 5:376–379 (1987)), which contains the lacZ promotor used to drive expression of fusion proteins, and the bacteriophage were amplified using the host strain XL1-Blue MRF' (Stratagene).

Source and Preparation of the Screening Sera

Dog sera: Adult *Ixodes scapularis* ticks collected from regions of the eastern United States having a high incidence of human Lyme disease were applied to dogs as described (Coughlin et al., *J. Infect. Dis.* 171:1049–1052 (1995)). Sera from the dogs was tested for immunoreactivity to *E. equi* by an immunofluorescence assay. Positive sera from infected dogs was pooled and used for immunoscreening of the GE genomic library.

Mouse sera: Proteins contained in SDS-disrupted whole GE were separated by SDS-PAGE and forty-six individual bands were excised from each of two gels, 10% and 15% acrylamide. Each gel fragment was mashed, added to buffer and Ribi adjuvant and used to immunize two mice. Sera with similar immunoreactivity patterns against GE antigen as determined by Western blot were pooled into 4 groups: A, B, C, and D.

Goat sera: A USG3 culture at approximately 80% host cell lysis was centrifuged at 500×g for 15 min at 4° C. to remove host HL60 cell debris. The GE was used to immunize each of two goats six times. Sera was collected after the last immunization and used for immunoscreening of the GE genomic library.

Screening of the Genomic DNA Library

Recombinant bacteriophage were diluted and plated with XL1-Blue MRF' cells on NZY agar plates. Twelve plates were prepared giving approximately 50,000 plaques per plate. Phage were induced to express cloned protein with 10 mM IPTG and transferred to nitrocellulose filters according to the Stratagene protocol. For immunoscreening, filters were blocked in TBS (25 mM Tris HCl, pH 7.5, 0.5M NaCl) containing 0.1% polyoxyethylene 20 cetyl ether (Brij 58) and incubated with either pooled dog sera, one of 4 pooled mouse sera, or the goat sera. The filters were washed and then reacted with either anti-dog HRP conjugated antibody, anti-mouse HRP conjugated antibody, or anti-goat HRP conjugated antibody. The filters were washed again-and developed with 4-chloronaphthol (Bio-Rad).

Positive plaques were isolated, replated and rescreened twice more to achieve purity. The pBluescript phagemids were excised using Stratagene's Exassist/SOLR system to allow characterization of each clone as a plasmid.

DNA Analysis

Restriction enzyme analysis: Standard techniques were followed according to the protocols of Sambrook et al., *Molecular Cloning* (2nd ed.), Cold Spring Harbor Laboratory Press, New York (1989)).

DNA sequencing: Individual clones prepared as pBluescript plasmids were sequenced by the primer walking method.

PCR amplification: DNA oligonucleotide primer sets were designed based on sequencing information from each individual clone (see Table 2). PCR primers were synthesized by Life Technologies, Maryland. Templates for PCR were either purified plasmid DNA, purified GE or HL60 genomic DNA, or phage lysates. All reactions were performed using a Gene Amp 9600 thermal cycler (Perkin-Elmer, Connecticut), GenAmp reagents from Perkin-Elmer, and TaqStart antibody (Clontech, California). The cycling program consisted of 30 cycles, each of 30 s at 94° C., 30 s at 55° C., and 1 min at 72° C., and an additional cycle of 10 min at 72° C.

TABLE 2

| Clone Name | Forward Primer | Reverse Primer |
|---|---|---|
| B3 | GGTGCCTGCGTATTTAACGATG | CGATTAACACGTCTACCAAACCCTC |
| E80 | TGGAAGGCAGTGTTGGTTATGG | CGTGACAGGTTTGGAAGTTCCC |
| E74.3 | GTGCTATTCCGCTGATTATGTCG | GCTCAAGAAAGGCAAATATCGCAG |
| E74.4 | GGATTCTAAAAACCCGTTGGTAGC | GGCTTCTCTCCCGTAGACATGAAC |
| E46.1 | TGTTGAATACGGGGAAAGGGAC | GCGGAGATTTCAGGAGAGAGCTG |
| E46.2 | TGGTTTGGATTACAGTCCAGCG | ACCTGCCCAGTTCACTTACATTC |
| E82.2 | CGGAATGCTCTATGACGTTTGG | CAAAGCAGCAATGTCTTTAGGAGC |
| E82.3 | GGTAGAGGGAATAACAAGTGCCG | GGAGATAGAGTGTGCGTAACGTGG |

TABLE 2-continued

| Clone Name | Forward Primer | Reverse Primer |
|---|---|---|
| W20.1 | TGGCAGAAGACGACTTG | CGTCAAAACACCACTGATCCG |
| W20.2 | GATGATATGGATGGGTTGCGG | AATGCACACCAAAAGCGGC |
| E8 | GCGTCACAGACGAATAAGACGG | AGCGGAGATTACAGGAGAGAGCTG |

Table 2: The sequences (SEQ ID NOS.20–41) of each primer set used to amplify regions of the listed clone are indicated. Each oligonucleotide sequence is shown in the 5' to 3' orientation.

Protein Analysis

Overnight cultures of individual pBluescript containing cultures were diluted 1:25 into TP broth (per liter: 20 g bactotryptone, 2 g $Na_2HPO_4$, 1 g $KH_2PO_4$, 8 g NaCl, 15 g yeast extract) and grown at 37° C. until an $OD_{600}$ of 0.5 to 1 was reached. A 1.5 ml aliquot of culture was taken and pelleted ($T_0$). IPTG was added to a concentration of 5 mM and growth was continued for 3 hours at 37° C. The $OD_{600}$ was read and 1.5 ml of each culture was pelleted ($T_3$). Pellets were resuspended in 5×Laemmli buffer (12% glycerol, 0.2 M Tris-HCl, pH 6.8, 5% SDS, 5% β-mercaptoethanol) at 200 μl per 1 OD unit. Samples were boiled and 10 μl of each were electrophoresed on SDS-PAGE gels. Proteins were transferred to nitrocellulose filters, the filters were blocked in TBS/Brij 58, and the blots were probed with antisera. Blots were then washed and incubated with HRP conjugated secondary antibody. After a final washing step, blots were developed with the Pierce Super Signal Chemiluminesence reagents.

Preparation of GE for Peptide Sequencing

Frozen GE pellets were suspended in 0.4% SD Sin 12.5 mM Tris, pH 6.8 and heated at 90–100° C. for 20 min. Fifty microliters of a cocktail consisting of RNase (33 μg/ml) and aprotinin (0.2 mg/ml) and 9 μl of DNase (0.17 mg/ml) was added per 5 mg pellet weight of GE. Twenty microliters of 25×Boehringer/Mannheim protease cocktail was added per 0.5 ml cell suspension and 2 μl of a PMSF solution (1 M in DMSO) was added just prior to cell disruption. Cells were disrupted in 30 second intervals for a total of 3 min in a mini-beadbeater cell disrupter, Type BX-4 (BioSpec), agitated at room temperature for 30 min and centrifuged at 15,000×g for 10 min. The pellet was suspended in Laemmli sample buffer and adjusted to 1.4 mg SDS per mg protein. Electrophoresis was performed on a 15% SDS-PAGE gel and proteins were transferred onto a 0.2 μm PVDF membrane. Half of the blot was probed with the anti-GE dog sera described above and the other half was stained with Ponceau S. Three protein bands which matched the molecular weights of the three most immunoreactive bands on the Western blot (54.7, 51, and 32.4 kDa) were excised and used for peptide and protein sequencing analysis.

Protein Sequencing

A portion of each band was used for direct N-terminal sequencing. The remaining material was digested with trypsin in situ and separated by RP-HPLC on a ZORBAX C18 (1 mm×150 mm) column. Potential candidates for sequencing were screened by MALDITOF Mass Spectrometry on a Finnigan Lasermat 2000 (Hemel, UK). Protein sequencing was performed by Edman degradation.

Example 1

Clones Isolated Using Convalescent Dog Sera

Over 1000 positive clones were isolated using pooled sera from adult *Ixodes scapularis* challenged, GE-infected dogs to screen the genomic library. This was described in the other provisional application filed concurrently herewith entitled "Granulocytic Ehrlichia Nucleic Acids, Proteins and Methods of Use." One clone (W20) was isolated that did not belong to either group I, II or III. DNA from this clone was sequenced by the primer walking method.

The complete sequence of W20 is shown in FIG. 1. Sequence analysis (MacVector, Oxford Molecular Group) showed that the clone contained two large open reading frames and one small open reading frame encoded by the plus strand of the insert (FIG. 2). There are also two additional small open reading frames in the W20 DNA insert, both on the minus strand. The amino acid sequences of open reading frames 1 and 2 (shown in FIG. 2) are shown underneath the DNA sequence in FIG. 1.

The DNA and amino acid sequences of W20 show that open reading frame 1 (orf 1) is a fusion protein with β-galactosidase. A database search revealed that the encoded protein is homologous to the YbaU protein of *E. coli* and a hypothetical protein of *H. influenzae*. These proteins contain 623 and 594 amino acids respectively compared to 546 amino acids contained in the nonβ-galactosidase portion of W20 orf 1. The W20 orf 2 consists of 514 amino acids and bears some similarity to a predicted coding region of *Methanococccus jannaschii*.

Based on the DNA sequences of each clone, PCR primers were designed to amplify specific regions of each open reading frame (see Table 2 for primer sequences). These reagents served two purposes: 1) to establish that the sequenced genes were derived from GE DNA and not HL60 DNA, and 2) to eliminate duplicate clones prior to plasmid rescue and DNA isolation by using them in PCR of phage lysates.

Primer pairs specific for W20 orf 1 and 2 were used in separate PCR reactions to amplify three different templates: GE DNA, HL60 DNA, or the purified plasmid DNA of the clone. FIG. 3 shows the results obtained for primers of W20-1 (A, lanes 15–17) and W20.2(A, lanes 18–20) using the PCR conditions outlined in the experimental protocols. The W20 clone was specific to GE and was not present in HL60 DNA. In each case, the size of the PCR product using genomic DNA as template was the same as that generated by the purified plasmid DNA.

Figure 4A:
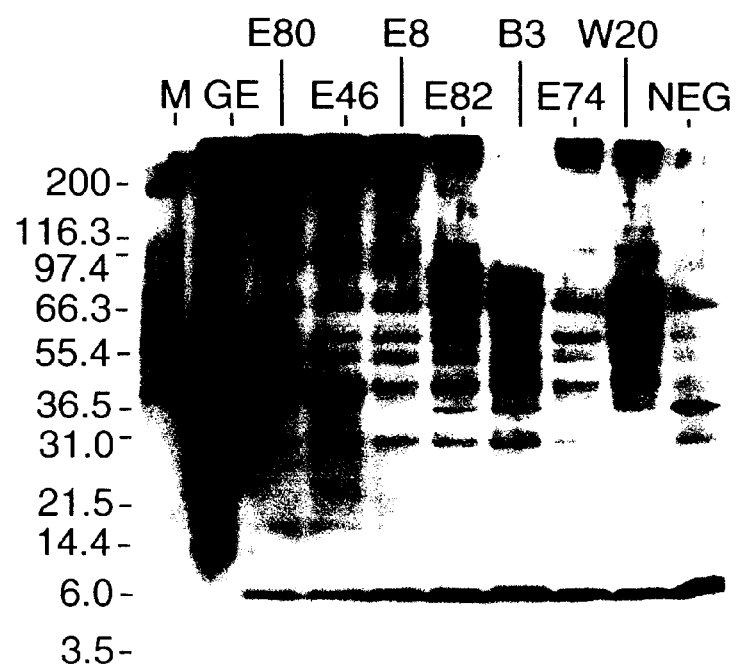
FIG. 4A shows a blot probed with dog sera and FIG. 4B shows a blot probed with goat sera. Individual recombinant clones E80, E46, E8, E82, B3, E76, and W20 were grown and induced by IPTG to induce protein expression according to the specification. Samples of each were electrophoresed on SDS-PAGE gels and transferred to nitrocellulose for Western blotting. SDS-disrupted GE was used as a positive control. Samples are indicated at the top of the gel, which were made in duplicate for the two blots. Molecular weight markers (in kilodaltons) are shown to the left of the blots.

A sample of the recombinant clone was induced to express the encoded protein(s) and bacterial extracts were prepared for SDS-PAGE as outlined in the experimental protocols. FIG. 4 shows two Western blots containing samples of W20 and other GE clones discussed below. SDS-disrupted whole GE was used as a positive control and a non-protein expressing clone was run as a negative control. Blot A was probed with the same pooled dog sera used to screen the library and blot B was probed with GE positive goat serum obtained as described in the experimental protocols. At least two immunoreactive W20 proteins were detected by the dog sera (A) with molecular weights in the range of 60 kDa. The blot probed with goat antisera (B) did not show any reactivity above background for the W20 sample. Based on the amino acid sequences of the proteins encoded by orfs 1 and 2, their calculated molecular weights are 61 kDa and 58 kDa respectively. This is consistent with the Western blot data shown here.

Example 2

Clones Isolated Using Sera from Vaccinated Mice

Four different pools of sera (designated A, B, C, and D) obtained from mice immunized with gel band samples of GE protein were used to screen the GE genomic DNA library. This method was described in the provisional application "Granulocytic Ehrlichia Nucleic Acids, Proteins and Methods of Use" filed herewith. Restriction enzyme analysis showed that all of the clones isolated using the D sera plus one of the clones isolated using the B sera contained the same gene.

Figure 6:
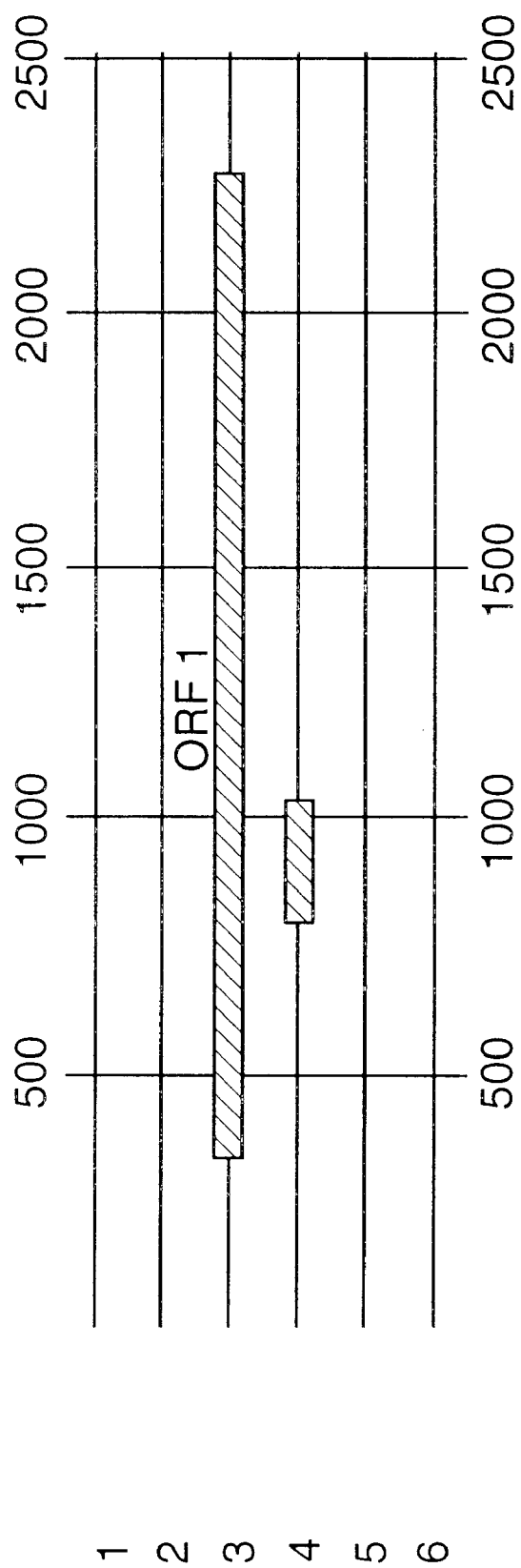
FIG. 6. The ORF map of B3 is shown. The insert contains one large orf (solid bar) on the plus strand and one small orf (hatched bar) on the minus strand.

One representative clone from this group (B3) was selected for DNA sequencing (FIG. 5). The insert contained one large open reading frame on the plus strand and a small open reading frame on the minus strand (FIG. 6). The protein sequence of the large orf is shown below the DNA sequence in FIG. 5. A search of the protein/nucleotide databases revealed that the amino acid sequence of B3 has significant homology to heat shock protein 70.

Figure 7A:
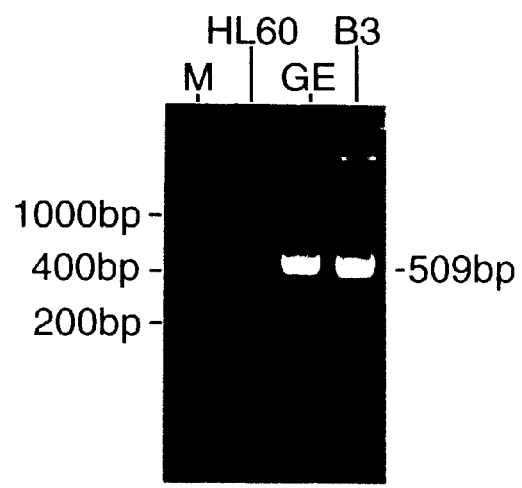
FIGS. 7A, B, and C. show the results of experiments performed with B3, E80, and E74 primers, respectively. B3 primers were used to amplify a 509 bp region of B3 DNA in FIG. 7A using as templates: HL60 DNA, GE DNA, and B3 plasmid DNA. E80 primers were used to amplify a 515 bp region of E80 DNA in FIG. 7B using as templates: HL60 DNA, GE DNA, and E80 plasmid DNA. E74.3 primers were used to amplify a 549 bp region of E74 DNA in FIG. 7C using as templates as shown from left to right after the molecular weight lane: HL60 DNA, GE DNA, and E74 plasmid DNA. E74.4 primers were used to amplify a 456 bp region of E74 DNA in FIG. 7C using as templates starting in the fourth lane moving left to right: HL60 DNA, GE DNA, and E74 plasmid DNA.

PCR primers were designed to amplify a region of the open reading frame contained in B3 (see Table 2 for primer sequences). FIG. 7A shows the results obtained with these primers using GE DNA, HL60 DNA or the B3 plasmid DNA as templates in a PCR reaction. The primer set amplified a region of the expected size using GE or plasmid templates but not the HL60 template. Thus, the B3 gene is GE specific.

The B3 primers were also used to amplify phage lysates from each of the other D clones isolated using the immune mouse sera. The B3 gene was also found in all eleven D clones. (Data not shown.)

The B3 clone was induced to express the encoded protein and a bacterial extract was prepared for SDS-PAGE as outlined in the experimental protocol. FIG. 4 shows Western blots of this sample electrophoresed next to SDS-disrupted whole GE. Both the dog sera (A) and the goat sera (B) reacted with a 70 kDa protein contained in the B3 sample.

Example 3

Clones Isolated Using Sera from Vaccinated Goats

A total of 50,000 plaques were plated and screened with sera from goats immunized with partially purified GE. Eighty-eight of these clones were purified by a secondary screen of the library. From this group sixty-two clones were purified as single plaques by a third immunoscreening. Phage supernatants were screened using PCR primer pairs specific for GE clones already sequenced (i.e., B3). Fifty-one of the clones contained the gene for the GE hsp70 protein (B3). Plasmids were rescued from the remaining eleven clones according to the Stratagene protocol and DNA was purified using Qiagen plasmid purification kits.

Restriction enzyme analysis was performed on each clone to assess their relatedness. Single enzyme digests were performed with EcoRI, Hind III, Bam HI, Hinc II, Xba I, Pst I, Eco RV and Acc I and in some cases a number of double digests were done. Based on these digests restriction maps were generated and several of the clones were found to be related. Two of the clones contained no insert. Four clones, E70, E15, E74, and E43, represented different fragments of the same genomic DNA, two clones (E8 and E33) were the same insert DNA with opposite orientation with respect to the lambda vector, two clones had several restriction fragments in common (E80 and E46) and one clone appeared to be unique (E82).

Figure 4B:
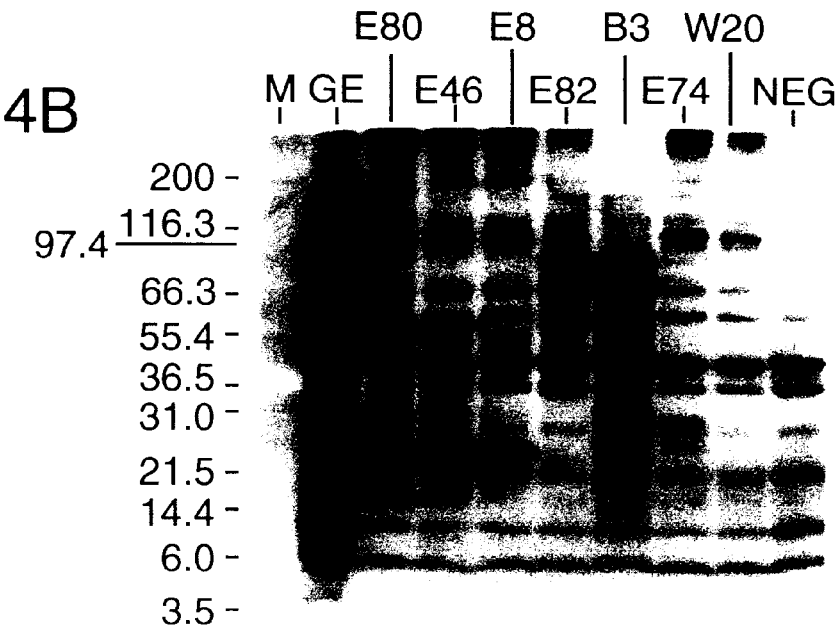
Figure 7B:
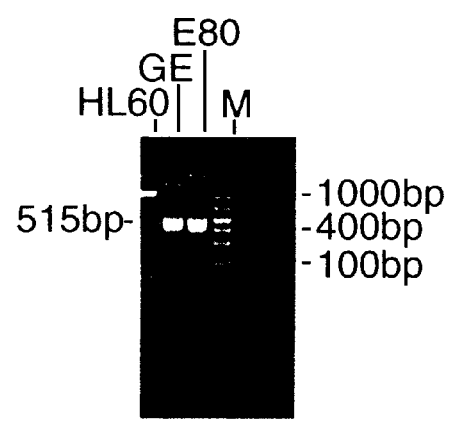
FIG. 7. PCR analysis of GE clones. PCR reactions were performed and the products analyzed using 4% Nusieve gels. Primer sequences are listed in Table 2.
Figure 7C:
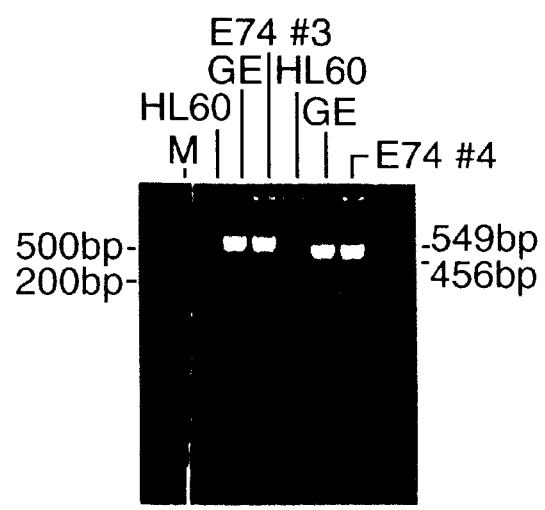
Figure 9:
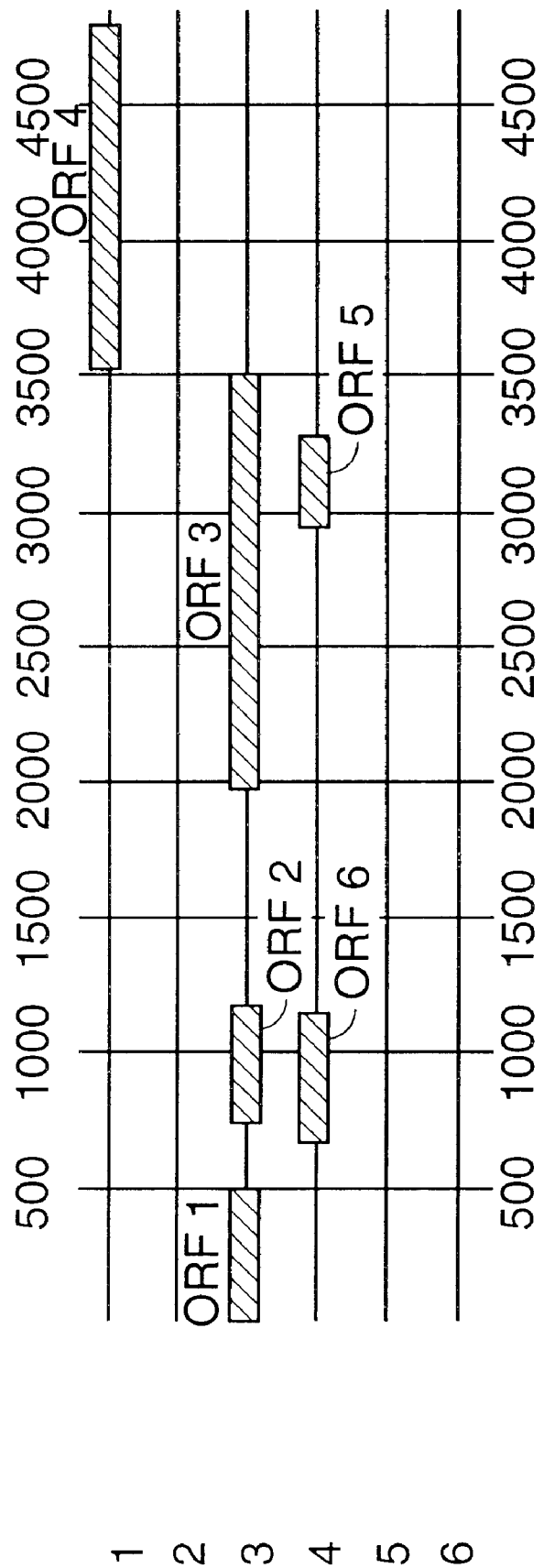
FIG. 9. The ORF map of E74 is shown. The insert contains two large and two small orfs (solid bars) encoded by the plus strand, as well as two small orfs (hatched bars) on the minus strand.

DNA sequencing was performed on the following clones: E74, E8, E80, E46, and E82. The sequence of E74 is shown in FIG. 8 and a diagram showing the open reading frames of 80 amino acids or more is shown in FIG. 9. When this sequence was compared with the other GE sequences obtained thus far it was found that the E74 orf 1 encoded the carboxy terminus of the GE hsp70 protein. This region of the open reading frame is outside the DNA region included in the B3 PCR product amplified by the primers listed in Table 2. Thus, all four clones (E70, E15, E74, and E43) were probably recognized by the goat sera because they contain the carboxy terminus of GE hsp 70. However, E74 does contain other open reading frames (see FIG. 9). Orf 3 potentially encodes a protein of 506 amino acids and 55.6 kDa, which is homologous to NADH dehydrogenase and E. coli HyfB. Orf 4 represents a truncated protein of 437 amino acids and 47.4 kDa, which is related to the E. coli signal recognition particle protein (453 amino acids, 48 kDa). PCR primers designed to amplify regions of these two genes (orfs 3 and 4) did amplify products of the correct size when either the plasmid E74 or GE DNA was used as template for the reaction (FIG. 7C). Western blots of E74 show no specific bands with the dog sera (FIG. 4A) but do show a minor immunoreactive band of about 25 kDa using the goat sera (FIG. 4B). This is consistent with the predicted size of the E74 orf 1 fusion protein.

Figure 3A:
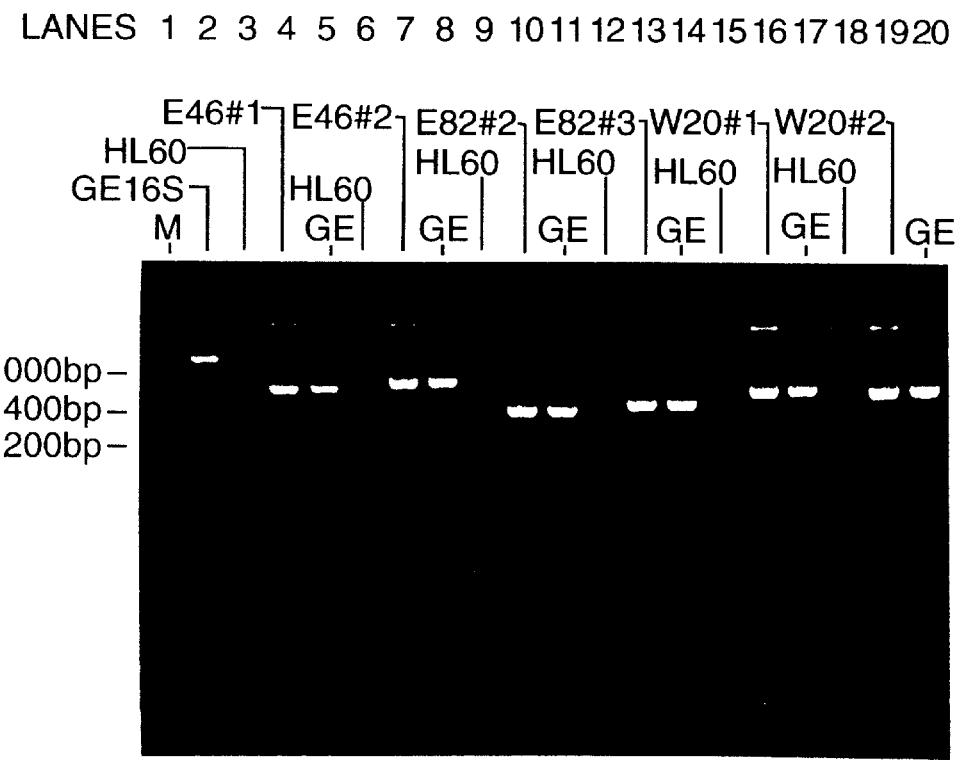
FIG. 3A shows the results of experiments performed with E46.1, E46.2, E82.2, E82.3, W20.1, and W20.2 primers. E46.1 primers were used to amplify a 509 bp region of E46 DNA using as templates: HL60 DNA (lane 3), E46 plasmid DNA (lane 4), and USG3 DNA (lane 5). E46.2 primers were used to amplify a 609 bp region of E46 DNA using as templates: HL60 DNA (lane 6), E46 plasmid DNA (lane 7), and GE DNA (lane 8). E82.2 primers were used to amplify a 371 bp region of E82 DNA using as templates: HL60 DNA (lane 9), E82 plasmid DNA (lane 10), and GE DNA (lane 11). E82.3 primers were used to amplify a 416 bp region of E82 DNA using as templates: HL60 DNA (lane 12), E82 plasmid DNA (lane 13), and GE DNA (lane 14). W20.1 primers were used to amplify a 524 bp region of W20 DNA using as templates: HL60 DNA (lane 15), W20 plasmid DNA (lane 16), and GE DNA (lane 17). W20.2 primers were used to amplify a 505 bp region of W20 DNA using as templates: HL60 DNA (lane 18), W20 plasmid DNA (lane 19), and GE DNA (lane 20). Lane 2 shows the amplification of a 919 bp region of 16S rDNA gene using GE DNA as template and primers specific for 16S rDNA.
Figure 11:
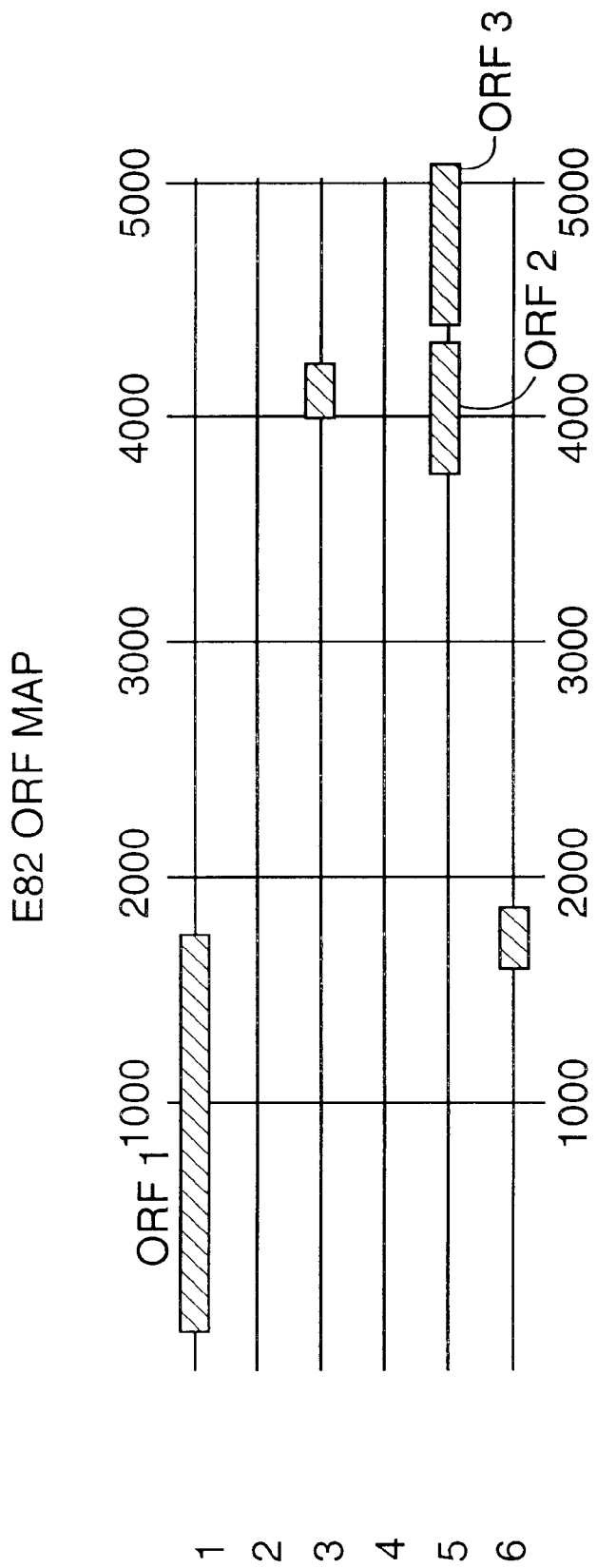
FIG. 11. The ORF map of E82 is shown. The insert contains one large and one small orf (solid bars) on the plus strand of DNA and three small orfs (hatched bars) on the minus strand of DNA.

The sequence of E82 is shown in FIG. 10 and the corresponding open reading frames are shown in FIG. 11. The first open reading frame corresponds to the C-terminal 573 amino acids of S2 (Murphy et al., "Granulocytic Ehrlichia Nucleic Acids, Proteins and Methods of Use" filed herewith). Again, the S2 specific PCR primer set failed to amplify this clone because the primer sequences are located upstream of the S2 insert in E82. There are, however, two additional potential genes located in E82, orf 2 and orf 3. Orf 2 encodes a predicted protein of 201 amino acids and 20.8 kDa, which could be a possible RNA binding protein based on the large number of glycine residues it contains. Orf 3 encodes a predicted protein of 238 amino acids and 27.4 kDa. It has homology to the E. coli yeiL protein (219 amino acids, 25.3 kDa, Reizer et al., FEMS Microbiol. Lett. 118:159–162, (1994)). Based on the E82 orf 2 and 3 sequences, PCR primers were designed to amplify regions of these genes (Table 2). PCR reactions using these primers showed that the genes are GE-specific (FIG. 3A, lanes 8–13).

The Western blots in FIG. 4 show an immunoreactive band at about 75 kDa which is consistent with the predicted size of E82 orf 1, the S2 truncated protein. No other specific immunoreactive bands could be detected with either sera.

Figure 13:
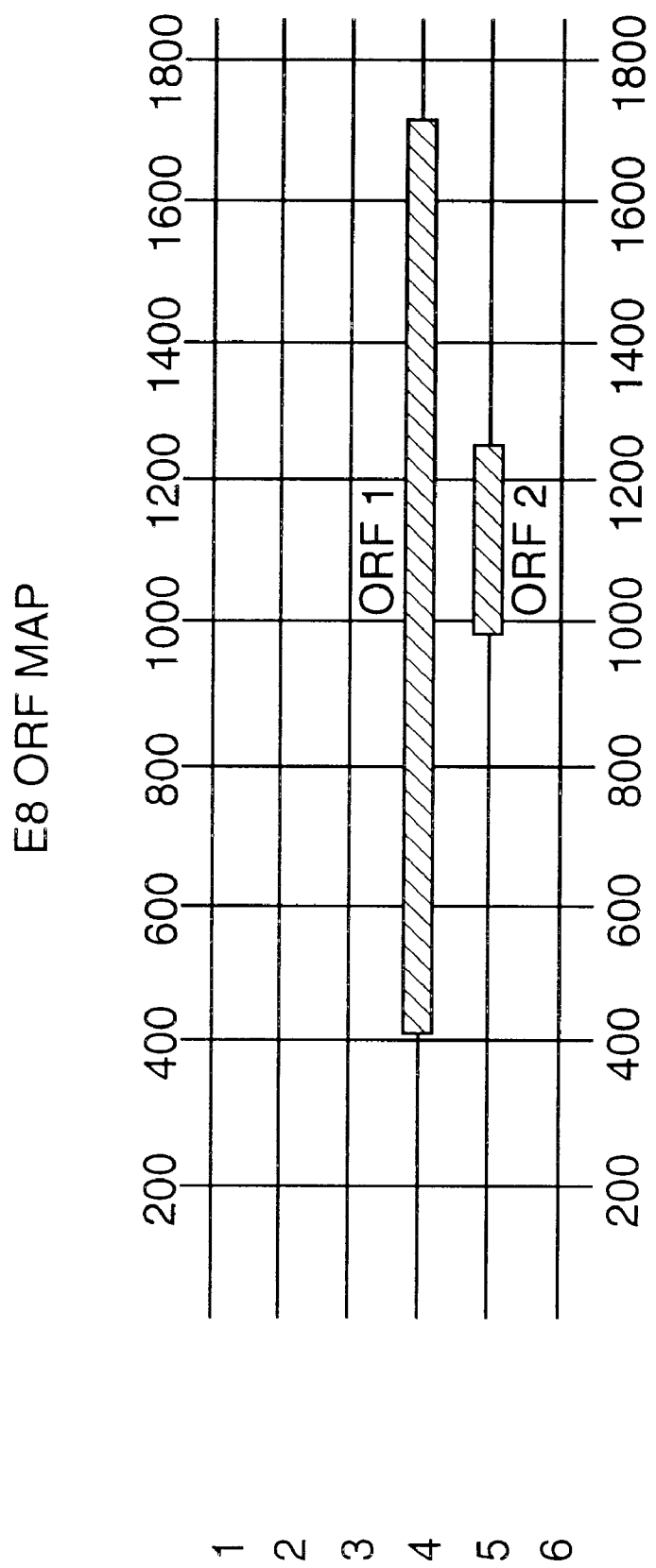
FIG. 13. The ORF map of E8 is shown. The insert contains one large and one small orf on the minus strand.
Figure 15:
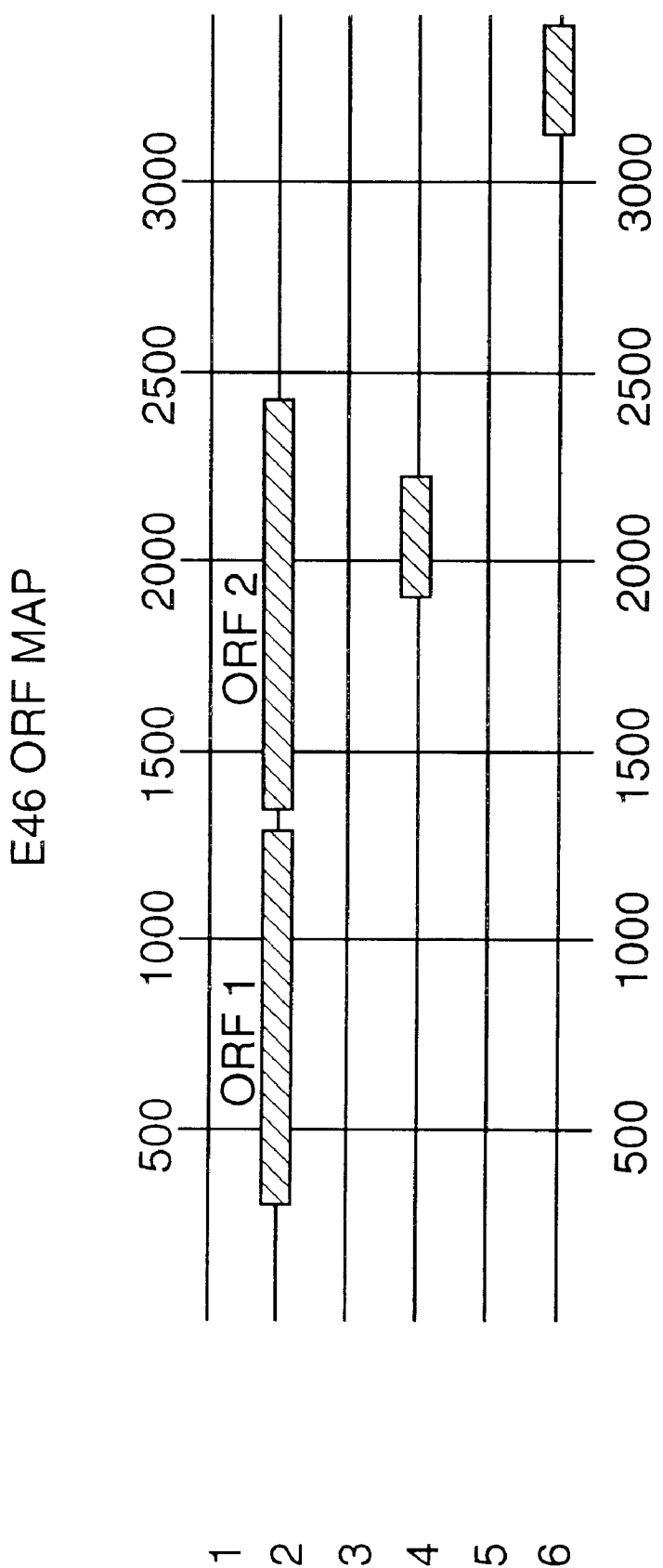
FIG. 15. The ORF map of E46 is shown. The insert contains two large orfs (solid bars) on the plus strand and two small orfs (hatched bars) on the minus strand.
Figure 17:
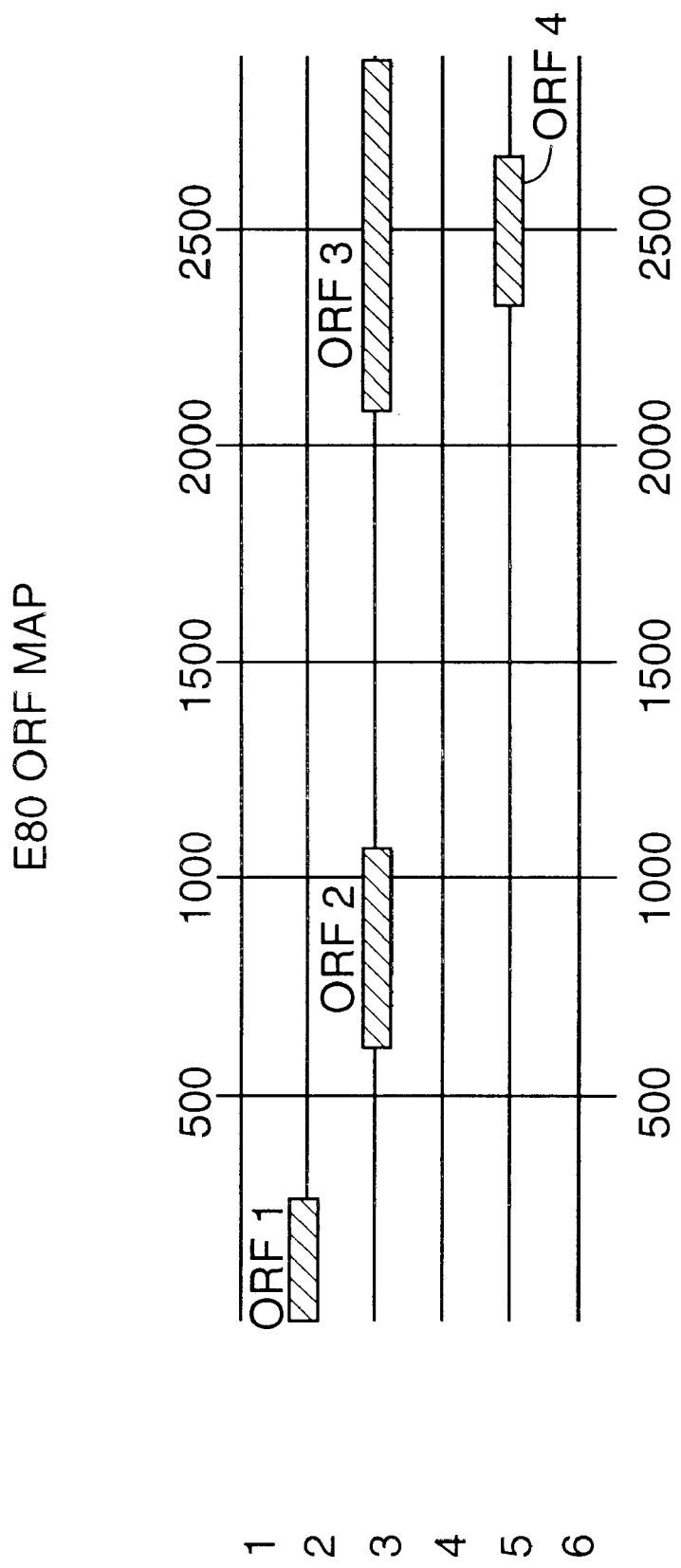
FIG. 17. The ORF map of E80 is shown. The insert contains three orfs (solid bars) on the plus strand and one orf (hatched bar) on the minus strand.

DNA sequences of the remaining three clones E8, E46, and E80, are shown in FIGS. 12, 14, and 16, respectively. The predicted amino acid sequences are shown underneath the corresponding DNA sequences and are depicted as open reading frames in FIGS. 13 (E8), 15 (E46), and 17 (E80). Comparison of E8 orf 1 (435 amino acids, 45.9 kDa), E46 orf 1 (326 amino acids, 34.3 kDa) and orf 2 (364 amino acids, 38.8 kDa), and E80 orf 3 (truncated, 26 kDa) revealed extensive sequence homology among these putative proteins.

Figure 3B:
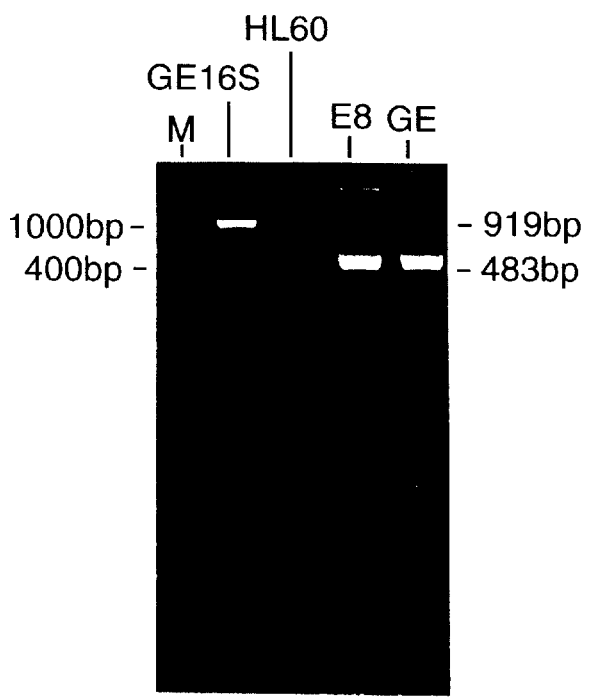
FIG. 3B shows the results of an experiment performed with an E8 primer. Primer sequences are shown in Table 2. E8 primers were used to amplify a 483 bp region of E8 DNA using as templates: HL60 DNA, E8 plasmid DNA, or GE DNA. The second lane shows the amplification of a 919 bp region of 16S rDNA gene using GE DNA as template and primers specific for 16S rDNA.

The protein sequences were aligned using Clustal W (MacVector 6.0, Oxford Molecular Group) and are shown in FIG. 18. Two of the proteins, E80 orf 3 and E46 orf 1, initiate at a methionine which is located approximately 100 amino acids from the N-terminus of E8 orf 1 and E46 orf 2. At this point, all four proteins are largely conserved for the next 90–95 amino acids and then diverge for the next 85 or so amino acids. They then share another large region of conservation at the carboxyl terminus. E80 orf 3 is identical to E46 orf 2 beginning at amino acid 102 of E46 orf 2 up until the point where the E80 insert ends with the exception of one amino acid difference at position 223 of E46 orf 2. All four genes are specific for GE as shown by PCR using sequence specific primers (FIGS. 3A, 3B, and 7B).

When these sequences were compared with those in the protein and nucleotide databases, they were found to share large regions of homology with the MSP-2 proteins of *Anaplasma marginale*. Regions of identity between the protein sequences of the GE MSP-like proteins and *A. marginale* MSP-2 (GenBank accession number UO7862) range from 40 to 46%. FIG. 19 shows a Clustal alignment of the amino acid sequences of E8 and *A. marginale* MSP-2. MSP-2 is part of a multigene family in *A. marginale* (Palmer et al., *Infection and Immunity* 62:3808–3816, (1994)) and it appears that the GE MSP-like genes described here are also part of a multigene family. The MSP-2 proteins *A. marginale* have been used with some success as vaccine candidates (Palmer et al., *Infection and Immunity* 56:1526–1531, (1988)) and thus the proteins encoded by E8, E46, and E80 would also be potential vaccine immunogens.

Samples of the E80, E46, and E8 recombinant clones were induced to express the encoded proteins and analyzed by SDS-PAGE and Western blotting. Immunoreactive bands were detected with the goat sera (FIG. 4B) but the molecular weights of these bands were lower (about 20 kDa) than the predicted sizes of the recombinant proteins. There was a higher molecular weight band in the E46 lane (also seen with the dog sera, FIG. 4A) which corresponds to the molecular weight of E46 orf 2 (38 kDa). The dog sera did not pick up the same lower molecular weight bands as the goat sera and only detected the one specific band for E46. Nothing specific was detected for E8 or E80 using the dog sera. The smaller proteins detected with the goat sera could be due to breakdown of the recombinant proteins at a specific site or to an internal initiation.

Example 4

Peptide Sequencing of GE Specific Proteins

Another approach to defining specific antigens of GE was to use GE proteins isolated by SDS-PAGE for peptide sequencing and design of degenerate primers for PCR. The method used for the preparation of these proteins (54.7, 51, and 32.4 kDa) is outlined in the experimental protocols above. These proteins react strongly with sera from both animals and humans infected with GE (see FIG. 4, GE lane) and are considered to be potential diagnostic targets.

Sequences of the N-terminal peptides and internal peptides from each of the three proteins are listed in Table 3. The 32.4 kDa protein had a blocked N-terminus and therefore could not be sequenced.

TABLE 3

| Protein | N-terminal sequence | Internal sequences |
| --- | --- | --- |
| 54.7 kDa | HDDVSALETGGAGYF | SGDNGSLADYTDGGASQTNK |
|  |  | AVGVSHPGIDK |
| 51 kDa | HDDVSALETGGAGYF | FDWNTPDPR |
|  |  | LSYQLSPVISAFAGGFYH |
| 32.4 kDa | Blocked | HDDVSALETGVAGYFYVGLD |

Other peptide sequences were obtained from the 51 and 32.4 kDa proteins but proved to be actin or trypsin peptides presumably from proteins contaminating the GE sample. When the peptides in Table 3 were compared with amino acid sequences obtained from the genomic library DNA sequencing, all of them, with the exception of the 32.4 kDa peptide, could be found in E8 orf 1, the GE MSP-like protein. FIG. 20 shows the amino acid sequence of E8 orf 1 with the location of these peptides underlined. The peptide sequence listed as N-terminal in Table 3 is an internal peptide in the E8 protein and may indicate that there is a signal sequence that is cleaved to form the mature protein. MSP-2 of *A. marginale* has a similar signal peptide sequence (Palmer et al., *Infection and Immunity* 62:3808–3816, (1994)). Since it is evident from the sequencing completed thus far that GE contains a multigene family composed of E8 and highly related proteins of molecular weights ranging from 32 kDa to 46 kDa, it is not surprising that all three proteins isolated from the protein blotting experiment detailed here contain MSP-like sequences.

The results from the DNA sequencing and the peptide sequencing also indicate that these proteins are not only immunodominant and useful as diagnostic reagents, but that they may be candidates for vaccine antigens as well.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

SEQUENCE LISTING (1) GENERAL INFORMATION:

(iii) NUMBER OF SEQUENCES: 41

(2) INFORMATION FOR SEQ ID NO: 1:

(i) SEQUENCE CHARACTERISTICS:

(A) LENGTH: 4833 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 1:

```
CCGCTCTAGA ACTAGTGGAT CCCCCGGGCT GCAGGAATTC CAAGGAAGTT GTCCTCAAGA        60
ACATGATAGC CGACATGGTC GTTGAAAAGT TTGCTCATGA CTTAGGCATA CGTGTTGGCT       120
CAAATAGCTT ACGGAGTCTG ATCAAAAATA TAAGAATATT TCAGGATGCT AATGGTGTCT       180
TCGACCAGGA GAGATATGAA GCCGTATTGG CTGACAGCGG AATGACTGAG TCGTCCTATG       240
TGAATAAAAT TCGCAATGCT TTACCTTCTA CTATTCTAAT GGAGTGTTTA TTCCCTAATA       300
GGGCGGAATT ACATATTCCT TATTATGATG CATTAGCAAA AGATGTTGTG TTGGGATTGC       360
TGCAGCATCG TGTGGCAGAC ATAGTGGAAA TATCTTCTGA TGCCGTAGAC ATTTCAGGAA       420
GTGATATATC TGATGATGAA TTGCAAAAAT TGTTTGAGGA GCAGTACAAG AATTCTCTAA       480
ATTTCCCTGA ATATCGCAGT GCTGATTATA TAATCATGGC AGAAGACGAC TTGCTTGCTG       540
ATGTCATTGT TTCGGATCAA GAGGTAGACG TTGAGATTAA AACAGTGAA CTACATGATC        600
AAAGAGATGT TCTAAATTTA GTATTTACAG ACAAAAATGA AGCTGAGCTA GCTTACAAAG       660
CTTACCAAGA GGGTAAGTCT TTTGAGGAAT TGGTTAGTGA TGCTGGCTAC ACCATAGAGG       720
ATATTGCACT CAATAATATC TCTAAGGATG TTCTTCCGGT AGGTGTGCGA AATGTGGTGT       780
TTGCACTAAA TGAAGGAGAA GTCAGTGAAA TGTTCCGTAG CGTTGTCGGC TGGCATATCA       840
TGAAGGTAAT AAGGAAGCAT GAGATCACTA AGGAAGACCT AGAAAAGCTG AAAGAGAAGA       900
TATCTTCAAA TATTAGAAGG CAGAAGGCAG GTGAGTTGCT AGTTAGCAAT GTGAAAAAAG       960
CAAACGATAT GATCAGCCGC GGGGCATCGC TGAATGAACT AAAGGATATG TTTGGTGCGC      1020
GGATCAGTGG TGTTTTGACG AATTTTGATA TGCATGGGCT CGATAAATCT GGCAACTTAG      1080
TGAAAGACTT TCCGTTGCAG CTTGGTATAA ACGCCTTTAC TACTTTGGCG TTTTCATCTG      1140
CCGTAGGAAA ACCGTCTCAT CTGGTTAGCA ATGGTGACGC TTATTTCGGC GTTCTTGTTA      1200
CTGAAGTAGT GCCTCCAAGA CCAAGGACAC TTGAAGAAAG CAGGTCTATT CTTACTGAAG      1260
AATGGAAGAG TGCATTACGT ATGAAGAAAA TACGTGAATT TGCTGTGGAG TTGCGCTCGA      1320
AGCTACAAAA TGGCACTGAA TTGTCCGTTG TAAATGGAGT TTCTTTTAAA AAGAATGTCA      1380
CGGTAAAAAA GTCAGATGGC TCTACCGACA ATGATAGCAA GTATCCTGAA CGCTTAGTCG      1440
ATGAGATATT CGCCATTAAC ATTGGTGGAG TAACGAAAGA AGTTATAGAT TCTGAATCTG      1500
AGACTGTATA CATTGCTCTG CTTAAAGAAA TAAAAGATGC TGAAATAAGT GAGGAGGATC      1560
TAGAGAGCTA CAAGGCACAT TTTGTTAGTA GTGGCATCCT ATCTATAAGA GAGCAGCTCT      1620
TAGGTTATTT GATGAAAAAA TACGGAGTAA CGATCGAAAA TAGTTTGCTA GAGAAAGTGT      1680
AATTACGTAC TTTCCTAAGG CTATTTTGTT TTTAGGATGA AGCGCGTTAG TGGATTTTAG      1740
TATCCTGTGT GTGCATCGTA TATGTACAGT ATATGCTTCG TTACATATGG ATATGATATT      1800
GTCGATGAAG GTTTTGCTTT CTGATATAGG AAAACTCTTG GCATTGCTGT TATATTACGA      1860
AGAGAGAGGC GTTTCGCAAG TAGGATAGTG TGCACGCAGA TAATGATTAA CTGTAAACTC      1920
ATGTGTCGCT GCTAAGTAGC TTATATTGCC GGATGATGAA ATTACAGGCA TTTTCTTAGT      1980
```

```
GCTGGGTAAC ATTGTAATTA AGTAAGTTAT ACTTATAAAA ATAATGAATA TTTGCATGCT      2040

GGTGGTGGAG CAAAACATAT GAAGGGAGAA GTGGTATCTT GGCCGTTTAT AGAAGCTGAA      2100

AAAATTTTAA AGGCATTTGG TGATAGCGAG GAAATAATAC TTGCTACAGG GTATGGTCCG      2160

TCCGGATTGC CTCATATAGG AACTTTTGGT GAAGTACAAA GAACAGTATA TGTAGCTAAT      2220

GCACTGCGAG AGATCTCTCC TAAAACTAAA ACAAGGATTT TAGCATTCTC TGATGATATG      2280

GATGGGTTGC GGAAAGTTCC TGATAACGTA CCAAACCGTG AAATGCTAGA GAAACATCTG      2340

GGACAGTTAC TGACCTCAAT ACCTGATCCG TTCGGCACAT CCTCAAGCTA TGGCCATCAT      2400

ATGAACGGCA CTTTCTGTGC TTTTTTAGAC AGATTTGGGT TTGAATACGA ATTTATTAGT      2460

GCAACAGAGT GCTACAGATC CGGTAGATAT GATGATGTAC TGCTACGGCT ACTAAGAAAT      2520

TATGATAAGG CCGTAAGCAT ACTGTTGCCA ACACTTGGCG AAGAGCGTCA AAAAACTTAT      2580

AGTCCGTTTC TGCCCATATG TGAAAAAACA TCTAGAGTGC TGCAGGTGAC TATAGTCAAA      2640

ACAGACGTAG AAAAAGGAAC TATTTTTTAT CAAAATGAAG ACGGAGACTT GGTAGAGGTA      2700

AAAGTAACCG GTGGACATTG TAAATTACAG TGGAAAGCTG ATTGGGGAAT GCGTTGGGCC      2760

GCTTTTGGTG TGCATTATGA ATCTCATGGT AAAGACCTAA CTCCTTCTGC TAAACCGTCT      2820

GCAGAAATCT GTAAACTCCT AGGTAGAAGG CCTCCTGTTC TGTTTCCATA TGAACTTTTT      2880

CTTGATAAAG AAGGGAAGAA AATTTCCAAA TCTAAGGGCA ATGGTTTCTC TGTAGAAGAG      2940

TGGCTTGCAT GCGCACCGTA TGAGAGCCTA GCCCTCTATA TGTTTCAAAA CCCGAAAAGG      3000

GCTAAGCGCT TGTGTTCTGA AGTAGTGCCA AAATTTGTAG ATGACTATCT GTCATTATTA      3060

CATAAATACA ATGAGGCTCC TAGTACTCAC AATCCTGTAT GGCATATACA CAACGGTAAT      3120

GTTCCTAAAG TAGAGCTGTA TGGTTTAACT TTTTGTCTAC TCATCAACAT AGCATCAGCG      3180

TGCAATGCAA ACGATGTTGC GATGTTGGAG CAACTCATAA AAATATATAG GGACGGGATT      3240

GATTTAGAGA ACAATACTCT ACTAAGTAGG TTATTAGAGT TCTCTGTTGC GTATTGCAGG      3300

GCATTTGTTA TGCCGTCTAG ATCATATAAA ACACCTACTG CTGAGGAGAG CAACATGTTA      3360

CTTGATCTAG CAAATACTCT TTCTTGCATG GATGACAGTA AATCACCTGA TGAAATACAA      3420

AATGAAGTAT TTGAGGTTGG AAAGAAGTAT CTACAGCCTA GTGATCTACG TATGTGGTTT      3480

AAGATGCTGT ACGAAGTGTT ACTTGGACAG AGTGATGGGC CTAGATTTGG GTCTTTTGTA      3540

AAATTGTATG GTATTGAGAA TACAGTACAG TTAATAAAGC GTAGTATTTC TGCTACTGAA      3600

TAGGAGGAGT CACACCATAA TATGAGTATT GTAGCATCTA TTTTTGGGTT GTTTTTTTGT      3660

GAGTAATGTT GACGAATCAG AGCTGGTGAA GTTCTCAAAT TTGGCTTCAG AATGGTGGGA      3720

TGGGGAGTCT TTTTCAGCTT TGCACAGGAT AAATCCTTTG CGCGTTCAGT ATATTCTTGA      3780

AAATTTACAA GAGGCTACTA ACTCAGGTAA AAGGCTTTTG GATATCGGTT GTGGTGGTGG      3840

GCTTATTTGC GAAGCCATGG CAAGGCTTGG TTTTAGTGTC ACTGGAGTAG ATCCATGTAG      3900

AGAAGGAATA GAAGCTGCTA GACAGCACGC TGCTATCGAA GGCTTAGATA TAGAGTACCA      3960

TTTTACGGAT ATAGAGTCTT TTATACACTC CTCAGAGTGT TCTTCTTACG ATATCATCAC      4020

CTTAATGGAA GTTGTAGAGC ATATCCCTGA TTTGACTGAA TTTTTATCTA GCTCCTGTAA      4080

GTTACTGAAA CCTGGAGGTA TGCTTTTCAT TTCTACACTA AACAGAACTA TCAAATCCAT      4140

GTTACTTGGT AAGATAGCTG CGGAGTATAT ACTTCGCATG GTGCCTCCTG GCACGCACCA      4200

GTGGAAGAAG TTTGTCAAGC CTTCAGAGAT TCACGATGCC CTATTAAAAA GCAGAGTGCT      4260

CGTTAAAGAT ATAAAAGGCA TTACCTATAA AATATTGCAT AACGATTGGG TCTTAAATGA      4320

TAGAGATATA AGTGTAAACT ACATATTAGC CGCTCAAAAA GAGCAATAAT CTACTTAGTG      4380
```

```
ATGTTTATAC GTAGTGTGTA CCACAGAATG TACTACTATT TAGGTTAGGT GTTATAGGCA        4440

TTTCTTTTGC CGTCGTGAAT ACCATATAGC CTTATTCTCT TGTACAAAAA TAGAGCTGCG        4500

CGCGCAGCTT CCACATACTT GCCATAGCTC TTACTTGCTT TTGCATCTTA TAAACCTCGT        4560

ATCTATGTTG AAATGGGAAA TTTAAATAGT TACGACACTA TATCCCCGCT CGACAGTAAA        4620

GCCCTCTTAG CGACTGAACC AGATATAGTA GAAAGAAGTA TTCAAGGGTT AAATACTGAG        4680

AAAAAACAAA ACCACTCATT TCATCTATAA CTGCTCATGC GAGGAAAAGG ATGTTATATC        4740

ACTATAAGTC TGCATAGGCG TAAACCAGGC TCAATAGCAT TTTCGCGTGT AAATAGTGGC        4800

TAGGAATTCG ATATCAAGCT TATCGATACC GTC                                    4833
```

(2) INFORMATION FOR SEQ ID NO: 2:

(i) SEQUENCE CHARACTERISTICS:
        (A) LENGTH: 546 amino acids
        (B) TYPE: amino acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 2:

```
Lys Glu Val Val Leu Lys Asn Met Ile Ala Asp Met Val Val Glu Lys
1               5                   10                  15

Phe Ala His Asp Leu Gly Ile Arg Val Gly Ser Asn Ser Leu Arg Ser
            20                  25                  30

Leu Ile Lys Asn Ile Arg Ile Phe Gln Asp Ala Asn Gly Val Phe Asp
        35                  40                  45

Gln Glu Arg Tyr Glu Ala Val Leu Ala Asp Ser Gly Met Thr Glu Ser
    50                  55                  60

Ser Tyr Val Asn Lys Ile Arg Asn Ala Leu Pro Ser Thr Ile Leu Met
65                  70                  75                  80

Glu Cys Leu Phe Pro Asn Arg Ala Glu Leu His Ile Pro Tyr Tyr Asp
                85                  90                  95

Ala Leu Ala Lys Asp Val Val Leu Gly Leu Leu Gln His Arg Val Ala
            100                 105                 110

Asp Ile Val Glu Ile Ser Ser Asp Ala Val Asp Ile Ser Gly Ser Asp
        115                 120                 125

Ile Ser Asp Asp Glu Leu Gln Lys Leu Phe Glu Glu Gln Tyr Lys Asn
    130                 135                 140

Ser Leu Asn Phe Pro Glu Tyr Arg Ser Ala Asp Tyr Ile Ile Met Ala
145                 150                 155                 160

Glu Asp Asp Leu Leu Ala Asp Val Ile Val Ser Asp Gln Glu Val Asp
                165                 170                 175

Val Glu Ile Lys Asn Ser Glu Leu His Asp Gln Arg Asp Val Leu Asn
            180                 185                 190

Leu Val Phe Thr Asp Lys Asn Glu Ala Glu Leu Ala Tyr Lys Ala Tyr
        195                 200                 205

Gln Glu Gly Lys Ser Phe Glu Glu Leu Val Ser Asp Ala Gly Tyr Thr
    210                 215                 220

Ile Glu Asp Ile Ala Leu Asn Asn Ile Ser Lys Asp Val Leu Pro Val
225                 230                 235                 240
```

-continued

```
Gly Val Arg Asn Val Val Phe Ala Leu Asn Glu Gly Glu Val Ser Glu
                245                 250                 255

Met Phe Arg Ser Val Val Gly Trp His Ile Met Lys Val Ile Arg Lys
                260                 265                 270

His Glu Ile Thr Lys Glu Asp Leu Glu Lys Leu Lys Glu Lys Ile Ser
                275                 280                 285

Ser Asn Ile Arg Arg Gln Lys Ala Gly Glu Leu Leu Val Ser Asn Val
                290                 295                 300

Lys Lys Ala Asn Asp Met Ile Ser Arg Gly Ala Ser Leu Asn Glu Leu
305                 310                 315                 320

Lys Asp Met Phe Gly Ala Arg Ile Ser Gly Val Leu Thr Asn Phe Asp
                325                 330                 335

Met His Gly Leu Asp Lys Ser Gly Asn Leu Val Lys Asp Phe Pro Leu
                340                 345                 350

Gln Leu Gly Ile Asn Ala Phe Thr Thr Leu Ala Phe Ser Ser Ala Val
                355                 360                 365

Gly Lys Pro Ser His Leu Val Ser Asn Gly Asp Ala Tyr Phe Gly Val
                370                 375                 380

Leu Val Thr Glu Val Val Pro Pro Arg Pro Arg Thr Leu Glu Glu Ser
385                 390                 395                 400

Arg Ser Ile Leu Thr Glu Glu Trp Lys Ser Ala Leu Arg Met Lys Lys
                405                 410                 415

Ile Arg Glu Phe Ala Val Glu Leu Arg Ser Lys Leu Gln Asn Gly Thr
                420                 425                 430

Glu Leu Ser Val Val Asn Gly Val Ser Phe Lys Lys Asn Val Thr Val
                435                 440                 445

Lys Lys Ser Asp Gly Ser Thr Asp Asn Asp Ser Lys Tyr Pro Glu Arg
                450                 455                 460

Leu Val Asp Glu Ile Phe Ala Ile Asn Ile Gly Gly Val Thr Lys Glu
465                 470                 475                 480

Val Ile Asp Ser Glu Ser Glu Thr Val Tyr Ile Ala Leu Leu Lys Glu
                485                 490                 495

Ile Lys Asp Ala Glu Ile Ser Glu Glu Asp Leu Glu Ser Tyr Lys Ala
                500                 505                 510

His Phe Val Ser Ser Gly Ile Leu Ser Ile Arg Glu Gln Leu Leu Gly
                515                 520                 525

Tyr Leu Met Lys Lys Tyr Gly Val Thr Ile Glu Asn Ser Leu Leu Glu
                530                 535                 540

Lys Val
545
```

(2) INFORMATION FOR SEQ ID NO: 3:

(i) SEQUENCE CHARACTERISTICS:
        (A) LENGTH: 514 amino acids
        (B) TYPE: amino acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 3:

```
Met Lys Gly Glu Val Val Ser Trp Pro Phe Ile Glu Ala Glu Lys Ile
1               5                   10                  15
```

-continued

```
Leu Lys Ala Phe Gly Asp Ser Glu Glu Ile Ile Leu Ala Thr Gly Tyr
             20                  25                  30

Gly Pro Ser Gly Leu Pro His Ile Gly Thr Phe Gly Glu Val Gln Arg
         35                  40                  45

Thr Val Tyr Val Ala Asn Ala Leu Arg Glu Ile Ser Pro Lys Thr Lys
         50                  55                  60

Thr Arg Ile Leu Ala Phe Ser Asp Asp Met Asp Gly Leu Arg Lys Val
65                  70                  75                  80

Pro Asp Asn Val Pro Asn Arg Glu Met Leu Glu Lys His Leu Gly Gln
             85                  90                  95

Leu Leu Thr Ser Ile Pro Asp Pro Phe Gly Thr Ser Ser Ser Tyr Gly
         100                 105                 110

His His Met Asn Gly Thr Phe Cys Ala Phe Leu Asp Arg Phe Gly Phe
         115                 120                 125

Glu Tyr Glu Phe Ile Ser Ala Thr Glu Cys Tyr Arg Ser Gly Arg Tyr
         130                 135                 140

Asp Asp Val Leu Leu Arg Leu Leu Arg Asn Tyr Asp Lys Ala Val Ser
145                 150                 155                 160

Ile Leu Leu Pro Thr Leu Gly Glu Glu Arg Gln Lys Thr Tyr Ser Pro
                 165                 170                 175

Phe Leu Pro Ile Cys Glu Lys Thr Ser Arg Val Leu Gln Val Thr Ile
             180                 185                 190

Val Lys Thr Asp Val Glu Lys Gly Thr Ile Phe Tyr Gln Asn Glu Asp
         195                 200                 205

Gly Asp Leu Val Glu Val Lys Val Thr Gly Gly His Cys Lys Leu Gln
         210                 215                 220

Trp Lys Ala Asp Trp Gly Met Arg Trp Ala Ala Phe Gly Val His Tyr
225                 230                 235                 240

Glu Ser His Gly Lys Asp Leu Thr Pro Ser Ala Lys Pro Ser Ala Glu
                 245                 250                 255

Ile Cys Lys Leu Leu Gly Arg Arg Pro Pro Val Leu Phe Pro Tyr Glu
             260                 265                 270

Leu Phe Leu Asp Lys Glu Gly Lys Lys Ile Ser Lys Ser Lys Gly Asn
         275                 280                 285

Gly Phe Ser Val Glu Glu Trp Leu Ala Cys Ala Pro Tyr Glu Ser Leu
         290                 295                 300

Ala Leu Tyr Met Phe Gln Asn Pro Lys Arg Ala Lys Arg Leu Cys Ser
305                 310                 315                 320

Glu Val Val Pro Lys Phe Val Asp Asp Tyr Leu Ser Leu Leu His Lys
                 325                 330                 335

Tyr Asn Glu Ala Pro Ser Thr His Asn Pro Val Trp His Ile His Asn
             340                 345                 350

Gly Asn Val Pro Lys Val Glu Leu Tyr Gly Leu Thr Phe Cys Leu Leu
         355                 360                 365

Ile Asn Ile Ala Ser Ala Cys Asn Ala Asn Asp Val Ala Met Leu Glu
         370                 375                 380

Gln Leu Ile Lys Ile Tyr Arg Asp Gly Ile Asp Leu Glu Asn Asn Thr
385                 390                 395                 400

Leu Leu Ser Arg Leu Leu Glu Phe Ser Val Ala Tyr Cys Arg Ala Phe
                 405                 410                 415

Val Met Pro Ser Arg Ser Tyr Lys Thr Pro Thr Ala Glu Glu Ser Asn
             420                 425                 430
```

```
Met Leu Leu Asp Leu Ala Asn Thr Leu Ser Cys Met Asp Asp Ser Lys
        435                 440                 445

Ser Pro Asp Glu Ile Gln Asn Glu Val Phe Glu Val Gly Lys Lys Tyr
        450                 455                 460

Leu Gln Pro Ser Asp Leu Arg Met Trp Phe Lys Met Leu Tyr Glu Val
465                 470                 475                 480

Leu Leu Gly Gln Ser Asp Gly Pro Arg Phe Gly Ser Phe Val Lys Leu
                485                 490                 495

Tyr Gly Ile Glu Asn Thr Val Gln Leu Ile Lys Arg Ser Ile Ser Ala
            500                 505                 510

Thr Glu (2) INFORMATION FOR SEQ ID NO: 4:

(i) SEQUENCE CHARACTERISTICS:
        (A) LENGTH: 2515 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 4:

AAAATGTTGC GGAGGTTGGA GAGAGCGTGG TTGCGGTGAC TTGGGTTGAT AAGTGGTTAA      60

CGCGGATGCT CTCTAAAATA TCGTAAGCAT AGTTAGTGGG GTATTTGAGG CTTTTGGTGC     120

TTCAATATAG AGCTAGTAAC GGGGCGTGAT GTTTGTTGGT AGCGTTTGTA TTACTAGTTT     180

CCTGACATGT ATTGTGCATA TCAGGTCTGT TGTGGTGTAA GGACACGTGT GTTGCTAGGT     240

ATCAGGGACA TATTTCTCTA ATTTTTAAAT AGGGGGTTGT AATTTGCAGC TTTGGTTATT     300

ATATCTACCG TGTCTGAGTT TTTTGTTTTT TTCGAATGGG GGTAGTCATG GCGGCTGAGC     360

GTATAATAGG TATAGATCTA GGTACTACGA ATTCCTGTGT TGCTGTTATG GAGGCTGGTA     420

CCGCAAAGGT GATAGAAAAC AGTGAAGGTT CGAGGACCAC CCCGTCTGTT GTTGCGTTTA     480

CTGATAATGA AAGGCTAGTA GGGGAATTGG CTAAGCGGCA AGCAAATATC AATGCTCAGA     540

ACACGATATA TGCGAGCAAA AGGATTATCG GCCGCAGATA CGATGACATG AGGGATTTGA     600

AGTGTCCTTA TGAGGTGTTT CCTGCAAAGA ACGTGATGC TTGGATAAGA GCAAAGGGTG      660

AGGGTTATTC TCCGGTTCAG ATTGGCGCGT TTGTCTTGGA AAAGATCAAG GAAACTGCTG     720

AGAGATACTT TGGTGCTCCA GTGAAGAAGG CGGTTATTAC GGTGCCTGCG TATTTTAACG     780

ATGCTCAACG TCAGGCAACA AAGGATGCTG GTACGATTGC TGGCCTAGAT GTTGTGAGAA     840

TAATTAATGA ACCTACAGCA GCAGCTTTGG CGTACGGGTT AGATAAGGGT GACAAGCAAA     900

GGACTATAGT AGTATACGAT CTTGGTGGTG GTACATTTGA CGTATCTGTT TTGGAGATAG     960

CTGACGGTGT ATTTGAAGTT AAAGCTACTA ATGGTGATAC TAAGCTTGGT GGTGAGGACT    1020

TTGATAATGC CATCATGGAA CATATGATGG AGAGTTTCCA AAAAGAAACA GGTATAAATC    1080

TACGTAATGA CCCTATGGCT GTTCAGCGGG TCAAGGAGGC TGCGGAGAAG CTAAGATTG     1140

AGTTATCTAC CAGGTTAGAG ACAGATATAA CTCTTCCGTT TATTTCTAGC GACAGCACTG    1200

GCGCGAAGCA CTTGAGTTTG AAGCTGAGTA GGGCTAAGTT TGAGGGTTTG GTAGACGAGT    1260

TAATCGAGCG CACTATAGAG CCATGTAAGA AGGCTTTGAG TGATGCGGGT ATTAAGGATA    1320

ACAGTAAGGT CGACGAGGTT GTGCTAGTTG GTGGTATGAC CAGGGTTCCT AAGGTTATTC    1380
```

```
AAAGGGTGAA AGACTTCTTT GGGAAAGAGC CATGTCAAGG TGTAAATCCA GATGAAGTTG      1440

TAGCTGTAGG TGCTGCGATA CAGGGTGGTA TCTTAACAGG TGATGTTCGT GATGTCTTGT      1500

TGTTGGATGT TGCTCCGCTA TCTTTGGGTA TAGAAACTTT GGGTGGTGTA TTTACGCCTT      1560

TGATTGAGCG TAATACTACA ATTCCTACTA GAAAGTCGCA GGTGTTCTCT ACGGCTGAAG      1620

ATGGTCAAAC TGCGGTGACT ATTAAGGTGT ACCAAGGTGA GCGTAAGATG GCAATCGACA      1680

ATAAGTTGTT GGGGCAGTTT AGTCTGGAGG GTATTCCTCA TGCTCCACGC GGAGTTCCTC      1740

AAATTGAGGT GACTTTTGAC ATAGACGCTA ATGGTATAGT GCACGTTTCA GCAAAGGATA      1800

AGGCTTCAGG TAAGGAGCAG ACTATTAAGA TACAGTCTTC TGGTGGCTTA AGTGATGAAG      1860

AAATCAAGAA GATGGTCAAA GATGCTCAGG ACCGGGCGGA AGACGATGAA AAGCGTAAGA      1920

AGCATGTGGA GCTGAAGAAT AGTTCTGAGG GGCTGATACA TTCTGTAGAG AAGTCTTTGA      1980

AGGATTATGG AGATAAGGTT GCGGGTGCTG ATAAGTCTAA TATCGAGAGC GCTATCAAGG      2040

ATTTGAGAGA GTGCTTGAAT GATAGCAACT GTAGTACTGA TACTCTGCAG CAGAAGTATG      2100

ATGCGCTTAT GAATCTATCC ATGAAGCTGG GAGAAGCTGC ATATGCGGCT AATAAGAATG      2160

ACGGTGCGGG AAGTGCTGAT CAATCTGGAA GCAGTAGTGG GGGTTCTGAT GGTAATCCGG      2220

AAGAGCGTGT TGTAGATTCC GAATATCAGG AGATTAATAA GGACGAGGAC AAGAAGAATA      2280

CTTAGGTGTT GATAAGTATT GGGTAGTTTG GTATCCTCCT GCGGGGGTCT GCGTTGTTCG      2340

TGTAGGTTGA AAGTGCCTCG AGCCCGATTT TGTTCTTATA GGGAGCCGTC ACTGGTAACC      2400

TCGAGTAGGT TATTACACGG CGCCCACCTT AGCTTTAGTC TCAGGACACT AAGCAAAGCG      2460

TTACGGCAAA TGCGGATCTC CTAGTTTCCT TTTTTAGCAG TGTGTGTAGG AATTC          2515

(2) INFORMATION FOR SEQ ID NO: 5:

(i) SEQUENCE CHARACTERISTICS:
        (A) LENGTH: 649 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 5:

Met Gly Val Val Met Ala Ala Glu Arg Ile Ile Gly Ile Asp Leu Gly
1               5                  10                  15

Thr Thr Asn Ser Cys Val Ala Val Met Glu Ala Gly Thr Ala Lys Val
                20                  25                  30

Ile Glu Asn Ser Glu Gly Ser Arg Thr Thr Pro Ser Val Val Ala Phe
            35                  40                  45

Thr Asp Asn Glu Arg Leu Val Gly Glu Leu Ala Lys Arg Gln Ala Asn
        50                  55                  60

Ile Asn Ala Gln Asn Thr Ile Tyr Ala Ser Lys Arg Ile Ile Gly Arg
65                  70                  75                  80

Arg Tyr Asp Asp Met Arg Asp Leu Lys Cys Pro Tyr Glu Val Phe Pro
                85                  90                  95

Ala Lys Asn Gly Asp Ala Trp Ile Arg Ala Lys Gly Glu Gly Tyr Ser
            100                 105                 110

Pro Val Gln Ile Gly Ala Phe Val Leu Glu Lys Ile Lys Glu Thr Ala
        115                 120                 125

Glu Arg Tyr Phe Gly Ala Pro Val Lys Lys Ala Val Ile Thr Val Pro
    130                 135                 140
```

-continued

```
Ala Tyr Phe Asn Asp Ala Gln Arg Gln Ala Thr Lys Asp Ala Gly Thr
145                 150                 155                 160

Ile Ala Gly Leu Asp Val Val Arg Ile Ile Asn Glu Pro Thr Ala Ala
            165                 170                 175

Ala Leu Ala Tyr Gly Leu Asp Lys Gly Asp Lys Gln Arg Thr Ile Val
        180                 185                 190

Val Tyr Asp Leu Gly Gly Gly Thr Phe Asp Val Ser Val Leu Glu Ile
    195                 200                 205

Ala Asp Gly Val Phe Glu Val Lys Ala Thr Asn Gly Asp Thr Lys Leu
210                 215                 220

Gly Gly Glu Asp Phe Asp Asn Ala Ile Met Glu His Met Met Glu Ser
225                 230                 235                 240

Phe Gln Lys Glu Thr Gly Ile Asn Leu Arg Asn Asp Pro Met Ala Val
                245                 250                 255

Gln Arg Val Lys Glu Ala Ala Glu Lys Ala Lys Ile Glu Leu Ser Thr
            260                 265                 270

Arg Leu Glu Thr Asp Ile Thr Leu Pro Phe Ile Ser Ser Asp Ser Thr
        275                 280                 285

Gly Ala Lys His Leu Ser Leu Lys Leu Ser Arg Ala Lys Phe Glu Gly
    290                 295                 300

Leu Val Asp Glu Leu Ile Glu Arg Thr Ile Glu Pro Cys Lys Lys Ala
305                 310                 315                 320

Leu Ser Asp Ala Gly Ile Lys Asp Asn Ser Lys Val Asp Glu Val Val
                325                 330                 335

Leu Val Gly Gly Met Thr Arg Val Pro Lys Val Ile Gln Arg Val Lys
            340                 345                 350

Asp Phe Phe Gly Lys Glu Pro Cys Gln Gly Val Asn Pro Asp Glu Val
        355                 360                 365

Val Ala Val Gly Ala Ala Ile Gln Gly Gly Ile Leu Thr Gly Asp Val
    370                 375                 380

Arg Asp Val Leu Leu Leu Asp Val Ala Pro Leu Ser Leu Gly Ile Glu
385                 390                 395                 400

Thr Leu Gly Gly Val Phe Thr Pro Leu Ile Glu Arg Asn Thr Thr Ile
                405                 410                 415

Pro Thr Lys Lys Ser Gln Val Phe Ser Thr Ala Glu Asp Gly Gln Thr
            420                 425                 430

Ala Val Thr Ile Lys Val Tyr Gln Gly Glu Arg Lys Met Ala Ile Asp
        435                 440                 445

Asn Lys Leu Leu Gly Gln Phe Ser Leu Glu Gly Ile Pro His Ala Pro
    450                 455                 460

Arg Gly Val Pro Gln Ile Glu Val Thr Phe Asp Ile Asp Ala Asn Gly
465                 470                 475                 480

Ile Val His Val Ser Ala Lys Asp Lys Ala Ser Gly Lys Glu Gln Thr
                485                 490                 495

Ile Lys Ile Gln Ser Ser Gly Gly Leu Ser Asp Glu Glu Ile Lys Lys
            500                 505                 510

Met Val Lys Asp Ala Gln Asp Arg Ala Glu Asp Glu Lys Arg Lys
        515                 520                 525

Lys His Val Glu Leu Lys Asn Ser Ser Glu Gly Leu Ile His Ser Val
    530                 535                 540

Glu Lys Ser Leu Lys Asp Tyr Gly Asp Lys Val Ala Gly Ala Asp Lys
545                 550                 555                 560

Ser Asn Ile Glu Ser Ala Ile Lys Asp Leu Arg Glu Cys Leu Asn Asp
```

-continued

```
                    565                 570                 575
Ser Asn Cys Ser Thr Asp Thr Leu Gln Gln Lys Tyr Asp Ala Leu Met
                580                 585                 590

Asn Leu Ser Met Lys Leu Gly Glu Ala Ala Tyr Ala Ala Asn Lys Asn
            595                 600                 605

Asp Gly Ala Gly Ser Ala Asp Gln Ser Gly Ser Ser Ser Gly Gly Ser
        610                 615                 620

Asp Gly Asn Pro Glu Glu Arg Val Val Asp Ser Glu Tyr Gln Glu Ile
625                 630                 635                 640

Asn Lys Asp Glu Asp Lys Lys Asn Thr
                645
```

(2) INFORMATION FOR SEQ ID NO: 6:

(i) SEQUENCE CHARACTERISTICS:
        (A) LENGTH: 4804 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 6:

```
AACTAGTGGA TCCCCCGGGC TGCAGGAATT CCTCAGGTAA GGAGCAGACT ATTAAGATAC      60

AGTCTTCTGG TGGCTTAAGT GATGAAGAAA TCAAGAAGAT GGTCAAAGAT GCTCAGGACC     120

GGGCGGAAGA CGATGAAAAG CGTAAGAAGC ATGTGGAGCT GAAGAATAGT TCTGAGGGGC     180

TGATACATTC TGTAGAGAAG TCTTTGAAGG ATTATGGAGA TAAGGTTGCG GGTGCTGATA     240

AGTCTAATAT CGAGAGCGCT ATCAAGGATT TGAGAGAGTG CTTGAATGAT AGCAACTGTA     300

GTACTGATAC TCTGCAGCAG AAGTATGATG CGCTTATGAA TCTATCCATG AAGCTGGGAG     360

AAGCTGCATA TGCGGCTAAT AAGAATGACG GTGCGGAAG TGCTGATCAA TCTGGAAGCA      420

GTAGTGGGGG TTCTGATGGT AATCCGGAAG AGCGTGTTGT AGATTCCGAA TATCAGGAGA     480

TTAATAAGGA CGAGGACAAG AAGAATACTT AGGTGTTGAT AAGTATTGGG TAGTTTGGTA     540

TCCTCCTGCG GGGGTCTGCG TTGTTCGTGT AGGTTGAAAG TGCCTCGAGC CCGATTTTGT     600

TCTTATAGGG AGCCGTCACT GGTAACCTCG AGTAGGTTAT TACACGGCGC CCACCTTAGC     660

TTTAGTCTCA GGACACTAAG CAAAGCGTTA CGGCAAATGC GGATCTCCTA GTTTCCTTTT     720

TTAGCAGTGT GTGTATGGTG CGAGCTAGGC GTGGGTTTAG CAAGAGCGAA GTGCTTAGTT     780

TTCCGGCAAA AGATATATTT TCCATTGTTC TTGATGTTGA GAAGTATCCC GCGTTTCTAC     840

CGTGGTGTAA GGAAGTAGTG ATTCTTGAAA GGCATGATGC TTCGATGTTT GTGAAGTTGG     900

TGGCGCAATT CATGTCACTT GAAGGTGCGT ATACTTCCGA AGTTAGTTTC TCTACTCCGA     960

CTTTAGAGAA CCCAGGGTGG ATAAGAGCTG TTTCTACTGA TGGAGTGTTT AATACTTTAT    1020

GTAGTGAGTG GAATTTCCTG CCTAAAAATG AAAGGGAGAC CTTGGTGACG TTTTTTGTGA    1080

ATTTTTCTTT CAAAAACAGA ATGTTGCAAT TTGCGTTCGA TATGGCATCA AGCATGGCTA    1140

TTTCTAACAT ATCTCGTGCG TTTAAAAACA GGGCGTACCA ATTGCTAAAA TAAGGTATGT    1200

GTGTAATTAG CTGTTGCTAT AACGCGCTGT GTTATATGTG CATGCTTTGG GACATAGATA    1260

TTGGAAGATT TCAGCATACA TTATGTGCTT GCGCTGGTAC AGCCAGCGTC TGAGGTTTGT    1320

GCTATAATGT TCTAGGGTCA GTAGCTTTTT TGTCATATGA GCCTGTAAAA CAACTATCTG    1380
```

-continued

| | |
|---|---|
| CTGGAATGCT TTCTCAAACA AAAGCAAATA TCTCGGCATA AAATATAGCT TCCTTACTAC | 1440 |
| TATAAATACA TCGCCTGTGG GCAATAAGTG TTTATATATC TCAGCGTATA GGTGCAGGTT | 1500 |
| AGATCAGAAG TTTCTATGGG CATGCACTAT TACAGCGTTT GCAAAGAATT ATGACTTTGA | 1560 |
| TAATGAGTCC ATGACGTAAT TGCAATAAAG GCTATTATCC CTGGTATCTA AATGGGTAGT | 1620 |
| TGTAAATTTG TGACGCAGCA TTGTGCTATA ATTCAGCAAA TAGTTACAGT GCTTTTATAG | 1680 |
| GGGTGATATA CCGCAACCTA AGCGCATAGA TGAGGGGTTA TAGAGGCGTC TATATATGCG | 1740 |
| TATTATATTG AGAAGTAGTT GATAAGAGCT ACAGCGGCGC AAAGTATTGG AATTTGCAGT | 1800 |
| GATGTGTTTT TTTGGTGCAG AGGACATGCG TTTACTGATT CAAGTAACAC GTGATGCATG | 1860 |
| TGCTATGATT CATGTCTTTG GTTTCGAAAT AATGTTTTAA CCTGTGGCGT TGGATATTGA | 1920 |
| CTTGTTAGCG TAGGATTGTG CGGGTATATA GAGTACAGGG GCTAGATGTT ACATTTTCCA | 1980 |
| TGGGTTCTTT GTATAATTTT ACGTTCAGTA ATATTTTTCA GGCATTGGGT GGTGAGAACG | 2040 |
| TGTTTTCATT AGACAAAGTC AGTGCTATTC CGCTGATTAT GTCGTTTCTT GCATCTATGT | 2100 |
| TTTGCATAGT TTGTAGGTGT AGGGTAGGTT TTAAGGAGCT CTTATGTTCT CTGCTATATT | 2160 |
| GCATTAGCAG TATTGCAGTA TTGTTATTTT CAAATCTCAC ATTGGTAACT ATTGGCTTTG | 2220 |
| AGATTATGGC GCTTACTGCA GTATGTATTG TAGCATTTGG GGCATATAAA GGCAGGGATT | 2280 |
| TTGCATTTTT ACATTATGCA TGTTTGCATT TTATTTCTGG CTTTTTGTTG CTTGTGGGTG | 2340 |
| CAAGTCAGCA TGCTCATTTA GGGGTTCTAG AGGGGATACC TAGATGGTTT TTTATGCTTG | 2400 |
| GTTTGATAAT AAATACAGCA GCTTTTCCTG CAGCATCATG GCTTGTGCGC GCATATCCGG | 2460 |
| TATCGTCAAG TTTTGGGATG CTGGTACTTT CCTTGTTCAC AACTAAAGTG GCATTGTATG | 2520 |
| TTTTGTTAAA GTTCTTTTCT GGCGAGTCCA TAATTTTATA CTTCGGTATT TCACTTCTA | 2580 |
| TATATGCTGC GATATTTGCC TTTCTTGAGC AGAATGTTCG TAGGCTGATG GCTTACATGT | 2640 |
| TTGTAGGGCA GGCAGGATTG CTTATGATGG CTATTGGGTG TCCGGGAATA CCATCAGACC | 2700 |
| TTATAATCGT GCAGTTATCA TTTTCAGTAT TATACCAGCT TCTTTTGGGG ATGTTTGCTG | 2760 |
| ATTCAGTGGT AAAACGTTCT GGGCATGTTG ATATTAACAG AATGGCTGGG TGTTTTAAAT | 2820 |
| TGGCATCTAT GGAAGCTATG GGTTGTATAG TGGCTCTGTT GAATTTAGGG GGCTTCCCGT | 2880 |
| GGACTGCTGG TTTTGTGACG AAAGGGCTAA TGTTACATAT GAACTTGCAG AGTTTTGACT | 2940 |
| ATATGCTCCT AAAGTATATG CAGCCTATGT TGGGATGGTT GTTATTTGCG AGTAATGGAA | 3000 |
| TGAAGCTTTT TTGGTTGGCA TGCTTAAAGC CGTGTTCTAC AACTCCGGAG TATGCGCCTA | 3060 |
| GTCCTTTTTC TTCTAAGCTC TCAATTATAA TGTTGTCGCT TATTATTACG GTGTCTGGTG | 3120 |
| TATTGTATGG CGAGGGCTTG CTTTTTTCAG AGCATAAATT TGTATATACA TTTGGTGCTG | 3180 |
| TAGCAACTAA GCTAATATGG CTCGGTGGCG TTGTTCTGTT TTTTATTTTG TTTAGAAGGC | 3240 |
| AGTTTTTGGG ACGGTACGAG TCTGCCATAG GTGATAGCTG GGTCTATCGG CAGTTTTTTA | 3300 |
| TAATGGCGGA AAAGTTTGCA CATGCTGCGT CACGCATGAG AGAGGTGTTG GGAGGCCTTT | 3360 |
| TTGCGGGGGG AGCTTTTAGC ATAGAAACTA GTGGTTCTAC TGTATTATCA GCCAGGTCGC | 3420 |
| CATCTGGGGT TGTTAGCTCT ACATTGCTTT TGGTTATGTT GAGTATTTGT ATTATTGTTT | 3480 |
| TGGTATGGGC TTATGTTTAA CTCTTTAACC AAGGGGTTTT CTTCTGCGCT GCAAAGGTTA | 3540 |
| AGTGGAAAGC GGGAGATATC CAGCAAGGAT TTTGATCTTG TAATAGAAGA TATAACTCAG | 3600 |
| GCATTGTTGG ATGCGGATGT TAATCTTGGT GTTGTTGACG AATTTATAGA GAACGTAAAA | 3660 |
| AGCAAGATCG TAGGGGGCGA TGTAGTTAAA GGGGTGCTCC CGGAGCAAAT GGTCATAAAG | 3720 |

-continued

```
CGTATAGAAG AGTGTTTGAT TGAAGTTTTA GGTAATGAGA GAGCGCTCT  TGATCTTAAG    3780

GGAAAGATTC CTGCAGTAAT CATGATGGTT GGGCTTCAAG GTGTTGGTAA GACTACTAAC    3840

ACAGTAAAAG TTGCACTGAG GTTAAAGAAG GATTCTAAAA ACCCGTTGGT AGCGTCTTTA    3900

GACGTATATC GTCCTGCAGC TCGAGAACAG CTGAAGGTTT TGGCTGATGG AGTTGGTATA    3960

GACAGTCTTC CCATCGTTGA GGAGCAAAAA CCACTTGATA TTGCGAAGCG TGCTATGAGG    4020

GAAGCGAGGC TCAAAGGGCA CGATGTGGTG CTTTTGGATA CAGCGGGGCG CTTGCATATC    4080

AATCAGGACA TGATAGATGA GCTGAAGTGT GTAAAGAAGG AGGTATCACC AGCTGAAATT    4140

GTATTGGTTG TAGACTCCTT AATGGGGCAA GATGCCGTCA CTATGGTGCG CAAGTTCAAT    4200

GAGGAGTTAG GCATTACTGG GACGATCTTT ACCAGGGCGG ATGGTGATCC TAGGGGTGGT    4260

GCTATCTTGT CTATGAAGTT GGTTGCTGGA TGTCCTATAA AGTTCATGTC TACGGGAGAG    4320

AAGCCTGAAG ATTTGGACGA TTTCTATCCT GATAGAAATA CTCGTAGAAT GTTAAATATG    4380

GGAGATGTCG CATCTCTTGT AGAAAAGGCG GTAGAAGCGG TTGGCAAGGA TACAATTAAT    4440

GAGCTACAGG CGAAGGCCAA GAAGGGTAAA TTCGATTTGG ATGATCTTGT TATTCAGCTG    4500

AAAGCTTTGA ATAAAATGGG TGGTATTGCT AATATAATGA AGTTTATACC CGCTTTCGGT    4560

AACGATATAA AACGCAAAGT TGCGGGGATA GCTGATGACA GCAAAGTCGA CATGTACATT    4620

GCGATTATTA ACTCAATGAC GAAGCAGGAG AGGGCGAATC CTGAGATACT GAATGGTGCG    4680

AGGAAGGCAA GGATAGCGAA GGGTGCGGGA GTTAAGGTTG ATGCTGTAAA TGCGTTGCTA    4740

AAGCAGTATA ATCAGATGAA TTCGATATCA AGCTTATCGA TACCGTCGAC CTCGAGGGGG    4800

CCCG                                                                4804
```

(2) INFORMATION FOR SEQ ID NO: 7:

(i) SEQUENCE CHARACTERISTICS:
        (A) LENGTH: 506 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 7:

```
Met Gly Ser Leu Tyr Asn Phe Thr Phe Ser Asn Ile Phe Gln Ala Leu
1               5                   10                  15

Gly Gly Glu Asn Val Phe Ser Leu Asp Lys Val Ser Ala Ile Pro Leu
            20                  25                  30

Ile Met Ser Phe Leu Ala Ser Met Phe Cys Ile Val Cys Arg Cys Arg
        35                  40                  45

Val Gly Phe Lys Glu Leu Leu Cys Ser Leu Leu Tyr Cys Ile Ser Ser
    50                  55                  60

Ile Ala Val Leu Leu Phe Ser Asn Leu Thr Leu Val Thr Ile Gly Phe
65                  70                  75                  80

Glu Ile Met Ala Leu Thr Ala Val Cys Ile Val Ala Phe Gly Ala Tyr
                85                  90                  95

Lys Gly Arg Asp Phe Ala Phe Leu His Tyr Ala Cys Leu His Phe Ile
            100                 105                 110

Ser Gly Phe Leu Leu Leu Val Gly Ala Ser Gln His Ala His Leu Gly
        115                 120                 125

Val Leu Glu Gly Ile Pro Arg Trp Phe Phe Met Leu Gly Leu Ile Ile
    130                 135                 140

Asn Thr Ala Ala Phe Pro Ala Ala Ser Trp Leu Val Arg Ala Tyr Pro
```

```
145                 150                 155                 160
Val Ser Ser Ser Phe Gly Met Leu Val Leu Ser Leu Phe Thr Thr Lys
                165                 170                 175
Val Ala Leu Tyr Val Leu Leu Lys Phe Phe Ser Gly Glu Ser Ile Ile
                180                 185                 190
Leu Tyr Phe Gly Ile Phe Thr Ser Ile Tyr Ala Ala Ile Phe Ala Phe
                195                 200                 205
Leu Glu Gln Asn Val Arg Arg Leu Met Ala Tyr Met Phe Val Gly Gln
    210                 215                 220
Ala Gly Leu Leu Met Met Ala Ile Gly Cys Pro Gly Ile Pro Ser Asp
225                 230                 235                 240
Leu Ile Ile Val Gln Leu Ser Phe Ser Val Leu Tyr Gln Leu Leu Leu
                245                 250                 255
Gly Met Phe Ala Asp Ser Val Val Lys Arg Ser Gly His Val Asp Ile
                260                 265                 270
Asn Arg Met Ala Gly Cys Phe Lys Leu Ala Ser Met Glu Ala Met Gly
            275                 280                 285
Cys Ile Val Ala Leu Leu Asn Leu Gly Gly Phe Pro Trp Thr Ala Gly
            290                 295                 300
Phe Val Thr Lys Gly Leu Met Leu His Met Asn Leu Gln Ser Phe Asp
305                 310                 315                 320
Tyr Met Leu Leu Lys Tyr Met Gln Pro Met Leu Gly Trp Leu Leu Phe
                325                 330                 335
Ala Ser Asn Gly Met Lys Leu Phe Trp Leu Ala Cys Leu Lys Pro Cys
            340                 345                 350
Ser Thr Thr Pro Glu Tyr Ala Pro Ser Pro Phe Ser Ser Lys Leu Ser
            355                 360                 365
Ile Ile Met Leu Ser Leu Ile Ile Thr Val Ser Gly Val Leu Tyr Gly
            370                 375                 380
Glu Gly Leu Leu Phe Ser Glu His Lys Phe Val Tyr Thr Phe Gly Ala
385                 390                 395                 400
Val Ala Thr Lys Leu Ile Trp Leu Gly Gly Val Val Leu Phe Phe Ile
                405                 410                 415
Leu Phe Arg Arg Gln Phe Leu Gly Arg Tyr Glu Ser Ala Ile Gly Asp
            420                 425                 430
Ser Trp Val Tyr Arg Gln Phe Phe Ile Met Ala Glu Lys Phe Ala His
            435                 440                 445
Ala Ala Ser Arg Met Arg Glu Val Leu Gly Leu Phe Ala Gly Gly
            450                 455                 460
Ala Phe Ser Ile Glu Thr Ser Gly Ser Thr Val Leu Ser Ala Arg Ser
465                 470                 475                 480
Pro Ser Gly Val Val Ser Ser Thr Leu Leu Val Met Leu Ser Ile
                485                 490                 495
Cys Ile Ile Val Leu Val Trp Ala Tyr Val
                500                 505

(2) INFORMATION FOR SEQ ID NO: 8:

(i) SEQUENCE CHARACTERISTICS:
        (A) LENGTH: 420 amino acids
        (B) TYPE: amino acid
        (C) STRANDEDNESS: <Unknown>
        (D) TOPOLOGY: linear (ii) MOLECULE TYPE: protein
```

(xi) SEQUENCE DESCRIPTION: SEQ ID NO: 8:

```
Met Phe Asn Ser Leu Thr Lys Gly Phe Ser Ala Leu Gln Arg Leu
1               5                   10                  15

Ser Gly Lys Arg Glu Ile Ser Ser Lys Asp Phe Asp Leu Val Ile Glu
            20                  25                  30

Asp Ile Thr Gln Ala Leu Leu Asp Ala Asp Val Asn Leu Gly Val Val
        35                  40                  45

Asp Glu Phe Ile Glu Asn Val Lys Ser Lys Ile Val Gly Gly Asp Val
50                  55                  60

Val Lys Gly Val Leu Pro Glu Gln Met Val Ile Lys Arg Ile Glu Glu
65                  70                  75                  80

Cys Leu Ile Glu Val Leu Gly Asn Glu Lys Ser Ala Leu Asp Leu Lys
                85                  90                  95

Gly Lys Ile Pro Ala Val Ile Met Met Val Gly Leu Gln Gly Val Gly
                100                 105                 110

Lys Thr Thr Asn Thr Val Lys Val Ala Leu Arg Leu Lys Lys Asp Ser
            115                 120                 125

Lys Asn Pro Leu Val Ala Ser Leu Asp Val Tyr Arg Pro Ala Ala Arg
        130                 135                 140

Glu Gln Leu Lys Val Leu Ala Asp Gly Val Gly Ile Asp Ser Leu Pro
145                 150                 155                 160

Ile Val Glu Glu Gln Lys Pro Leu Asp Ile Ala Lys Arg Ala Met Arg
                165                 170                 175

Glu Ala Arg Leu Lys Gly His Asp Val Val Leu Leu Asp Thr Ala Gly
            180                 185                 190

Arg Leu His Ile Asn Gln Asp Met Ile Asp Glu Leu Lys Cys Val Lys
        195                 200                 205

Lys Glu Val Ser Pro Ala Glu Ile Val Leu Val Asp Ser Leu Met
210                 215                 220

Gly Gln Asp Ala Val Thr Met Val Arg Lys Phe Asn Glu Glu Leu Gly
225                 230                 235                 240

Ile Thr Gly Thr Ile Phe Thr Arg Ala Asp Gly Asp Pro Arg Gly Gly
                245                 250                 255

Ala Ile Leu Ser Met Lys Leu Val Ala Gly Cys Pro Ile Lys Phe Met
            260                 265                 270

Ser Thr Gly Glu Lys Pro Glu Asp Leu Asp Asp Phe Tyr Pro Asp Arg
        275                 280                 285

Ile Ala Arg Arg Met Leu Asn Met Gly Asp Val Ala Ser Leu Val Glu
290                 295                 300

Lys Ala Val Glu Ala Val Gly Lys Asp Thr Ile Asn Glu Leu Gln Ala
305                 310                 315                 320

Lys Ala Lys Lys Gly Lys Phe Asp Leu Asp Asp Leu Val Ile Gln Leu
                325                 330                 335

Lys Ala Leu Asn Lys Met Gly Gly Ile Ala Asn Ile Met Lys Phe Ile
            340                 345                 350

Pro Ala Phe Gly Asn Asp Ile Lys Arg Lys Val Ala Gly Ile Ala Asp
        355                 360                 365

Asp Ser Lys Val Asp Met Tyr Ile Ala Ile Ile Asn Ser Met Thr Lys
370                 375                 380

Gln Glu Arg Ala Asn Pro Glu Ile Leu Asn Gly Ala Arg Lys Ala Arg
385                 390                 395                 400

Ile Ala Lys Gly Ala Gly Val Lys Val Asp Ala Val Asn Ala Leu Leu
                405                 410                 415
```

Lys Gln Tyr Asn
            420

(2) INFORMATION FOR SEQ ID NO: 9:

(i) SEQUENCE CHARACTERISTICS:
        (A) LENGTH: 5174 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 9:

```
TCTAGAACTA GTGGATCCCC CGGGCTGAAT TCCGTAGAAG CTGGGGCACA TATAAATACT    60
CCTACCGGAT CTATGAGCCC TTTAGCTGCT GCAGTTCAAG CGGCAAATGA GGCAAGTAAC   120
CTTAAAGAGG CTAATAAGAT TGTAAATTTC CTTTTACATA GGGGTGCAGA TCTTTCGTCT   180
ACGGAACACA CTGGAACTCC AGCCTTGCAT TTAGCAACAG CTGCTGGCAA CCATAGGACT   240
GCTATGTTGC TCTTGGATAA AGGGGCTCCA GCAACGCAGA GAGATGCTAG GGGTAGGACG   300
GCTTTACATA TAGCAGCTGC TAATGGTGAC GGTAAGCTAT ATAGGATGAT TGCGAAAAAA   360
TGCCCAGATA GCTGTCAACC ACTCTGTTCT GATATGGGAG ATACAGCGTT ACATGAGGCT   420
TTATATTCTG ATAATGTTAC AGAAAAATGC TTTTTAAAGA TGCTTAAAGA GTCTCGAAAG   480
CATTTGTCAA ACTCATCTTT TTTCGGAGAC TTGCTTAATA CTCCTCAAGA AGCAAATGGT   540
GACACGTTAC TGCATCTGGC TGCATCGCGT GGTTTCGGTA AAGCATGTAA AATACTACTA   600
AAGGCTGGGG CGTCAGTATC AGTCGTGAAT GTAGAGGGAA AAACACCGGT AGATGTTGCG   660
GATCCATCAT TGAAAACTCG TCCGTGGTTT TTTGGAAAGT CCGTTGTCAC AATGATGGCT   720
GAACGTGTTC AAGTTCCTGA AGGGGATTCC CCACCATATC TGCCGCCTGA AAGTCCAACT   780
CCTTCTTTAG GATCTATTTC AAGTTTTGAG AGTGTCTCTG CGCTATCATC CTTGGGTAGT   840
GGCCTAGATA CTGCAGGAGC TGAGGAGTCT ATCTACGAAG AAATTAAGGA TACAGCAAAA   900
GGTACAACGG AAGTTGAAAG CACATATACA ACTGTAGGAG CTGAGGAGTC TATCTACGAA   960
GAAATTAAGG ATACAGCAAA AGGTACAACG GAAGTTGAAA GCACATATAC AACTGTAGGA  1020
GCTGAAGGTC CGAGAACACC AGAAGGTGAA GATCTGTATG CTACTGTGGG AGCTGCAATT  1080
ACTTCCGAGG CGCAAGCATC AGATGCGGCG TCATCTAAGG GAGAAAGGCC GGAATCCATT  1140
TATGCTGATC CATTTGATAT AGTGAAACCT AGGCAGGAAA GGCCTGAATC TATCTATGCT  1200
GACCCATTTG CTGCGGAACG AACATCTTCT GGAGTAACGA CATTTGGCCC TAAGGAAGAG  1260
CCGATTTATG CAACAGTGAA AAAGGGTCCT AAGAAGAGTG ATACTTCTCA AAAAGAAGGA  1320
ACAGCTTCTG AAAAAGTCTG CTCAACAATA ACTGTGATTA GAAGAAAAGT GAAACCTCAG  1380
GTTCCAGCTA GGACAAGTAG TTTGCCTACT AAAGAAGGTA TAGGTTCTGA TAAAGACCTG  1440
AGTTCAGGAA CTAGTAGCTC TTTTGCAGCT GAGCTGCAAG CACAAAGGGG TAAATTGCGT  1500
CCTGTGAAGG GAGGTGCTCC GGATTCTACC AAAGACAAAA CAGCTACTTC TATATTCTCC  1560
AGTAAAGAGT TCAAAAGGA ACTAACAAAA GCTGCCGAAG GATTACAGGG AGCAGTTGAA  1620
GAAGCTCAGA AGGGTGATGG AGGAGCTGCA AAGGCAAAGC AAGATCTTGG CATGGAATCT  1680
GGTGCCCCAG GATCTCAACC AGAAGCTCCT CAAAGTGAAG GCCCTAAGTC TGTAAAAGGA  1740
GGTCGCGGTA GGTAGAATTA TACCGAAAAA TCGCTGAGGT ACTTTGATCA ATATAATTCG  1800
```

```
CGCTTCTGAG TATTTAGGCG ATGATCTCGC CACTTTAATA ATACCCCTTT TAGAGTACAT    1860

AACGCTCTAA AGGGGGCAGA TTATTTTAAG TAGTAGGGTT TTGATTCTGA GATCTTTTGA    1920

GTACAACTAT TCCTTAGTGT TTTTTTGGAA TGCTATGTGC TTGATAAAGA AAAAACTTGC    1980

TCTGGGGTGG GATGCACTCT TGAGTACTTT CCGCGCTCTG TATATTCCTT TTTTTGCATC    2040

TGCATAATCT GCTGCATATG TGATTATGTG ATAATGACGG AATTACCCAG AAAAGTTTTA    2100

GCGTGTGAGG CTATCATTCT CAGTAAAGTT ACAGTAGGAA ACTTGTCATT TTCATCTTGT    2160

ATTTTTGTAA GTTGGCTAAG AGCACTAGCT ATAACAAATG CATCTATGGC ATTTTTTGAG    2220

AGTTATAATA ATGAGCAACA AAGGGTGGTA CTATTGTTCA AAATTTGTTT ATGTGCTTTG    2280

TCTCACAATG GAGTTTAAAG TCATCTCCGT GTAGTACTAC GACTTTAAGT AGAGAATACT    2340

TTGTATTTTC TTTATAGAAG CTCAGAGATA TACTTCAGTA TGTGTCGGAG GTTGTTCCCT    2400

TGGGAAAAAG GGCATTTTAT CAACTGTGAA CTATCGCTAC TATGGCTGAG GAAAAGTAGA    2460

TAGCAACAAA GATAGTATTC TGGTTTTATA ATCAAACCGT AATCTTTCAA CATGTTCGAA    2520

GATCGCTTTC ACTTTATAAT CCTTTTTGAC TGCCCTGCTG AAAGGGCTTT TTTGTTATGA    2580

AACTATCCTC GCTCGATTTT CTTATCTTTG GATTCTATTA CCACGGATAA TGTTTGTTGG    2640

AATTATTTTA GAAGAAGCTT AGGCATTGCG TTATTTCTTT AACTCTTATG GTACTTGTAC    2700

AGTTTTCAGC AGCTTTAATT AAATCTTTTT CAATGTGGGC TCAAAGAGTT GAGAATATAA    2760

GATTACGCTT ATACTGTGAC CATTTCTCTA CTTTGCGCTG TAAGGGAAGT TCTTATGTTT    2820

GACTTCGTAT TTAAGGTGCT TTACGCGACC TCGCGTGTGG GTAGATAGAT AAATTTGCTA    2880

TGGAGAGGAG GGATTTGCTT TGCATGCCAA ATGCCGCATA ATGTTCTGCA TCGCGTGAAC    2940

GATACGTTAA TACTTTTTGC GTTGTTTTTG AGTTACGTAA TCAATAAATT CACTGTTGTA    3000

ATTTAAGAGA TGCAAGATGT ACACTCAGGC GTATATACTT ATGGAATACT TCACATACCG    3060

CGTGATTAGG TAATAAAAAG GCCTCAGCTT TTCTAGAAGA ATGTTCGCAG AAGCATTTAG    3120

TGATGTTTCA GGGTTTGTTT TTTATGCTAG GCGGACTTCC TTATGATCAT CCCATGTAGG    3180

TATGCGGTTT TCAAATGGGC ATGTAACGAA AAAATTCAAT TTTTTTATTT ATAAACATCT    3240

TGCTACTGTC TCAATAATTT GGTACATAGG AGAAAGTTGC ACGGGTTTGT ATGCAGCGCT    3300

TTCTTTTCGC GGGGTGGAGC AGTGGTAGCT CATCAGGCTC ATAACCTGAA GGTCGATGGT    3360

TCGAGTCCGT CCCCCGCAAC TTGTATTTCC TTAGTTCGCT ATGTAGTGTT GTCCTAAGGG    3420

GCGGAATGTC TTTATCTCTA GCTATTGCTT TATCTTTAAC TACTTGCGTG TTGTAGTAAA    3480

GCTGTTGTAT CTATTGCAGC TCAGTAGAGT TCGTGGGGTA GAAGTACTAA CGAAAAGTTT    3540

GAGATTAATA TCAAAATGGC GGCTAATTTT ATTCACCATC TACCGTATAC TAACGCTTGG    3600

CTGCGCAATA TCCGTATAGC TTAGCGGAAT TATACTGTGT AAATAATATT CACTCAAAAG    3660

TGTGATGATT TTAAGATAAC ACAGGTTTTC ACTTCGCTTA CCACTAAGTG TTTATCTACA    3720

TACCTCTTCC TTCGGAATGC TCTATGACGT TTGGCGAAGG AGAAGGGGAG ACATGGTGCT    3780

CATGGCCTCT TTCTTCATGT GATACACCAT CTAATCCTTG TGCTGCTCTT CCAATAGATT    3840

CGTCAGCATG TGGATACTGG TCAAAATCCC AAGGATCATA TAGATGCGGG TCATTTCTTC    3900

CATCTAAATA TCTCTCATCA TCGCCACCGT CAGTATAATC TTCTCCTCCT TCGCCACCTC    3960

CTGATGCTGC TTCATCTCCT CCTTCTCCCC CTCCCTTTAT GGAGTCAAAA AGTATAGGAA    4020

AGCCAAAAGC TAATGATGTT TTAGAAGGTC CATATATGCT AAACTGCGCT GATAGATTAG    4080

CTCCTAAAGA CATTGCTGCT TTGTCTATAT TACCAAGCAG GCTTCCTACA AGATCAGCCT    4140

TCATCGCTTC TACAGGGGTT GCCAGTACTG CATTCATTAT TGCTAGAGAA GATCTATCAT    4200
```

```
CTCCTTCTTC ACCTCCTCCA GCGGCTTCAG CGCGCTCTTG AGTAGCATGC ATTAAGGACT      4260

GTACACTAGC TATATTTGGT CCCATACCCA TATCGGCACC GCCACCACCA GGTTTATGCA      4320

TAATCACCTC TCAAGTAACA TAGAAAATTC AAGGCATATC CTAACTACAT CTACCATGCA      4380

ATAGTGAATA TTTTTAAAAC GCCTCTTCCT CATATATAAG GGCTGTCATT TCTTTGCGCT      4440

GCTCTAGGAA TTTTGAATCA TCTGATAGTA AATGTCTATG GAGAAAATAT CCTAGGATTT      4500

GTAAGCAGAG CAAAAACTCT TTTCGTGAAC ACTGTTCGGT GTGAGTTCCA TTATGAAGAT      4560

CGCGTAATAT TTGTGGTAGA GGGAATAACA AGTGCCGATA TGATACGCCA GCTCTTTCAG      4620

ATATTGCGCG ACCTGTTTTA GGAGATATGT ACAATAGATT ATCTTCGCAA TGGTAAACAG      4680

CGCATCTTGA GAGATCTAAG GCGAAGCCCA GCTGGGATAA AATTTCAAGT TCAAGCTTTA      4740

AGTACTCGTT GTACCAATGG CCTCCACATT CTGCAGCTTC AGCAAACTCT ATAAGATAGT      4800

CATATAGTAT AGGATGTGCA TCATTTGTGG GGACGGACTT GTATATTGTG GATGTAACAG      4860

AGGATAGACA CAGCAACTTT GAATGATCTT GAAAATACGC ATAAAAAGCT GATGAAATAA      4920

TTTCACAGGA GTTAAAATAC CCAAGGTTAT TAGCTAATCT CGCACGCCAC GTTACGCACA      4980

CTCTATCTCC AATCTGCAGA GACTGCTTCT TTTTGTTTAG TCTGATCATG GCATTGCAAA      5040

TTCCGTGATT ACGCGTAAAT ACAGACAATA TACTTCGAGT ATCCCCATAA GGCGTCATGC      5100

TTACGATCAT TCCATGGTCT TGCCATGGAA TTCGATATCA AGCTTATCGA TACCGTCGAC      5160

CTCGAGGGGG GCCC                                                        5174
```

(2) INFORMATION FOR SEQ ID NO: 10:

(i) SEQUENCE CHARACTERISTICS:
        (A) LENGTH: 201 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 10:

```
Met His Lys Pro Gly Gly Gly Ala Asp Met Gly Met Gly Pro Asn
1               5                  10                  15

Ile Ala Ser Val Gln Ser Leu Met His Ala Thr Gln Glu Arg Ala Glu
            20                  25                  30

Ala Ala Gly Gly Gly Glu Glu Gly Asp Asp Arg Ser Ser Leu Ala Ile
        35                  40                  45

Met Asn Ala Val Leu Ala Thr Pro Val Glu Ala Met Lys Ala Asp Leu
    50                  55                  60

Val Gly Ser Leu Leu Gly Asn Ile Asp Lys Ala Ala Met Ser Leu Gly
65                  70                  75                  80

Ala Asn Leu Ser Ala Gln Phe Ser Ile Tyr Gly Pro Ser Lys Thr Ser
                85                  90                  95

Leu Ala Phe Gly Phe Pro Ile Leu Phe Asp Ser Ile Lys Gly Gly Gly
            100                 105                 110

Glu Gly Gly Asp Glu Ala Ala Ser Gly Gly Gly Glu Gly Gly Glu Asp
        115                 120                 125

Tyr Thr Asp Gly Gly Asp Asp Glu Arg Tyr Leu Asp Gly Arg Asn Asp
    130                 135                 140

Pro His Leu Tyr Asp Pro Trp Asp Phe Asp Gln Tyr Pro His Ala Asp
145                 150                 155                 160

Glu Ser Ile Gly Arg Ala Ala Gln Gly Leu Asp Gly Val Ser His Glu
```

165                 170                 175
Glu Arg Gly His Glu His His Val Ser Pro Ser Pro Asn Val
            180                 185                 190

Ile Glu His Ser Glu Gly Arg Gly Met
            195                 200

(2) INFORMATION FOR SEQ ID NO: 11:

(i) SEQUENCE CHARACTERISTICS:
        (A) LENGTH: 238 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 11:

Met Ile Val Ser Met Thr Pro Tyr Gly Asp Thr Arg Ser Ile Leu Ser
1               5                  10                  15

Val Phe Thr Arg Asn His Gly Ile Cys Asn Ala Met Ile Arg Leu Asn
            20                  25                  30

Lys Lys Lys Gln Ser Leu Gln Ile Gly Asp Arg Val Cys Val Thr Trp
        35                  40                  45

Arg Ala Arg Leu Ala Asn Asn Leu Gly Tyr Phe Asn Ser Cys Glu Ile
    50                  55                  60

Ile Ser Ser Ala Phe Tyr Ala Tyr Phe Gln Asp His Ser Lys Leu Leu
65                  70                  75                  80

Cys Leu Ser Ser Val Thr Ser Thr Ile Tyr Lys Ser Val Pro Thr Asn
                85                  90                  95

Asp Ala His Pro Ile Leu Tyr Asp Tyr Leu Ile Glu Phe Ala Glu Ala
            100                 105                 110

Ala Glu Cys Gly Gly His Trp Tyr Asn Glu Tyr Leu Lys Leu Glu Leu
        115                 120                 125

Glu Ile Leu Ser Gln Leu Gly Phe Ala Leu Asp Leu Ser Arg Cys Ala
    130                 135                 140

Val Tyr His Cys Glu Asp Asn Leu Leu Tyr Ile Ser Pro Lys Thr Gly
145                 150                 155                 160

Arg Ala Ile Ser Glu Arg Ala Gly Val Ser Tyr Arg His Leu Leu Phe
                165                 170                 175

Pro Leu Pro Gln Ile Leu Arg Asp Leu His Asn Gly Thr His Thr Glu
            180                 185                 190

Gln Cys Ser Arg Lys Glu Phe Leu Leu Cys Leu Gln Ile Leu Gly Tyr
        195                 200                 205

Phe Leu His Arg His Leu Leu Ser Asp Asp Ser Lys Phe Leu Glu Gln
    210                 215                 220

Arg Lys Glu Met Thr Ala Leu Ile Tyr Glu Glu Glu Ala Phe
225                 230                 235

(2) INFORMATION FOR SEQ ID NO: 12:

(i) SEQUENCE CHARACTERISTICS:
        (A) LENGTH: 1843 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 12:

| | | | | | | |
|---|---|---|---|---|---|---|
| GGGCTATTCT | GCAGCCTCAT | AATAGATCCA | CGCCCAAAAG | CGCGTTCAAT | CTGACCAATA | 60 |
| GCAGCATCAA | CAGCCCGCTG | CTTATCAGAG | GGGGAGTCCT | TCATTTCAAC | CATGGGGTAT | 120 |
| CACAAGAATT | TTAACTGCTC | AACAATAGAC | ATTGAAGCCA | AAAGTGTCAA | GATTTGTACA | 180 |
| AATGGGAGCG | ATGCGATTTG | CACTATAAAA | ACACGCCAAA | TCCCCATCAA | GCACTGATAG | 240 |
| AAACCTTCTA | ACCTGAGCAG | CAAGAAAATA | AATAATAGGA | ACGGTCACGG | AGTAATAATT | 300 |
| AATGGTAGCA | GAACCAGAAG | AAGTCAGGAA | GAGGGTGAAG | TACCGCAGGA | AGTAGAATTA | 360 |
| AAGTAGAAAA | GGGGAGCCCT | TAGCCCCCCT | CTTTAGATAA | GCAAGCTTAA | AAAGCAAACC | 420 |
| TAACACCAAA | TTCCCCACCG | ACATAAGCCA | TGGAGAAGTT | AGCAATAGCA | GTATCCTTAG | 480 |
| TACGACCCGC | CGGACTAGTA | TCATCTACAA | GACGTTGAGC | CGGCAGATCA | TCATAAACGC | 540 |
| CATCTCCCAC | AACGCGATGG | TAGAATCCAC | CCGCAAAAGC | GGAGATTACA | GGAGAGAGCT | 600 |
| GATAACTCAA | CCCAGCCTTT | AATCTATAAG | CAAGCTTAGG | AGTGATATGG | CCATCAACCA | 660 |
| CGCCCACGAA | GTTACCGCCA | AGACCAACAC | AAGCATAAGG | AACAACACCT | AAACCTTCAC | 720 |
| TAAGAAGATC | ATAACAAGCA | TTGACCATTA | CGGAAGTAGA | AGAAACCGCC | CTGATCTCAA | 780 |
| CAACTTCACC | CCCTTCAATA | GTCTTAGCTA | GTAACCCTGC | TACTATGGTT | TTTTCTTCAG | 840 |
| GGGTTAGCTC | CTGTACTAGG | TCTTTAGCTA | CGGCTTCGGC | GTTACCATTC | GTATCGCCGA | 900 |
| GCACATTAAC | GTTGTCGCCA | TCATTAACGT | ACCCGTTGG | CCAATTCTTA | CCTTCTCCAA | 960 |
| CCTTTGTTTT | GTTAACAAAC | TCAGTCAAGC | CCAATCCTCT | CTTGCCGGCT | TTGCCGGTTC | 1020 |
| CCATACCACT | ACACTGAGCC | GTCTTATTCG | TCTGTGACGC | GCCACCATCC | GTATAGTCGG | 1080 |
| CCAGCGAGCC | ATTATCTCCA | CTCTTTTTTC | CCCGTGCATG | ACCCCCATCA | CAAACCTTCT | 1140 |
| TATCAATACC | GGGATGAGAA | ACCCCAACCG | CCTTAGCAAA | CTGAACAATA | TCTTTACCAG | 1200 |
| AGGTCTTGGC | AAGAGCAGCA | GCAAGGTTAT | CAGTCTGCCC | AGTAACAACA | TCATAAGCTA | 1260 |
| ACTCCTTAGC | TAGTAGATAT | ACTGTATCAG | CTTCATCTTC | CTTACTACCA | CTATCTCTAA | 1320 |
| TACCCTTGGT | CTTGAAGCGC | TCGTAACCAA | TCTCAAGCTC | AACCCTGGCA | CCACCAATAC | 1380 |
| CATAACCAAC | ACTACCTTCC | ATAGCTACAA | GCATGTTGTC | CTTAAACCCA | ATCCGAGGAT | 1440 |
| CAGGAGTGTT | CCAGTCAAAC | TTGTGTGACT | CTAGCTTTAC | ACTCTTTCCA | TCCTTTAAGT | 1500 |
| ATGGATATAC | TGCCTTAGTC | TCTCCGTTAC | TCTCCCTTAT | ACTAAAATCT | CTTATCTTGC | 1560 |
| TAAACGCTGG | ACTGTAATCC | AAGCCAACAT | AGAAATATCC | CGCACCACCA | GTCTCCAAAG | 1620 |
| CGCTAACGTC | ATCATGAGCC | CTGACATCAT | TCCCAGCCAT | GACTATAGCC | ATCGACATCA | 1680 |
| TTACGCTTCC | TAAGATTATC | TTTCCTTTTC | TCATACTTTT | CAACTTCTCC | AAATTCCTTC | 1740 |
| TTTTTCTTCG | TCTCCTCACT | TCAGCCGGTC | CACTCAAGGG | CTAACCCCCT | CTAACATCTC | 1800 |
| CAGCCAGGAA | TTCGATATCA | AGCTTATCGA | TACCGTCGAC | CTC | | 1843 |

(2) INFORMATION FOR SEQ ID NO: 13:

(i) SEQUENCE CHARACTERISTICS:
        (A) LENGTH: 435 amino acids
        (B) TYPE: amino acid
        (C) STRANDEDNESS: <Unknown>
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO: 13:

```
Met Arg Lys Gly Lys Ile Ile Leu Gly Ser Val Met Met Ser Met Ala
1               5                   10                  15

Ile Val Met Ala Gly Asn Asp Val Arg Ala His Asp Val Ser Ala
            20                  25                  30

Leu Glu Thr Gly Gly Ala Gly Tyr Phe Tyr Val Gly Leu Asp Tyr Ser
            35                  40                  45

Pro Ala Phe Ser Lys Ile Arg Asp Phe Ser Ile Arg Glu Ser Asn Gly
        50                  55                  60

Glu Thr Lys Ala Val Tyr Pro Tyr Leu Lys Asp Gly Lys Ser Val Lys
65                  70                  75                  80

Leu Glu Ser His Lys Phe Asp Trp Asn Thr Pro Asp Pro Arg Ile Gly
                85                  90                  95

Phe Lys Asp Asn Met Leu Val Ala Met Glu Gly Ser Val Gly Tyr Gly
                100                 105                 110

Ile Gly Gly Ala Arg Val Glu Leu Glu Ile Gly Tyr Glu Arg Phe Lys
            115                 120                 125

Thr Lys Gly Ile Arg Asp Ser Gly Ser Lys Glu Asp Glu Ala Asp Thr
        130                 135                 140

Val Tyr Leu Leu Ala Lys Glu Leu Ala Tyr Asp Val Val Thr Gly Gln
145                 150                 155                 160

Thr Asp Asn Leu Ala Ala Ala Leu Ala Lys Thr Ser Gly Lys Asp Ile
                165                 170                 175

Val Gln Phe Ala Lys Ala Val Gly Val Ser His Pro Gly Ile Asp Lys
            180                 185                 190

Lys Val Cys Asp Gly Gly His Ala Arg Gly Lys Lys Ser Gly Asp Asn
            195                 200                 205

Gly Ser Leu Ala Asp Tyr Thr Asp Gly Gly Ala Ser Gln Thr Asn Lys
        210                 215                 220

Thr Ala Gln Cys Ser Gly Met Gly Thr Gly Lys Ala Gly Lys Arg Gly
225                 230                 235                 240

Leu Gly Leu Thr Glu Phe Val Asn Lys Thr Lys Val Gly Glu Gly Lys
                245                 250                 255

Asn Trp Pro Thr Gly Tyr Val Asn Asp Gly Asp Asn Val Asn Val Leu
                260                 265                 270

Gly Asp Thr Asn Gly Asn Ala Glu Ala Val Ala Lys Asp Leu Val Gln
            275                 280                 285

Glu Leu Thr Pro Glu Glu Lys Thr Ile Val Ala Gly Leu Leu Ala Lys
        290                 295                 300

Thr Ile Glu Gly Gly Glu Val Val Glu Ile Arg Ala Val Ser Ser Thr
305                 310                 315                 320

Ser Val Met Val Asn Ala Cys Tyr Asp Leu Leu Ser Glu Gly Leu Gly
                325                 330                 335

Val Val Pro Tyr Ala Cys Val Gly Leu Gly Gly Asn Phe Val Gly Val
                340                 345                 350

Val Asp Gly His Ile Thr Pro Lys Leu Ala Tyr Arg Leu Lys Ala Gly
            355                 360                 365

Leu Ser Tyr Gln Leu Ser Pro Val Ile Ser Ala Phe Ala Gly Gly Phe
        370                 375                 380

Tyr His Arg Val Val Gly Asp Gly Val Tyr Asp Asp Leu Pro Ala Gln
385                 390                 395                 400
```

-continued

```
Arg Leu Val Asp Asp Thr Ser Pro Ala Gly Arg Thr Lys Asp Thr Ala
            405                 410                 415

Ile Ala Asn Phe Ser Met Ala Tyr Val Gly Gly Glu Phe Gly Val Arg
            420                 425                 430

Phe Ala Phe
        435
```

(2) INFORMATION FOR SEQ ID NO: 14:

(i) SEQUENCE CHARACTERISTICS:
        (A) LENGTH: 3435 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 14:

```
TTTTTATATC TGGAGCTCTT GTACTGTGTT TACCACGGGA TTTATTATTG GGTAGGCTTG      60

ATATTCAGGC TCTATCAACG CAGCTATTCA TGGCATTATT ACAGATAAAT TTGGCATTTT     120

GGAGATAGGC GATCTAGGGT TCTATTATTA GGAATCTATT ATTTAGATAT ATAGGGATAT     180

AAGGGAGAGT AACGGAGAGA CTAAGGCAGT ATATCCATAC TTAAAGGATG GAAAGAGTTG     240

AAAGCTAGAG TCACACAAGT TTGACTGGAA CACTCCTGAT CCTCGGATTG GGTTTAAGGA     300

CAACATGCTT GTAGCTATGG AAGGCAGTGT TGGTTATGGT ATTGGTGGTG CCAGGGTTGA     360

GCTTGAGATT GGTTACGAGC GCTTCAAGAC CAAGGGTATT AGAGATAGTG GTAGTAAGGA     420

AGATGAAGCA GATACAGTAT ATCTACTAGC TAAGGAGTTA GCTTATGATG TTGTTACTGG     480

ACAGACTGAT AACCTTGCCG CTGCTCTTGC CAAAACCTCG GGGAAGGACA TCGTTCAGTT     540

TGCCAATGCT GTGAAAATTT CTTACCCTAA AATTGATGAG CAGGTTTGTA ATAAAAATCA     600

TACAGTGTTG AATACGGGGA AAGGGACAAC CTTTAATCCA GATCCCAAGA CAACCGAAGA     660

TAATACAGCG CAGTGCAGTG GGTTGAACAC GAAGGGAACG AATAAGTTTA GCGATTTTGC     720

TGAAGGTGTA GGTTTGAAAG ATAATAAGAA TTGGCCTACT GGTCAGGCTG GAAGAGCAG     780

TGGTGGTCCT GTGGTGGGTG CATCTAATAG TAATGCCAAC GCTATGGCTA GAGACCTAGT     840

AGATCTTAAT CGAGACGAAA AAACCATAGT AGCAGGGTTA CTAGCTAAAA CTATTGAAGG     900

TGGTGAGGTT GTTGAGATTA GGGCGGTTTC TTCTACTTCT GTAATGGTCA ATGCTTGTTA     960

TGATCTTCTT AGTGAAGGTC TAGGCGTTGT TCCTTACGCT TGTGTCGGTC TTGGAGGTAA    1020

CTTCGTGGGC GTTGTTGATG GCATATCAC TCCTAAGCTT GCTTATAGAT TAAAGGCTGG    1080

GTTGAGTTAT CAGCTCTCTC CTGAAATCTC CGCTTTTGCT GGGGGATTCT ATCATCGCGT    1140

TGTGGGAGAT GGTGTCTATG ATGATCTTCC AGCTCAACGT CTTGTAGATG ATACTAGTCC    1200

GGCGGGTCGT ACTAAGGATA CTGCTATTGC TAACTTCTCC ATGGCTTATG TCGGTGGGGA    1260

ATTTGGTGTT AGGTTTGCTT TTTAAGGTGG TTTGTTGGAA GCGGGGTAAG TCAAACTTAC    1320

CCCGCTTCTA TTAGGGAGTT AGTATATGAG ATCTAGAAGT AAGCTATTTT TAGGAAGCGT    1380

AATGATGTCG TTGGCTATAG TCATGGCTGG GAATGATGTC AGGGCTCATG ATGACGTTAG    1440

CGCTTTGGAT ACTGGTGGTG CGGGATATTT CTATGTTGGT TTGGATTACA GTCCAGCGTT    1500

TAGCAAGATA AGAGATTTTA GTATAAGGGA GAGTAACGGA GAGACTAAGG CAGTATATCC    1560

ATACTTAAAG GATGGAAAGA GTGTAAAGCT AGAGTCACAC AAGTTTGACT GGAACACTCC    1620
```

```
TGATCCTCGG ATTGGGTTTA AGGACAACAT GCTTGTAGCT ATGGAAGGTA GTGTTGGTTA       1680

TGGTATTGGT GGTGCCAGGG TTGAGCTTGA GATTGGTTAC GAGCGCTTCA AGACCAAGGG       1740

TATTAGAGAT AGTGGTAGTA AGGAAGATGA AGCTGATACA GTATATCTAC TAGCTAAGGA       1800

GTTAGCTTAT GATGTTGTTA CTGGGCAGAC TGATAACCTT GCCGCTGCTC TGGCCAAAAC       1860

CTCCGGTAAA GACTTTGTCC AGTTTGCTAA GGCGGTTGGG GTTTCTCATC CTAGTATTGA       1920

TGGGAAGGTT TGTAAGACGA AGGCGGATAG CTCGAAGAAA TTTCCGTTAT ATAGTGACGA       1980

AACGCACACG AAGGGGGCAA GTGAGGGGAG AACGTCTTTG TGCGGTGACA ATGGTAGTTC       2040

TACGATAACA AACAGTGGTG CGAATGTAAG TGAAACTGGG CAGGTTTTTA GGGATTTTAT       2100

CAGGGCAACG CTGAAAGAGG ATGGTAGTAA AAACTGGCCA ACTTCAAGCG GCACGGGAAC       2160

TCCAAAACCT GTCACGAACG ACAACGCCAA AGCCGTAGCT AAAGACCTAG TACAGGAGCT       2220

AACCCCTGAA GAAAAAACCA TAGTAGCAGG GTTACTAGCT AAAACTATTG AAGGTGGTGA       2280

GGTTATTGAA ATCAGGGCGG TTTCTTCTAC TTCTGTGATG GTCAATGCTT GTTATGATCT       2340

TCTTAGTGAA GGTTTAGGTG TTGTCCCTTA TGCTTGTGTT GGTCTCGGTG GTAACTTCGT       2400

GGGCGTGGTT GATGGAATTC ATTACACAAA CCATCTTTAA CTCTGAATAC CCTAGTTAAG       2460

GTAAGTGAAG TAACTAGGCA AATTAGTGCT GCACCACTCG TGAAACAAAC TACGATCAGC       2520

GATTCACCAT ACTTAGTAAG TCCGTACAGT GGCTTTACGC TCTTACCCAT CATGAAAAAT       2580

ACTTGCTATC TAGGAATCTC CTCTAAAACT TTACAGAGGT TATCTGTACT TCGAGAGGAA       2640

GCTAATCTGT GGCTCATGAG GATGGTATTT AGCGTATCAC AGGTTCCAGC TGTCTTACAG       2700

TCTCTGGAGA TGTTATAAGG GTGCACATAT AAAACTATGC AATATTTCGC TGCAATACGA       2760

TTCCGATTCG AAAACACTGA AAAGTATTCC CATTATCTAT GAATCTCTGT GTAGATATAA       2820

ATAAGGGTAT ACGCAGTAAC TCTTACTTGT TAAAAACAAG ACCAATGGTA TAAGGAAAAA       2880

GCCTCAGTGT TGTTCCTCAT GCTTGCAGCT TACCCGATGC ACTCTTATTT AATAAGGTTG       2940

AATGTTAATC AGTGTTTCTG GGAAGGGAAT ATCTTATTGC AAAAACCTCA GCAGCTGCTT       3000

AGATATTGAA ACAAATGCGA TCATGCCGTC AGCACAATTA TGACATCTCT TAAGGCTCTG       3060

TAGTGCGCTT ATTTAGTCTA ACATGTGGTA AAGCTTTGCC AGTTCTTTAC CACATGTTCA       3120

CCATCAGTTA ATTGAAAGCA AATCTTGCTC CTATGTTGAA GCCGTAACTA GCTATATTTG       3180

CCTTTACCTT GGCTGCAGCA CCACCTGCTA TGTTTACACG GTTACTAGCG GGAATACCTG       3240

CATACTGTTC ATCGAAAATT CCGTGGTAAA AACCTCCAGC TATTAAAGAT ATTTCAGGAG       3300

TAAGCTTGTA ACTTACGCCT ACCTTTCCTC TATAAGCCAA CTTACTTGTA ACGTGATCGG       3360

CGATATTAAT AAAGCTCGCC CCTAACCCAG CACACATGTA AGGAGGGAAT TCGATATCAA       3420

GCTTATCGAT ACCGT                                                       3435

(2) INFORMATION FOR SEQ ID NO: 15:

(i) SEQUENCE CHARACTERISTICS:
        (A) LENGTH: 326 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 15:

Met Leu Val Ala Met Glu Gly Ser Val Gly Tyr Gly Ile Gly Gly Ala
1               5                   10                  15
```

```
Arg Val Glu Leu Glu Ile Gly Tyr Glu Arg Phe Lys Thr Lys Gly Ile
            20                  25                  30

Arg Asp Ser Gly Ser Lys Glu Asp Glu Ala Asp Thr Val Tyr Leu Leu
            35                  40                  45

Ala Lys Glu Leu Ala Tyr Asp Val Val Thr Gly Gln Thr Asp Asn Leu
 50                  55                  60

Ala Ala Ala Leu Ala Lys Thr Ser Gly Lys Asp Ile Val Gln Phe Ala
 65                  70                  75                  80

Asn Ala Val Lys Ile Ser Tyr Pro Lys Ile Asp Glu Gln Val Cys Asn
                 85                  90                  95

Lys Asn His Thr Val Leu Asn Thr Gly Lys Gly Thr Thr Phe Asn Pro
            100                 105                 110

Asp Pro Lys Thr Thr Glu Asp Asn Thr Ala Gln Cys Ser Gly Leu Asn
            115                 120                 125

Thr Lys Gly Thr Asn Lys Phe Ser Asp Phe Ala Glu Gly Val Gly Leu
        130                 135                 140

Lys Asp Asn Lys Asn Trp Pro Thr Gly Gln Ala Gly Lys Ser Ser Gly
145                 150                 155                 160

Gly Pro Val Val Gly Ala Ser Asn Ser Asn Ala Asn Ala Met Ala Arg
                165                 170                 175

Asp Leu Val Asp Leu Asn Arg Asp Glu Lys Thr Ile Val Ala Gly Leu
                180                 185                 190

Leu Ala Lys Thr Ile Glu Gly Gly Glu Val Val Glu Ile Arg Ala Val
        195                 200                 205

Ser Ser Thr Ser Val Met Val Asn Ala Cys Tyr Asp Leu Leu Ser Glu
210                 215                 220

Gly Leu Gly Val Val Pro Tyr Ala Cys Val Gly Leu Gly Gly Asn Phe
225                 230                 235                 240

Val Gly Val Val Asp Gly His Ile Thr Pro Lys Leu Ala Tyr Arg Leu
                245                 250                 255

Lys Ala Gly Leu Ser Tyr Gln Leu Ser Pro Glu Ile Ser Ala Phe Ala
            260                 265                 270

Gly Gly Phe Tyr His Arg Val Val Gly Asp Gly Val Tyr Asp Asp Leu
        275                 280                 285

Pro Ala Gln Arg Leu Val Asp Asp Thr Ser Pro Ala Gly Arg Thr Lys
        290                 295                 300

Asp Thr Ala Ile Ala Asn Phe Ser Met Ala Tyr Val Gly Gly Glu Phe
305                 310                 315                 320

Gly Val Arg Phe Ala Phe
                325

(2) INFORMATION FOR SEQ ID NO: 16:

(i) SEQUENCE CHARACTERISTICS:
        (A) LENGTH: 364 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 16:

Met Arg Ser Arg Ser Lys Leu Phe Leu Gly Ser Val Met Met Ser Leu
 1               5                  10                  15

Ala Ile Val Met Ala Gly Asn Asp Val Arg Ala His Asp Asp Val Ser
            20                  25                  30
```

```
Ala Leu Asp Thr Gly Gly Ala Gly Tyr Phe Tyr Val Gly Leu Asp Tyr
         35                  40                  45

Ser Pro Ala Phe Ser Lys Ile Arg Asp Phe Ser Ile Arg Glu Ser Asn
 50                  55                  60

Gly Glu Thr Lys Ala Val Tyr Pro Tyr Leu Lys Asp Gly Lys Ser Val
 65                  70                  75                  80

Lys Leu Glu Ser His Lys Phe Asp Trp Asn Thr Pro Asp Pro Arg Ile
                 85                  90                  95

Gly Phe Lys Asp Asn Met Leu Val Ala Met Glu Gly Ser Val Gly Tyr
                100                 105                 110

Gly Ile Gly Gly Ala Arg Val Glu Leu Glu Ile Gly Tyr Glu Arg Phe
             115                 120                 125

Lys Thr Lys Gly Ile Arg Asp Ser Gly Ser Lys Glu Asp Glu Ala Asp
         130                 135                 140

Thr Val Tyr Leu Leu Ala Lys Glu Leu Ala Tyr Asp Val Val Thr Gly
145                 150                 155                 160

Gln Thr Asp Asn Leu Ala Ala Leu Ala Lys Thr Ser Gly Lys Asp
                165                 170                 175

Phe Val Gln Phe Ala Lys Ala Val Gly Val Ser His Pro Ser Ile Asp
             180                 185                 190

Gly Lys Val Cys Lys Thr Lys Ala Asp Ser Ser Lys Lys Phe Pro Leu
         195                 200                 205

Tyr Ser Asp Glu Thr His Thr Lys Gly Ala Ser Glu Gly Arg Thr Ser
210                 215                 220

Leu Cys Gly Asp Asn Gly Ser Ser Thr Ile Thr Asn Ser Gly Ala Asn
225                 230                 235                 240

Val Ser Glu Thr Gly Gln Val Phe Arg Asp Phe Ile Arg Ala Thr Leu
                245                 250                 255

Lys Glu Asp Gly Ser Lys Asn Trp Pro Thr Ser Ser Gly Thr Gly Thr
                260                 265                 270

Pro Lys Pro Val Thr Asn Asp Asn Ala Lys Ala Val Ala Lys Asp Leu
         275                 280                 285

Val Gln Glu Leu Thr Pro Glu Glu Lys Thr Ile Val Ala Gly Leu Leu
 290                 295                 300

Ala Lys Thr Ile Glu Gly Gly Glu Val Ile Glu Ile Arg Ala Val Ser
305                 310                 315                 320

Ser Thr Ser Val Met Val Asn Ala Cys Tyr Asp Leu Leu Ser Glu Gly
                325                 330                 335

Leu Gly Val Val Pro Tyr Ala Cys Val Gly Leu Gly Gly Asn Phe Val
             340                 345                 350

Gly Val Val Asp Gly Ile His Tyr Thr Asn His Leu
         355                 360
```

(2) INFORMATION FOR SEQ ID NO: 17:

(i) SEQUENCE CHARACTERISTICS:
        (A) LENGTH: 2900 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 17:

-continued

| | | | | | |
|---|---|---|---|---|---|
| CTCCACCGCG | GTGGCGGCCG | CTCTAGAACT | AGTGGATCCC | CCGGGCTGCA | GGAATTCCGG | 60 |
| AATTCCGGAA | TTCGGCCCTC | CGGACAGTAT | AAAAGCTGCT | ATTTTTTTCC | CTTGCGCAAG | 120 |
| TAAAGCAGGG | AAGTCAGTAT | CTACAGAAAA | AACCTCACTA | TACACTCCAA | GTTCTCTTAC | 180 |
| TCTGCGTGCA | ATCAGCTGGG | TAACCTGTGA | ACCAAAGTCA | ATTATGGCAA | TCGTTAACAC | 240 |
| TTACTACTCC | AATATACTCA | CACACATTGT | AAGACATTAG | TGCTCAGTGG | ACAATGCACA | 300 |
| TACACAGGGA | AGAGCAACGC | TTATTGTTCA | AAAGGAGAAG | TAATCTCCCT | CTTAGTATAG | 360 |
| GGAAGAGGCT | ACCACGGAAG | ATACAGGGTA | TGTCACCTTG | AGTGTTACCA | CACTTAGACG | 420 |
| CAAGCGAAGC | ATGCAATAGC | ATTTGGTGTA | TTGATAGTAT | AAATATTAAA | ATTTTCTTTT | 480 |
| TTTACTACTT | TACGTAGAGT | GCGCCTATAG | GGAATACCAC | TTTCATTAGT | TCTGTCATCA | 540 |
| ATTTACTAAA | GTTATAAATT | TATTAATGAA | TTTCCCATAA | CCTCGGTAGT | GACAATATTT | 600 |
| TGGTGAATGG | TATGAAAACT | GAACCGCAAA | GCCACAATTC | TACAACAGTA | AATGATACTA | 660 |
| CTTCTTCATC | TAGAACAAGG | AGTGACGTTA | TGAAAGGAAA | GTCAGATTCT | GAAATACGTA | 720 |
| CGTCTTCTTC | AATACGTACA | TCTTCTTCAG | ACGATAGCGA | GAGTTCGGAT | GACAGCACAC | 780 |
| GTATTCGTGC | TTCTAAAACT | CATCCTCAAG | CACCTAGCGA | CAACAGCAGC | ATACTCTCAT | 840 |
| CTGAGGATAT | TGAGAGCGTA | ATGCGGTGCC | TAGAAGAGGA | ATATGGCCAA | AAGCTTAGCA | 900 |
| GTGAGCTTAA | GAAATCAATG | CGTGAAGAAA | TTTCTACAGC | TGTGCCAGAA | TTGACAAGAG | 960 |
| CGCTTATACC | ATTATTAGCA | TCTGCTAGTG | ATAGTGATTC | AAGCTCTAGA | AAGCTGCAAG | 1020 |
| AAGAATGGGT | GAAAACATTC | ATGGCTATTA | TGTTGCCGCA | TATGCAGAAA | ATTGTGGCAT | 1080 |
| CGACCCAAGG | TTAGGTTTAG | CCCAGGAGAC | TGCTGCAGTT | CAAGCACAGC | GCCTAACCGG | 1140 |
| CAGCAGGTGC | TGCATGCACA | GTCAGTAAAT | GTTGTTTGAT | AGATGCCTGG | AGCAGATCTA | 1200 |
| GTAGCATCGC | CCCAGGCATC | TCTCCCATTC | CAAGCTCGCA | ATTCTCTTCA | GATTCTTTTT | 1260 |
| TCCACAAAGG | ATATCTATAT | ATTAGTCAGC | TGCTTCTCGT | TTTAGTGTGT | GTGTAGAGCG | 1320 |
| GTGCTAAATC | TCCTAATCTC | CCATAGGTAG | TAGCACCGTA | CCTTTACCGA | TATGCAAGTG | 1380 |
| TGTGCTGCGA | GCGCTACCAT | AGGCATATCG | GTGGAGGTCT | AACAAAACAA | GGCGTATATC | 1440 |
| AAGTGCGTTT | ATTACATAGA | TCACGTCTGT | ATTGATAGTG | AGCGTGCACA | CACAGTTCTA | 1500 |
| TCATTAGGTT | GACACAGCTT | TCATGTAGCG | TCATAAACGT | CGCATTTTAC | TATGAAGTAG | 1560 |
| CTTATTTTAA | CCATTCAAGT | ATGTACTTTG | TGCAAGAGAT | TCTCCATTGG | CATCACAGGA | 1620 |
| TTCGCTCTGT | AAGTCTTGTG | AGTACATTAC | CATTGATTCC | AGATTTTAAA | TCTGTGCTTC | 1680 |
| CTTCCATACG | TTCAGTGCCT | TTGTAGCCTT | ATAGGCAGGT | ACTGGGTTTG | TATCTATGGC | 1740 |
| TCGTGTATTT | ACATTGAGTT | TTGTAATCAG | GTACAGGTTT | TTATATCTGG | AGCTCTTGTA | 1800 |
| CTGTGTTTAC | CACGGGATTT | ATTATTGGGT | AGGCTTGATA | TTCAGGCTCT | ATCAACGCAG | 1860 |
| CTATTCATGG | CATTATTACA | GATAAATTTG | GCATTTGGA | GATAGGCGAT | CTAGGGTTCT | 1920 |
| ATTATTAGGA | ATCTATTATT | TAGATATATA | GGGATATAAG | GGAGAGTAAC | GGAGAGACTA | 1980 |
| AGGCAGTATA | TCCATACTTA | AAGGATGGAA | AGAGTGTAAA | GCTAGAGTCA | CACAAGTTTG | 2040 |
| ACTGGAACAC | TCCTGATCCT | CGGATTGGGT | TTAAGGACAA | CATGCTTGTA | GCTATGGAAG | 2100 |
| GCAGTGTTGG | TTATGGTATT | GGTGGTGCCA | GGGTTGAGCT | TGAGATTGGT | TACGAGCGCT | 2160 |
| TCAAGACCAA | GGGTATTAGA | GATAGTGGTA | GTAAGGAAGA | TGAAGCTGAT | ACAGTATATC | 2220 |
| TACTAGCTAA | GGAGTTAGCT | TATGATGTTG | TTACTGGGCA | GACTGATAAC | CTTGCCGCTG | 2280 |
| CTCTGGCCAA | AACCTCCGGT | AAAGACTTTG | TCCAGTTTGC | TAAGGCGGTT | GGGGTTTCTC | 2340 |

```
ATCCTAGTAT TGATGGGAAG GTTTGTAAGA CGAAGGCGGA TAGCTCGAAG AAATTTCCGT     2400

TATATAGTGA CGAAACGCAC ACGAAGGGGG CAAGTGAGGG GAGAAGCTCT TTGTGCGGTG     2460

ACAATGGTAG TTCTACGATA ACAAACAGTG GTGCGAATGT AAGTGAAACT GGGCAGGTTT     2520

TTAGGGATTT TATCAGGGCA ACGCTGAAAG AGGATGGTAG TAAAAACTGG CCAACTTCAA     2580

GCGGCACGGG AACTCCAAAA CCTGTCACGA ACGACAACGC CAAAGCCGTA GCTAAAGACC     2640

TAGTACAGGA GCTAACCCCT GAAGAAAAAA CCATAGTAGC AGGGTTACTA GCTAAAACTA     2700

TTGAAGGTGG TGAGGTTATT GAAATCAGGG CGGTTTCTTC TACTTCTGTG ATGGTCAATG     2760

CTTGTTATGA TCTTCTTAGT GAAGGTTTAG GTGTTGTCCC TTATGCTTGT GTTGGTCTCG     2820

GTGGTAACTT CGTGGGCGTG GTTGATGGAA TTCGATATCA AGCTTATCGA TACCGTCGAC     2880

CTCGAGGGGG GGCCCGGTAC                                                2900
```

(2) INFORMATION FOR SEQ ID NO: 18:

(i) SEQUENCE CHARACTERISTICS:
        (A) LENGTH: 256 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 18:

```
Met Leu Val Ala Met Glu Gly Ser Val Gly Tyr Gly Ile Gly Gly Ala
  1               5                  10                  15

Arg Val Glu Leu Glu Ile Gly Tyr Glu Arg Phe Lys Thr Lys Gly Ile
             20                  25                  30

Arg Asp Ser Gly Ser Lys Glu Asp Glu Ala Asp Thr Val Tyr Leu Leu
         35                  40                  45

Ala Lys Glu Leu Ala Tyr Asp Val Val Thr Gly Gln Thr Asp Asn Leu
     50                  55                  60

Ala Ala Ala Leu Ala Lys Thr Ser Gly Lys Asp Phe Val Gln Phe Ala
 65                  70                  75                  80

Lys Ala Val Gly Val Ser His Pro Ser Ile Asp Gly Lys Val Cys Lys
                 85                  90                  95

Thr Lys Ala Asp Ser Ser Lys Lys Phe Pro Leu Tyr Ser Asp Glu Thr
            100                 105                 110

His Thr Lys Gly Ala Ser Glu Gly Arg Ser Ser Leu Cys Gly Asp Asn
        115                 120                 125

Gly Ser Ser Thr Ile Thr Asn Ser Gly Ala Asn Val Ser Glu Thr Gly
    130                 135                 140

Gln Val Phe Arg Asp Phe Ile Arg Ala Thr Leu Lys Glu Asp Gly Ser
145                 150                 155                 160

Lys Asn Trp Pro Thr Ser Ser Gly Thr Gly Thr Pro Lys Pro Val Thr
                165                 170                 175

Asn Asp Asn Ala Lys Ala Val Ala Lys Asp Leu Val Gln Glu Leu Thr
            180                 185                 190

Pro Glu Glu Lys Thr Ile Val Ala Gly Leu Leu Ala Lys Thr Ile Glu
        195                 200                 205

Gly Gly Glu Val Ile Glu Ile Arg Ala Val Ser Ser Thr Ser Val Met
    210                 215                 220

Val Asn Ala Cys Tyr Asp Leu Leu Ser Glu Gly Leu Gly Val Val Pro
225                 230                 235                 240

Tyr Ala Cys Val Gly Leu Gly Gly Asn Phe Val Gly Val Val Asp Gly
```

-continued (2) INFORMATION FOR SEQ ID NO: 19:

(i) SEQUENCE CHARACTERISTICS:
        (A) LENGTH: 409 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 19:

```
Met Ser Ala Val Ser Asn Arg Lys Leu Pro Leu Gly Gly Val Leu Met
  1               5                  10                  15

Ala Leu Ala Ala Ala Val Ala Pro Ile His Ser Leu Leu Ala Ala Pro
             20                  25                  30

Ala Ala Gly Ala Gly Ala Gly Gly Glu Gly Leu Phe Ser Gly Ala Gly
         35                  40                  45

Ala Gly Ser Phe Tyr Ile Gly Leu Asp Tyr Ser Pro Ala Phe Gly Ser
     50                  55                  60

Ile Lys Asp Phe Lys Val Gln Glu Ala Gly Gly Thr Thr Arg Gly Val
 65                  70                  75                  80

Phe Pro Tyr Lys Arg Asp Ala Ala Gly Arg Val Asp Phe Lys Val His
                 85                  90                  95

Asn Phe Asp Trp Ser Ala Pro Glu Pro Lys Ile Ser Phe Lys Asp Ser
            100                 105                 110

Met Leu Thr Ala Leu Glu Gly Ser Ile Gly Tyr Ser Ile Gly Gly Ala
            115                 120                 125

Arg Val Glu Val Glu Val Gly Tyr Glu Arg Phe Val Ile Lys Gly Gly
        130                 135                 140

Lys Lys Ser Asn Glu Asp Thr Ala Ser Val Phe Leu Leu Gly Lys Glu
145                 150                 155                 160

Leu Ala Tyr His Thr Ala Arg Gly Gln Val Asp Arg Leu Ala Thr Ala
                165                 170                 175

Leu Gly Lys Met Thr Lys Ser Glu Ala Lys Lys Trp Gly Asn Ala Ile
            180                 185                 190

Glu Ser Ala Thr Gly Thr Thr Ser Gly Asp Glu Leu Ser Lys Lys Val
        195                 200                 205

Cys Gly Lys Gly Thr Thr Ser Gly Ser Thr Asn Gln Cys Gly Thr Thr
    210                 215                 220

Asp Ser Thr Ala Thr Thr Lys Ile Ser Ala Val Phe Thr Glu Asp Ala
225                 230                 235                 240

Ala Ala Gln Leu Ser Thr Met Asp Asn Thr Thr Ile Asn Thr Thr Gly
                245                 250                 255

Met Ala Asn Asn Ile Asn Ser Leu Thr Lys Asp Glu Lys Ala Ile Val
            260                 265                 270

Ala Gly Ala Phe Ala Arg Ala Val Glu Gly Ala Glu Val Ile Glu Val
        275                 280                 285

Arg Ala Ile Gly Ser Thr Ser Val Met Leu Asn Ala Cys Tyr Asp Leu
    290                 295                 300

Leu Thr Asp Gly Ile Gly Val Val Pro Tyr Ala Cys Ala Gly Ile Gly
305                 310                 315                 320

Gly Asn Phe Val Ser Val Val Asp Gly His Ile Asn Pro Lys Phe Ala
                325                 330                 335

Tyr Arg Val Lys Ala Gly Leu Ser Tyr Ala Leu Thr Pro Glu Ile Ser
```

```
                    340              345              350
Ala Phe Ala Gly Ala Phe Tyr His Lys Val Leu Gly Asp Gly Asp Tyr
            355              360              365
Asp Glu Leu Pro Leu Ser His Ile Ser Asp Tyr Thr Gly Thr Ala Gly
        370              375              380
Lys Asn Lys Asp Thr Gly Ile Ala Ser Phe Asn Phe Ala Tyr Phe Gly
385              390              395              400
Gly Glu Ile Gly Val Arg Phe Ala Phe
                405
```

(2) INFORMATION FOR SEQ ID NO: 20:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 20:

```
GGTGCCTGCG TATTTAACGA TG                                      22
```

(2) INFORMATION FOR SEQ ID NO: 21:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 21:

```
CGATTAACAC GTCTACCAAA ACCCTC                                  26
```

(2) INFORMATION FOR SEQ ID NO: 22:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 22:

```
TGGAAGGCAG TGTTGGTTAT GG                                      22
```

(2) INFORMATION FOR SEQ ID NO: 23:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 23:

```
CGTGACAGGT TTGGAAGTTC CC                                      22
```

(2) INFORMATION FOR SEQ ID NO: 24:

(i) SEQUENCE CHARACTERISTICS:
        (A) LENGTH: 23 base pairs

```
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 24:

GTGCTATTCC GCTGATTATG TCG                                              23

(2) INFORMATION FOR SEQ ID NO: 25:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 25:

GCTCAAGAAA GGCAAATATC GCAG                                             24

(2) INFORMATION FOR SEQ ID NO: 26:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 26:

GGATTCTAAA AACCCGTTGG TAGC                                             24

(2) INFORMATION FOR SEQ ID NO: 27:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 27:

GGCTTCTCTC CCGTAGACAT GAAC                                             24

(2) INFORMATION FOR SEQ ID NO: 28:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 28:

TGTTGAATAC GGGGAAAGGG AC                                               22

(2) INFORMATION FOR SEQ ID NO: 29:

(i) SEQUENCE CHARACTERISTICS:
        (A) LENGTH: 23 base pairs
        (B) TYPE: nucleic acid
        (C) STRANDEDNESS: single
        (D) TOPOLOGY: linear
```

```
    (ii) MOLECULE TYPE: DNA (genomic)

(xi) SEQUENCE DESCRIPTION: SEQ ID NO: 29:

GCGGAGATTT CAGGAGAGAG CTG                                          23

(2) INFORMATION FOR SEQ ID NO: 30:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 30:

TGTTTGGATT ACAGTCCAGC G                                            21

(2) INFORMATION FOR SEQ ID NO: 31:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 31:

ACCTGCCCAG TTCACTTACA TTC                                          23

(2) INFORMATION FOR SEQ ID NO: 32:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 32:

CGGAATGCTC TATGACGTTT GG                                           22

(2) INFORMATION FOR SEQ ID NO: 33:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 33:

CAAAGCAGCA ATGTCTTTAG GAGC                                         24

(2) INFORMATION FOR SEQ ID NO: 34:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 34:
```

```
GGTAGAGGGA ATAACAAGTG CCG                                                   23
```

(2) INFORMATION FOR SEQ ID NO: 35:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 35:

```
GGAGATAGAG TGTGCGTAAC GTGG                                                  24
```

(2) INFORMATION FOR SEQ ID NO: 36:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 36:

```
TGGCAGAAGA CGACTTG                                                          17
```

(2) INFORMATION FOR SEQ ID NO: 37:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 37:

```
CGTCAAAACA CCACTGATCC G                                                     21
```

(2) INFORMATION FOR SEQ ID NO: 38:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 38:

```
GATGATATGG ATGGGTTGCG G                                                     21
```

(2) INFORMATION FOR SEQ ID NO: 39:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 39:

```
AATGCACACC AAAAGCGGC                                                        19
```

(2) INFORMATION FOR SEQ ID NO: 40:

```
    (i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 40:

GCGTCACAGA CGAATAAGAC GG                                               22

(2) INFORMATION FOR SEQ ID NO: 41:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 41:

AGCGGAGATT ACAGGAGAGA GCTG                                             24
```

What is claimed is:

1. A purified polypeptide comprising an amino acid sequence selected from the group of amino acid sequences set forth as SEQ ID NOS: 2, 3, 5, 7, 8, 10, and 11, corresponding to granulocytic Ehrlichia polypeptide W20.1, W20.2, B3, E74.3, E74.4, E82.2, and E82.3, respectively.

2. A composition comprising the polypeptide of claim 1, and a carrier.

3. A composition comprising the polypeptide of claim 1, together with a pharmaceutically acceptable diluent, carrier, or excipient, wherein said polypeptide is present in an amount effective to elicit immune responses in an animal to granulocytic Ehrlichia.

4. A purified polypeptide having at least 85% amino acid sequence identity to the amino acid sequence set forth as SEQ ID NO: 2, 3, 5, 7, 8, 10, or 11.

5. A purified polypeptide having at least 90% amino acid sequence identity to the amino acid sequence set forth as SEQ ID NO: 2, 3, 5, 7, 8, 10, or 11.

6. A purified polypeptide, comprising an immunologically reactive fragment of the amino acid sequence set forth in SEQ ID NO: 2, 3, 5, 7, 8, 10, or 11.

7. A composition comprising the polypeptide according to claim 6, and a carrier.

8. A composition comprising the polypeptide according to claim 6, together with a pharmaceutically acceptable diluent, carrier, or excipient, wherein said fragment is present in an amount effective to elicit immune responses in an animal to granulocytic Ehrlichia.

9. A method of producing an immune response which recognizes GE in a host comprising administering to the host the composition according to claim 7.

* * * * *